United States Patent
Caligiuri et al.

(10) Patent No.: US 11,459,378 B2
(45) Date of Patent: Oct. 4, 2022

(54) PASSIVE ANTIBODY DEPENDENT CELL-MEDIATED ACTIVATION

(71) Applicant: Ohio State Innovation Foundation, Columbus, OH (US)

(72) Inventors: Michael Caligiuri, Columbus, OH (US); Jianhua Yu, Columbus, OH (US); Hongsheng Dai, Columbus, OH (US)

(73) Assignee: OHIO STATE INNOVATION FOUNDATION, Columbus, OH (US)

( * ) Notice: Subject to any disclaimer, the term of this patent is extended or adjusted under 35 U.S.C. 154(b) by 0 days.

(21) Appl. No.: 16/480,293

(22) PCT Filed: Jan. 30, 2018

(86) PCT No.: PCT/US2018/016035
§ 371 (c)(1),
(2) Date: Jul. 23, 2019

(87) PCT Pub. No.: WO2018/140974
PCT Pub. Date: Aug. 2, 2018

(65) Prior Publication Data
US 2020/0040064 A1 Feb. 6, 2020

Related U.S. Application Data

(60) Provisional application No. 62/452,111, filed on Jan. 30, 2017.

(51) Int. Cl.
| | |
|---|---|
| *C07K 16/08* | (2006.01) |
| *C07K 16/30* | (2006.01) |
| *C12N 5/0786* | (2010.01) |
| *A61K 38/08* | (2019.01) |

(52) U.S. Cl.
CPC .......... *C07K 16/087* (2013.01); *A61K 38/08* (2013.01); *C07K 16/088* (2013.01); *C07K 16/30* (2013.01); *C12N 5/0645* (2013.01); *C07K 2317/52* (2013.01); *C07K 2317/72* (2013.01); *C07K 2317/732* (2013.01); *C12N 2533/50* (2013.01)

(58) Field of Classification Search
CPC .... C07K 16/087; C07K 16/088; C07K 16/30; C07K 2317/52; C07K 2317/72; C07K 2317/732; C07K 2317/31; C07K 2319/30; C07K 14/005; A61K 38/08; C12N 5/0645; C12N 2533/50; C12N 2710/16222; C12N 2710/16622; A61P 25/00; A61P 29/00; A61P 31/22; A61P 35/00

See application file for complete search history.

(56) References Cited

U.S. PATENT DOCUMENTS

| | | | | |
|---|---|---|---|---|
| 2007/0036799 | A1* | 2/2007 | Stavenhagen | A61P 35/00 424/155.1 |
| 2012/0244578 | A1* | 9/2012 | Kannan | C07K 16/00 435/69.6 |
| 2013/0177555 | A1* | 7/2013 | Wilkinson | C07K 14/00 424/133.1 |
| 2015/0368668 | A1 | 12/2015 | Marcotrigiano et al. | |

FOREIGN PATENT DOCUMENTS

| | | | |
|---|---|---|---|
| CN | 105669838 A | 6/2016 | |
| JP | 2009-507470 | 2/2009 | |
| WO | WO-2007/021841 | 2/2007 | |
| WO | WO-2012/022985 A1 | 2/2012 | |
| WO | WO-2013138643 A1 * | 9/2013 | ........... G01N 33/573 |

OTHER PUBLICATIONS

Olinescu A, Hristescu S, Sjöquist J, Gheţie V. Correlation between the triggering of proliferation and the potentiation of NK activity induced by protein A in human lymphocytes. Immunol Lett. Apr. 1983;6(4):231-7.*
Huvenne W, Callebaut I, Plantinga M, Vanoirbeek JA, Krysko O, Bullens DM, Gevaert P, Van Cauwenberge P, Lambrecht BN, Ceuppens JL, Bachert C, Hellings PW. *Staphylococcus aureus* enterotoxin B facilitates allergic sensitization in experimental asthma. Clin Exp Allergy. Jul. 2010;40(7):1079-90. Epub Mar. 1, 2010.*
Pauli NT, Kim HK, Falugi F, Huang M, Dulac J, Henry Dunand C, Zheng NY, Kaur K, Andrews SF, Huang Y, DeDent A, Frank KM, Charnot-Katsikas A, Schneewind O, Wilson PC. *Staphylococcus aureus* infection induces protein A-mediated immune evasion in humans. J Exp Med. Nov. 17, 2014;211(12):2331-9. Epub Oct. 27, 2014.*
Hook LM, Friedman HM. Subversion of innate and adaptive immunity: immune evasion from antibody and complement. In: Arvin A, Campadelli-Fiume G, Mocarski E, et al., editors. Human Herpesviruses: Biology, Therapy, and Immunoprophylaxis. Cambridge: Cambridge University Press; 2007. Chapter 63. (Year: 2007).*

(Continued)

*Primary Examiner* — Rachel B Gill
(74) *Attorney, Agent, or Firm* — Foley & Lardner LLP

(57) ABSTRACT

In certain embodiments, described herein is a method of treating a subject infected with a pathogen encoding an Fc-binding protein comprising administering to the subject a therapeutically effective amount of a pharmaceutical composition comprising an Fc region of an immunoglobulin G antibody. Also described herein is a method for treating cancer in a subject undergoing oncolytic viral therapy comprising administering to the subject a therapeutically effective amount of a pharmaceutical composition comprising an Fc region of an immunoglobulin G antibody. Further described herein is a method of activating natural killer (NK) cells in a subject infected with a pathogen, comprising administering to the subject a pharmaceutical composition comprising an Fc region of an immunoglobulin G antibody.

13 Claims, 67 Drawing Sheets
Specification includes a Sequence Listing.

(56) References Cited

OTHER PUBLICATIONS

Sugano S, Suzuki Y. Unnamed protein product [*Homo sapiens*]. GenBank: BAC85237.1. Dep. Sep. 14, 2006. (Year: 2006).*

Silva-Martin N, Bartual SG, Ramierz-Aportela E, Chacon P, Park CG, Hermoso JA. Chain A, Ig Gamma-1 Chain C Region. PDB: 4CDH_A. Dep. Nov. 13, 2014. (Year: 2014).*

Alvarez-Breckenridge CA, Yu J, Price R, Wojton J, Pradarelli J, Mao H, Wei M, Wang Y, He S, Hardcastle J, Fernandez SA, Kaur B, Lawler SE, et al. NK cells impede glioblastoma virotherapy through NKp30 and NKp46 natural cytotoxicity receptors. Nat Med. Dec. 2012;18(12):1827-34. Epub Nov. 25, 2012.; (Year: 2012).*

Chen W, Gong R, Ying T, Prabakaran P, Zhu Z, Feng Y, Dimitrov DS. Discovery of novel candidate therapeutics and diagnostics based on engineered human antibody domains. Curr Drug Discov Technol. Mar. 2014;11(1):28-40. (Year: 2014).*

Mi W, Wanjie S, Lo ST, Gan Z, Pickl-Herk B, Ober RJ, Ward ES. Targeting the neonatal fc receptor for antigen delivery using engineered fc fragments. J Immunol. Dec. 1, 2008;181(11):7550-61. (Year: 2008).*

Gong R, Xiao G. Engineered antibody variable and constant domains as therapeutic candidates. Pharm Pat Anal. Sep. 2013;2(5):637-46. (Year: 2013).*

Corrales-Aguilar E, Trilling M, Hunold K, Fiedler M, Le VT, Reinhard H, Ehrhardt K, Mercé-Maldonado E, Aliyev E, Zimmermann A, Johnson DC, Hengel H. Human cytomegalovirus Fcγ binding proteins gp34 and gp68 antagonize Fcγ receptors I, II and III. PLoS Pathog. May 15, 2014;10(5):e1004131. (Year: 2014).*

Knopp GW, Stadlmayr G, Ruker F. IgG Fc Fragment as a Scaffold for Development of Targeted Therapeutics. Curr Pharm Biotechnol. 2016;17(15):1315-1323. (Year: 2016).*

Aiba N, Shiraki A, Yajima M, Oyama Y, Yoshida Y, Ohno A, Yamada H, Takemoto M, Daikoku T, Shiraki K. Interaction of Immunoglobulin with Cytomegalovirus-Infected Cells. Viral Immunol. Sep. 2017;30(7):500-507. Epub Jun. 9, 2017. (Year: 2017).*

Maidji E, McDonagh S, Genbacev O, Tabata T, Pereira L. Maternal antibodies enhance or prevent cytomegalovirus infection in the placenta by neonatal Fc receptor-mediated transcytosis. Am J Pathol. Apr. 2006;168(4):1210-26. (Year: 2006).*

Dai et al, "Molecular Basis for the Recognition of Herpes Simplex Virus Type 1 Infection by Human Natural Killer Cells", Frontiers in Immunology, vol. 9, Feb. 12, 2018 (Feb. 12, 2018), pp. 1-8.

Dai et al, "The Fc Domain of Immunoglobulin is Sufficient to Bridge NK Cells with Virally Infected Cells", Immunity, Cell Press, Amsterdam, NL, vol. 47, No. 1, Jul. 18, 2017 (Jul. 18, 2017) p. 159.

Foreign Search Report on EP 18744927.7 dated Oct. 30, 2020.

Frank et al, "A novel function of the herpes simplex virus type 1 Fc receptor: participation in bipolar bridging of antiviral immunoglobulin G.", Journal of Virology, vol. 63, No. 11, Nov. 1, 1989 (Nov. 1, 1989), pp. 4479-4488.

Kumel et al, "Passive Immune protection by herpes simplex virus-specific monoclonal antibodies and monoclonal antibody-resistant mutants altered in pathogenicity", Journal of Virology, The American Society for Microbiology, vol. 56, No. 3, Dec. 1, 1985 (Dec. 1, 1985), pp. 930-937.

Rector et al, "Use of monoclonal antibodies for analysis of antibody-dependent immunity to ocular herpes simplex virus type 1 infection", Infection and Immunity, vol. 38, No. 1, Jan. 1, 1982 (Jan. 1, 1982), pp. 168-174.

Awasthi et al., "Blocking Herpes Simplex Virus 2 Glycoprotein E Immune Evasion as an Approach to Enhance Efficacy of a Trivalent Subunit Antigen Vaccine for Genital Herpes", Journal of Virology, May 2014, 88(15), pp. 8421-8432.

Ghiasi et al., "Corneal Macrophage Infiltrates Following Ocular Herpes Simplex Virus Type 1 Challenge Vary in BALB/c Mice Vaccinated with Different Vaccines", Vacccine, 2001, 19(9-10), pp. 1266-1273.

International Search Report and Written Opinion issued in PCT Application No. PCT/US2018/016035 dated Jun. 11, 2018, 16 pages.

Kebriaei et al., "Construction and immunogenicity of a new Fc-based subunit vaccine candidate against *Mycobacterium tuberculosis*", Mol Biol Rep., 2016, 43(9), pp. 911-922.

Lubinski et al., "The Herpes Simplex Virus 1 IgG Fc Receptor Blocks Antibody-Mediated Complement Activation and Antibody-Dependent Cellular Cytotoxicity in Vivo," Journal of Virology, Apr. 2011, 85(7), pp. 3239-3249.

Mobergslien et al., "Cancer cell-binding peptide fused Fc domain activates immune effector cells and blocks tumor growth", Oncotarget, 2016, 7(46), pp. 75940-75953.

Wines et al., "The IgG Fc contains distinct Fc receptor (FcR) binding sites: the leukocyte receptors Fc gamma RI and Fc gamma RIIa Bind to a Region in the Fc Distinct from That Recognized by Neonatal FcR and Protein A", The Journal of Immunology, 2000, 164(10), pp. 5313-5318.

Yin et al., "Protein A immunoadsorption combined with rituximab in highly sensitized kidney transplant recipients", Chin Med J., 2009, 122(22), pp. 2752-2756.

Eugenia Corrales-Aguilar, et al., "Human Cytomegalovirus Fcγ Binding Proteins gp34 and gp68, Antagonize Fcγ Receptors I, II and III", PLOS Pathogens, vol. 10, No. 5, May 15, 2014, pp. 1-7.

Foreign Search Report on EP 18744927.7 dated Mar. 25, 2021.

Igor Puzanov, et al, "Talimogene Laherparepvec in Combination With Ipilimumab in Previously Untreated, Unresectable Stage IIIB-IV Melanoma", Journal of Clinical Oncology, vol. 34, No. 22, Aug. 1, 2016, pp. 2619-2626.

Paul M. Foreman, et al, "Oncolytic Virotherapy for the Treatment of Malignant Glioma", Neurntherapeutics, Elsevier Inc, vol. 14, No. 2, Mar. 6, 2017, pp. 333-344.

Xing Zhao, et al., "Strategic Combinations: The Future of Oncolytic Virotherapy with Reovirus", Molecular Cancer, vol. 15, No. 5, Apr. 14, 2016, pp. 767-773.

\* cited by examiner

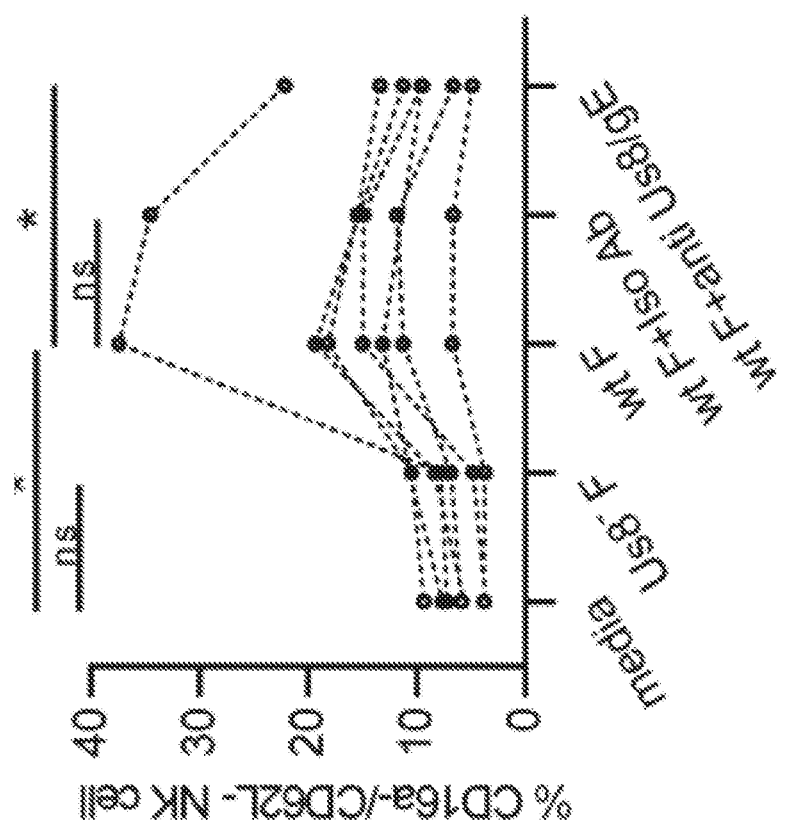
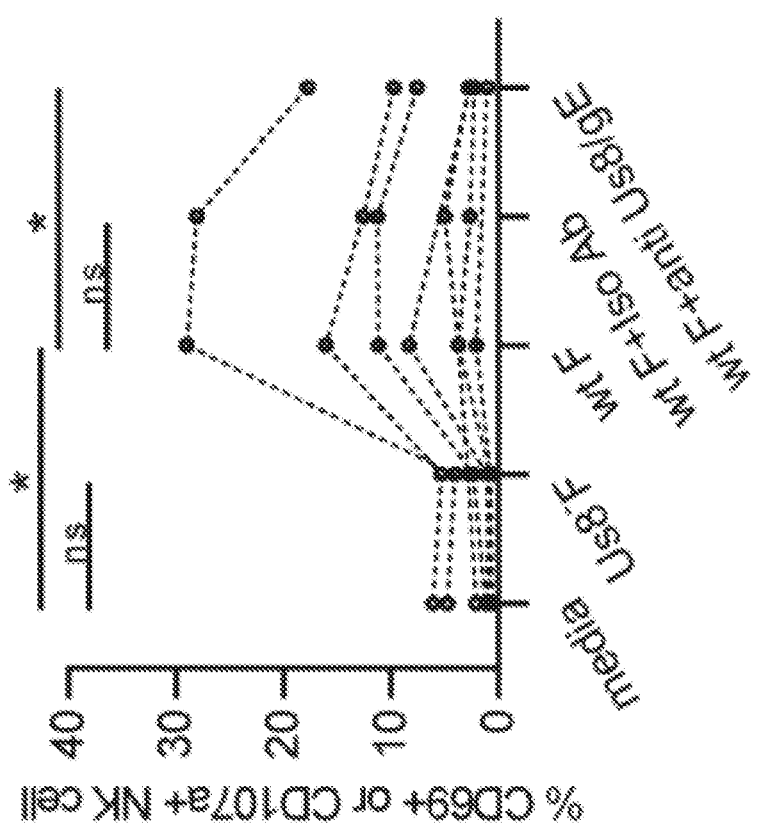
FIG. 11

FIG. 16

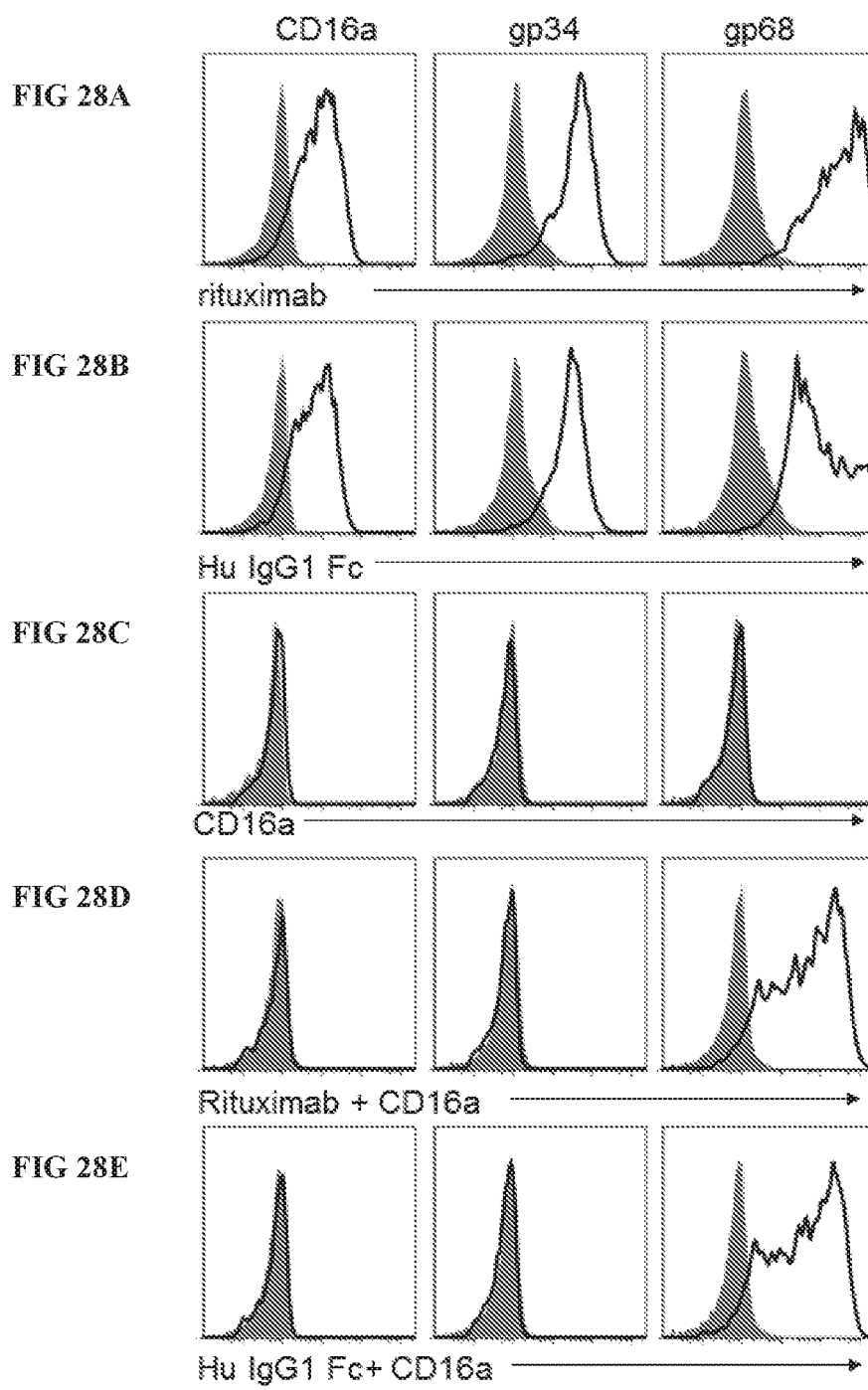

SEQUENCE LISTING

<160> NUMBER OF SEQ ID NOS: 171

<210> SEQ ID NO 1
<211> LENGTH: 232
<212> TYPE: PRT
<213> ORGANISM: Homo sapiens

<400> SEQUENCE: 1

```
Glu Pro Lys Ser Cys Asp Lys Thr His Thr Cys Pro Pro Cys Pro Ala
1               5                   10                  15

Pro Glu Leu Leu Gly Gly Pro Ser Val Phe Leu Phe Pro Pro Lys Pro
            20                  25                  30

Lys Asp Thr Leu Met Ile Ser Arg Thr Pro Glu Val Thr Cys Val Val
        35                  40                  45

Val Asp Val Ser His Glu Asp Pro Glu Val Lys Phe Asn Trp Tyr Val
    50                  55                  60

Asp Gly Val Glu Val His Asn Ala Lys Thr Lys Pro Arg Glu Glu Gln
65                  70                  75                  80

Tyr Asn Ser Thr Tyr Arg Val Val Ser Val Leu Thr Val Leu His Gln
                85                  90                  95

Asp Trp Leu Asn Gly Lys Glu Tyr Lys Cys Lys Val Ser Asn Lys Ala
            100                 105                 110

Leu Pro Ala Pro Ile Glu Lys Thr Ile Ser Lys Ala Lys Gly Gln Pro
        115                 120                 125

Arg Glu Pro Gln Val Tyr Thr Leu Pro Pro Ser Arg Asp Glu Leu Thr
    130                 135                 140

Lys Asn Gln Val Ser Leu Thr Cys Leu Val Lys Gly Phe Tyr Pro Ser
145                 150                 155                 160

Asp Ile Ala Val Glu Trp Glu Ser Asn Gly Gln Pro Glu Asn Asn Tyr
                165                 170                 175

Lys Thr Thr Pro Pro Val Leu Asp Ser Asp Gly Ser Phe Phe Leu Tyr
            180                 185                 190

Ser Lys Leu Thr Val Asp Lys Ser Arg Trp Gln Gln Gly Asn Val Phe
        195                 200                 205

Ser Cys Ser Val Met His Glu Ala Leu His Asn His Tyr Thr Gln Lys
    210                 215                 220

Ser Leu Ser Leu Ser Pro Gly Lys
225                 230
```

<210> SEQ ID NO 2
<211> LENGTH: 205
<212> TYPE: PRT
<213> ORGANISM: Homo sapiens -continued

<400> SEQUENCE: 2

Phe Pro Pro Lys Pro Lys Asp Thr Leu Met Ile Ser Arg Thr Pro Glu
1               5                   10                  15

Val Thr Cys Val Val Val Asp Val Ser His Glu Asp Pro Glu Val Lys
            20                  25                  30

Phe Asn Trp Tyr Val Asp Gly Val Glu Val His Asn Ala Lys Thr Lys
        35                  40                  45

Pro Arg Glu Glu Gln Tyr Asn Ser Thr Tyr Arg Val Val Ser Val Leu
    50                  55                  60

Thr Val Leu His Gln Asp Trp Leu Asn Gly Lys Glu Tyr Lys Cys Lys
65                  70                  75                  80

Val Ser Asn Lys Ala Leu Pro Ala Pro Ile Glu Lys Thr Ile Ser Lys
                85                  90                  95

Ala Lys Gly Gln Pro Arg Glu Pro Gln Val Tyr Thr Leu Pro Pro Ser
            100                 105                 110

Arg Asp Glu Leu Thr Lys Asn Gln Val Ser Leu Thr Cys Leu Val Lys
        115                 120                 125

Gly Phe Tyr Pro Ser Asp Ile Ala Val Glu Trp Glu Ser Asn Gly Gln
    130                 135                 140

Pro Glu Asn Asn Tyr Lys Thr Thr Pro Pro Val Leu Asp Ser Asp Gly
145                 150                 155                 160

Ser Phe Phe Leu Tyr Ser Lys Leu Thr Val Asp Lys Ser Arg Trp Gln
                165                 170                 175

Gln Gly Asn Val Phe Ser Cys Ser Val Met His Glu Ala Leu His Asn
            180                 185                 190

His Tyr Thr Gln Lys Ser Leu Ser Leu Ser Pro Gly Lys
        195                 200                 205

<210> SEQ ID NO 3
<211> LENGTH: 450
<212> TYPE: PRT
<213> ORGANISM: Staphylococcus aureus

<400> SEQUENCE: 3

Met Lys Lys Asn Ile Tyr Ser Ile Arg Lys Leu Gly Val Gly Ile
1               5                   10                  15

Ala Ser Val Thr Leu Gly Thr Leu Leu Ile Ser Gly Gly Val Thr Pro
            20                  25                  30

Ala Ala Asn Ala Ala Gln His Asp Glu Ala Gln Gln Asn Ala Phe Tyr
        35                  40                  45

Gln Val Leu Asn Met Pro Asn Leu Asn Ala Asp Gln Arg Asn Gly Phe
    50                  55                  60

Ile Gln Ser Leu Lys Asp Asp Pro Ser Gln Ser Ala Asn Val Leu Gly
65                  70                  75                  80

Glu Ala Gln Lys Leu Asn Asp Ser Gln Ala Pro Lys Ala Asp Ala Gln
                85                  90                  95

Gln Asn Asn Phe Asn Lys Asp Gln Gln Ser Ala Phe Tyr Glu Ile Leu
            100                 105                 110

Asn Met Pro Asn Leu Asn Glu Ala Gln Arg Asn Gly Phe Ile Gln Ser
        115                 120                 125

Leu Lys Asp Asp Pro Ser Gln Ser Thr Asn Val Leu Gly Glu Ala Lys
    130                 135                 140

Lys Leu Asn Glu Ser Gln Ala Pro Lys Ala Asp Asn Asn Phe Asn Lys
145                 150                 155                 160

Glu Gln Gln Asn Ala Phe Tyr Glu Ile Leu Asn Met Pro Asn Leu Asn
                165                 170                 175

Glu Glu Gln Arg Asn Gly Phe Ile Gln Ser Leu Lys Asp Asp Pro Ser
            180                 185                 190

Gln Ser Ala Asn Leu Leu Ser Glu Ala Lys Lys Leu Asn Glu Ser Gln
        195                 200                 205

Ala Pro Lys Ala Asp Asn Lys Phe Asn Lys Glu Gln Gln Asn Ala Phe
    210                 215                 220

Tyr Glu Ile Leu His Leu Pro Asn Leu Asn Glu Gln Arg Asn Gly
225                 230                 235                 240

Phe Ile Gln Ser Leu Lys Asp Asp Pro Ser Val Ser Lys Glu Ile Leu
                245                 250                 255

Ala Glu Ala Lys Lys Leu Asn Asp Ala Gln Ala Pro Lys Glu Glu Asp
            260                 265                 270

Asn Lys Lys Pro Gly Lys Glu Asp Gly Asn Lys Pro Gly Lys Glu Asp
        275                 280                 285

Gly Asn Lys Pro Gly Lys Glu Asp Asn Lys Pro Gly Lys Glu Asp
    290                 295                 300

Gly Asn Lys Pro Gly Lys Glu Asp Asn Lys Pro Gly Lys Glu Asp
305                 310                 315                 320

Gly Asn Lys Pro Gly Lys Glu Asp Asn Lys Pro Gly Lys Glu Asp
                325                 330                 335

Gly Asn Lys Pro Gly Lys Glu Asp Gly Asn Lys Pro Gly Lys Glu Asp
            340                 345                 350

Gly Asn Gly Val His Val Val Lys Pro Gly Asp Thr Val Asn Asp Ile
        355                 360                 365

Ala Lys Ala Asn Gly Thr Thr Ala Asp Lys Ile Ala Ala Asp Asn Lys
    370                 375                 380

Leu Ala Asp Lys Asn Met Ile Lys Pro Gly Gln Glu Leu Val Val Asp
385                 390                 395                 400

Lys Lys Gln Pro Ala Asn His Ala Asp Ala Asn Lys Ala Gln Ala Leu
                405                 410                 415

Pro Glu Thr Gly Glu Glu Asn Pro Phe Ile Gly Thr Thr Val Phe Gly
            420                 425                 430

Gly Leu Ser Leu Ala Leu Gly Ala Ala Leu Leu Ala Gly Arg Arg Arg
        435                 440                 445

Glu Leu
    450

<210> SEQ ID NO 4
<211> LENGTH: 448
<212> TYPE: PRT
<213> ORGANISM: Streptococcus sp.

<400> SEQUENCE: 4

Met Glu Lys Glu Lys Lys Val Lys Tyr Phe Leu Arg Lys Ser Ala Phe
1               5                   10                  15

Gly Leu Ala Ser Val Ser Ala Ala Phe Leu Val Gly Ser Thr Val Phe
            20                  25                  30

Ala Val Asp Ser Pro Ile Glu Asp Thr Pro Ile Ile Arg Asn Gly Gly
        35                  40                  45

Glu Leu Thr Asn Leu Leu Gly Asn Ser Glu Thr Thr Leu Ala Leu Arg
    50                  55                  60

Asn Glu Glu Ser Ala Thr Ala Asp Leu Thr Ala Ala Val Ala Asp
65                  70                  75                  80

Thr Val Ala Ala Ala Ala Glu Asn Ala Gly Ala Ala Ala Trp Glu
                85                  90                  95

Ala Ala Ala Ala Ala Asp Ala Leu Ala Lys Ala Lys Ala Asp Ala Leu
                100                 105                 110

Lys Glu Phe Asn Lys Tyr Gly Val Ser Asp Tyr Tyr Lys Asn Leu Ile
            115                 120                 125

Asn Asn Ala Lys Thr Val Glu Gly Ile Lys Asp Leu Gln Ala Gln Val
        130                 135                 140

Val Glu Ser Ala Lys Lys Ala Arg Ile Ser Glu Ala Thr Asp Gly Leu
145                 150                 155                 160

Ser Asp Phe Leu Lys Ser Gln Thr Pro Ala Glu Asp Thr Val Lys Ser
                165                 170                 175

Ile Glu Leu Ala Glu Ala Lys Val Leu Ala Asn Arg Glu Leu Asp Lys
            180                 185                 190

Tyr Gly Val Ser Asp Tyr His Lys Asn Leu Ile Asn Asn Ala Lys Thr
        195                 200                 205

Val Glu Gly Val Lys Glu Leu Ile Asp Glu Ile Leu Ala Ala Leu Pro
210                 215                 220

Lys Thr Asp Thr Tyr Lys Leu Ile Leu Asn Gly Lys Thr Leu Lys Gly
225                 230                 235                 240

Glu Thr Thr Thr Glu Ala Val Asp Ala Ala Thr Ala Glu Lys Val Phe
                245                 250                 255

Lys Gln Tyr Ala Asn Asp Asn Gly Val Asp Gly Glu Trp Thr Tyr Asp
            260                 265                 270

Asp Ala Thr Lys Thr Phe Thr Val Thr Glu Lys Pro Glu Val Ile Asp
        275                 280                 285

Ala Ser Glu Leu Thr Pro Ala Val Thr Thr Tyr Lys Leu Val Ile Asn
290                 295                 300

Gly Lys Thr Leu Lys Gly Glu Thr Thr Thr Lys Ala Val Asp Ala Glu
305                 310                 315                 320

Thr Ala Glu Lys Ala Phe Lys Gln Tyr Ala Asn Asp Asn Gly Val Asp
                325                 330                 335

Gly Val Trp Thr Tyr Asp Asp Ala Thr Lys Thr Phe Thr Val Thr Glu
            340                 345                 350

Met Val Thr Glu Val Pro Gly Asp Ala Pro Thr Glu Pro Glu Lys Pro
        355                 360                 365

Glu Ala Ser Ile Pro Leu Val Pro Leu Thr Pro Ala Thr Pro Ile Ala
370                 375                 380

Lys Asp Asp Ala Lys Lys Asp Asp Thr Lys Lys Glu Asp Ala Lys Lys
385                 390                 395                 400

Pro Glu Ala Lys Lys Asp Asp Ala Lys Lys Ala Glu Thr Leu Pro Thr
                405                 410                 415

Thr Gly Glu Gly Ser Asn Pro Phe Phe Thr Ala Ala Leu Ala Val
            420                 425                 430

Met Ala Gly Ala Gly Ala Leu Ala Val Ala Ser Lys Arg Lys Glu Asp
        435                 440                 445

<210> SEQ ID NO 5
<211> LENGTH: 548
<212> TYPE: PRT
<213> ORGANISM: Human herpesvirus 2

<400> SEQUENCE: 5

Met Ala Arg Gly Ala Gly Leu Val Phe Phe Val Gly Val Trp Val Val

-continued

```
1               5                   10                  15
Ser Cys Leu Ala Ala Pro Arg Thr Ser Trp Lys Arg Val Thr Ser
                20                  25                  30
Gly Glu Asp Val Val Leu Leu Pro Ala Pro Gly Pro Glu Glu Arg
                35                  40                  45
Thr Arg Ala His Lys Leu Leu Trp Ala Ala Glu Pro Leu Asp Ala Cys
    50                  55                  60
Gly Pro Leu Arg Pro Ser Trp Val Ala Leu Trp Pro Pro Arg Arg Val
65                  70                  75                  80
Leu Glu Thr Val Val Asp Ala Ala Cys Met Arg Ala Pro Glu Pro Leu
                    85                  90                  95
Ala Ile Ala Tyr Ser Pro Pro Phe Pro Ala Gly Asp Glu Gly Leu Tyr
                100                 105                 110
Ser Glu Leu Ala Trp Arg Asp Arg Val Ala Val Val Asn Glu Ser Leu
                115                 120                 125
Val Ile Tyr Gly Ala Leu Glu Thr Asp Ser Gly Leu Tyr Thr Leu Ser
            130                 135                 140
Val Val Gly Leu Ser Asp Glu Ala Arg Gln Val Ala Ser Val Val Leu
145                 150                 155                 160
Val Val Glu Pro Ala Pro Val Pro Thr Pro Thr Pro Asp Asp Tyr Asp
                    165                 170                 175
Glu Glu Asp Asp Ala Gly Val Ser Glu Arg Thr Pro Val Ser Val Pro
                180                 185                 190
Pro Pro Thr Pro Pro Arg Arg Pro Pro Val Ala Pro Pro Thr His Pro
                195                 200                 205
Arg Val Ile Pro Glu Val Ser His Val Arg Gly Val Thr Val His Met
                210                 215                 220
Glu Thr Pro Glu Ala Ile Leu Phe Ala Pro Gly Glu Thr Phe Gly Thr
225                 230                 235                 240
Asn Val Ser Ile His Ala Ile His Asp Asp Gly Pro Tyr Ala Met
                    245                 250                 255
Asp Val Val Trp Met Arg Phe Asp Val Pro Ser Ser Cys Ala Glu Met
                260                 265                 270
Arg Ile Tyr Glu Ala Cys Leu Tyr His Pro Gln Leu Pro Glu Cys Leu
                275                 280                 285
Ser Pro Ala Asp Ala Pro Cys Ala Val Ser Ser Trp Ala Tyr Arg Leu
                290                 295                 300
Ala Val Arg Ser Tyr Ala Gly Cys Ser Arg Thr Thr Pro Pro Pro Arg
305                 310                 315                 320
Cys Phe Ala Glu Ala Arg Met Glu Pro Val Pro Gly Leu Ala Trp Leu
                    325                 330                 335
Ala Ser Thr Val Asn Leu Glu Phe Gln His Ala Ser Pro Gln His Ala
                    340                 345                 350
Gly Leu Tyr Leu Cys Val Val Tyr Val Asp Asp His Ile His Ala Trp
                355                 360                 365
Gly His Met Thr Ile Ser Thr Ala Ala Gln Tyr Arg Asn Ala Val Val
                370                 375                 380
Glu Gln His Leu Pro Gln Arg Gln Pro Glu Pro Val Glu Pro Thr Arg
385                 390                 395                 400
Pro His Val Arg Ala Pro Pro Ala Pro Ser Ala Arg Gly Pro Leu
                    405                 410                 415
Arg Leu Gly Ala Val Leu Gly Ala Ala Leu Leu Leu Ala Ala Leu Gly
                420                 425                 430
```

```
Leu Ser Ala Trp Ala Cys Met Thr Cys Trp Arg Arg Arg Ser Trp Arg
            435                 440                 445

Ala Val Lys Ser Arg Ala Ser Ala Thr Gly Pro Thr Tyr Ile Arg Val
450                 455                 460

Ala Asp Ser Glu Leu Tyr Ala Asp Trp Ser Ser Asp Ser Glu Gly Glu
465                 470                 475                 480

Arg Asp Gly Ser Leu Trp Gln Asp Pro Pro Glu Arg Pro Asp Ser Pro
                485                 490                 495

Ser Thr Asn Gly Ser Gly Phe Glu Ile Leu Ser Pro Thr Ala Pro Ser
            500                 505                 510

Val Tyr Pro His Ser Glu Gly Arg Lys Ser Arg Arg Pro Leu Thr Thr
            515                 520                 525

Phe Gly Ser Gly Ser Pro Gly Arg Arg His Ser Gln Ala Ser Tyr Ser
            530                 535                 540

Ser Val Leu Trp
545

<210> SEQ ID NO 6
<211> LENGTH: 330
<212> TYPE: PRT
<213> ORGANISM: Homo sapiens

<400> SEQUENCE: 6

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
        115                 120                 125

Lys Pro Lys Asp Thr Leu Met Ile Ser Arg Thr Pro Glu Val Thr Cys
130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Ala Pro Ile Glu Lys Thr Ile Ser Lys Ala Lys Gly
    210                 215                 220

Gln Pro Arg Glu Pro Gln Val Tyr Thr Leu Pro Pro Ser Arg Asp Glu
225                 230                 235                 240

Leu Thr Lys Asn Gln Val Ser Leu Thr Cys Leu Val Lys Gly Phe Tyr
```

```
            245                 250                 255
Pro Ser Asp Ile Ala Val Glu Trp Glu Ser Asn Gly Gln Pro Glu Asn
                260                 265                 270

Asn Tyr Lys Thr Thr Pro Pro Val Leu Asp Ser Asp Gly Ser Phe Phe
            275                 280                 285

Leu Tyr Ser Lys Leu Thr Val Asp Lys Ser Arg Trp Gln Gln Gly Asn
        290                 295                 300

Val Phe Ser Cys Ser Val Met His Glu Ala Leu His Asn His Tyr Thr
305                 310                 315                 320

Gln Lys Ser Leu Ser Leu Ser Pro Gly Lys
                325                 330

<210> SEQ ID NO 7
<211> LENGTH: 326
<212> TYPE: PRT
<213> ORGANISM: Homo sapiens

<400> SEQUENCE: 7

Ala Ser Thr Lys Gly Pro Ser Val Phe Pro Leu Ala Pro Cys Ser Arg
1               5                   10                  15

Ser Thr Ser Glu Ser Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Asn Phe Gly Thr Gln Thr
65                  70                  75                  80

Tyr Thr Cys Asn Val Asp His Lys Pro Ser Asn Thr Lys Val Asp Lys
                85                  90                  95

Thr Val Glu Arg Lys Cys Cys Val Glu Cys Pro Pro Cys Pro Ala Pro
            100                 105                 110

Pro Val Ala Gly Pro Ser Val Phe Leu Phe Pro Pro Lys Pro Lys Asp
        115                 120                 125

Thr Leu Met Ile Ser Arg Thr Pro Glu Val Thr Cys Val Val Val Asp
    130                 135                 140

Val Ser His Glu Asp Pro Glu Val Gln Phe Asn Trp Tyr Val Asp Gly
145                 150                 155                 160

Val Glu Val His Asn Ala Lys Thr Lys Pro Arg Glu Glu Gln Phe Asn
                165                 170                 175

Ser Thr Phe Arg Val Val Ser Val Leu Thr Val Val His Gln Asp Trp
            180                 185                 190

Leu Asn Gly Lys Glu Tyr Lys Cys Lys Val Ser Asn Lys Gly Leu Pro
        195                 200                 205

Ala Pro Ile Glu Lys Thr Ile Ser Lys Thr Lys Gly Gln Pro Arg Glu
    210                 215                 220

Pro Gln Val Tyr Thr Leu Pro Pro Ser Arg Glu Glu Met Thr Lys Asn
225                 230                 235                 240

Gln Val Ser Leu Thr Cys Leu Val Lys Gly Phe Tyr Pro Ser Asp Ile
                245                 250                 255

Ser Val Glu Trp Glu Ser Asn Gly Gln Pro Glu Asn Asn Tyr Lys Thr
            260                 265                 270

Thr Pro Pro Met Leu Asp Ser Asp Gly Ser Phe Phe Leu Tyr Ser Lys
        275                 280                 285
```

-continued

```
Leu Thr Val Asp Lys Ser Arg Trp Gln Gln Gly Asn Val Phe Ser Cys
    290                 295                 300
Ser Val Met His Glu Ala Leu His Asn His Tyr Thr Gln Lys Ser Leu
305                 310                 315                 320
Ser Leu Ser Pro Gly Lys
                325

<210> SEQ ID NO 8
<211> LENGTH: 377
<212> TYPE: PRT
<213> ORGANISM: Homo sapiens

<400> SEQUENCE: 8

Ala Ser Thr Lys Gly Pro Ser Val Phe Pro Leu Ala Pro Cys Ser Arg
1               5                   10                  15
Ser Thr Ser Gly Gly Thr Ala Ala Leu Gly Cys Leu Val Lys Asp Tyr
            20                  25                  30
Phe Pro Glu Pro Val Thr Val Ser Trp Asn Ser Gly Ala Leu Thr Ser
        35                  40                  45
Gly Val His Thr Phe Pro Ala Val Leu Gln Ser Ser Gly Leu Tyr Ser
    50                  55                  60
Leu Ser Ser Val Val Thr Val Pro Ser Ser Ser Leu Gly Thr Gln Thr
65                  70                  75                  80
Tyr Thr Cys Asn Val Asn His Lys Pro Ser Asn Thr Lys Val Asp Lys
                85                  90                  95
Arg Val Glu Leu Lys Thr Pro Leu Gly Asp Thr Thr His Thr Cys Pro
            100                 105                 110
Arg Cys Pro Glu Pro Lys Ser Cys Asp Thr Pro Pro Pro Cys Pro Arg
        115                 120                 125
Cys Pro Glu Pro Lys Ser Cys Asp Thr Pro Pro Pro Cys Pro Arg Cys
    130                 135                 140
Pro Glu Pro Lys Ser Cys Asp Thr Pro Pro Pro Cys Pro Arg Cys Pro
145                 150                 155                 160
Ala Pro Glu Leu Leu Gly Gly Pro Ser Val Phe Leu Phe Pro Pro Lys
                165                 170                 175
Pro Lys Asp Thr Leu Met Ile Ser Arg Thr Pro Glu Val Thr Cys Val
            180                 185                 190
Val Val Asp Val Ser His Glu Asp Pro Glu Val Gln Phe Lys Trp Tyr
        195                 200                 205
Val Asp Gly Val Glu Val His Asn Ala Lys Thr Lys Pro Arg Glu Glu
    210                 215                 220
Gln Tyr Asn Ser Thr Phe Arg Val Val Ser Val Leu Thr Val Leu His
225                 230                 235                 240
Gln Asp Trp Leu Asn Gly Lys Glu Tyr Lys Cys Lys Val Ser Asn Lys
                245                 250                 255
Ala Leu Pro Ala Pro Ile Glu Lys Thr Ile Ser Lys Thr Lys Gly Gln
            260                 265                 270
Pro Arg Glu Pro Gln Val Tyr Thr Leu Pro Pro Ser Arg Glu Glu Met
        275                 280                 285
Thr Lys Asn Gln Val Ser Leu Thr Cys Leu Val Lys Gly Phe Tyr Pro
    290                 295                 300
Ser Asp Ile Ala Val Glu Trp Glu Ser Ser Gly Gln Pro Glu Asn Asn
305                 310                 315                 320
Tyr Asn Thr Thr Pro Pro Met Leu Asp Ser Asp Gly Ser Phe Phe Leu
                325                 330                 335
```

```
Tyr Ser Lys Leu Thr Val Asp Lys Ser Arg Trp Gln Gln Gly Asn Ile
            340                 345                 350

Phe Ser Cys Ser Val Met His Glu Ala Leu His Asn Arg Phe Thr Gln
            355                 360                 365

Lys Ser Leu Ser Leu Ser Pro Gly Lys
            370                 375

<210> SEQ ID NO 9
<211> LENGTH: 327
<212> TYPE: PRT
<213> ORGANISM: Homo sapiens

<400> SEQUENCE: 9

Ala Ser Thr Lys Gly Pro Ser Val Phe Pro Leu Ala Pro Cys Ser Arg
1               5                   10                  15

Ser Thr Ser Glu Ser Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Lys Thr
65                  70                  75                  80

Tyr Thr Cys Asn Val Asp His Lys Pro Ser Asn Thr Lys Val Asp Lys
                85                  90                  95

Arg Val Glu Ser Lys Tyr Gly Pro Pro Cys Pro Ser Cys Pro Ala Pro
            100                 105                 110

Glu Phe Leu Gly Gly Pro Ser Val Phe Leu Phe Pro Pro Lys Pro Lys
        115                 120                 125

Asp Thr Leu Met Ile Ser Arg Thr Pro Glu Val Thr Cys Val Val Val
    130                 135                 140

Asp Val Ser Gln Glu Asp Pro Glu Val Gln Phe Asn Trp Tyr Val Asp
145                 150                 155                 160

Gly Val Glu Val His Asn Ala Lys Thr Lys Pro Arg Glu Glu Gln Phe
                165                 170                 175

Asn Ser Thr Tyr Arg Val Val Ser Val Leu Thr Val Leu His Gln Asp
            180                 185                 190

Trp Leu Asn Gly Lys Glu Tyr Lys Cys Lys Val Ser Asn Lys Gly Leu
        195                 200                 205

Pro Ser Ser Ile Glu Lys Thr Ile Ser Lys Ala Lys Gly Gln Pro Arg
    210                 215                 220

Glu Pro Gln Val Tyr Thr Leu Pro Pro Ser Gln Glu Glu Met Thr Lys
225                 230                 235                 240

Asn Gln Val Ser Leu Thr Cys Leu Val Lys Gly Phe Tyr Pro Ser Asp
                245                 250                 255

Ile Ala Val Glu Trp Glu Ser Asn Gly Gln Pro Glu Asn Asn Tyr Lys
            260                 265                 270

Thr Thr Pro Pro Val Leu Asp Ser Asp Gly Ser Phe Phe Leu Tyr Ser
        275                 280                 285

Arg Leu Thr Val Asp Lys Ser Arg Trp Gln Glu Gly Asn Val Phe Ser
    290                 295                 300

Cys Ser Val Met His Glu Ala Leu His Asn His Tyr Thr Gln Lys Ser
305                 310                 315                 320

Leu Ser Leu Ser Leu Gly Lys
```

<210> SEQ ID NO 10
<211> LENGTH: 466
<212> TYPE: PRT
<213> ORGANISM: Homo sapiens

<400> SEQUENCE: 10

Met Glu Phe Gly Leu Ser Trp Leu Phe Leu Val Ala Ile Leu Lys Gly
1               5                   10                  15

Val Gln Cys Glu Val Gln Leu Leu Glu Ser Gly Gly Asp Leu Val Gln
            20                  25                  30

Pro Gly Gly Ser Leu Arg Leu Ser Cys Ala Ala Ser Gly Phe Thr Phe
        35                  40                  45

Ser Thr Tyr Ala Met Ser Trp Val Arg Gln Ala Pro Gly Lys Gly Leu
    50                  55                  60

Glu Trp Val Ser Gly Ile Gly Asp Ser Gly His Ser Ile Tyr Tyr Ala
65                  70                  75                  80

Asp Ser Val Lys Gly Arg Phe Thr Ile Ser Arg Asp Asn Ser Lys Asn
                85                  90                  95

Thr Leu Tyr Leu Gln Met Asn Ser Leu Arg Ala Glu Asp Thr Ala Val
            100                 105                 110

Tyr Tyr Cys Ala Thr Gly Ser Gln Trp Pro Gly Asp Tyr Trp Gly Gln
        115                 120                 125

Gly Thr Leu Val Thr Val Ser Ser Ala Ser Thr Lys Gly Pro Ser Val
    130                 135                 140

Phe Pro Leu Ala Pro Ser Ser Lys Ser Thr Ser Gly Gly Thr Ala Ala
145                 150                 155                 160

Leu Gly Cys Leu Val Lys Asp Tyr Phe Pro Glu Pro Val Thr Val Ser
                165                 170                 175

Trp Asn Ser Gly Ala Leu Thr Ser Gly Val His Thr Phe Pro Ala Val
            180                 185                 190

Leu Gln Ser Ser Gly Leu Tyr Ser Leu Ser Ser Val Val Thr Val Pro
        195                 200                 205

Ser Ser Ser Leu Gly Thr Gln Thr Tyr Ile Cys Asn Val Asn His Lys
    210                 215                 220

Pro Ser Asn Thr Lys Val Asp Lys Arg Val Glu Pro Lys Ser Cys Asp
225                 230                 235                 240

Lys Thr His Thr Cys Pro Pro Cys Pro Ala Pro Glu Leu Leu Gly Gly
                245                 250                 255

Pro Ser Val Phe Leu Phe Pro Pro Lys Pro Lys Asp Thr Leu Met Ile
            260                 265                 270

Ser Arg Thr Pro Glu Val Thr Cys Val Val Val Asp Val Ser His Glu
        275                 280                 285

Asp Pro Glu Val Lys Phe Asn Trp Tyr Val Asp Gly Val Glu Val His
    290                 295                 300

Asn Ala Lys Thr Lys Pro Arg Glu Glu Gln Tyr Asn Ser Thr Tyr Arg
305                 310                 315                 320

Val Val Ser Val Leu Thr Val Leu His Gln Asp Trp Leu Asn Gly Lys
                325                 330                 335

Glu Tyr Lys Cys Lys Val Ser Asn Lys Ala Leu Pro Ala Pro Ile Glu
            340                 345                 350

Lys Thr Ile Ser Lys Ala Lys Gly Gln Pro Arg Glu Pro Gln Val Tyr
        355                 360                 365

```
Thr Leu Pro Pro Ser Arg Asp Glu Leu Thr Lys Asn Gln Val Ser Leu
    370                 375                 380

Thr Cys Leu Val Lys Gly Phe Tyr Pro Ser Asp Ile Ala Val Glu Trp
385                 390                 395                 400

Glu Ser Asn Gly Gln Pro Glu Asn Asn Tyr Lys Thr Thr Pro Pro Val
                405                 410                 415

Leu Asp Ser Asp Gly Ser Phe Phe Leu Tyr Ser Lys Leu Thr Val Asp
            420                 425                 430

Lys Ser Arg Trp Gln Gln Gly Asn Val Phe Ser Cys Ser Val Met His
        435                 440                 445

Glu Ala Leu His Asn His Tyr Thr Gln Lys Ser Leu Ser Leu Ser Pro
    450                 455                 460

Gly Lys
465

<210> SEQ ID NO 11
<211> LENGTH: 6
<212> TYPE: PRT
<213> ORGANISM: Homo sapiens

<400> SEQUENCE: 11

Met Gly Lys His Arg Tyr
1               5

<210> SEQ ID NO 12
<211> LENGTH: 626
<212> TYPE: PRT
<213> ORGANISM: Human herpesvirus 1

<400> SEQUENCE: 12

Met Glu Ser Thr Val Gly Pro Ala Cys Pro Pro Gly Arg Thr Val Thr
1               5                   10                  15

Lys Arg Pro Trp Ala Leu Ala Glu Asp Thr Pro Arg Gly Pro Asp Ser
            20                  25                  30

Pro Pro Lys Arg Pro Arg Pro Asn Ser Leu Pro Leu Thr Thr Thr Phe
        35                  40                  45

Arg Pro Leu Pro Pro Pro Gln Thr Thr Ser Ala Val Asp Pro Ser
    50                  55                  60

Ser His Ser Pro Val Asn Pro Pro Arg Asp Gln His Ala Thr Asp Thr
65                  70                  75                  80

Ala Asp Glu Lys Pro Arg Ala Ala Ser Pro Ala Leu Ser Asp Ala Ser
                85                  90                  95

Gly Pro Pro Thr Pro Asp Ile Pro Leu Ser Pro Gly Gly Thr His Ala
            100                 105                 110

Arg Asp Pro Asp Ala Asp Pro Asp Ser Pro Asp Leu Asp Ser Met Trp
        115                 120                 125

Ser Ala Ser Val Ile Pro Asn Ala Leu Pro Ser His Ile Leu Ala Glu
    130                 135                 140

Thr Phe Glu Arg His Leu Arg Gly Leu Leu Gly Val Arg Ala Pro
145                 150                 155                 160

Leu Ala Ile Gly Pro Leu Trp Ala Arg Leu Asp Tyr Leu Cys Ser Leu
                165                 170                 175

Ala Val Val Leu Glu Glu Ala Gly Met Val Asp Arg Gly Leu Gly Arg
            180                 185                 190

His Leu Trp Arg Leu Thr Arg Arg Gly Pro Pro Ala Ala Ala Asp Ala
        195                 200                 205
```

```
Val Ala Pro Arg Pro Leu Met Gly Phe Tyr Glu Ala Thr Gln Asn
210                 215                 220

Gln Ala Asp Cys Gln Leu Trp Ala Leu Arg Arg Gly Leu Thr Thr
225                 230                 235                 240

Ala Ser Thr Leu Arg Trp Gly Pro Gln Gly Pro Cys Phe Ser Pro Gln
                245                 250                 255

Trp Leu Lys His Asn Ala Ser Leu Arg Pro Asp Val Gln Ser Ser Ala
                260                 265                 270

Val Met Phe Gly Arg Val Asn Glu Pro Thr Ala Arg Ser Leu Leu Phe
                275                 280                 285

Arg Tyr Cys Val Gly Arg Ala Asp Asp Gly Glu Ala Gly Ala Asp
290                 295                 300

Thr Arg Arg Phe Ile Phe His Glu Pro Ser Asp Leu Ala Glu Glu Asn
305                 310                 315                 320

Val His Thr Cys Gly Val Leu Met Asp Gly His Thr Gly Met Val Gly
                325                 330                 335

Ala Ser Leu Asp Ile Leu Val Cys Pro Arg Asp Ile His Gly Tyr Leu
                340                 345                 350

Ala Pro Val Pro Lys Thr Pro Leu Ala Phe Tyr Glu Val Lys Cys Arg
                355                 360                 365

Ala Lys Tyr Ala Phe Asp Pro Met Asp Pro Ser Asp Pro Thr Ala Ser
370                 375                 380

Ala Tyr Glu Asp Leu Met Ala His Arg Ser Pro Glu Ala Phe Arg Ala
385                 390                 395                 400

Phe Ile Arg Ser Ile Pro Lys Pro Ser Val Arg Tyr Phe Ala Pro Gly
                405                 410                 415

Arg Val Pro Gly Pro Glu Glu Ala Leu Val Thr Gln Asp Gln Ala Trp
                420                 425                 430

Ser Glu Ala His Ala Ser Gly Glu Lys Arg Arg Cys Ser Ala Ala Asp
                435                 440                 445

Arg Ala Leu Val Glu Leu Asn Ser Gly Val Val Ser Glu Val Leu Leu
450                 455                 460

Phe Gly Ala Pro Asp Leu Gly Arg His Thr Ile Ser Pro Val Ser Trp
465                 470                 475                 480

Ser Ser Gly Asp Leu Val Arg Arg Glu Pro Val Phe Ala Asn Pro Arg
                485                 490                 495

His Pro Asn Phe Lys Gln Ile Leu Val Gln Gly Tyr Val Leu Asp Ser
                500                 505                 510

His Phe Pro Asp Cys Pro Pro His Pro His Leu Val Thr Phe Ile Gly
                515                 520                 525

Arg His Arg Thr Ser Ala Glu Glu Gly Val Thr Phe Arg Leu Glu Asp
                530                 535                 540

Gly Ala Gly Ala Leu Gly Ala Ala Gly Pro Ser Lys Ala Ser Ile Leu
545                 550                 555                 560

Pro Asn Gln Ala Val Pro Ile Ala Leu Ile Ile Thr Pro Val Arg Ile
                565                 570                 575

Asp Pro Glu Ile Tyr Lys Ala Ile Gln Arg Ser Ser Arg Leu Ala Phe
                580                 585                 590

Asp Asp Thr Leu Ala Glu Leu Trp Ala Ser Arg Ser Pro Gly Pro Gly
                595                 600                 605

Pro Ala Ala Ala Glu Thr Thr Ser Ser Ser Pro Thr Thr Gly Arg Ser
610                 615                 620

Ser Arg
```

<210> SEQ ID NO 13
<211> LENGTH: 1235
<212> TYPE: PRT
<213> ORGANISM: Human herpesvirus 1

<400> SEQUENCE: 13

```
Met Phe Ser Gly Gly Gly Pro Leu Ser Pro Gly Gly Lys Ser Ala
1               5                   10                  15

Ala Arg Ala Ala Ser Gly Phe Phe Ala Pro Ala Gly Pro Arg Gly Ala
            20                  25                  30

Ser Arg Gly Pro Pro Pro Cys Leu Arg Gln Asn Phe Tyr Asn Pro Tyr
            35                  40                  45

Leu Ala Pro Val Gly Thr Gln Gln Lys Pro Thr Gly Pro Thr Gln Arg
    50                  55                  60

His Thr Tyr Tyr Ser Glu Cys Asp Glu Phe Arg Phe Ile Ala Pro Arg
65              70                  75                  80

Val Leu Asp Glu Asp Ala Pro Pro Glu Lys Arg Ala Gly Val His Asp
                85                  90                  95

Gly His Leu Lys Arg Ala Pro Lys Val Tyr Cys Gly Gly Asp Glu Arg
            100                 105                 110

Asp Val Leu Arg Val Gly Ser Gly Gly Phe Trp Pro Arg Arg Ser Arg
            115                 120                 125

Leu Trp Gly Gly Val Asp His Ala Pro Ala Gly Phe Asn Pro Thr Val
130                 135                 140

Thr Val Phe His Val Tyr Asp Ile Leu Glu Asn Val Glu His Ala Tyr
145                 150                 155                 160

Gly Met Arg Ala Ala Gln Phe His Ala Arg Phe Met Asp Ala Ile Thr
                165                 170                 175

Pro Thr Gly Thr Val Ile Thr Leu Leu Gly Leu Thr Pro Glu Gly His
            180                 185                 190

Arg Val Ala Val His Val Tyr Gly Thr Arg Gln Tyr Phe Tyr Met Asn
            195                 200                 205

Lys Glu Glu Val Asp Arg His Leu Gln Cys Arg Ala Pro Arg Asp Leu
210                 215                 220

Cys Glu Arg Met Ala Ala Ala Leu Arg Glu Ser Pro Gly Ala Ser Phe
225                 230                 235                 240

Arg Gly Ile Ser Ala Asp His Phe Glu Ala Glu Val Val Glu Arg Thr
                245                 250                 255

Asp Val Tyr Tyr Tyr Glu Thr Arg Pro Ala Leu Phe Tyr Arg Val Tyr
            260                 265                 270

Val Arg Ser Gly Arg Val Leu Ser Tyr Leu Cys Asp Asn Phe Cys Pro
            275                 280                 285

Ala Ile Lys Lys Tyr Glu Gly Gly Val Asp Ala Thr Thr Arg Phe Ile
290                 295                 300

Leu Asp Asn Pro Gly Phe Val Thr Phe Gly Trp Tyr Arg Leu Lys Pro
305                 310                 315                 320

Gly Arg Asn Asn Thr Leu Ala Gln Pro Ala Ala Pro Met Ala Phe Gly
                325                 330                 335

Thr Ser Ser Asp Val Glu Phe Asn Cys Thr Ala Asp Asn Leu Ala Ile
            340                 345                 350

Glu Gly Gly Met Ser Asp Leu Pro Ala Tyr Lys Leu Met Cys Phe Asp
            355                 360                 365
```

-continued

```
Ile Glu Cys Lys Ala Gly Gly Glu Asp Glu Leu Ala Phe Pro Val Ala
    370                 375                 380

Gly His Pro Glu Asp Leu Val Ile Gln Ile Ser Cys Leu Leu Tyr Asp
385                 390                 395                 400

Leu Ser Thr Thr Ala Leu Glu His Val Leu Leu Phe Ser Leu Gly Ser
                405                 410                 415

Cys Asp Leu Pro Glu Ser His Leu Asn Glu Leu Ala Ala Arg Gly Leu
                420                 425                 430

Pro Thr Pro Val Val Leu Glu Phe Asp Ser Glu Phe Glu Met Leu Leu
            435                 440                 445

Ala Phe Met Thr Leu Val Lys Gln Tyr Gly Pro Glu Phe Val Thr Gly
450                 455                 460

Tyr Asn Ile Ile Asn Phe Asp Trp Pro Phe Leu Leu Ala Lys Leu Thr
465                 470                 475                 480

Asp Ile Tyr Lys Val Pro Leu Asp Gly Tyr Gly Arg Met Asn Gly Arg
                485                 490                 495

Gly Val Phe Arg Val Trp Asp Ile Gly Gln Ser His Phe Gln Lys Arg
                500                 505                 510

Ser Lys Ile Lys Val Asn Gly Met Val Asn Ile Asp Met Tyr Gly Ile
            515                 520                 525

Ile Thr Asp Lys Ile Lys Leu Ser Ser Tyr Lys Leu Asn Ala Val Ala
530                 535                 540

Glu Ala Val Leu Lys Asp Lys Lys Asp Leu Ser Tyr Arg Asp Ile
545                 550                 555                 560

Pro Ala Tyr Tyr Ala Ala Gly Pro Ala Gln Arg Gly Val Ile Gly Glu
                565                 570                 575

Tyr Cys Ile Gln Asp Ser Leu Leu Val Gly Gln Leu Phe Phe Lys Phe
                580                 585                 590

Leu Pro His Leu Glu Leu Ser Ala Val Ala Arg Leu Ala Gly Ile Asn
            595                 600                 605

Ile Thr Arg Thr Ile Tyr Asp Gly Gln Gln Ile Arg Val Phe Thr Cys
610                 615                 620

Leu Leu Arg Leu Ala Asp Gln Lys Gly Phe Ile Leu Pro Asp Thr Gln
625                 630                 635                 640

Gly Arg Phe Arg Gly Ala Gly Gly Glu Ala Pro Lys Arg Pro Ala Ala
                645                 650                 655

Ala Arg Glu Asp Glu Glu Arg Pro Glu Glu Glu Gly Glu Asp Glu Asp
                660                 665                 670

Glu Arg Glu Glu Gly Gly Gly Glu Arg Glu Pro Glu Gly Ala Arg Glu
            675                 680                 685

Thr Ala Gly Arg His Val Gly Tyr Gln Gly Ala Arg Val Leu Asp Pro
690                 695                 700

Thr Ser Gly Phe His Val Asn Pro Val Val Phe Asp Phe Ala Ser
705                 710                 715                 720

Leu Tyr Pro Ser Ile Ile Gln Ala His Asn Leu Cys Phe Ser Thr Leu
                725                 730                 735

Ser Leu Arg Ala Asp Ala Val Ala His Leu Glu Ala Gly Lys Asp Tyr
                740                 745                 750

Leu Glu Ile Glu Val Gly Gly Arg Arg Leu Phe Phe Val Lys Ala His
            755                 760                 765

Val Arg Glu Ser Leu Leu Ser Ile Leu Leu Arg Asp Trp Leu Ala Met
770                 775                 780

Arg Lys Gln Ile Arg Ser Arg Ile Pro Gln Ser Ser Pro Glu Glu Ala
```

-continued

```
            785                 790                 795                 800
Val Leu Leu Asp Lys Gln Gln Ala Ala Ile Lys Val Val Cys Asn Ser
                805                 810                 815

Val Tyr Gly Phe Thr Gly Val Gln His Gly Leu Leu Pro Cys Leu His
                820                 825                 830

Val Ala Ala Thr Val Thr Thr Ile Gly Arg Glu Met Leu Leu Ala Thr
                835                 840                 845

Arg Glu Tyr Val His Ala Arg Trp Ala Ala Phe Glu Gln Leu Leu Ala
        850                 855                 860

Asp Phe Pro Glu Ala Ala Asp Met Arg Ala Pro Gly Pro Tyr Ser Met
865                 870                 875                 880

Arg Ile Ile Tyr Gly Asp Thr Asp Ser Ile Phe Val Leu Cys Arg Gly
                885                 890                 895

Leu Thr Ala Ala Gly Leu Thr Ala Val Gly Asp Lys Met Ala Ser His
                900                 905                 910

Ile Ser Arg Ala Leu Phe Leu Pro Pro Ile Lys Leu Glu Cys Glu Lys
                915                 920                 925

Thr Phe Thr Lys Leu Leu Leu Ile Ala Lys Lys Lys Tyr Ile Gly Val
        930                 935                 940

Ile Tyr Gly Gly Lys Met Leu Ile Lys Gly Val Asp Leu Val Arg Lys
945                 950                 955                 960

Asn Asn Cys Ala Phe Ile Asn Arg Thr Ser Arg Ala Leu Val Asp Leu
                965                 970                 975

Leu Phe Tyr Asp Asp Thr Val Ser Gly Ala Ala Ala Leu Ala Glu
                980                 985                 990

Arg Pro Ala Glu Glu Trp Leu Ala Arg Pro Leu Pro Glu Gly Leu Gln
        995                 1000                1005

Ala Phe Gly Ala Val Leu Val Asp Ala His Arg Arg Ile Thr Asp
        1010                1015                1020

Pro Glu Arg Asp Ile Gln Asp Phe Val Leu Thr Ala Glu Leu Ser
        1025                1030                1035

Arg His Pro Arg Ala Tyr Thr Asn Lys Arg Leu Ala His Leu Thr
        1040                1045                1050

Val Tyr Tyr Lys Leu Met Ala Arg Arg Ala Gln Val Pro Ser Ile
        1055                1060                1065

Lys Asp Arg Ile Pro Tyr Val Ile Val Ala Gln Thr Arg Glu Val
        1070                1075                1080

Glu Glu Thr Val Ala Arg Leu Ala Ala Leu Arg Glu Leu Asp Ala
        1085                1090                1095

Ala Ala Pro Gly Asp Glu Pro Ala Pro Ala Ala Leu Pro Ser
        1100                1105                1110

Pro Ala Lys Arg Pro Arg Glu Thr Pro Ser Pro Ala Asp Pro Pro
        1115                1120                1125

Gly Gly Ala Ser Lys Pro Arg Lys Leu Leu Val Ser Glu Leu Ala
        1130                1135                1140

Glu Asp Pro Ala Tyr Ala Ile Ala His Gly Val Ala Leu Asn Thr
        1145                1150                1155

Asp Tyr Tyr Phe Ser His Leu Leu Gly Ala Ala Cys Val Thr Phe
        1160                1165                1170

Lys Ala Leu Phe Gly Asn Asn Ala Lys Ile Thr Glu Ser Leu Leu
        1175                1180                1185

Lys Arg Phe Ile Pro Glu Val Trp His Pro Pro Asp Asp Val Ala
        1190                1195                1200
```

Ala Arg Leu Arg Thr Ala Gly Phe Gly Ala Val Gly Ala Gly Ala
    1205                1210                1215

Thr Ala Glu Glu Thr Arg Arg Met Leu His Arg Ala Phe Asp Thr
    1220                1225                1230

Leu Ala
    1235

<210> SEQ ID NO 14
<211> LENGTH: 92
<212> TYPE: PRT
<213> ORGANISM: Human herpesvirus 1

<400> SEQUENCE: 14

Met Ser Leu Arg Ala Val Trp His Leu Gly Leu Leu Gly Ser Leu Val
1               5                   10                  15

Gly Ala Val Leu Ala Ala Thr His Arg Gly Pro Ala Ala Asn Thr Thr
            20                  25                  30

Asp Pro Leu Thr His Ala Pro Val Ser Pro His Pro Ser Pro Leu Gly
        35                  40                  45

Gly Phe Ala Val Pro Leu Val Val Gly Gly Leu Cys Ala Val Val Leu
50                  55                  60

Gly Ala Ala Cys Leu Leu Glu Leu Leu Arg Arg Thr Cys Arg Gly Trp
65                  70                  75                  80

Gly Arg Tyr His Pro Tyr Met Asp Pro Val Val Val
                85                  90

<210> SEQ ID NO 15
<211> LENGTH: 186
<212> TYPE: PRT
<213> ORGANISM: Human herpesvirus 5

<400> SEQUENCE: 15

Met Lys Pro Val Leu Val Leu Ala Ile Leu Ala Val Leu Phe Leu Arg
1               5                   10                  15

Leu Ala Asp Ser Val Pro Arg Pro Leu Asp Val Val Val Ser Glu Ile
            20                  25                  30

Arg Ser Ala His Phe Arg Val Glu Glu Asn Gln Cys Trp Phe His Met
        35                  40                  45

Gly Met Leu Tyr Phe Lys Gly Arg Met Ser Gly Asn Phe Thr Glu Lys
50                  55                  60

His Phe Val Asn Val Gly Ile Val Ser Gln Ser Tyr Met Asp Arg Leu
65                  70                  75                  80

Gln Val Ser Gly Glu Gln Tyr His His Asp Glu Arg Gly Ala Tyr Phe
                85                  90                  95

Glu Trp Asn Ile Gly Gly His Pro Val Thr His Thr Val Asp Met Val
            100                 105                 110

Asp Ile Thr Leu Ser Thr Arg Trp Gly Asp Pro Lys Lys Tyr Ala Ala
        115                 120                 125

Cys Val Pro Gln Val Arg Met Asp Tyr Ser Ser Gln Thr Ile Asn Trp
130                 135                 140

Tyr Leu Gln Arg Ser Met Arg Asp Asp Asn Trp Gly Leu Leu Phe Arg
145                 150                 155                 160

Thr Leu Leu Val Tyr Leu Phe Ser Leu Val Val Leu Val Leu Leu Thr
                165                 170                 175

Val Gly Val Ser Ala Arg Leu Arg Phe Ile
            180                 185

<210> SEQ ID NO 16
<211> LENGTH: 281
<212> TYPE: PRT
<213> ORGANISM: Human herpesvirus 5

<400> SEQUENCE: 16

Met Val Gln Ile Gln Phe His Gln Gly Glu Pro Leu Gly His Lys Lys
1               5                   10                  15

Glu Lys Pro Pro Val Ser Pro Ser Pro Pro Ile Arg Arg
            20                  25                  30

Val Thr Val Ile Thr Lys Asp Glu Asp Thr Leu Arg Ser Val Gln His
        35                  40                  45

Phe Leu Trp Met Val Arg Leu Tyr Gly Thr Val Val Phe Gln Thr Ser
    50                  55                  60

Ala Thr Ile Ala Thr Thr Ile Leu Phe Met Leu Ile Pro Trp Arg Val
65                  70                  75                  80

Thr Thr Pro Tyr Leu Arg Asp Thr Leu Pro Phe Trp Ser Thr Leu Leu
                85                  90                  95

Pro Cys Ala Leu Arg Cys His Ala Tyr Trp Leu Glu Arg Gln Arg Arg
            100                 105                 110

Pro Gly Thr Leu Met Leu Val Met Val Tyr Thr Thr Leu Thr Thr Ile
        115                 120                 125

Ser Val Ser Thr Ile Gly Leu Cys Phe Asp Arg Thr Val Val Ile Gln
    130                 135                 140

Ala Tyr Val Leu Ser Ser Met Leu Cys Val Trp Cys Thr Gly Leu Ala
145                 150                 155                 160

Trp Leu Met Ala Trp Asn Met Gln Arg Arg Leu Ala Ile Leu Cys Leu
                165                 170                 175

Leu Ser Phe Met Leu Pro Ile Leu Trp Leu Phe Ile Ala Val Gln Ser
            180                 185                 190

Trp Glu Pro Tyr Gln Arg Ile Ile Leu Ala Leu Thr Val Ser Phe Ile
        195                 200                 205

Tyr Gly Leu Lys Ile Val Leu Ile Arg Asp Thr Leu Thr Val Leu Tyr
    210                 215                 220

Arg Ser Pro Ser Asn Cys Tyr Thr Asp Gly Asp Leu Leu Arg Thr Ala
225                 230                 235                 240

Met Leu Leu Tyr Met Asp Gln Val Ile Met Phe Leu Leu Val Val Val
                245                 250                 255

Pro Leu Thr Ala Pro Ile Trp Tyr Pro Asn Tyr Ala Gly Ala Leu Gly
            260                 265                 270

Arg Thr Ala His Trp Leu Phe His Lys
        275                 280

<210> SEQ ID NO 17
<211> LENGTH: 225
<212> TYPE: PRT
<213> ORGANISM: Human herpesvirus 5

<400> SEQUENCE: 17

Met Arg Ile Gln Leu Leu Leu Val Ser Thr Leu Val Ala Ser Ile Val
1               5                   10                  15

Ala Thr Arg Val Glu Asp Met Ala Thr Phe Arg Thr Glu Lys Gln Trp
            20                  25                  30

Gln Gln Asp Leu Gln Tyr Arg Arg Glu Phe Val Lys Arg Gln Leu Ala
        35                  40                  45

```
Pro Lys Pro Lys Ser Asn Ile Val Val Ser His Thr Val Ser Cys Val
    50                  55                  60

Ile Asp Gly Gly Asn Met Thr Ser Val Trp Arg Phe Glu Gly Gln Phe
65                  70                  75                  80

Asn Pro His Ile Ala Ser Glu Val Ile Leu His Asp Thr Ser Gly Leu
                85                  90                  95

Tyr Asn Val Pro His Glu Val Gln Asn Asp Gly Gln Val Leu Thr Val
                100                 105                 110

Thr Val Lys Arg Ser Ala Pro Ala Asp Ile Ala Lys Val Leu Ile Ser
                115                 120                 125

Leu Lys Pro Val Gln Leu Ser Ser Gly Gln Tyr Glu Cys Arg Pro Gln
    130                 135                 140

Leu Gln Leu Pro Trp Val Pro Arg Pro Ser Ser Phe Met Tyr Asp Ser
145                 150                 155                 160

Tyr Arg Leu Trp Tyr Glu Lys Arg Trp Leu Thr Ile Ile Leu Tyr Val
                165                 170                 175

Phe Met Trp Thr Tyr Leu Val Thr Leu Leu Gln Tyr Cys Ile Val Arg
                180                 185                 190

Phe Ile Gly Thr Arg Leu Phe Tyr Phe Leu Gln Arg Asn Ile Thr Ile
                195                 200                 205

Arg Phe Thr Gly Lys Pro Thr Tyr Asn Leu Leu Thr Tyr Pro Val Lys
    210                 215                 220

Gly
225

<210> SEQ ID NO 18
<211> LENGTH: 227
<212> TYPE: PRT
<213> ORGANISM: Human herpesvirus 5

<400> SEQUENCE: 18

Met Arg Arg Trp Leu Arg Leu Leu Val Gly Leu Gly Cys Cys Trp Val
1               5                   10                  15

Thr Leu Ala His Ala Gly Asn Pro Tyr Glu Asp Asp Asp Tyr Tyr Tyr
                20                  25                  30

Tyr Arg Glu Asp Glu Pro Arg Gln His Gly Glu Pro Asn Tyr Val Ala
            35                  40                  45

Pro Pro Ala Arg Gln Phe Arg Phe Pro Pro Leu Asn Asn Val Ser Ser
    50                  55                  60

Tyr Gln Ala Ser Cys Val Val Lys Asp Gly Val Leu Asp Ala Val Trp
65                  70                  75                  80

Arg Val Gln Gly Thr Phe Tyr Pro Glu Lys Gly Ile Val Ala Arg Val
                85                  90                  95

Gly Trp Ser Gly Arg Arg Gly Arg Lys Trp Gly Arg Leu His Ala Pro
                100                 105                 110

Glu Cys Leu Val Glu Thr Thr Glu Ala Val Phe Arg Leu Arg Gln Trp
            115                 120                 125

Val Pro Thr Asp Leu Asp His Leu Thr Leu His Leu Val Pro Cys Thr
    130                 135                 140

Lys Cys Lys Pro Met Trp Cys Gln Pro Arg Tyr His Ile Arg Tyr Phe
145                 150                 155                 160

Ser Tyr Gly Asn Ser Val Asp Asn Leu Arg Arg Leu His Tyr Glu Tyr
                165                 170                 175

Arg His Leu Glu Leu Gly Val Val Ile Ala Ile Gln Met Ala Met Val
```

```
              180                 185                 190
Leu Leu Leu Gly Tyr Val Leu Ala Arg Thr Val Tyr Arg Val Ser Ser
            195                 200                 205

Ala Tyr Tyr Leu Arg Trp His Ala Cys Val Pro Gln Lys Cys Glu Lys
        210                 215                 220

Ser Leu Cys
225

<210> SEQ ID NO 19
<211> LENGTH: 183
<212> TYPE: PRT
<213> ORGANISM: Human herpesvirus 5

<400> SEQUENCE: 19

Met Asp Leu Leu Ile Arg Leu Gly Phe Leu Leu Met Cys Ala Leu Pro
1               5                   10                  15

Thr Pro Gly Glu Arg Ser Arg Asp Pro Lys Thr Leu Leu Ser Leu
            20                  25                  30

Ser Pro Arg Gln Gln Ala Cys Val Pro Arg Thr Lys Ser His Arg Pro
        35                  40                  45

Val Cys Tyr Asn Asp Thr Gly Asp Cys Thr Ala Asp Asp Ser Trp
50                  55                  60

Lys Gln Leu Gly Glu Asp Phe Ala His Gln Cys Leu Gln Ala Ala Lys
65                  70                  75                  80

Lys Arg Pro Lys Thr His Lys Ser Arg Pro Asn Asp Arg Asn Leu Glu
                85                  90                  95

Gly Arg Leu Thr Cys Gln Arg Val Arg Arg Leu Pro Cys Asp Leu
            100                 105                 110

Asp Ile His Pro Ser His Arg Leu Leu Thr Leu Met Asn Asn Cys Val
        115                 120                 125

Cys Asp Gly Ala Val Trp Asn Ala Phe Arg Leu Ile Glu Arg His Gly
    130                 135                 140

Phe Phe Ala Val Thr Leu Tyr Leu Cys Cys Gly Ile Thr Leu Leu Val
145                 150                 155                 160

Val Ile Leu Ala Leu Leu Cys Ser Ile Thr Tyr Glu Ser Thr Gly Arg
                165                 170                 175

Gly Ile Arg Arg Cys Gly Ser
            180

<210> SEQ ID NO 20
<211> LENGTH: 490
<212> TYPE: PRT
<213> ORGANISM: Human herpesvirus 1

<400> SEQUENCE: 20

Met Asp Leu Leu Val Asp Glu Leu Phe Ala Asp Met Asn Ala Asp Gly
1               5                   10                  15

Ala Ser Pro Pro Pro Arg Pro Ala Gly Gly Pro Lys Asn Thr Pro
            20                  25                  30

Ala Ala Pro Pro Leu Tyr Ala Thr Gly Arg Leu Ser Gln Ala Gln Leu
        35                  40                  45

Met Pro Ser Pro Pro Met Pro Val Pro Pro Ala Ala Leu Phe Asn Arg
    50                  55                  60

Leu Leu Asp Asp Leu Gly Phe Ser Ala Gly Pro Ala Leu Cys Thr Met
65                  70                  75                  80

Leu Asp Thr Trp Asn Glu Asp Leu Phe Ser Ala Leu Pro Thr Asn Ala
```

```
                            85                  90                  95
Asp Leu Tyr Arg Glu Cys Lys Phe Leu Ser Thr Leu Pro Ser Asp Val
                    100                 105                 110

Val Glu Trp Gly Asp Ala Tyr Val Pro Glu Arg Thr Gln Ile Asp Ile
            115                 120                 125

Arg Ala His Gly Asp Val Ala Phe Pro Thr Leu Pro Ala Thr Arg Asp
    130                 135                 140

Gly Leu Gly Leu Tyr Tyr Glu Ala Leu Ser Arg Phe Phe His Ala Glu
145                 150                 155                 160

Leu Arg Ala Arg Glu Glu Ser Tyr Arg Thr Val Leu Ala Asn Phe Cys
                165                 170                 175

Ser Ala Leu Tyr Arg Tyr Leu Arg Ala Ser Val Arg Gln Leu His Arg
            180                 185                 190

Gln Ala His Met Arg Gly Arg Asp Arg Asp Leu Gly Glu Met Leu Arg
        195                 200                 205

Ala Thr Ile Ala Asp Arg Tyr Tyr Arg Glu Thr Ala Arg Leu Ala Arg
    210                 215                 220

Val Leu Phe Leu His Leu Tyr Leu Phe Leu Thr Arg Glu Ile Leu Trp
225                 230                 235                 240

Ala Ala Tyr Ala Glu Gln Met Met Arg Pro Asp Leu Phe Asp Cys Leu
                245                 250                 255

Cys Cys Asp Leu Glu Ser Trp Arg Gln Leu Ala Gly Leu Phe Gln Pro
            260                 265                 270

Phe Met Phe Val Asn Gly Ala Leu Thr Val Arg Gly Val Pro Ile Glu
        275                 280                 285

Ala Arg Arg Leu Arg Glu Leu Asn His Ile Arg Glu His Leu Asn Leu
    290                 295                 300

Pro Leu Val Arg Ser Ala Ala Thr Glu Glu Pro Gly Ala Pro Leu Thr
305                 310                 315                 320

Thr Pro Pro Thr Leu His Gly Asn Gln Ala Arg Ala Ser Gly Tyr Phe
                325                 330                 335

Met Val Leu Ile Arg Ala Lys Leu Asp Ser Tyr Ser Ser Phe Thr Thr
            340                 345                 350

Ser Pro Ser Glu Ala Val Met Arg Glu His Ala Tyr Ser Arg Ala Arg
        355                 360                 365

Thr Lys Asn Asn Tyr Gly Ser Thr Ile Glu Gly Leu Leu Asp Leu Pro
    370                 375                 380

Asp Asp Asp Ala Pro Glu Glu Ala Gly Leu Ala Ala Pro Arg Leu Ser
385                 390                 395                 400

Phe Leu Pro Ala Gly His Thr Arg Arg Leu Ser Thr Ala Pro Pro Thr
                405                 410                 415

Asp Val Ser Leu Gly Asp Glu Leu His Leu Asp Gly Glu Asp Val Ala
            420                 425                 430

Met Ala His Ala Asp Ala Leu Asp Asp Phe Asp Leu Asp Met Leu Gly
        435                 440                 445

Asp Gly Asp Ser Pro Gly Pro Gly Phe Thr Pro His Asp Ser Ala Pro
    450                 455                 460

Tyr Gly Ala Leu Asp Met Ala Asp Phe Glu Phe Glu Gln Met Phe Thr
465                 470                 475                 480

Asp Ala Leu Gly Ile Asp Glu Tyr Gly Gly
                485                 490

<210> SEQ ID NO 21
```

<211> LENGTH: 317
<212> TYPE: PRT
<213> ORGANISM: Homo sapiens

<400> SEQUENCE: 21

```
Met Thr Met Glu Thr Gln Met Ser Gln Asn Val Cys Pro Arg Asn Leu
1               5                   10                  15

Trp Leu Leu Gln Pro Leu Thr Val Leu Leu Leu Ala Ser Ala Asp Ser
                20                  25                  30

Ser Gln Ala Ala Ala Pro Pro Lys Ala Val Leu Lys Leu Glu Pro Pro
            35                  40                  45

Trp Ile Asn Val Leu Gln Glu Asp Ser Val Thr Leu Thr Cys Gln Gly
    50                  55                  60

Ala Arg Ser Pro Glu Ser Asp Ser Ile Gln Trp Phe His Asn Gly Asn
65                  70                  75                  80

Leu Ile Pro Thr His Thr Gln Pro Ser Tyr Arg Phe Lys Ala Asn Asn
                85                  90                  95

Asn Asp Ser Gly Glu Tyr Thr Cys Gln Thr Gly Gln Thr Ser Leu Ser
            100                 105                 110

Asp Pro Val His Leu Thr Val Leu Ser Glu Trp Leu Val Leu Gln Thr
        115                 120                 125

Pro His Leu Glu Phe Gln Glu Gly Glu Thr Ile Met Leu Arg Cys His
    130                 135                 140

Ser Trp Lys Asp Lys Pro Leu Val Lys Val Thr Phe Phe Gln Asn Gly
145                 150                 155                 160

Lys Ser Gln Lys Phe Ser His Leu Asp Pro Thr Phe Ser Ile Pro Gln
                165                 170                 175

Ala Asn His Ser His Ser Gly Asp Tyr His Cys Thr Gly Asn Ile Gly
            180                 185                 190

Tyr Thr Leu Phe Ser Ser Lys Pro Val Thr Ile Thr Val Gln Val Pro
        195                 200                 205

Ser Met Gly Ser Ser Ser Pro Met Gly Ile Ile Val Ala Val Val Ile
    210                 215                 220

Ala Thr Ala Val Ala Ala Ile Val Ala Ala Val Val Ala Leu Ile Tyr
225                 230                 235                 240

Cys Arg Lys Lys Arg Ile Ser Ala Asn Ser Thr Asp Pro Val Lys Ala
                245                 250                 255

Ala Gln Phe Glu Pro Pro Gly Arg Gln Met Ile Ala Ile Arg Lys Arg
            260                 265                 270

Gln Leu Glu Glu Thr Asn Asn Asp Tyr Glu Thr Ala Asp Gly Gly Tyr
        275                 280                 285

Met Thr Leu Asn Pro Arg Ala Pro Thr Asp Asp Asp Lys Asn Ile Tyr
    290                 295                 300

Leu Thr Leu Pro Pro Asn Asp His Val Asn Ser Asn Asn
305                 310                 315
```

<210> SEQ ID NO 22
<211> LENGTH: 310
<212> TYPE: PRT
<213> ORGANISM: Homo sapiens

<400> SEQUENCE: 22

```
Met Gly Ile Leu Ser Phe Leu Pro Val Leu Ala Thr Glu Ser Asp Trp
1               5                   10                  15

Ala Asp Cys Lys Ser Pro Gln Pro Trp Gly His Met Leu Leu Trp Thr
                20                  25                  30
```

```
Ala Val Leu Phe Leu Ala Pro Val Ala Gly Thr Pro Ala Pro Pro
        35                  40                  45

Lys Ala Val Leu Lys Leu Glu Pro Gln Trp Ile Asn Val Leu Gln Glu
 50                  55                  60

Asp Ser Val Thr Leu Thr Cys Arg Gly Thr His Ser Pro Glu Ser Asp
 65                  70                  75                  80

Ser Ile Gln Trp Phe His Asn Gly Asn Leu Ile Pro Thr His Thr Gln
                 85                  90                  95

Pro Ser Tyr Arg Phe Lys Ala Asn Asn Asn Asp Ser Gly Glu Tyr Thr
            100                 105                 110

Cys Gln Thr Gly Gln Thr Ser Leu Ser Asp Pro Val His Leu Thr Val
        115                 120                 125

Leu Ser Glu Trp Leu Val Leu Gln Thr Pro His Leu Glu Phe Gln Glu
130                 135                 140

Gly Glu Thr Ile Val Leu Arg Cys His Ser Trp Lys Asp Lys Pro Leu
145                 150                 155                 160

Val Lys Val Thr Phe Phe Gln Asn Gly Lys Ser Lys Lys Phe Ser Arg
                165                 170                 175

Ser Asp Pro Asn Phe Ser Ile Pro Gln Ala Asn His Ser His Ser Gly
            180                 185                 190

Asp Tyr His Cys Thr Gly Asn Ile Gly Tyr Thr Leu Tyr Ser Ser Lys
        195                 200                 205

Pro Val Thr Ile Thr Val Gln Ala Pro Ser Ser Ser Pro Met Gly Ile
210                 215                 220

Ile Val Ala Val Val Thr Gly Ile Ala Val Ala Ala Ile Val Ala Ala
225                 230                 235                 240

Val Val Ala Leu Ile Tyr Cys Arg Lys Lys Arg Ile Ser Ala Leu Pro
                245                 250                 255

Gly Tyr Pro Glu Cys Arg Glu Met Gly Glu Thr Leu Pro Glu Lys Pro
            260                 265                 270

Ala Asn Pro Thr Asn Pro Asp Glu Ala Asp Lys Val Gly Ala Glu Asn
        275                 280                 285

Thr Ile Thr Tyr Ser Leu Leu Met His Pro Asp Ala Leu Glu Glu Pro
290                 295                 300

Asp Asp Gln Asn Arg Ile
305                 310

<210> SEQ ID NO 23
<211> LENGTH: 390
<212> TYPE: PRT
<213> ORGANISM: Human herpesvirus 1

<400> SEQUENCE: 23

Met Pro Cys Arg Pro Leu Gln Gly Leu Val Leu Val Gly Leu Trp Val
 1               5                  10                  15

Cys Ala Thr Ser Leu Val Val Arg Gly Pro Thr Val Ser Leu Val Ser
                 20                  25                  30

Asn Ser Phe Val Asp Ala Gly Ala Leu Gly Pro Asp Gly Val Val Glu
            35                  40                  45

Glu Asp Leu Leu Ile Leu Gly Glu Leu Arg Phe Val Gly Asp Gln Val
 50                  55                  60

Pro His Thr Thr Tyr Tyr Asp Gly Gly Val Glu Leu Trp His Tyr Pro
 65                  70                  75                  80

Met Gly His Lys Cys Pro Arg Val Val His Val Val Thr Val Thr Ala
```

```
                    85                  90                  95
Cys Pro Arg Arg Pro Ala Val Ala Phe Ala Leu Cys Arg Ala Thr Asp
                100                 105                 110

Ser Thr His Ser Pro Ala Tyr Pro Thr Leu Glu Leu Asn Leu Ala Gln
            115                 120                 125

Gln Pro Leu Leu Arg Val Gln Arg Ala Thr Arg Asp Tyr Ala Gly Val
        130                 135                 140

Tyr Val Leu Arg Val Trp Val Gly Asp Ala Pro Asn Ala Ser Leu Phe
145                 150                 155                 160

Val Leu Gly Met Ala Ile Ala Ala Glu Gly Thr Leu Ala Tyr Asn Gly
                165                 170                 175

Ser Ala Tyr Gly Ser Cys Asp Pro Lys Leu Leu Pro Ser Ser Ala Pro
            180                 185                 190

Arg Leu Ala Pro Ala Ser Val Tyr Gln Pro Ala Pro Asn Gln Ala Ser
        195                 200                 205

Thr Pro Ser Thr Thr Thr Ser Thr Pro Ser Thr Thr Ile Pro Ala Pro
    210                 215                 220

Ser Thr Thr Ile Pro Ala Pro Gln Ala Ser Thr Thr Pro Phe Pro Thr
225                 230                 235                 240

Gly Asp Pro Lys Pro Gln Pro Pro Gly Val Asn His Glu Pro Pro Ser
                245                 250                 255

Asn Ala Thr Arg Ala Thr Arg Asp Ser Arg Tyr Ala Leu Thr Val Thr
            260                 265                 270

Gln Ile Ile Gln Ile Ala Ile Pro Ala Ser Ile Ile Ala Leu Val Phe
        275                 280                 285

Leu Gly Ser Cys Ile Cys Phe Ile His Arg Cys Gln Arg Arg Tyr Arg
    290                 295                 300

Arg Ser Arg Arg Pro Ile Tyr Ser Pro Gln Met Pro Thr Gly Ile Ser
305                 310                 315                 320

Cys Ala Val Asn Glu Ala Ala Met Ala Arg Leu Gly Ala Glu Leu Lys
                325                 330                 335

Ser His Pro Ser Thr Pro Pro Lys Ser Arg Arg Arg Ser Ser Arg Thr
            340                 345                 350

Pro Met Pro Ser Leu Thr Ala Ile Ala Glu Glu Ser Glu Pro Ala Gly
        355                 360                 365

Ala Ala Gly Leu Pro Thr Pro Pro Val Asp Pro Thr Thr Pro Thr Pro
    370                 375                 380

Thr Pro Pro Leu Leu Val
385                 390

<210> SEQ ID NO 24
<211> LENGTH: 254
<212> TYPE: PRT
<213> ORGANISM: Homo sapiens

<400> SEQUENCE: 24

Met Trp Gln Leu Leu Leu Pro Thr Ala Leu Leu Leu Leu Val Ser Ala
1               5                   10                  15

Gly Met Arg Thr Glu Asp Leu Pro Lys Ala Val Val Phe Leu Glu Pro
            20                  25                  30

Gln Trp Tyr Arg Val Leu Glu Lys Asp Ser Val Thr Leu Lys Cys Gln
        35                  40                  45

Gly Ala Tyr Ser Pro Glu Asp Asn Ser Thr Gln Trp Phe His Asn Glu
    50                  55                  60
```

```
Ser Leu Ile Ser Ser Gln Ala Ser Ser Tyr Phe Ile Asp Ala Ala Thr
 65                  70                  75                  80

Val Asp Asp Ser Gly Glu Tyr Arg Cys Gln Thr Asn Leu Ser Thr Leu
                 85                  90                  95

Ser Asp Pro Val Gln Leu Glu Val His Ile Gly Trp Leu Leu Leu Gln
            100                 105                 110

Ala Pro Arg Trp Val Phe Lys Glu Glu Asp Pro Ile His Leu Arg Cys
        115                 120                 125

His Ser Trp Lys Asn Thr Ala Leu His Lys Val Thr Tyr Leu Gln Asn
    130                 135                 140

Gly Lys Gly Arg Lys Tyr Phe His His Asn Ser Asp Phe Tyr Ile Pro
145                 150                 155                 160

Lys Ala Thr Leu Lys Asp Ser Gly Ser Tyr Phe Cys Arg Gly Leu Val
                165                 170                 175

Gly Ser Lys Asn Val Ser Ser Glu Thr Val Asn Ile Thr Ile Thr Gln
            180                 185                 190

Gly Leu Ala Val Ser Thr Ile Ser Ser Phe Phe Pro Pro Gly Tyr Gln
        195                 200                 205

Val Ser Phe Cys Leu Val Met Val Leu Leu Phe Ala Val Asp Thr Gly
    210                 215                 220

Leu Tyr Phe Ser Val Lys Thr Asn Ile Arg Ser Ser Thr Arg Asp Trp
225                 230                 235                 240

Lys Asp His Lys Phe Lys Trp Arg Lys Asp Pro Gln Asp Lys
                245                 250

<210> SEQ ID NO 25
<211> LENGTH: 36
<212> TYPE: DNA
<213> ORGANISM: Artificial Sequence
<220> FEATURE:
<223> OTHER INFORMATION: Description of Artificial Sequence: Synthetic
      UL1 forward primer

<400> SEQUENCE: 25
gtctacacta gtatggggat tttggttgg gtcggg                              36

<210> SEQ ID NO 26
<211> LENGTH: 1137
<212> TYPE: PRT
<213> ORGANISM: Human herpesvirus 1

<400> SEQUENCE: 26

Met Ala Ser Arg Pro Ala Ala Ser Pro Val Glu Arg Ala Pro
 1               5                  10                  15

Val Gly Gly Gln Glu Ala Gly Gly Pro Ser Ala Ala Thr Gln Gly Glu
                20                  25                  30

Ala Ala Gly Ala Pro Leu Ala His Gly His His Val Tyr Cys Gln Arg
            35                  40                  45

Val Asn Gly Val Met Val Leu Ser Asp Lys Thr Pro Gly Ser Ala Ser
        50                  55                  60

Tyr Arg Ile Ser Asp Ser Asn Phe Val Gln Cys Gly Ser Asn Cys Thr
 65                  70                  75                  80

Met Ile Ile Asp Gly Asp Val Val Arg Gly Arg Pro Gln Asp Pro Gly
                 85                  90                  95

Ala Ala Ala Ser Pro Ala Pro Phe Val Ala Val Thr Asn Ile Gly Ala
            100                 105                 110

Gly Ser Asp Gly Gly Thr Ala Val Val Ala Phe Gly Gly Thr Pro Arg
```

```
            115                 120                 125
Arg Ser Ala Gly Thr Ser Thr Gly Thr Gln Thr Ala Asp Val Pro Ala
130                 135                 140

Glu Ala Leu Gly Gly Pro Pro Pro Pro Arg Phe Thr Leu Gly Gly
145                 150                 155                 160

Gly Cys Cys Ser Cys Arg Asp Thr Arg Arg Ser Ala Val Phe Gly
                165                 170                 175

Gly Glu Gly Asp Pro Val Gly Pro Ala Glu Phe Val Ser Asp Asp Arg
                180                 185                 190

Ser Ser Asp Ser Asp Ser Asp Ser Glu Asp Thr Asp Ser Glu Thr
        195                 200                 205

Leu Ser His Ala Ser Ser Asp Val Ser Gly Gly Ala Thr Tyr Asp Asp
        210                 215                 220

Ala Leu Asp Ser Asp Ser Ser Asp Asp Ser Leu Gln Ile Asp Gly
225                 230                 235                 240

Pro Val Cys Arg Pro Trp Ser Asn Asp Thr Ala Pro Leu Asp Val Cys
                245                 250                 255

Pro Gly Thr Pro Gly Pro Gly Ala Asp Ala Gly Gly Pro Ser Ala Val
                260                 265                 270

Asp Pro His Ala Pro Thr Thr Gly Ala Gly Ala Gly Leu Ala Ala Asp
                275                 280                 285

Pro Ala Val Ala Arg Asp Asp Ala Glu Gly Leu Ser Asp Pro Arg Pro
290                 295                 300

Arg Leu Gly Thr Gly Thr Ala Tyr Pro Val Pro Leu Glu Leu Thr Pro
305                 310                 315                 320

Glu Asn Ala Glu Ala Val Ala Arg Phe Leu Gly Asp Ala Val Asn Arg
                325                 330                 335

Glu Pro Ala Leu Met Leu Glu Tyr Phe Cys Arg Cys Ala Arg Glu Glu
                340                 345                 350

Thr Lys Arg Val Pro Pro Arg Thr Phe Cys Ser Pro Arg Leu Thr
        355                 360                 365

Glu Asp Asp Phe Gly Leu Leu Asn Tyr Ala Leu Val Glu Met Gln Arg
370                 375                 380

Leu Cys Leu Asp Val Pro Val Pro Pro Asn Ala Tyr Met Pro Tyr
385                 390                 395                 400

Tyr Leu Arg Glu Tyr Val Thr Arg Leu Val Asn Gly Phe Lys Pro Leu
                405                 410                 415

Val Ser Arg Ser Val Arg Leu Tyr Arg Ile Leu Gly Val Leu Val His
                420                 425                 430

Leu Arg Ile Arg Thr Arg Glu Ala Ser Phe Glu Glu Trp Leu Arg Ser
            435                 440                 445

Lys Glu Val Ala Leu Asp Phe Gly Leu Thr Glu Arg Leu Arg Glu His
        450                 455                 460

Glu Ala Gln Leu Val Ile Leu Ala Gln Ala Leu Asp His Tyr Asp Cys
465                 470                 475                 480

Leu Ile His Ser Thr Pro His Thr Leu Val Glu Arg Gly Leu Gln Ser
                485                 490                 495

Ala Leu Lys Tyr Glu Glu Phe Tyr Leu Lys Arg Phe Gly Gly His Tyr
                500                 505                 510

Met Glu Ser Val Phe Gln Met Tyr Thr Arg Ile Ala Gly Phe Leu Ala
            515                 520                 525

Cys Arg Ala Thr Arg Gly Met Arg His Ile Ala Leu Gly Arg Glu Gly
530                 535                 540
```

```
Ser Trp Trp Glu Met Phe Lys Phe Phe Phe His Arg Leu Tyr Asp His
545                 550                 555                 560

Gln Ile Val Pro Ser Thr Pro Ala Met Leu Asn Leu Gly Thr Arg Asn
                565                 570                 575

Tyr Tyr Thr Ser Ser Cys Tyr Leu Val Asn Pro Gln Ala Thr Thr Asn
            580                 585                 590

Lys Ala Thr Leu Arg Ala Ile Thr Ser Asn Val Ser Ala Ile Leu Ala
        595                 600                 605

Arg Asn Gly Gly Ile Gly Leu Cys Val Gln Ala Phe Asn Asp Ser Gly
    610                 615                 620

Pro Gly Thr Ala Ser Val Met Pro Ala Leu Lys Val Leu Asp Ser Leu
625                 630                 635                 640

Val Ala Ala His Asn Lys Glu Ser Ala Arg Pro Thr Gly Ala Cys Val
                645                 650                 655

Tyr Leu Glu Pro Trp His Thr Asp Val Arg Ala Val Leu Arg Met Lys
            660                 665                 670

Gly Val Leu Ala Gly Glu Glu Ala Gln Arg Cys Asp Asn Ile Phe Ser
        675                 680                 685

Ala Leu Trp Met Pro Asp Leu Phe Phe Lys Arg Leu Ile Arg His Leu
    690                 695                 700

Asp Gly Glu Lys Asn Val Thr Trp Thr Leu Phe Asp Arg Asp Thr Ser
705                 710                 715                 720

Met Ser Leu Ala Asp Phe His Gly Glu Glu Phe Glu Lys Leu Tyr Gln
                725                 730                 735

His Leu Glu Val Met Gly Phe Gly Glu Gln Ile Pro Ile Gln Glu Leu
            740                 745                 750

Ala Tyr Gly Ile Val Arg Ser Ala Ala Thr Thr Gly Ser Pro Phe Val
        755                 760                 765

Met Phe Lys Asp Ala Val Asn Arg His Tyr Ile Tyr Asp Thr Gln Gly
    770                 775                 780

Ala Ala Ile Ala Gly Ser Asn Leu Cys Thr Glu Ile Val His Pro Ala
785                 790                 795                 800

Ser Lys Arg Ser Ser Gly Val Cys Asn Leu Gly Ser Val Asn Leu Ala
                805                 810                 815

Arg Cys Val Ser Arg Gln Thr Phe Asp Phe Gly Arg Leu Arg Asp Ala
            820                 825                 830

Val Gln Ala Cys Val Leu Met Val Asn Ile Met Ile Asp Ser Thr Leu
        835                 840                 845

Gln Pro Thr Pro Gln Cys Thr Arg Gly Asn Asp Asn Leu Arg Ser Met
    850                 855                 860

Gly Ile Gly Met Gln Gly Leu His Thr Ala Cys Leu Lys Leu Gly Leu
865                 870                 875                 880

Asp Leu Glu Ser Ala Glu Phe Gln Asp Leu Asn Lys His Ile Ala Glu
                885                 890                 895

Val Met Leu Leu Ser Ala Met Lys Thr Ser Asn Ala Leu Cys Val Arg
            900                 905                 910

Gly Ala Arg Pro Phe Asn His Phe Lys Arg Ser Met Tyr Arg Ala Gly
        915                 920                 925

Arg Phe His Trp Glu Arg Phe Pro Asp Ala Arg Pro Arg Tyr Glu Gly
    930                 935                 940

Glu Trp Glu Met Leu Arg Gln Ser Met Met Lys His Gly Leu Arg Asn
945                 950                 955                 960
```

```
Ser Gln Phe Val Ala Leu Met Pro Thr Ala Ala Ser Ala Gln Ile Ser
            965                 970                 975

Asp Val Ser Glu Gly Phe Ala Pro Leu Phe Thr Asn Leu Phe Ser Lys
        980                 985                 990

Val Thr Arg Asp Gly Glu Thr Leu Arg Pro Asn Thr Leu Leu Leu Lys
    995                 1000                1005

Glu Leu Glu Arg Thr Phe Ser Gly Lys Arg Leu Leu Glu Val Met
    1010                1015                1020

Asp Ser Leu Asp Ala Lys Gln Trp Ser Val Ala Gln Ala Leu Pro
    1025                1030                1035

Cys Leu Glu Pro Thr His Pro Leu Arg Arg Phe Lys Thr Ala Phe
    1040                1045                1050

Asp Tyr Asp Gln Lys Leu Leu Ile Asp Leu Cys Ala Asp Arg Ala
    1055                1060                1065

Pro Tyr Val Asp His Ser Gln Ser Met Thr Leu Tyr Val Thr Glu
    1070                1075                1080

Lys Ala Asp Gly Thr Leu Pro Ala Ser Thr Leu Val Arg Leu Leu
    1085                1090                1095

Val His Ala Tyr Lys Arg Gly Leu Lys Thr Gly Met Tyr Tyr Cys
    1100                1105                1110

Lys Val Arg Lys Ala Thr Asn Ser Gly Val Phe Gly Gly Asp Asp
    1115                1120                1125

Asn Ile Val Cys Thr Ser Cys Ala Leu
    1130                1135

<210> SEQ ID NO 27
<211> LENGTH: 36
<212> TYPE: DNA
<213> ORGANISM: Artificial Sequence
<220> FEATURE:
<223> OTHER INFORMATION: Description of Artificial Sequence: Synthetic
      UL1 forward primer

<400> SEQUENCE: 27
gtctacacta gtatggggat tttgggttgg gtcggg                            36

<210> SEQ ID NO 28
<211> LENGTH: 37
<212> TYPE: DNA
<213> ORGANISM: Artificial Sequence
<220> FEATURE:
<223> OTHER INFORMATION: Description of Artificial Sequence: Synthetic
      UL1 reverse primer

<400> SEQUENCE: 28
gtctacttaa ttaagatgcg ccgggagtgg ggtcgtc                           37

<210> SEQ ID NO 29
<211> LENGTH: 35
<212> TYPE: DNA
<213> ORGANISM: Artificial Sequence
<220> FEATURE:
<223> OTHER INFORMATION: Description of Artificial Sequence: Synthetic
      UL2 forward primer

<400> SEQUENCE: 29
gtctacacta gtatgaagcg ggcctgcagc cgaag                             35

<210> SEQ ID NO 30
<211> LENGTH: 34
<212> TYPE: DNA
```

-continued

```
<213> ORGANISM: Artificial Sequence
<220> FEATURE:
<223> OTHER INFORMATION: Description of Artificial Sequence: Synthetic
      UL2 reverse primer

<400> SEQUENCE: 30
gtctacttaa ttaaaaccga ccagtcgatg ggtg                              34

<210> SEQ ID NO 31
<211> LENGTH: 36
<212> TYPE: DNA
<213> ORGANISM: Artificial Sequence
<220> FEATURE:
<223> OTHER INFORMATION: Description of Artificial Sequence: Synthetic
      UL3 forward primer

<400> SEQUENCE: 31
gtctacacta gtatggttaa acctctggtc tcatac                            36

<210> SEQ ID NO 32
<211> LENGTH: 36
<212> TYPE: DNA
<213> ORGANISM: Artificial Sequence
<220> FEATURE:
<223> OTHER INFORMATION: Description of Artificial Sequence: Synthetic
      UL3 reverse primer

<400> SEQUENCE: 32
gtctacttaa ttaactcggc ccccgaggcc agcatg                            36

<210> SEQ ID NO 33
<211> LENGTH: 36
<212> TYPE: DNA
<213> ORGANISM: Artificial Sequence
<220> FEATURE:
<223> OTHER INFORMATION: Description of Artificial Sequence: Synthetic
      UL4 forward primer

<400> SEQUENCE: 33
gtctacacta gtatgtccaa tccacagacg accatc                            36

<210> SEQ ID NO 34
<211> LENGTH: 36
<212> TYPE: DNA
<213> ORGANISM: Artificial Sequence
<220> FEATURE:
<223> OTHER INFORMATION: Description of Artificial Sequence: Synthetic
      UL4 reverse primer

<400> SEQUENCE: 34
gtctacttaa ttaaggaccc caaaagtttg tctgcg                            36

<210> SEQ ID NO 35
<211> LENGTH: 33
<212> TYPE: DNA
<213> ORGANISM: Artificial Sequence
<220> FEATURE:
<223> OTHER INFORMATION: Description of Artificial Sequence: Synthetic
      UL5 forward primer

<400> SEQUENCE: 35
gtctacacta gtatggcggc ggccggcggg gag                               33

<210> SEQ ID NO 36
<211> LENGTH: 39
<212> TYPE: DNA
<213> ORGANISM: Artificial Sequence
```

```
<220> FEATURE:
<223> OTHER INFORMATION: Description of Artificial Sequence: Synthetic
      UL5 reverse primer

<400> SEQUENCE: 36
gtctacttaa ttaaatatac aatgaccacg ttcggatcg                              39

<210> SEQ ID NO 37
<211> LENGTH: 33
<212> TYPE: DNA
<213> ORGANISM: Artificial Sequence
<220> FEATURE:
<223> OTHER INFORMATION: Description of Artificial Sequence: Synthetic
      UL6 forward primer

<400> SEQUENCE: 37
gtctacacta gtatgaccgc accacgctcg cgg                                    33

<210> SEQ ID NO 38
<211> LENGTH: 39
<212> TYPE: DNA
<213> ORGANISM: Artificial Sequence
<220> FEATURE:
<223> OTHER INFORMATION: Description of Artificial Sequence: Synthetic
      UL6 reverse primer

<400> SEQUENCE: 38
gtctacttaa ttaatcgtcg gccgtcgcgg cggccatcc                              39

<210> SEQ ID NO 39
<211> LENGTH: 33
<212> TYPE: DNA
<213> ORGANISM: Artificial Sequence
<220> FEATURE:
<223> OTHER INFORMATION: Description of Artificial Sequence: Synthetic
      UL7 forward primer

<400> SEQUENCE: 39
gtctacacta gtatggccgc cgcgacggcc gac                                    33

<210> SEQ ID NO 40
<211> LENGTH: 37
<212> TYPE: DNA
<213> ORGANISM: Artificial Sequence
<220> FEATURE:
<223> OTHER INFORMATION: Description of Artificial Sequence: Synthetic
      UL7 reverse primer

<400> SEQUENCE: 40
gtctacttaa ttaaacaaaa ctgataaaac agcgacg                                37

<210> SEQ ID NO 41
<211> LENGTH: 36
<212> TYPE: DNA
<213> ORGANISM: Artificial Sequence
<220> FEATURE:
<223> OTHER INFORMATION: Description of Artificial Sequence: Synthetic
      UL8 forward primer

<400> SEQUENCE: 41
gtctacacta gtatggacac cgcagatatc gtgtgg                                 36

<210> SEQ ID NO 42
<211> LENGTH: 36
<212> TYPE: DNA
<213> ORGANISM: Artificial Sequence
<220> FEATURE:
```

```
<223> OTHER INFORMATION: Description of Artificial Sequence: Synthetic
      UL8 reverse primer

<400> SEQUENCE: 42
gtctacttaa ttaaggcaaa cagaaacgac atcttg                                36

<210> SEQ ID NO 43
<211> LENGTH: 36
<212> TYPE: DNA
<213> ORGANISM: Artificial Sequence
<220> FEATURE:
<223> OTHER INFORMATION: Description of Artificial Sequence: Synthetic
      UL9 forward primer

<400> SEQUENCE: 43
gtctacacta gtatgccttt cgtgggggc gcggag                                 36

<210> SEQ ID NO 44
<211> LENGTH: 34
<212> TYPE: DNA
<213> ORGANISM: Artificial Sequence
<220> FEATURE:
<223> OTHER INFORMATION: Description of Artificial Sequence: Synthetic
      UL9 reverse primer

<400> SEQUENCE: 44
gtctacttaa ttaatagggt gctaaagttc accg                                  34

<210> SEQ ID NO 45
<211> LENGTH: 32
<212> TYPE: DNA
<213> ORGANISM: Artificial Sequence
<220> FEATURE:
<223> OTHER INFORMATION: Description of Artificial Sequence: Synthetic
      UL10 forward primer

<400> SEQUENCE: 45
gtctacacta gtatgggacg cccggccccc ag                                    32

<210> SEQ ID NO 46
<211> LENGTH: 36
<212> TYPE: DNA
<213> ORGANISM: Artificial Sequence
<220> FEATURE:
<223> OTHER INFORMATION: Description of Artificial Sequence: Synthetic
      UL10 reverse primer

<400> SEQUENCE: 46
gtctacttaa ttaaccaacg gcggacggtg ctgtac                                36

<210> SEQ ID NO 47
<211> LENGTH: 35
<212> TYPE: DNA
<213> ORGANISM: Artificial Sequence
<220> FEATURE:
<223> OTHER INFORMATION: Description of Artificial Sequence: Synthetic
      UL11 forward primer

<400> SEQUENCE: 47
gtctacacta gtatgggcct ctcgttctcc ggggc                                 35

<210> SEQ ID NO 48
<211> LENGTH: 37
<212> TYPE: DNA
<213> ORGANISM: Artificial Sequence
<220> FEATURE:
<223> OTHER INFORMATION: Description of Artificial Sequence: Synthetic
```

UL11 reverse primer

<400> SEQUENCE: 48
gtctacttaa ttaattcgct atcggacatg gggggtg                                    37

<210> SEQ ID NO 49
<211> LENGTH: 32
<212> TYPE: DNA
<213> ORGANISM: Artificial Sequence
<220> FEATURE:
<223> OTHER INFORMATION: Description of Artificial Sequence: Synthetic
      UL12 forward primer

<400> SEQUENCE: 49
gtctacacta gtatggagtc cacggtaggc cc                                         32

<210> SEQ ID NO 50
<211> LENGTH: 34
<212> TYPE: DNA
<213> ORGANISM: Artificial Sequence
<220> FEATURE:
<223> OTHER INFORMATION: Description of Artificial Sequence: Synthetic
      UL12 reverse primer

<400> SEQUENCE: 50
gtctacttaa ttaagcgaga cgacctcccc gtcg                                       34

<210> SEQ ID NO 51
<211> LENGTH: 35
<212> TYPE: DNA
<213> ORGANISM: Artificial Sequence
<220> FEATURE:
<223> OTHER INFORMATION: Description of Artificial Sequence: Synthetic
      UL13 forward primer

<400> SEQUENCE: 51
gtctacacta gtatggatga gtcccgcaga cagcg                                      35

<210> SEQ ID NO 52
<211> LENGTH: 36
<212> TYPE: DNA
<213> ORGANISM: Artificial Sequence
<220> FEATURE:
<223> OTHER INFORMATION: Description of Artificial Sequence: Synthetic
      UL13 reverse primer

<400> SEQUENCE: 52
gtctacttaa ttaacgacag cgcgtgccgc gcgcac                                     36

<210> SEQ ID NO 53
<211> LENGTH: 34
<212> TYPE: DNA
<213> ORGANISM: Artificial Sequence
<220> FEATURE:
<223> OTHER INFORMATION: Description of Artificial Sequence: Synthetic
      UL14 forward primer

<400> SEQUENCE: 53
gtctacacta gtatggaccg agatgccgcc cacg                                       34

<210> SEQ ID NO 54
<211> LENGTH: 35
<212> TYPE: DNA
<213> ORGANISM: Artificial Sequence
<220> FEATURE:
<223> OTHER INFORMATION: Description of Artificial Sequence: Synthetic
      UL14 reverse primer

<400> SEQUENCE: 54
gtctacttaa ttaattcgcc atcgggatag tcccg					35

<210> SEQ ID NO 55
<211> LENGTH: 35
<212> TYPE: DNA
<213> ORGANISM: Artificial Sequence
<220> FEATURE:
<223> OTHER INFORMATION: Description of Artificial Sequence: Synthetic
      UL15 forward primer

<400> SEQUENCE: 55
gtctacacta gtatgtttgg tcagcagctg gcgtc					35

<210> SEQ ID NO 56
<211> LENGTH: 36
<212> TYPE: DNA
<213> ORGANISM: Artificial Sequence
<220> FEATURE:
<223> OTHER INFORMATION: Description of Artificial Sequence: Synthetic
      UL15 reverse primer

<400> SEQUENCE: 56
gtctacttaa ttaacgaaac gcgtgtgatg ggagcg					36

<210> SEQ ID NO 57
<211> LENGTH: 35
<212> TYPE: DNA
<213> ORGANISM: Artificial Sequence
<220> FEATURE:
<223> OTHER INFORMATION: Description of Artificial Sequence: Synthetic
      UL16 forward primer

<400> SEQUENCE: 57
gtctacacta gtatggcgca gctgggaccc cggcg					35

<210> SEQ ID NO 58
<211> LENGTH: 38
<212> TYPE: DNA
<213> ORGANISM: Artificial Sequence
<220> FEATURE:
<223> OTHER INFORMATION: Description of Artificial Sequence: Synthetic
      UL16 reverse primer

<400> SEQUENCE: 58
gtctacttaa ttaattcggg atcgcttgag gaggcccg					38

<210> SEQ ID NO 59
<211> LENGTH: 39
<212> TYPE: DNA
<213> ORGANISM: Artificial Sequence
<220> FEATURE:
<223> OTHER INFORMATION: Description of Artificial Sequence: Synthetic
      UL17 forward primer

<400> SEQUENCE: 59
gtctacacta gtatgaacgc gcacttggcc aacgaggtc					39

<210> SEQ ID NO 60
<211> LENGTH: 35
<212> TYPE: DNA
<213> ORGANISM: Artificial Sequence
<220> FEATURE:
<223> OTHER INFORMATION: Description of Artificial Sequence: Synthetic
      UL17 reverse primer

<400> SEQUENCE: 60
gtctacttaa ttaagcgaga acggccgttc ccgga                                35

<210> SEQ ID NO 61
<211> LENGTH: 35
<212> TYPE: DNA
<213> ORGANISM: Artificial Sequence
<220> FEATURE:
<223> OTHER INFORMATION: Description of Artificial Sequence: Synthetic
      UL18 forward primer

<400> SEQUENCE: 61
gtctacacta gtatgctggc ggacggcttt gaaac                                35

<210> SEQ ID NO 62
<211> LENGTH: 32
<212> TYPE: DNA
<213> ORGANISM: Artificial Sequence
<220> FEATURE:
<223> OTHER INFORMATION: Description of Artificial Sequence: Synthetic
      UL18 reverse primer

<400> SEQUENCE: 62
gtctacttaa ttaagggata gcgtataacg gg                                   32

<210> SEQ ID NO 63
<211> LENGTH: 35
<212> TYPE: DNA
<213> ORGANISM: Artificial Sequence
<220> FEATURE:
<223> OTHER INFORMATION: Description of Artificial Sequence: Synthetic
      UL19 forward primer

<400> SEQUENCE: 63
gtctacacta gtatggccgc tcccaaccgc gaccc                                35

<210> SEQ ID NO 64
<211> LENGTH: 40
<212> TYPE: DNA
<213> ORGANISM: Artificial Sequence
<220> FEATURE:
<223> OTHER INFORMATION: Description of Artificial Sequence: Synthetic
      UL19 reverse primer

<400> SEQUENCE: 64
gtctacttaa ttaacagagc cagtcccttg agcggggatg                           40

<210> SEQ ID NO 65
<211> LENGTH: 37
<212> TYPE: DNA
<213> ORGANISM: Artificial Sequence
<220> FEATURE:
<223> OTHER INFORMATION: Description of Artificial Sequence: Synthetic
      UL20 forward primer

<400> SEQUENCE: 65
gtctacacta gtatgaccat gcgggatgac cttcctc                              37

<210> SEQ ID NO 66
<211> LENGTH: 36
<212> TYPE: DNA
<213> ORGANISM: Artificial Sequence
<220> FEATURE:
<223> OTHER INFORMATION: Description of Artificial Sequence: Synthetic
      UL20 reverse primer

<400> SEQUENCE: 66
gtctacttaa ttaagaacgc gacgggtgca ttcaag                                    36

<210> SEQ ID NO 67
<211> LENGTH: 33
<212> TYPE: DNA
<213> ORGANISM: Artificial Sequence
<220> FEATURE:
<223> OTHER INFORMATION: Description of Artificial Sequence: Synthetic
      UL21 forward primer

<400> SEQUENCE: 67
gtctacacta gtatggagct tagctacgcc acc                                       33

<210> SEQ ID NO 68
<211> LENGTH: 34
<212> TYPE: DNA
<213> ORGANISM: Artificial Sequence
<220> FEATURE:
<223> OTHER INFORMATION: Description of Artificial Sequence: Synthetic
      UL21 reverse primer

<400> SEQUENCE: 68
gtctacttaa ttaacacaga ctgtccgtgt ttgg                                      34

<210> SEQ ID NO 69
<211> LENGTH: 34
<212> TYPE: DNA
<213> ORGANISM: Artificial Sequence
<220> FEATURE:
<223> OTHER INFORMATION: Description of Artificial Sequence: Synthetic
      UL22 forward primer

<400> SEQUENCE: 69
gtctacacta gtatggggaa tggtttatgg ttcg                                      34

<210> SEQ ID NO 70
<211> LENGTH: 40
<212> TYPE: DNA
<213> ORGANISM: Artificial Sequence
<220> FEATURE:
<223> OTHER INFORMATION: Description of Artificial Sequence: Synthetic
      UL22 reverse primer

<400> SEQUENCE: 70
gtctacttaa ttaattcgcg tctccaaaaa aacgggacac                                40

<210> SEQ ID NO 71
<211> LENGTH: 34
<212> TYPE: DNA
<213> ORGANISM: Artificial Sequence
<220> FEATURE:
<223> OTHER INFORMATION: Description of Artificial Sequence: Synthetic
      UL23 forward primer

<400> SEQUENCE: 71
gtctacacta gtatggcttc gtacccctgc catc                                      34

<210> SEQ ID NO 72
<211> LENGTH: 43
<212> TYPE: DNA
<213> ORGANISM: Artificial Sequence
<220> FEATURE:
<223> OTHER INFORMATION: Description of Artificial Sequence: Synthetic
      UL23 reverse primer

<400> SEQUENCE: 72

```
gtctacttaa ttaagttagc ctcccccatc tcccgggcaa acg          43
```

<210> SEQ ID NO 73
<211> LENGTH: 33
<212> TYPE: DNA
<213> ORGANISM: Artificial Sequence
<220> FEATURE:
<223> OTHER INFORMATION: Description of Artificial Sequence: Synthetic
      UL24 forward primer

<400> SEQUENCE: 73

```
gtctacacta gtatggccgc gagaacgcgc agc                     33
```

<210> SEQ ID NO 74
<211> LENGTH: 36
<212> TYPE: DNA
<213> ORGANISM: Artificial Sequence
<220> FEATURE:
<223> OTHER INFORMATION: Description of Artificial Sequence: Synthetic
      UL24 reverse primer

<400> SEQUENCE: 74

```
gtctacttaa ttaattcgga ggcggctcgg ggtttg                  36
```

<210> SEQ ID NO 75
<211> LENGTH: 34
<212> TYPE: DNA
<213> ORGANISM: Artificial Sequence
<220> FEATURE:
<223> OTHER INFORMATION: Description of Artificial Sequence: Synthetic
      UL25 forward primer

<400> SEQUENCE: 75

```
gtctacacta gtatggaccc gtactgccca tttg                    34
```

<210> SEQ ID NO 76
<211> LENGTH: 35
<212> TYPE: DNA
<213> ORGANISM: Artificial Sequence
<220> FEATURE:
<223> OTHER INFORMATION: Description of Artificial Sequence: Synthetic
      UL25 reverse primer

<400> SEQUENCE: 76

```
gtctacttaa ttaaaaccgc cgacaggtac tgtgg                   35
```

<210> SEQ ID NO 77
<211> LENGTH: 34
<212> TYPE: DNA
<213> ORGANISM: Artificial Sequence
<220> FEATURE:
<223> OTHER INFORMATION: Description of Artificial Sequence: Synthetic
      UL26 forward primer

<400> SEQUENCE: 77

```
gtctacacta gtatggcagc cgatgccccg ggag                    34
```

<210> SEQ ID NO 78
<211> LENGTH: 36
<212> TYPE: DNA
<213> ORGANISM: Artificial Sequence
<220> FEATURE:
<223> OTHER INFORMATION: Description of Artificial Sequence: Synthetic
      UL26 reverse primer

<400> SEQUENCE: 78

```
gtctacttaa ttaagcgggc ccccatcatc tgagag                  36
```

<210> SEQ ID NO 79
<211> LENGTH: 36
<212> TYPE: DNA
<213> ORGANISM: Artificial Sequence
<220> FEATURE:
<223> OTHER INFORMATION: Description of Artificial Sequence: Synthetic
    UL26.5 forward primer

<400> SEQUENCE: 79
gtctacacta gtatgaaccc cgttccggca tcgggc                              36

<210> SEQ ID NO 80
<211> LENGTH: 36
<212> TYPE: DNA
<213> ORGANISM: Artificial Sequence
<220> FEATURE:
<223> OTHER INFORMATION: Description of Artificial Sequence: Synthetic
    UL26.5 reverse primer

<400> SEQUENCE: 80
gtctacttaa ttaagcgggc ccccatcatc tgagag                              36

<210> SEQ ID NO 81
<211> LENGTH: 32
<212> TYPE: DNA
<213> ORGANISM: Artificial Sequence
<220> FEATURE:
<223> OTHER INFORMATION: Description of Artificial Sequence: Synthetic
    UL27 forward primer

<400> SEQUENCE: 81
gtctacacta gtatgcgcca gggcgccccc gc                                  32

<210> SEQ ID NO 82
<211> LENGTH: 35
<212> TYPE: DNA
<213> ORGANISM: Artificial Sequence
<220> FEATURE:
<223> OTHER INFORMATION: Description of Artificial Sequence: Synthetic
    UL27 reverse primer

<400> SEQUENCE: 82
gtctacttaa ttaacaggtc gtcctcgtcg gcgtc                               35

<210> SEQ ID NO 83
<211> LENGTH: 36
<212> TYPE: DNA
<213> ORGANISM: Artificial Sequence
<220> FEATURE:
<223> OTHER INFORMATION: Description of Artificial Sequence: Synthetic
    UL28 forward primer

<400> SEQUENCE: 83
gtctacacta gtatggccgc cccggtgtcc gagccc                              36

<210> SEQ ID NO 84
<211> LENGTH: 34
<212> TYPE: DNA
<213> ORGANISM: Artificial Sequence
<220> FEATURE:
<223> OTHER INFORMATION: Description of Artificial Sequence: Synthetic
    UL28 reverse primer

<400> SEQUENCE: 84
gtctacttaa ttaacgggg cccgtcgtgc cccc                                 34

<210> SEQ ID NO 85
<211> LENGTH: 35
<212> TYPE: DNA
<213> ORGANISM: Artificial Sequence
<220> FEATURE:
<223> OTHER INFORMATION: Description of Artificial Sequence: Synthetic
      UL29 forward primer

<400> SEQUENCE: 85
gtctacacta gtatggagac aaagcccaag acggc                              35

<210> SEQ ID NO 86
<211> LENGTH: 37
<212> TYPE: DNA
<213> ORGANISM: Artificial Sequence
<220> FEATURE:
<223> OTHER INFORMATION: Description of Artificial Sequence: Synthetic
      UL29 reverse primer

<400> SEQUENCE: 86
gtctacttaa ttaacagcat atccaacgtc aggtctc                            37

<210> SEQ ID NO 87
<211> LENGTH: 32
<212> TYPE: DNA
<213> ORGANISM: Artificial Sequence
<220> FEATURE:
<223> OTHER INFORMATION: Description of Artificial Sequence: Synthetic
      UL30 forward primer

<400> SEQUENCE: 87
gtctacacta gtatgttttc cggtggcggc gg                                 32

<210> SEQ ID NO 88
<211> LENGTH: 34
<212> TYPE: DNA
<213> ORGANISM: Artificial Sequence
<220> FEATURE:
<223> OTHER INFORMATION: Description of Artificial Sequence: Synthetic
      UL30 reverse primer

<400> SEQUENCE: 88
gtctacttaa ttaatgctag agtatcaaag gctc                               34

<210> SEQ ID NO 89
<211> LENGTH: 34
<212> TYPE: DNA
<213> ORGANISM: Artificial Sequence
<220> FEATURE:
<223> OTHER INFORMATION: Description of Artificial Sequence: Synthetic
      UL31 forward primer

<400> SEQUENCE: 89
gtctacacta gtatgtatga caccgacccc catc                               34

<210> SEQ ID NO 90
<211> LENGTH: 37
<212> TYPE: DNA
<213> ORGANISM: Artificial Sequence
<220> FEATURE:
<223> OTHER INFORMATION: Description of Artificial Sequence: Synthetic
      UL31 reverse primer

<400> SEQUENCE: 90
gtctacttaa ttaacggcgg aggaaactcg tcgaatg                            37

```
<210> SEQ ID NO 91
<211> LENGTH: 32
<212> TYPE: DNA
<213> ORGANISM: Artificial Sequence
<220> FEATURE:
<223> OTHER INFORMATION: Description of Artificial Sequence: Synthetic
      UL32 forward primer

<400> SEQUENCE: 91
gtctacacta gtgcccagcc atggcaactt cg                                    32

<210> SEQ ID NO 92
<211> LENGTH: 36
<212> TYPE: DNA
<213> ORGANISM: Artificial Sequence
<220> FEATURE:
<223> OTHER INFORMATION: Description of Artificial Sequence: Synthetic
      UL32 reverse primer

<400> SEQUENCE: 92
gtctacttaa ttaatacata ggtacacagg gtgtgc                                36

<210> SEQ ID NO 93
<211> LENGTH: 31
<212> TYPE: DNA
<213> ORGANISM: Artificial Sequence
<220> FEATURE:
<223> OTHER INFORMATION: Description of Artificial Sequence: Synthetic
      UL33 forward primer

<400> SEQUENCE: 93
gtctacacta gtgaagttgc catggctggg c                                     31

<210> SEQ ID NO 94
<211> LENGTH: 38
<212> TYPE: DNA
<213> ORGANISM: Artificial Sequence
<220> FEATURE:
<223> OTHER INFORMATION: Description of Artificial Sequence: Synthetic
      UL33 reverse primer

<400> SEQUENCE: 94
gtctacttaa ttaagccccg cagaatctgg tgcaggtc                              38

<210> SEQ ID NO 95
<211> LENGTH: 33
<212> TYPE: DNA
<213> ORGANISM: Artificial Sequence
<220> FEATURE:
<223> OTHER INFORMATION: Description of Artificial Sequence: Synthetic
      UL34 forward primer

<400> SEQUENCE: 95
gtctacacta gtatggcggg actgggcaag ccc                                   33

<210> SEQ ID NO 96
<211> LENGTH: 35
<212> TYPE: DNA
<213> ORGANISM: Artificial Sequence
<220> FEATURE:
<223> OTHER INFORMATION: Description of Artificial Sequence: Synthetic
      UL34 reverse primer

<400> SEQUENCE: 96
gtctacttaa ttaataggcg cgcgccagca ccaac                                 35

<210> SEQ ID NO 97
```

<210> LENGTH: 33
<212> TYPE: DNA
<213> ORGANISM: Artificial Sequence
<220> FEATURE:
<223> OTHER INFORMATION: Description of Artificial Sequence: Synthetic
UL35 forward primer

<400> SEQUENCE: 97
gtctacacta gtatggccgt cccgcaattt cac                                    33

<210> SEQ ID NO 98
<211> LENGTH: 35
<212> TYPE: DNA
<213> ORGANISM: Artificial Sequence
<220> FEATURE:
<223> OTHER INFORMATION: Description of Artificial Sequence: Synthetic
UL35 reverse primer

<400> SEQUENCE: 98
gtctacttaa ttaacggggt cccgggcgtc gaagg                                  35

<210> SEQ ID NO 99
<211> LENGTH: 36
<212> TYPE: DNA
<213> ORGANISM: Artificial Sequence
<220> FEATURE:
<223> OTHER INFORMATION: Description of Artificial Sequence: Synthetic
UL36 forward primer

<400> SEQUENCE: 99
gtctacacta gtatgatcgc gggcacccca ccgcac                                 36

<210> SEQ ID NO 100
<211> LENGTH: 38
<212> TYPE: DNA
<213> ORGANISM: Artificial Sequence
<220> FEATURE:
<223> OTHER INFORMATION: Description of Artificial Sequence: Synthetic
UL36 reverse primer

<400> SEQUENCE: 100
gtctacttaa ttaagcccag taacatgcgc acgtgatg                               38

<210> SEQ ID NO 101
<211> LENGTH: 37
<212> TYPE: DNA
<213> ORGANISM: Artificial Sequence
<220> FEATURE:
<223> OTHER INFORMATION: Description of Artificial Sequence: Synthetic
UL37 forward primer

<400> SEQUENCE: 101
gtctacacta gtatggcaga ccgcggtctc ccgtccg                                37

<210> SEQ ID NO 102
<211> LENGTH: 38
<212> TYPE: DNA
<213> ORGANISM: Artificial Sequence
<220> FEATURE:
<223> OTHER INFORMATION: Description of Artificial Sequence: Synthetic
UL37 reverse primer

<400> SEQUENCE: 102
gtctacttaa ttaattggta actcgttaac ggcaagtc                               38

<210> SEQ ID NO 103
<211> LENGTH: 34

```
<212> TYPE: DNA
<213> ORGANISM: Artificial Sequence
<220> FEATURE:
<223> OTHER INFORMATION: Description of Artificial Sequence: Synthetic
      UL38 forward primer

<400> SEQUENCE: 103
gtctacacta gtatgaagac caatccgcta cccg                              34

<210> SEQ ID NO 104
<211> LENGTH: 35
<212> TYPE: DNA
<213> ORGANISM: Artificial Sequence
<220> FEATURE:
<223> OTHER INFORMATION: Description of Artificial Sequence: Synthetic
      UL38 reverse primer

<400> SEQUENCE: 104
gtctacttaa ttaacgcgca tgcccgccac tcgcc                             35

<210> SEQ ID NO 105
<211> LENGTH: 32
<212> TYPE: DNA
<213> ORGANISM: Artificial Sequence
<220> FEATURE:
<223> OTHER INFORMATION: Description of Artificial Sequence: Synthetic
      UL39 forward primer

<400> SEQUENCE: 105
gtctacacta gtatggccag ccgcccagcc gc                                32

<210> SEQ ID NO 106
<211> LENGTH: 35
<212> TYPE: DNA
<213> ORGANISM: Artificial Sequence
<220> FEATURE:
<223> OTHER INFORMATION: Description of Artificial Sequence: Synthetic
      UL39 reverse primer

<400> SEQUENCE: 106
gtctacttaa ttaacagcgc gcagctcgtg cagac                             35

<210> SEQ ID NO 107
<211> LENGTH: 31
<212> TYPE: DNA
<213> ORGANISM: Artificial Sequence
<220> FEATURE:
<223> OTHER INFORMATION: Description of Artificial Sequence: Synthetic
      UL40 forward primer

<400> SEQUENCE: 107
gtctacacta gtatggattc cgcggcccca g                                 31

<210> SEQ ID NO 108
<211> LENGTH: 32
<212> TYPE: DNA
<213> ORGANISM: Artificial Sequence
<220> FEATURE:
<223> OTHER INFORMATION: Description of Artificial Sequence: Synthetic
      UL40 reverse primer

<400> SEQUENCE: 108
gtctacttaa ttaacagatc gttgacgacc gc                                32

<210> SEQ ID NO 109
<211> LENGTH: 36
<212> TYPE: DNA
```

```
<213> ORGANISM: Artificial Sequence
<220> FEATURE:
<223> OTHER INFORMATION: Description of Artificial Sequence: Synthetic
      UL41 forward primer

<400> SEQUENCE: 109
gtctacacta gtatgggttt gttcgggatg atgaag                                36

<210> SEQ ID NO 110
<211> LENGTH: 35
<212> TYPE: DNA
<213> ORGANISM: Artificial Sequence
<220> FEATURE:
<223> OTHER INFORMATION: Description of Artificial Sequence: Synthetic
      UL41 reverse primer

<400> SEQUENCE: 110
gtctacttaa ttaactcgtc ccagaatttg gccag                                 35

<210> SEQ ID NO 111
<211> LENGTH: 34
<212> TYPE: DNA
<213> ORGANISM: Artificial Sequence
<220> FEATURE:
<223> OTHER INFORMATION: Description of Artificial Sequence: Synthetic
      UL42 forward primer

<400> SEQUENCE: 111
gtctacacta gtatgacgga ttcccctggc ggtg                                  34

<210> SEQ ID NO 112
<211> LENGTH: 33
<212> TYPE: DNA
<213> ORGANISM: Artificial Sequence
<220> FEATURE:
<223> OTHER INFORMATION: Description of Artificial Sequence: Synthetic
      UL42 reverse primer

<400> SEQUENCE: 112
gtctacttaa ttaaggggaa tccaaaacca gac                                   33

<210> SEQ ID NO 113
<211> LENGTH: 34
<212> TYPE: DNA
<213> ORGANISM: Artificial Sequence
<220> FEATURE:
<223> OTHER INFORMATION: Description of Artificial Sequence: Synthetic
      UL43 forward primer

<400> SEQUENCE: 113
gtctacacta gtatgctccg caacgacagc cacc                                  34

<210> SEQ ID NO 114
<211> LENGTH: 37
<212> TYPE: DNA
<213> ORGANISM: Artificial Sequence
<220> FEATURE:
<223> OTHER INFORMATION: Description of Artificial Sequence: Synthetic
      UL43 reverse primer

<400> SEQUENCE: 114
gtctacttaa ttaaatcgcc cgaccgcccg cccgttg                               37

<210> SEQ ID NO 115
<211> LENGTH: 32
<212> TYPE: DNA
<213> ORGANISM: Artificial Sequence
```

<220> FEATURE:
<223> OTHER INFORMATION: Description of Artificial Sequence: Synthetic
      UL44 forward primer

<400> SEQUENCE: 115
gtctacacta gtgctttgcc gggaacgcta gc                               32

<210> SEQ ID NO 116
<211> LENGTH: 36
<212> TYPE: DNA
<213> ORGANISM: Artificial Sequence
<220> FEATURE:
<223> OTHER INFORMATION: Description of Artificial Sequence: Synthetic
      UL44 reverse primer

<400> SEQUENCE: 116
gtctacttaa ttaaccgccg atgacgctgc cgcgac                           36

<210> SEQ ID NO 117
<211> LENGTH: 34
<212> TYPE: DNA
<213> ORGANISM: Artificial Sequence
<220> FEATURE:
<223> OTHER INFORMATION: Description of Artificial Sequence: Synthetic
      UL45 forward primer

<400> SEQUENCE: 117
gtctacacta gtatgcctct gcgggcatcg gaac                             34

<210> SEQ ID NO 118
<211> LENGTH: 34
<212> TYPE: DNA
<213> ORGANISM: Artificial Sequence
<220> FEATURE:
<223> OTHER INFORMATION: Description of Artificial Sequence: Synthetic
      UL45 reverse primer

<400> SEQUENCE: 118
gtctacttaa ttaacggcag ccccagcgcg ttgc                             34

<210> SEQ ID NO 119
<211> LENGTH: 34
<212> TYPE: DNA
<213> ORGANISM: Artificial Sequence
<220> FEATURE:
<223> OTHER INFORMATION: Description of Artificial Sequence: Synthetic
      UL46 forward primer

<400> SEQUENCE: 119
gtctacacta gtctggacgc ggcataactc cgac                             34

<210> SEQ ID NO 120
<211> LENGTH: 41
<212> TYPE: DNA
<213> ORGANISM: Artificial Sequence
<220> FEATURE:
<223> OTHER INFORMATION: Description of Artificial Sequence: Synthetic
      UL46 reverse primer

<400> SEQUENCE: 120
gtctacttaa ttaaccggct ccggcgtcct tcgcgtttaa g                     41

<210> SEQ ID NO 121
<211> LENGTH: 32
<212> TYPE: DNA
<213> ORGANISM: Artificial Sequence
<220> FEATURE:

```
<223> OTHER INFORMATION: Description of Artificial Sequence: Synthetic
      UL47 forward primer

<400> SEQUENCE: 121
gtctacacta gtatgtcggc tcgcgaaccc gc                                     32

<210> SEQ ID NO 122
<211> LENGTH: 35
<212> TYPE: DNA
<213> ORGANISM: Artificial Sequence
<220> FEATURE:
<223> OTHER INFORMATION: Description of Artificial Sequence: Synthetic
      UL47 reverse primer

<400> SEQUENCE: 122
gtctacttaa ttaatgggcg tggcgggcct cccag                                  35

<210> SEQ ID NO 123
<211> LENGTH: 36
<212> TYPE: DNA
<213> ORGANISM: Artificial Sequence
<220> FEATURE:
<223> OTHER INFORMATION: Description of Artificial Sequence: Synthetic
      UL48 forward primer

<400> SEQUENCE: 123
gtctacacta gtatggacct cttggtcgac gagctg                                 36

<210> SEQ ID NO 124
<211> LENGTH: 38
<212> TYPE: DNA
<213> ORGANISM: Artificial Sequence
<220> FEATURE:
<223> OTHER INFORMATION: Description of Artificial Sequence: Synthetic
      UL48 reverse primer

<400> SEQUENCE: 124
gtctacttaa ttaacccacc gtactcgtca attccaag                               38

<210> SEQ ID NO 125
<211> LENGTH: 36
<212> TYPE: DNA
<213> ORGANISM: Artificial Sequence
<220> FEATURE:
<223> OTHER INFORMATION: Description of Artificial Sequence: Synthetic
      UL49 forward primer

<400> SEQUENCE: 125
gtctacacta gtatgaccctc tcgccgctcc gtgaag                                36

<210> SEQ ID NO 126
<211> LENGTH: 31
<212> TYPE: DNA
<213> ORGANISM: Artificial Sequence
<220> FEATURE:
<223> OTHER INFORMATION: Description of Artificial Sequence: Synthetic
      UL49 reverse primer

<400> SEQUENCE: 126
gtctacttaa ttaactcgac gggccgtctg g                                      31

<210> SEQ ID NO 127
<211> LENGTH: 36
<212> TYPE: DNA
<213> ORGANISM: Artificial Sequence
<220> FEATURE:
<223> OTHER INFORMATION: Description of Artificial Sequence: Synthetic
```

UL49A forward primer

<400> SEQUENCE: 127
gtctacacta gtctcatctt cctgttaggg acgatg                                36

<210> SEQ ID NO 128
<211> LENGTH: 35
<212> TYPE: DNA
<213> ORGANISM: Artificial Sequence
<220> FEATURE:
<223> OTHER INFORMATION: Description of Artificial Sequence: Synthetic
      UL49A reverse primer

<400> SEQUENCE: 128
gtctacttaa ttaaggcgtg cccggcagcc agtag                                 35

<210> SEQ ID NO 129
<211> LENGTH: 36
<212> TYPE: DNA
<213> ORGANISM: Artificial Sequence
<220> FEATURE:
<223> OTHER INFORMATION: Description of Artificial Sequence: Synthetic
      UL50 forward primer

<400> SEQUENCE: 129
gtctacacta gtgtccctaa caggaagatg agtcag                                36

<210> SEQ ID NO 130
<211> LENGTH: 35
<212> TYPE: DNA
<213> ORGANISM: Artificial Sequence
<220> FEATURE:
<223> OTHER INFORMATION: Description of Artificial Sequence: Synthetic
      UL50 reverse primer

<400> SEQUENCE: 130
gtctacttaa ttaaaatacc ggtagagcca aaacc                                 35

<210> SEQ ID NO 131
<211> LENGTH: 32
<212> TYPE: DNA
<213> ORGANISM: Artificial Sequence
<220> FEATURE:
<223> OTHER INFORMATION: Description of Artificial Sequence: Synthetic
      UL51 forward primer

<400> SEQUENCE: 131
gtctacacta gtatggcttc tcttctcggg gc                                    32

<210> SEQ ID NO 132
<211> LENGTH: 38
<212> TYPE: DNA
<213> ORGANISM: Artificial Sequence
<220> FEATURE:
<223> OTHER INFORMATION: Description of Artificial Sequence: Synthetic
      UL51 reverse primer

<400> SEQUENCE: 132
gtctacttaa ttaattgacc caaaacacac ggagctgc                              38

<210> SEQ ID NO 133
<211> LENGTH: 33
<212> TYPE: DNA
<213> ORGANISM: Artificial Sequence
<220> FEATURE:
<223> OTHER INFORMATION: Description of Artificial Sequence: Synthetic
      UL52 forward primer

```
<400> SEQUENCE: 133
gtctacacta gtatggggca ggaagacggg aac                              33

<210> SEQ ID NO 134
<211> LENGTH: 37
<212> TYPE: DNA
<213> ORGANISM: Artificial Sequence
<220> FEATURE:
<223> OTHER INFORMATION: Description of Artificial Sequence: Synthetic
      UL52 reverse primer

<400> SEQUENCE: 134
gtctacttaa ttaaagacga cggttgagag gtgctgc                          37

<210> SEQ ID NO 135
<211> LENGTH: 36
<212> TYPE: DNA
<213> ORGANISM: Artificial Sequence
<220> FEATURE:
<223> OTHER INFORMATION: Description of Artificial Sequence: Synthetic
      UL53 forward primer

<400> SEQUENCE: 135
gtctacacta gtatgctcgc cgtccgttcc ctgcag                           36

<210> SEQ ID NO 136
<211> LENGTH: 39
<212> TYPE: DNA
<213> ORGANISM: Artificial Sequence
<220> FEATURE:
<223> OTHER INFORMATION: Description of Artificial Sequence: Synthetic
      UL53 reverse primer

<400> SEQUENCE: 136
gtctacttaa ttaatacatc aaacaggcgc ctctggatc                        39

<210> SEQ ID NO 137
<211> LENGTH: 40
<212> TYPE: DNA
<213> ORGANISM: Artificial Sequence
<220> FEATURE:
<223> OTHER INFORMATION: Description of Artificial Sequence: Synthetic
      UL54 forward primer

<400> SEQUENCE: 137
gtctacacta gtatggcgac tgacattgat atgctaattg                       40

<210> SEQ ID NO 138
<211> LENGTH: 43
<212> TYPE: DNA
<213> ORGANISM: Artificial Sequence
<220> FEATURE:
<223> OTHER INFORMATION: Description of Artificial Sequence: Synthetic
      UL54 reverse primer

<400> SEQUENCE: 138
gtctacttaa ttaaaaacag ggagttgcaa taaaaatatt tgc                   43

<210> SEQ ID NO 139
<211> LENGTH: 34
<212> TYPE: DNA
<213> ORGANISM: Artificial Sequence
<220> FEATURE:
<223> OTHER INFORMATION: Description of Artificial Sequence: Synthetic
      UL55 forward primer
```

```
<400> SEQUENCE: 139
gtctacacta gtcttttgca ctatgacagc gacc                                    34

<210> SEQ ID NO 140
<211> LENGTH: 35
<212> TYPE: DNA
<213> ORGANISM: Artificial Sequence
<220> FEATURE:
<223> OTHER INFORMATION: Description of Artificial Sequence: Synthetic
      UL55 reverse primer

<400> SEQUENCE: 140
gtctacttaa ttaacgcctt aattttaatc ttgac                                   35

<210> SEQ ID NO 141
<211> LENGTH: 36
<212> TYPE: DNA
<213> ORGANISM: Artificial Sequence
<220> FEATURE:
<223> OTHER INFORMATION: Description of Artificial Sequence: Synthetic
      UL56 forward primer

<400> SEQUENCE: 141
gtctacacta gtcatccatg gcttcggagg cggcgc                                  36

<210> SEQ ID NO 142
<211> LENGTH: 39
<212> TYPE: DNA
<213> ORGANISM: Artificial Sequence
<220> FEATURE:
<223> OTHER INFORMATION: Description of Artificial Sequence: Synthetic
      UL56 reverse primer

<400> SEQUENCE: 142
gtctacttaa ttaaccgcca caggaatacc agaataatg                               39

<210> SEQ ID NO 143
<211> LENGTH: 35
<212> TYPE: DNA
<213> ORGANISM: Artificial Sequence
<220> FEATURE:
<223> OTHER INFORMATION: Description of Artificial Sequence: Synthetic
      RS1 forward primer

<400> SEQUENCE: 143
gtctacacta gtatggcgtc ggagaacaag cagcg                                   35

<210> SEQ ID NO 144
<211> LENGTH: 39
<212> TYPE: DNA
<213> ORGANISM: Artificial Sequence
<220> FEATURE:
<223> OTHER INFORMATION: Description of Artificial Sequence: Synthetic
      RS1 reverse primer

<400> SEQUENCE: 144
gtctacttaa ttaacagcac cccgtccccc tcgaacgcg                               39

<210> SEQ ID NO 145
<211> LENGTH: 32
<212> TYPE: DNA
<213> ORGANISM: Artificial Sequence
<220> FEATURE:
<223> OTHER INFORMATION: Description of Artificial Sequence: Synthetic
      US1 forward primer

<400> SEQUENCE: 145
```
gtctacacta gtatggccga catttcccca gg        32

<210> SEQ ID NO 146
<211> LENGTH: 36
<212> TYPE: DNA
<213> ORGANISM: Artificial Sequence
<220> FEATURE:
<223> OTHER INFORMATION: Description of Artificial Sequence: Synthetic
      US1 reverse primer

<400> SEQUENCE: 146
gtctacttaa ttaacggccg gagaaacgtg tcgctg        36

<210> SEQ ID NO 147
<211> LENGTH: 34
<212> TYPE: DNA
<213> ORGANISM: Artificial Sequence
<220> FEATURE:
<223> OTHER INFORMATION: Description of Artificial Sequence: Synthetic
      US2 forward primer

<400> SEQUENCE: 147
gtctacacta gtatgggcgt tgttgtcgtc aacg        34

<210> SEQ ID NO 148
<211> LENGTH: 39
<212> TYPE: DNA
<213> ORGANISM: Artificial Sequence
<220> FEATURE:
<223> OTHER INFORMATION: Description of Artificial Sequence: Synthetic
      US2 reverse primer

<400> SEQUENCE: 148
gtctacttaa ttaacagggt ggtaaccgga tagcagatg        39

<210> SEQ ID NO 149
<211> LENGTH: 35
<212> TYPE: DNA
<213> ORGANISM: Artificial Sequence
<220> FEATURE:
<223> OTHER INFORMATION: Description of Artificial Sequence: Synthetic
      US3 forward primer

<400> SEQUENCE: 149
gtctacacta gtatggcctg tcgtaagttt tgtcg        35

<210> SEQ ID NO 150
<211> LENGTH: 37
<212> TYPE: DNA
<213> ORGANISM: Artificial Sequence
<220> FEATURE:
<223> OTHER INFORMATION: Description of Artificial Sequence: Synthetic
      US3 reverse primer

<400> SEQUENCE: 150
gtctacttaa ttaatttctg ttgaaacagc ggcaaac        37

<210> SEQ ID NO 151
<211> LENGTH: 34
<212> TYPE: DNA
<213> ORGANISM: Artificial Sequence
<220> FEATURE:
<223> OTHER INFORMATION: Description of Artificial Sequence: Synthetic
      US4 forward primer

<400> SEQUENCE: 151

```
gtctacacta gtcatcatgt cgccgggcgc catg                                  34
```

<210> SEQ ID NO 152
<211> LENGTH: 36
<212> TYPE: DNA
<213> ORGANISM: Artificial Sequence
<220> FEATURE:
<223> OTHER INFORMATION: Description of Artificial Sequence: Synthetic
      US4 reverse primer

<400> SEQUENCE: 152

```
gtctacttaa ttaacccgcg ttcggacggc aggcac                                36
```

<210> SEQ ID NO 153
<211> LENGTH: 32
<212> TYPE: DNA
<213> ORGANISM: Artificial Sequence
<220> FEATURE:
<223> OTHER INFORMATION: Description of Artificial Sequence: Synthetic
      US5 forward primer

<400> SEQUENCE: 153

```
gtctacacta gtatgtctct gcgcgcagtc tg                                    32
```

<210> SEQ ID NO 154
<211> LENGTH: 37
<212> TYPE: DNA
<213> ORGANISM: Artificial Sequence
<220> FEATURE:
<223> OTHER INFORMATION: Description of Artificial Sequence: Synthetic
      US5 reverse primer

<400> SEQUENCE: 154

```
gtctacttaa ttaatacgac aactgggtcc atgtagg                               37
```

<210> SEQ ID NO 155
<211> LENGTH: 32
<212> TYPE: DNA
<213> ORGANISM: Artificial Sequence
<220> FEATURE:
<223> OTHER INFORMATION: Description of Artificial Sequence: Synthetic
      US6 forward primer

<400> SEQUENCE: 155

```
gtctacacta gtgtgtggtg cgttccggta tg                                    32
```

<210> SEQ ID NO 156
<211> LENGTH: 36
<212> TYPE: DNA
<213> ORGANISM: Artificial Sequence
<220> FEATURE:
<223> OTHER INFORMATION: Description of Artificial Sequence: Synthetic
      US6 reverse primer

<400> SEQUENCE: 156

```
gtctacttaa ttaagtaaaa caagggctgg tgcgag                                36
```

<210> SEQ ID NO 157
<211> LENGTH: 33
<212> TYPE: DNA
<213> ORGANISM: Artificial Sequence
<220> FEATURE:
<223> OTHER INFORMATION: Description of Artificial Sequence: Synthetic
      US7 forward primer

<400> SEQUENCE: 157

```
gtctacacta gtgtcccgtt ccgggatgcc gtg                                   33
```

<210> SEQ ID NO 158
<211> LENGTH: 34
<212> TYPE: DNA
<213> ORGANISM: Artificial Sequence
<220> FEATURE:
<223> OTHER INFORMATION: Description of Artificial Sequence: Synthetic
      US7 reverse primer

<400> SEQUENCE: 158
gtctacttaa ttaataccaa caggggaggc gttg                                34

<210> SEQ ID NO 159
<211> LENGTH: 33
<212> TYPE: DNA
<213> ORGANISM: Artificial Sequence
<220> FEATURE:
<223> OTHER INFORMATION: Description of Artificial Sequence: Synthetic
      US8 forward primer

<400> SEQUENCE: 159
gtctacacta gtgacatgga tcgcggggcg gtg                                 33

<210> SEQ ID NO 160
<211> LENGTH: 34
<212> TYPE: DNA
<213> ORGANISM: Artificial Sequence
<220> FEATURE:
<223> OTHER INFORMATION: Description of Artificial Sequence: Synthetic
      US8 reverse primer

<400> SEQUENCE: 160
gtctacttaa ttaaccagaa gacggacgaa tcgg                                34

<210> SEQ ID NO 161
<211> LENGTH: 32
<212> TYPE: DNA
<213> ORGANISM: Artificial Sequence
<220> FEATURE:
<223> OTHER INFORMATION: Description of Artificial Sequence: Synthetic
      US8A forward primer

<400> SEQUENCE: 161
gtctacacta gtatggatcc ggctttgaga tc                                  32

<210> SEQ ID NO 162
<211> LENGTH: 36
<212> TYPE: DNA
<213> ORGANISM: Artificial Sequence
<220> FEATURE:
<223> OTHER INFORMATION: Description of Artificial Sequence: Synthetic
      US8A reverse primer

<400> SEQUENCE: 162
gtctacttaa ttaatgcgcc tcgggcaatt gacgtc                              36

<210> SEQ ID NO 163
<211> LENGTH: 31
<212> TYPE: DNA
<213> ORGANISM: Artificial Sequence
<220> FEATURE:
<223> OTHER INFORMATION: Description of Artificial Sequence: Synthetic
      US9 forward primer

<400> SEQUENCE: 163
gtctacacta gtatgacgtc ccggctctcc g                                   31

```
<210> SEQ ID NO 164
<211> LENGTH: 35
<212> TYPE: DNA
<213> ORGANISM: Artificial Sequence
<220> FEATURE:
<223> OTHER INFORMATION: Description of Artificial Sequence: Synthetic
      US9 reverse primer

<400> SEQUENCE: 164
gtctacttaa ttaagcggag cagccacatc aggag                              35

<210> SEQ ID NO 165
<211> LENGTH: 33
<212> TYPE: DNA
<213> ORGANISM: Artificial Sequence
<220> FEATURE:
<223> OTHER INFORMATION: Description of Artificial Sequence: Synthetic
      US10 forward primer

<400> SEQUENCE: 165
gtctacacta gtgtgataat gatcaagcgg cgg                                33

<210> SEQ ID NO 166
<211> LENGTH: 33
<212> TYPE: DNA
<213> ORGANISM: Artificial Sequence
<220> FEATURE:
<223> OTHER INFORMATION: Description of Artificial Sequence: Synthetic
      US10 reverse primer

<400> SEQUENCE: 166
gtctacttaa ttaagcacag gggtggggtt agg                                33

<210> SEQ ID NO 167
<211> LENGTH: 33
<212> TYPE: DNA
<213> ORGANISM: Artificial Sequence
<220> FEATURE:
<223> OTHER INFORMATION: Description of Artificial Sequence: Synthetic
      US11 forward primer

<400> SEQUENCE: 167
gtctacacta gtgtggctct cgagatgagc cag                                33

<210> SEQ ID NO 168
<211> LENGTH: 37
<212> TYPE: DNA
<213> ORGANISM: Artificial Sequence
<220> FEATURE:
<223> OTHER INFORMATION: Description of Artificial Sequence: Synthetic
      US11 reverse primer

<400> SEQUENCE: 168
gtctacttaa ttaatacaga cccgcgagcc gtacgtg                            37

<210> SEQ ID NO 169
<211> LENGTH: 35
<212> TYPE: DNA
<213> ORGANISM: Artificial Sequence
<220> FEATURE:
<223> OTHER INFORMATION: Description of Artificial Sequence: Synthetic
      US12 forward primer

<400> SEQUENCE: 169
gtctacacta gtatgtcgtg ggccctggaa atggc                              35
```

-continued

```
<210> SEQ ID NO 170
<211> LENGTH: 37
<212> TYPE: DNA
<213> ORGANISM: Artificial Sequence
<220> FEATURE:
<223> OTHER INFORMATION: Description of Artificial Sequence: Synthetic
      US12 reverse primer

<400> SEQUENCE: 170
gtctacttaa ttaaacgggt taccggatta cggggac                              37

<210> SEQ ID NO 171
<211> LENGTH: 550
<212> TYPE: PRT
<213> ORGANISM: Human herpesvirus 1

<400> SEQUENCE: 171
```

Met Asp Arg Gly Ala Val Val Gly Phe Leu Leu Gly Val Cys Val Val
1               5                   10                  15

Ser Cys Leu Ala Gly Thr Pro Lys Thr Ser Trp Arg Arg Val Ser Val
                20                  25                  30

Gly Glu Asp Val Ser Leu Leu Pro Ala Pro Gly Pro Thr Gly Arg Gly
            35                  40                  45

Pro Thr Gln Lys Leu Leu Trp Ala Val Glu Pro Leu Asp Gly Cys Gly
        50                  55                  60

Pro Leu His Pro Ser Trp Val Ser Leu Met Pro Pro Lys Gln Val Pro
65                  70                  75                  80

Glu Thr Val Val Asp Ala Ala Cys Met Arg Ala Pro Val Pro Leu Ala
                85                  90                  95

Met Ala Tyr Ala Pro Pro Ala Pro Ser Ala Thr Gly Gly Leu Arg Thr
                100                 105                 110

Asp Phe Val Trp Gln Glu Arg Ala Ala Val Val Asn Arg Ser Leu Val
            115                 120                 125

Ile His Gly Val Arg Glu Thr Asp Ser Gly Leu Tyr Thr Leu Ser Val
        130                 135                 140

Gly Asp Ile Lys Asp Pro Ala Arg Gln Val Ala Ser Val Val Leu Val
145                 150                 155                 160

Val Gln Pro Ala Pro Val Pro Thr Pro Pro Thr Pro Ala Asp Tyr
                165                 170                 175

Asp Glu Asp Asp Asn Asp Glu Gly Glu Asp Glu Ser Leu Ala Gly Thr
                180                 185                 190

Pro Ala Ser Gly Thr Pro Arg Leu Pro Pro Pro Ala Pro Pro Arg
            195                 200                 205

Ser Trp Pro Ser Ala Pro Glu Val Ser His Val Arg Gly Val Thr Val
        210                 215                 220

Arg Met Glu Thr Pro Glu Ala Ile Leu Phe Ser Pro Gly Glu Thr Phe
225                 230                 235                 240

Ser Thr Asn Val Ser Ile His Ala Ile Ala His Asp Asp Gln Thr Tyr
                245                 250                 255

Ser Met Asp Val Val Trp Leu Arg Phe Asp Val Pro Thr Ser Cys Ala
                260                 265                 270

Glu Met Arg Ile Tyr Glu Ser Cys Leu Tyr His Pro Gln Leu Pro Glu
            275                 280                 285

Cys Leu Ser Pro Ala Asp Ala Pro Cys Ala Ala Ser Thr Trp Thr Ser
        290                 295                 300

Arg Leu Ala Val Arg Ser Tyr Ala Gly Cys Ser Arg Thr Asn Pro Pro
305                 310                 315                 320

-continued

```
Pro Arg Cys Ser Ala Glu Ala His Met Glu Pro Val Pro Gly Leu Ala
                325                 330                 335

Trp Gln Ala Ala Ser Val Asn Leu Glu Phe Arg Asp Ala Ser Pro Gln
            340                 345                 350

His Ser Gly Leu Tyr Leu Cys Val Val Tyr Val Asn Asp His Ile His
        355                 360                 365

Ala Trp Gly His Ile Thr Ile Ser Thr Ala Ala Gln Tyr Arg Asn Ala
    370                 375                 380

Val Val Glu Gln Pro Leu Pro Gln Arg Gly Ala Asp Leu Ala Glu Pro
385                 390                 395                 400

Thr His Pro His Val Gly Ala Pro Pro His Ala Pro Pro Thr His Gly
                405                 410                 415

Ala Leu Arg Leu Gly Ala Val Met Gly Ala Ala Leu Leu Leu Ser Ala
            420                 425                 430

Leu Gly Leu Ser Val Trp Ala Cys Met Thr Cys Trp Arg Arg Arg Ala
            435                 440                 445

Trp Arg Ala Val Lys Ser Arg Ala Ser Gly Lys Gly Pro Thr Tyr Ile
        450                 455                 460

Arg Val Ala Asp Ser Glu Leu Tyr Ala Asp Trp Ser Ser Asp Ser Glu
465                 470                 475                 480

Gly Glu Arg Asp Gln Val Pro Trp Leu Ala Pro Pro Glu Arg Pro Asp
                485                 490                 495

Ser Pro Ser Thr Asn Gly Ser Gly Phe Glu Ile Leu Ser Pro Thr Ala
                500                 505                 510

Pro Ser Val Tyr Pro Arg Ser Asp Gly His Gln Ser Arg Arg Gln Leu
            515                 520                 525

Thr Thr Phe Gly Ser Gly Arg Pro Asp Arg Arg Tyr Ser Gln Ala Ser
    530                 535                 540

Asp Ser Ser Val Phe Trp
545             550
```

PASSIVE ANTIBODY DEPENDENT CELL-MEDIATED ACTIVATION

CROSS-REFERENCE TO RELATED APPLICATIONS

This application is a national stage entry under 35 U.S.C. § 371 of International Application No. PCT/US2018/016035, filed Jan. 30, 2018, which in turn claims priority under 35 U.S.C. § 119(e) to U.S. Provisional Application No. 62/452,111, filed Jan. 30, 2017, the content of which is hereby incorporated by reference in its entirety.

STATEMENT REGARDING FEDERALLY SPONSORED RESEARCH OR DEVELOPMENT

This invention was made with Government Support under Grant No. 5P01CA163205 awarded by the National Institutes of Health. The Government has certain rights in the invention.

BACKGROUND

Natural killer (NK) cells are innate lymphoid cells that lack the ability to rearrange germline immunoglobulin genes to generate an adaptive immune response, and can recognize virally infected cells or cancer cells without prior antigen exposure (Orr et al., 2010, *Cell* 142, 847-856). The functional status of NK cells is regulated by signal inputs from a wide variety of NK cell activating/inhibitory receptors and cytokines. NK cells are also the major effector cells for antibody-dependent cell-mediated cytotoxicity (ADCC), and express the low affinity FcγRIIIA/CD16a protein (CD16a hereafter) that binds an IgG molecule at that molecule's hinge region and initiates NK cell activation via the resulting antigen-antibody complex (Sondermann et al., 2000, *Nature* 406, 267-273). CD16a is coupled in NK cells with the signal transducer protein CD3ζ (Anderson et al., 1990, *Proc Natl Acad Sci USA* 87, 2274-2278; Lanier et al., 1989, *Nature* 342, 803-805). NK cell activation through CD16a minimally requires two CD16a binding sites physically close enough to cluster CD3ζ, whose phosphorylation in turn results in the activation of NK cells and lysis of antibody-coated target cells (O'Shea et al., 1991, *Proc Natl Acad Sci USA* 88, 350-354).

There is substantial evidence in mice and in humans that NK cells can act as a first line of defense against a broad array of infectious pathogens and against malignant transformation. "First line of defense" connotes protection arising days to weeks before the adaptive, antigen-specific immune system of T-cells and B-cells can detect a pathogen and attack it, and quickly recall its response when the pathogen or tumor itself is present in the body again at a later time. The mechanisms behind this early recognition of pathogens and tumor cells by NK cells and other innate immune cells are largely but not completely unknown (Dai, et al., 2017, *Immunity* 47(1), 159-170). Understanding how NK cells and other innate immune cells can see such dangers will improve understanding of how to treat such diseases early, thus saving more lives.

As one example, NK cells constitute the first line of defense against herpesviruses infection and patients with NK cell deficiencies often suffer severe, recurrent and sometimes fatal HSV infection (Orange, 2012, *Journal of Clinical Investigation* 122, 798-801). The herpesviridae family includes many significant human pathogens that are yet to have approved vaccines (Gilden et al., 2007, *Nat Clin Pract Neurol* 3, 82-94), and oncolytic HSV1 has recently been clinically approved for treating melanoma (albeit with moderate therapeutic effects; Andtbacka et al., 2015, *J Clin Oncol*. Talimogene Laherparepvec Improves Durable Response Rate in Patients With Advanced Melanoma"). Thus, there remains a need in the art to develop reagents, methods, and pharmaceutical compositions for providing effective antiviral treatments and maximizing efficacy of oncolytic HSV1 therapy.

SUMMARY

The disclosure provides reagents, methods, and pharmaceutical compositions for promoting immunological activation of immune effector cells. In particular embodiments, provided herein are immunological polypeptides comprising a domain that binds an Fc gamma receptor (FcγR) on immune effector cells and a non-overlapping domain that binds Fc binding proteins on target cells. The polypeptides described herein are capable of forming a bridge between an immune effector cell and a target cell without use of the antigen-binding region (the so-called IgG Fab region) of the antibody. This type of immune effector cell activation is referred to herein as passive antibody dependent cell-mediated cytotoxicity (ADCC). Passive ADCC can have both beneficial and deleterious effects in subjects infected with pathogens that encode Fc binding proteins, subjects who express genes that encode Fc binding proteins other than FcγR, and in subjects undergoing treatment with antibody. Therefore, also disclosed are methods of enhancing or inhibiting passive ADCC in subjects.

In particular embodiments, a pharmaceutical composition for treating a subject infected with a pathogen encoding an Fc-binding protein is provided. In particular embodiments, the composition comprises an immunological polypeptide comprising a domain that binds an Fc gamma receptor (FcγR) on an immune effector cell and a non-overlapping domain that binds the pathogen-encoded Fc binding protein. In certain embodiments the immunological polypeptide is an antibody, more specifically an IgG antibody and in particular an Fc fragment of an IgG antibody. Also within the scope of such immunological polypeptides is IgG-containing antisera. A feature of the immunological polypeptides useful in the methods and comprising the pharmaceutical compositions disclosed herein is that the efficacy and utility of said IgG antibodies is independent of their antigenic specificity.

In particular embodiments, the invention also provides reagents, methods and pharmaceutical compositions for preventing neurologic damage in a subject with HSV1 infection. In particular embodiments, the invention further provides reagents, methods and pharmaceutical compositions for preventing death in a subject with HSV1 infection. In particular embodiments, a pharmaceutical composition comprising an immunological polypeptide comprising a domain that binds an FcγR on an immune effector cell and a non-overlapping domain that binds a HSV1-encoded Fc binding protein is provided. In certain embodiments the immunological polypeptide is an antibody, more specifically an IgG antibody and in particular an Fc fragment of an IgG antibody. Also within the scope of such immunological polypeptides is IgG-containing antisera. A feature of the immunological polypeptides useful in the methods and comprising the pharmaceutical compositions disclosed herein is that the efficacy and utility of said IgG antibodies is independent of their antigenic specificity.

In some embodiments, provided herein are polypeptides comprising an Fc region of an immunoglobulin G (IgG)

antibody but do not comprise an Fab region of an antibody. For example, the polypeptide can be a fragment of an IgG1, IgG2, IgG3, or IgG4 immunoglobulin. In some embodiments, the polypeptide comprises a single Fc region of an IgG immunoglobulin. In some embodiments, the polypeptide comprises two or more Fc regions of one or a plurality of IgG immunoglobulins. In some embodiments, the polypeptide comprises an Fc gamma receptor binding site that has been modified to enhance binding to an Fc gamma receptor, and in some embodiments, the polypeptide comprises an Fc gamma receptor binding site that has been modified to delete binding to an Fc gamma receptor or delete binding to an Fc binding protein other than an Fc gamma receptor.

In some embodiments, the immune effector cell is an immune cell that expresses an Fc gamma receptor. Fc gamma receptors include CD16a, CD16b, CD32, and CD64. Therefore in some embodiments, the immune effector cell is a T cell, a B cell, a natural killer (NK) cell, a monocyte, a macrophage, a granulocyte, a neutrophil, or a dendritic cell.

The disclosed reagents, methods and pharmaceutical compositions can be used in some embodiments to treat a subject infected with a pathogen expressing an Fc binding protein, wherein the methods comprise administering to the subject a therapeutically effective amount of the pharmaceutical compositions disclosed herein. In some cases, the pathogen is a virus. In a non-limiting example, the pathogen is herpes simplex virus 1 (HSV1) or HSV2 that expresses the Fc binding protein glycoprotein E (gE). In other embodiments, the pathogen is human cytomegalovirus (CMV) that expresses the Fc binding protein comprises a 68 kDa-glycoprotein (gp68). In other embodiments, the pathogen is Varicella zoster virus (VZV).

In some cases, the pathogen is a bacterium, such as *Staphylococcus aureus, Streptococcus*, or *Escherichia coli*. In such embodiments, the Fc binding protein expressed by the pathogen comprises protein A, protein G, protein H, or M1 protein.

In particular embodiments, the methods provided herein are applied to a subject undergoing oncolytic viral therapy. While it may be advantageous to inhibit passive ADCC early after oncolytic viral infection of a tumor to allow the virus to spread to other tumor cells, the disclosed methods can also be used to enhance passive ADCC after the tumor cells are infected to enhance killing and clearing of tumor cells.

Also disclosed are reagents, methods and pharmaceutical compositions for reducing or inhibiting passive ADCC. In such embodiments, the polypeptide is a fragment of an IgG immunoglobulin modified to bind Fc binding proteins but not bind an FcγR, which will cause them to bind the Fc binding proteins of target cells and prevent them from crosslinking FcγR and activating passive ADCC. For example, the polypeptide can be an IgG fragment that lacks or has been engineered to lack a CD16a, CD32, or CD64 binding site. The Fc binding site for HSV1 gE, protein A and protein G and M1 protein of *Streptococcus* is known to be the CH2-CH3 interface of an IgG molecule. Therefore, in some embodiments, the polypeptide is a fragment of an IgG immunoglobulin comprising the CH2-CH3 interface of IgG but not comprising the FcγR binding region.

In other embodiments, the polypeptide can be a fragment of an IgG1, IgG2, IgG3 or IgG4 immunoglobulin. In some embodiments, the polypeptide is a fragment from more than one subclass of antibody. Regions of FcγRIIIa/CD16a involved in binding Fc are B/C loop (Trp 131 to Ala 135), F/G loop (Val 176 to Lys 179), C strand (His 137 to Thr 140) and C' strand (Asp 147 to His 153) of SEQ ID NO: 24). Additionally, Arg 173 and the connector (Ile 106 to Trp 108) region are also involved in binding. On the other hand, Cγ2 hinge (Leu 235 to Ser 239) and residue Asp 265 to Glu 269 of Fc are known to be the main contact residues for CD16a (Sondermann et al., 2000, *Nature* 406, 267-273)). Thus, modification on the interacting interface can change binding between CD16a and IgG. For example, replacement of FcγRIII FG-loop with that of FcγRI (MGKHRY; SEQ ID NO: 11) resulted in a 15-fold increase in IgG1 binding affinity (Lu et al., 2011, *JBC* 286, 40608-40613). Another example is an Fc fragment comprising human IgG1 Fc amino acids 262-470 of SEQ ID NO: 10, which bind HSV1 gE, protein A and protein G, but completely failed to bind human Fcγ receptors (CD16a, CD32, CD64).

In some embodiments, the methods disclosed herein involve administering an Fc binding protein, such as protein A or protein G, which will bind antibodies and prevent bridging immune effector cells and target cells by passive ADCC.

In some embodiments, the polypeptide is a fragment of an IgG immunoglobulin modified to bind FcγR but not bind an Fc binding protein, which will bind immune effector cells and prevent them from interacting with bridging antibodies. For example, the polypeptide can be a fragment of an IgG immunoglobulin that binds FcγR but has a mutation in the CH2-CH3 interface causing it to not bind HSV1 gE, protein A and protein G. For example, human IgG 4 binds gE while IgG4 mutant H435R is unable to bind gE.

In particular embodiments, the invention provides reagents, methods and pharmaceutical compositions for reducing inflammation in a subject receiving anti-cancer therapy. These embodiments can comprise administering a therapeutically effective amount of a polypeptide comprising a region that binds to an Fc binding protein but does not comprise a region that binds to an FcγR and administering an anti-cancer therapy comprising a monoclonal antibody drug. In particular embodiments the antibody drug is rituximab, tocilizumab, tositumomab, trastuzumab bevacizumab, brentuximab vedotin, cetuximab, daratumumab, ipilimumab, ofatumumab, panitumumab, alemtuzumab or pembrolizumab. In other embodiments, the pharmaceutical composition is administered prior to treatment with the monoclonal antibody drug.

In some embodiments, the subject is being treated with a therapeutic antibody. Most therapeutic monoclonal antibody drugs are produced from mammalian host cell lines to target specific antigens. Side effects and reduce therapeutic efficacy can be caused by sequestration of the antibody by various Fc binding proteins endogenously present in a patient, and interacting via passive ADCC with FcγR-bearing immune cells. The disclosed methods can decrease such side effects of antibody mediated infusion toxicity (the so-called first dose effect), yet enhance antibody-based immunotherapy.

The disclosed methods can also be used to prevent cytokine release from FcγR-bearing immune cells, hypotension and multiple organ failure in patients with infection from organisms that have Fc binding proteins.

In some embodiments of this use of the reagents, methods and pharmaceutical compositions disclosed herein, the subject has, or is at risk of having viremia with a virus that encodes an Fc binding protein. These disclosed methods can be used to treat or prevent viremia by enhancing viral clearance by FcγR-bearing immune cells using IgG Fc fragments or antibodies with higher-than-normal affinity for Fc binding proteins and/or FcγR, and utilizing passive ADCC for clearance.

In some embodiments provided herein, are reagents, methods and pharmaceutical compositions for treating cancer in a subject undergoing oncolytic viral therapy. The methods can be used to inhibit passive ADCC early after oncolytic viral infection of a tumor so the oncolytic virus can spread to other tumor cells. In particular embodiments, the immunological polypeptide can be administered prior to treatment with an oncolytic viral therapeutic agent, an in others the immunological polypeptide can be co-administered with an oncolytic viral therapeutic agent. In particular embodiments, a pharmaceutical composition comprising a polypeptide comprising a region that binds to an Fc binding protein on a target cell but does not comprise a region that binds to an FcγR is provided for inhibiting passive ADCC in a patient undergoing oncolytic viral therapy. A feature of the immunological polypeptides useful in the methods and comprising the pharmaceutical compositions disclosed herein is that the efficacy and utility of said IgG antibodies is independent of their antigenic specificity.

Subsequent to viral infection of a tumor cell, reagents, methods, and pharmaceutical compositions provided herein for enhancement of passive ADCC can be used to improve destruction of virally infected tumor cells by FcγR-bearing immune cells. For example, a pharmaceutical composition comprising an immunological polypeptide comprising a domain that binds an FcγR on an immune effector cell and a non-overlapping domain that binds an Fc binding protein on a target cell can be used to enhance passive ADCC to improve destruction of virally-infected tumor cells. In certain embodiments the immunological polypeptide is an antibody, more specifically an IgG antibody and in particular an Fc fragment of an IgG antibody. Also within the scope of such immunological polypeptides is IgG-containing antisera. A feature of the immunological polypeptides useful in the methods and comprising the pharmaceutical compositions disclosed herein is that the efficacy and utility of said IgG antibodies is independent of their antigenic specificity.

Also disclosed herein is a method for identifying viral genes that modulate the interaction of a virally-infected cell and an immune effector cell. The disclosed method can involve transfecting a host cell with an expression vector comprising a candidate viral gene and a reporter gene operably linked to an expression control sequence, exposing the transfected host cells and non-transfected host cells to a cytotoxic immune effector cell, and assaying the exposed transfected host cells and non-transfected host cells to measure cell death as a function of reporter gene expression or activity. In these methods, a decrease in cell death by the transfected host cells compared to non-transfected host cells is an indication that the viral gene protected the host cell from the immune effector cell, and an increase in cell death by the transfected host cells compared to non-transfected host cells is an indication that the viral gene made the host cell susceptible to the immune effector cell. These methods can be used with any immune effector cell(s) that is/are cytotoxic. For example, the cytotoxic immune effector cell can be a CD4+ T-cell, a CD8+ T-cell, a natural killer (NK) cell, a macrophage, a granulocyte, or a dendritic cell.

In particular embodiments, the reporter gene is a fluorescence gene, wherein the exposed transfected host cells and non-transfected host cells are assayed, inter alia, by flow cytometry to measure cell death as a function of fluorescence, wherein an increase in the percentage of fluorescent transfected host cells compared to non-transfected host cells is an indication that the viral gene protected the host cell from the immune effector cell, and wherein a decrease in mean fluorescence by the transfected host cells compared to non-transfected host cells is an indication that the viral gene made the host cell susceptible to the immune effector cell.

The process can be repeated for each gene in a viral genome. For example, the method can further comprising repeating the process for combinations of 2, 3, 4, 5, 6, 7, 8, 9, 10, 20, 30, 40, 50, or more genes in a viral genome.

The host cell is preferably selected based on its known susceptibility or resistance to killing by an immune effector cell when virally infected.

Also disclosed herein is a recombinant oncolytic Herpes Simplex Virus (oHSV), comprising one or more activating mutations in an Us8 gene (SEQ ID NO: 18), one or more activating mutations in an UL12 gene (SEQ ID NO: 12), one or more activating mutations in an UL30 gene (SEQ ID NO: 13), one or more activating mutations in an Us3 gene (SEQ ID NO: 15), one or more activating mutations in an Us5 gene (SEQ ID NO: 14), one or more activating mutations in an Us12 gene (SEQ ID NO: 16), or any combination thereof.

Also disclosed is a recombinant HSV1 vector, comprising a CMV immediate-early enhancer upstream of the promoter for HSV1 Us7 and HSV1 Us8.

Also disclosed herein is a method for using particular IgG-binding proteins, specifically protein A and protein G, to capture monocytes and increase the efficacy of generating dendritic cells and macrophages in vitro. The disclosed methods can comprise coating culture plates with recombinant protein A or protein G, culturing human (or mouse) peripheral blood mononuclear cells (PBMC) or purified monocytes with cytokines in the protein A or G-coated plate to generate macrophage or dendritic cells. The disclosed methods can also include culturing human (or mouse) peripheral blood mononuclear cells (PBMC) or purified monocytes with any polymerized form of protein A, protein G, or other IgG-binding proteins. These methods can similarly comprise coating culture plates with recombinant protein A or protein G, culturing human (or mouse) peripheral blood mononuclear cells (PBMC) or purified monocytes with cytokines in the protein A or G-coated plate to generate macrophage or dendritic cells.

The details of one or more embodiments of the invention are set forth in the accompanying drawings and the description below. Other features, objects, and advantages of the invention will be apparent from the description and drawings, and from the claims.

DESCRIPTION OF DRAWINGS

FIGS. 1A to 1I show differential cytolysis mediated by ectopic gene expression (DC-MEGE) that identified HSV1 gE as an NK cell-activating molecule. FIG. 1A is a flow diagram of the DC-MEGE assay. FIG. 1B shows representative graphs of the DC-MEGE assay for representative HSV1 genes. FIG. 1C is a bar graph showing DC-MEGE results for all 65 HSV1 genes (n≥4), wherein expression of HSV1 genes UL12, UL30, Us3, Us8 and Us12 promoted NK cytolysis, while expression of UL48, Us5 and Us6 inhibited NK cytolysis. FIG. 1D shows cytotoxicity against transfected human glioma cell lines at the specified Effector: Target ratio (E:T, x-axis). FIG. 1E shows that IFNγ is secreted by primary human NK cells after 20 hours culture with transfected glioma cells (mean of triplicates, n=5). FIGS. 1F and 1G show phenotypes of primary human NK cells after culturing with transfected glioma cells for 7 hours. FIG. 1H shows cytotoxicity of primary human NK cells against glioma cells expressing Us8 in the presence of isotype or Us8/gE-specific antibody. FIG. 1I shows phenotypes of primary human NK cells after culturing in plates precoated with inactivated pure wild type F strain or Us8 deficient F strain for 7 hours, or in the presence of isotype or gE-specific antibody (n=7). Data in FIGS. 1C, 1D, and 1H are set forth as mean±sem. Each dotted line in FIGS. 1E, 1H and 1I links data acquired from the same donor. * p<0.05, ** p<0.01.

FIG. 2A shows phenotypes of primary human NK cells after culturing with transfected glioma cells for 7 hours. Percentages of NK cells gaining expression of CD69 or CD107a, or NK cells losing both CD16a and CD62L expression are summarized for 14 donors. FIG. 2B shows primary human NK cells treated as in FIG. 2A, wherein supernatants were collected at 20 h and measured for human IFNγ (mean of triplicates, n=5). FIGS. 2C and 2D show human PBMC washed with pH 7.4 or pH 4 media, and subsequently stained with lineage markers and human IgG Fc antibody; mean intensity of cell markers and Fc are shown and one representative of at least five donors is shown. FIG. 2E shows the presence of human IgG on NK cells from human donors. FIG. 2F shows phenotypes of NK cells from donors in FIG. 2E after culturing with transfected glioma cells or K562 cells for 7 hour. FIG. 2G shows the percentage of NK cells positive for CD69 or CD107a after co-culturing with glioma cells or K562, plotted against surface IgG intensity of corresponding human donors. Correlation analysis was conducted using linear regression (n≥20). Each dotted line in FIGS. 2A and 2B links data acquired from the same donor. * p<0.05, ** p<0.01.

FIG. 3A shows a model structure of a gE-IgGFc-CD16a ternary complex. Front view, side view and top view are shown respectively. CD16a is shown as a stick, gE is shown as a sphere, and two monomers of IgG Fc dimer are shown as a ribbon. FIG. 3B shows binding of human IgG products (FIG. 3B) or CD16a with or without human IgG products (FIG. 3C) to transfected glioma cells. FIG. 3D shows binding of CD16a to infected glioma cells in the presence of human IgG products. FIG. 3E shows phosphorylation of CD3ζ following NK cell stimulation as described in 1H. FIGS. 3F and 3G show staining of lineage markers and protein A (FIG. 3F) or protein G (FIG. 3G) in human PBMC following a brief wash with pH 7.4 or pH 4 media. The numbers in these Figures are mean intensity of each staining. FIG. 3H shows primary human NK cells that were first incubated with protein A or protein G, and then the phenotypes were assessed after culturing with transfected glioma cells, K562 or interleukins IL12+IL18 for 7 h (n=7-8). FIG. 3I shows primary human NK cells incubated with protein A or protein G, and subsequently assessed for cytotoxicity against glioma Us7+Us8 (FIG. 3I). FIG. 3J shows NK cells treated as in (FIG. 3H), wherein IFNγ secretion was assessed at 20 hours of culture (mean of triplicates, n=5). FIG. 3K shows an action model for immunostimulation mediated by IgG Fc (ADCC as an example). Each dotted line in FIGS. 3H and 3J links data acquired from the same donor. FIGS. 3B, 3C, 3D, 3E, 3F and 3G were repeated at least 3 times. * p<0.01.

FIG. 4A shows cytotoxicity of primary human NK cells against infected glioma cells in the presence or absence of human IgG products. FIG. 4B shows cytotoxicity of primary human NK cells against transfected glioma cells in the presence or absence of human IgG1 Fc. FIG. 4C shows cytotoxicity of primary mouse NK cells against glioma Us7+Us8 in the presence or absence of human IgG1 Fc. FIG. 4D shows protection of mice against lethal HSV1 infection by human IgG products. FIGS. 4E and 4F show HSV1 virus load at 18 h and 84 h post infection (n=5). The data in FIGS. 4A, 4B and 4C are set forth as the mean±sem. * p<0.05, ** p<0.001.

FIGS. 5A and 5B show phenotype (FIG. 5A) and IFN γ production (FIG. 5B) of primary human NK cells after being cultured with soluble protein A, or in plates coated with protein A, or in protein A-coated plates that were blocked with mouse serum before NK cell culture. Each dotted line in FIG. 5B represents one donor (mean of triplicates, n=6). FIG. 5C shows human NK cells cultured in plates coated with media or protein A for 30 min, wherein cytotoxicity was assessed against glioma cells; the results shown are mean±sem. FIG. 5D shows phosphorylation of CD3ζ after exposing primary human NK cells to stimuli indicated in the Figure for 1 h. FIG. 5E shows the phenotype of primary human NK cells after culture with bacteria for 7 hours. In some cases NK cells were pretreated with soluble protein A or protein G, or soluble protein A was pre-incubated with mouse serum or human IgG. FIG. 5F shows IFN γ production in mouse NK cells after being cultured with bacteria (mean of triplicates, n=5), each dotted line representing one mouse. FIG. 5G shows the phenotype of mouse NK cells after culturing in plates pre-coated with media or protein A. FIG. 5H shows the phenotypes of NK cells from BALB/c mice that were injected with control silicone beads or protein A-conjugated silicone beads. FIGS. 5A, 5D, and 5E were repeated minimally on 4 donors.

Figure 16:
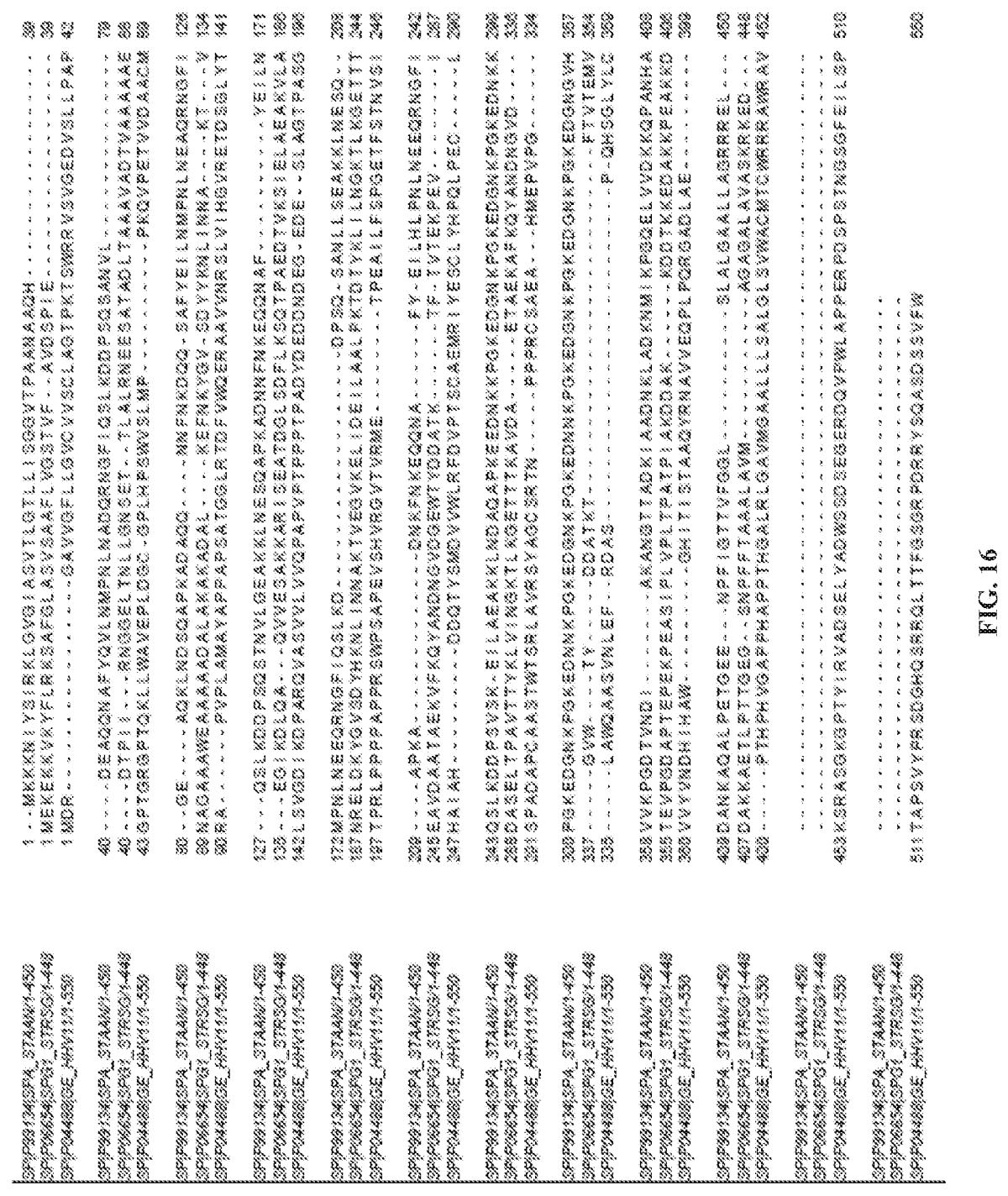

FIG. 16 shows sequence alignment of protein A (UniProtKB: P99134) (SEQ ID NO: 3), protein G (UniProtKB: P06654) (SEQ ID NO: 4) and HSV1 gE (UniProtKB: P04488) (SEQ ID NO: 171).

FIG. 17A shows the morphology of human monocytes cultured in plates pre-coated with media, protein A, or protein G for 3 h or 18 h. FIG. 7B shows the result of a monocyte respiratory burst assay, in which human primary monocytes were cultured in plates coated with bovine serum (BSA), or protein A, or stimulated with phorbol 12-myristate 13-acetate (PMA; positive control) for a specified time. FIG. 17C shows intracellular IL1beta staining of monocytes as treated in FIG. 17B.

FIGS. 28A-28E show that CMV IgG binding protein gp68 is capable of forming a ternary complex with human IgG1 Fc and CD16a. FIG. 28A illustrates the results obtained from glioma cells transfected with individual IgG binding proteins and incubated with fluorescently labeled rituximab. FIG. 28B illustrates the results obtained from glioma cells transfected with individual IgG binding proteins and incubated with human IgG1 Fc. FIGS. 28C, 28D, and 28E illustrate the results obtained from transfected glioma cells incubated with fluorescently labeled CD16a alone (FIG. 28C) or in the presence of rituximab (FIG. 28D) or human IgG1 Fc (FIG. 28E). Filled gray areas represent cells not expressing IgG binding proteins. Heavy black lines represent cells expressing IgG binding proteins.

FIG. 29A shows the percentages of NK cells gaining expression of CD69 or CD107a and cells losing both CD16a and CD62L. FIG. 29B is a graphical summary of the results for 6 donors. * p<0.05.

DETAILED DESCRIPTION

Definitions

Figure 1A:
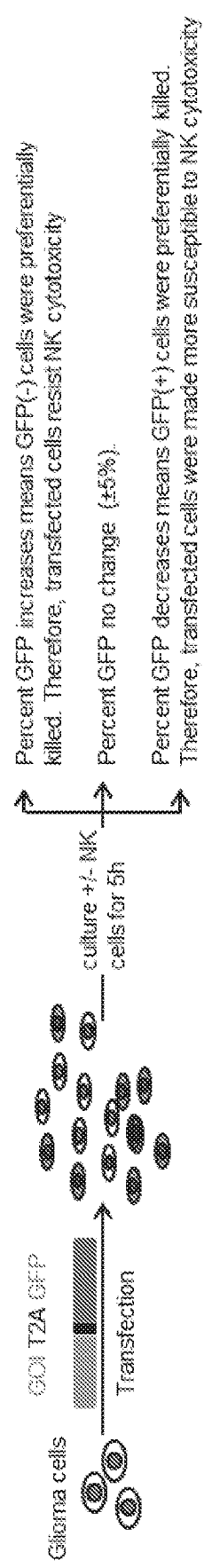

In this specification and in the claims that follow, reference will be made to a number of terms, which shall be defined to have the following meanings:

As used in the description and the appended claims, the singular forms "a," "an," and "the" include plural referents unless the context clearly dictates otherwise. Thus, for example, reference to "a composition" includes mixtures of two or more such compositions, reference to "the compound" includes mixtures of two or more such compounds, reference to "an agent" includes mixture of two or more such agents, and the like.

"Optional" or "optionally" means that the subsequently described event or circumstance can or cannot occur, and that the description includes instances where the event or circumstance occurs and instances where it does not.

Ranges can be expressed herein and when such a range is expressed, another aspect includes from the one particular value and/or to the other particular value. Similarly, when values are expressed as approximations, it will be understood that the particular value forms another aspect. It will be further understood that the endpoints of each of the ranges are significant both in relation to the other endpoint, and independently of the other endpoint. It is also understood that when a value is disclosed, then "less than or equal to" the value, "greater than or equal to the value," and possible ranges between values are also disclosed, as appropriately understood by the skilled artisan. It is also understood that throughout the application data are provided in a number of different formats and that this data represent endpoints and starting points and ranges for any combination of the data points. It is also understood that each unit between two particular units are also disclosed. For example, if 10 and 15 are disclosed, then 11, 12, 13, and 14 are also disclosed.

The term "subject" or "patient" refers to any individual who is the target of administration of a pharmaceutical composition of the invention or treatment using a method as disclosed herein. The subject can be a vertebrate, for example, a mammal. Thus, the subject can be a human or veterinary patient. The term "patient" specifically refers to a subject under the treatment of a clinician, e.g., physician.

By "prevent" or other forms of the word, such as "preventing" or "prevention," is meant to stop a particular event or characteristic, to stabilize or delay the development or progression of a particular event or characteristic, or to minimize the chances that a particular event or characteristic will occur. Prevent does not require comparison to a control as it is typically more absolute than, for example, the term "reduce." As used herein, something could be reduced but not prevented, but something that is reduced could also be prevented. Likewise, something could be prevented but not reduced, but something that is prevented could also be reduced. It is understood that where reduce or prevent are used, unless specifically indicated otherwise, the use of the other word is also expressly disclosed.

The term "treatment" or "treating" refers to the medical management of a subject with the intent to cure, ameliorate, stabilize, or prevent a disease, pathological condition, or disorder. This term includes active treatment, that is, treatment directed specifically toward the improvement of a disease, pathological condition, or disorder, and also includes causal treatment, that is, treatment directed toward removal of the cause of the associated disease, pathological condition, or disorder. In addition, this term includes palliative treatment, that is, treatment designed for the relief of symptoms rather than the curing of the disease, pathological condition, or disorder; preventative treatment, that is, treatment directed to minimizing or partially or completely inhibiting the development of the associated disease, pathological condition, or disorder; and supportive treatment, that is, treatment employed to supplement another specific therapy directed toward the improvement of the associated disease, pathological condition, or disorder.

As used herein, a "target cell" refers to a target of an immune effector cell that expresses an Fc binding protein. This includes virally infected cells and also microorganisms, such as bacteria and fungi.

A "host cell" includes an individual cell or cell culture which can be or has been a recipient of a virus and/or viral vector. Host cells include progeny of a single host cell, and the progeny may not necessarily be completely identical (in morphology or of total DNA complement) to the original parent cell due to natural, accidental, or deliberate mutation and/or change.

The term "gene" is well understood in the art to mean a polynucleotide encoding a polypeptide. In addition to the polypeptide coding regions, a gene can include non-coding regions including, but not limited to, introns, transcribed but untranslated segments, and regulatory elements upstream and downstream of the coding segments.

The terms "polypeptide," "peptide" and "protein" are used interchangeably to refer to polymers of amino acids of any length. These terms also include proteins that are post-translationally modified through reactions that include glycosylation, acetylation, myristoylation, and phosphorylation.

The term "antibody" specifically covers monoclonal antibodies (including full length monoclonal antibodies), polyclonal antibodies, multispecific antibodies (e.g., bispecific antibodies), and antibody fragments so long as they exhibit the desired biological activity.

A "native sequence Fc region" comprises an amino acid sequence identical to the amino acid sequence of an Fc region found in nature (e.g., SEQ ID NO: 1), with the caveat that naturally occurring Fc regions and fragments can be heterogeneous in amino acid sequence as the consequence, inter alia, of population-related genetic heterogeneity (although species-specific "canonical" sequences have been derived. Human immunoglobulins, specifically IgG embodiments thereof, are known to exhibit sequence polymorphisms classically termed allotypes. See, Jefferis and Lefranc, 209, Human immunoglobulin allotypes: Possible implications for immunogenicity, *mAbs* 1: 1-7. As used herein, IgG isotypes (IgG1, IgG2, IgG3, and IgG4) comprise such allotypes throughout the scope of naturally occurring variability, including combinations and mixtures thereof as well as isolated and purified allotypes of such isotypes.

A "variant Fc region" as appreciated by one of ordinary skill in the art comprises an amino acid sequence which differs from that of a native sequence Fc region by virtue of at least one "amino acid modification." Preferably, the variant Fc region has at least one amino acid substitution compared to a native sequence Fc region or to the Fc region of a parent polypeptide, e.g., from about one to about ten amino acid substitutions, and preferably from about one to about five amino acid substitutions in a native sequence Fc region or in the Fc region of the parent polypeptide. The variant Fc region herein will preferably possess at least about 80% sequence identity with a native sequence Fc region and/or with an Fc region of a parent polypeptide, and more preferably at least about 90% sequence identity therewith, more preferably at least about 95% sequence identity therewith, even more preferably, at least about 99% sequence identity therewith.

The terms "Fc receptor" or "FcR" are used to describe a receptor that binds to the Fc region of an antibody. An FcγR is a receptor that binds to the Fc region of an IgG antibody. FcγRs includes receptors of the FcγRI, FcγRII, and FcγRIII subclasses, including allelic variants and alternatively spliced forms of these receptors. FcγRII receptors include FcγRIIA (an "activating receptor") (e.g., SEQ ID NO: 21) and FcγRIIB (an "inhibiting receptor") (e.g., SEQ ID NO: 22), which have similar amino acid sequences that differ primarily in the cytoplasmic domains thereof. Activating receptor FcγRIIA contains an immunoreceptor tyrosine-based activation motif (ITAM) in its cytoplasmic domain. Inhibiting receptor FcγRIIB contains an immunoreceptor tyrosine-based inhibition motif (ITIM) in its cytoplasmic domain.

The term "Fc binding protein" refers to any protein that binds IgG Fc region outside of the FcγR binding sites. In particular embodiments, the Fc binding protein binds a region of the Fc region of IgG without interfering with the binding of FcγR to the IgG Fc.

By "effective amount" is meant an amount sufficient to bring about a beneficial or desired clinical result (e.g. improvement in clinical condition).

A "promoter" is generally a sequence or sequences of DNA that function when in a relatively fixed location in regard to the transcription start site. A "promoter" contains core elements required for basic interaction of RNA polymerase and transcription factors and can contain upstream elements and response elements.

"Enhancer" generally refers to a sequence of DNA that functions at no fixed distance from the transcription start site and can be either 5' or 3' to the transcription unit. Furthermore, enhancers can be within an intron as well as within the coding sequence itself. They are usually between 10 and 300 bp in length, and they function in cis. Enhancers function to increase transcription from nearby promoters. Enhancers, like promoters, also often contain response elements that mediate the regulation of transcription. Enhancers often determine the regulation of expression.

Enhancing Passive ADCC

Disclosed herein are reagents, methods, and pharmaceutical compositions for enhancing passive ADCC in a subject. In particular embodiments, provided herein are methods for treating a subject infected with a pathogen encoding a Fc-binding protein wherein the subject is administered a pharmaceutical composition of the invention comprising a domain that binds an FcγR on an immune effector cell and a non-overlapping domain that binds the pathogen-encoded Fc binding protein. In other embodiments, reagents, methods, and pharmaceutical compositions for preventing neurologic damage in a subject with HSV1 infection and for preventing death in a subject with HSV1 infection are provided. In certain embodiments the immunological polypeptide is an antibody, more specifically an IgG antibody and in particular an Fc fragment of an IgG antibody. Also within the scope of such immunological polypeptides is IgG-containing antisera. A feature of the immunological polypeptides useful in the methods and comprising the pharmaceutical compositions disclosed herein is that the efficacy and utility of said IgG antibodies is independent of their antigenic specificity.

Fc Fragments

In some embodiments, the immunological polypeptide comprises an Fc region of an immunoglobulin G (IgG) antibody but does not comprise the antigen-binding region of an antibody, e.g., Fab region. For example, the immunological polypeptide can be a fragment of an IgG1 (e.g., SEQ ID NO: 6), IgG2 (e.g., SEQ ID NO: 7), IgG3 (e.g., SEQ ID NO: 8) or IgG4 (e.g., SEQ ID NO: 9) immunoglobulin; the sequences set forth herein are exemplary, and the skilled worker will recognize that the claimed reagents, methods, and pharmaceutical compositions comprise allotypic variation of IgG isotyopes. In some embodiments, the immunological polypeptide comprises an Fc region of an IgG immunoglobulin, or a fragment thereof capable of simultaneously binding an FcγR and an Fc binding protein, or a fragment thereof capable of binding either an FcγR or an Fc binding protein, but not both (e.g., IgG3) and does not comprise the antigen-binding region of an antibody, e.g., Fab region. In particular embodiments, the immunological polypeptides of the disclosure comprise a domain that has been altered (naturally, by genetic engineering, or otherwise) to bind the FcγR on an immune effector cell with a higher affinity than IgG found in nature and/or a non-overlapping domain that binds the pathogen-encoded Fc binding protein with a higher affinity than an IgG found in nature. The immunological polypeptide can be a recombinant protein, containing fragments of human IgG1 (S6B291; SEQ ID NO: 10). For example, in particular embodiments the recombinant protein comprises residue 235-466 of human IgG1 (S6B291) (SEQ ID NO: 2), or equivalent homologue sequence of IgG2, IgG3, or IgG4. The immunological polypeptide also can be made by papain or plasmin digestion of human IgG1, IgG2, IgG3 or IgG4 as known in the art (see, for example, Goding, J. (1983). Monoclonal Antibodies. Principles and Practice. Academic Press Inc., London, U.K.).

The polypeptide can be a recombinant protein, containing residue 262-466 of human IgG1 (S6B291) (SEQ ID NO: 1), or equivalent homologue sequence of IgG2, IgG3, or IgG4.

Fc Variants

Also disclosed are synthetic or recombinant polypeptides capable of simultaneously binding an FcγR and an Fc binding protein. In some embodiments, the immunological polypeptide comprises two or more Fc regions of an IgG immunoglobulin. In particular embodiments, the Fc region is modified by for example PEGylation or myrisoylation.

In some embodiments, the immunological polypeptide comprises an Fc gamma receptor binding site that has been modified to enhance binding to an Fc gamma receptor. In some embodiments, this involves a structure-guided design of the IgG-Fcγ receptor interface to produce a higher binding affinity. In some embodiments, this involves removal of the fucose linked to Asn297 of an IgG molecule. In some embodiments, this involves chemically modifying the polypeptide to enhance Fcγ receptor binding (see, for example, Konno et al. (2010) Controlling Fucosylation Levels of Antibodies with Osmolality during Cell Culture. In: Kamihira M., Katakura Y., Ito A. (eds) Animal Cell Technology: Basic & Applied Aspects. Animal Cell Technology: Basic & Applied Aspects, vol 16. Springer, Dordrecht).

In some embodiments, the immune effector cell is an immune cell that expresses an Fc gamma receptor. Fc gamma receptors include CD16a, CD16b, CD32, and CD64. Therefore in some embodiments, the immune effector cell is a T-cell, a B cell, a natural killer (NK) cell, a monocyte, a macrophage, a neutrophil or granulocyte, or a dendritic cell.

Diseases/Disorders

The methods disclosed herein are broadly applicable to any disease or condition in which killing or interruption of target cells or pathogens expressing Fc binding proteins is desirable.

In some embodiments, a virus or an infected target cell infected with a virus expresses an Fc binding protein. For example, the herpes simplex viruses 1 (HSV1) and HSV2 expresses the Fc binding protein glycoprotein E (gE)(SEQ ID NO: 5) that can induce passive ADCC. The herpes virus cytomegalovirus (CMV) expresses the Fc binding protein 68 kDa-glycoprotein (gp68) that can induce passive ADCC. Note that CMV gp32 also binds IgG Fc, but it competes with the same binding site on IgG Fc as CD16a, so it does not induce passive ADCC. Additionally, Varicella zoster virus (VZV) expresses the IgG binding protein gE, which is a homologue of HSV1 gE (reference PMC241147 and PMID: 2167554).

Viruses that can be targeted by the reagents, methods, and pharmaceutical compositions of the invention in general include but are not limited to those in the following families: picornaviridae; caliciviridae; togaviridae; flaviviridae; coronaviridae; rhabdoviridae; filoviridae; paramyxoviridae; orthomyxoviridae; bunyaviridae; arenaviridae; reoviridae; retroviridae; hepadnaviridae; parvoviridae; papovaviridae; adenoviridae; herpesviridae; and poxyviridae.

In some embodiments, the pathogen is a bacterium, such as *Staphylococcus aureus, Streptococcus*, or *Escherichia coli*. *Staphylococcus aureus* expresses the Fc binding protein A, *Streptococcus* expresses the Fc binding proteins protein G, protein H, and M1 protein, and *Escherichia coli* expresses the Fc binding protein M1 protein. Therefore, in some embodiments, the Fc binding protein comprises protein G, protein H, or M1 protein.

Bacteria in general include but are not limited to: *P. aeruginosa; E. coli, Klebsiella* sp.; *Serratia* sp.; *Pseudomanas* sp.; *P. cepacia; Acinetobacter* sp.; *S. epidermis; E. faecalis; S. pneumonias; S. aureus; Haemophilus* sp.; *Neisseria* Sp.; *N. meningitidis; Bacteroides* sp.; *Citrobacter* sp.; *Branhamella* sp.; *Salmonella* sp.; *Shigella* sp.; *S. pyogenes; Proteus* sp.; *Clostridium* sp.; *Erysipelothrix* sp.; *Lesteria* sp.; *Pasteurella multocida; Streptobacillus* sp.; *Spirillum* sp.; *Fusospirochetasp.; Treponema pallidum;*
*Borrelia* sp.; *Actinomycetes;*
*Mycoplasma* sp.; *Chlamydia* sp.; *Rickettsia* sp.; *Spirochaeta;*
*Legionella* sp.; Mycobacteria sp.; *Ureaplasma* sp.; *Streptomyces* sp.; *Trichomonas* sp.; and *P. mirabilis*.

Parasites include but are not limited to: *Plasmodium falciparum, P. vivax, P. ovale, P. malaria; Toxoplasma gondii; Leishmania mexicana, L. tropica, L. major, L. aethiopica, L. donovani, Trypanosoma cruzi, T. brucei, Schistosoma mansoni, S. haematobium, S. japonium; Trichinella spiralis; Wuchereria bancrofti; Brugia malayli; Entamoeba histolytica; Enterobius vermiculoarus; Taenia solium, T. saginata, Trichomonas vaginatis, T. hominis, T. tenax; Giardia lamblia; Cryptosporidium parvum; Pneumocytis carinii, Babesia bovis, B. divergens, B. microti, Isospore belli, L hominis; Dientamoeba fragiles; Onchocerca volvulus; Ascaris lumbricoides, Necator americanis; Ancylostoma duodenale; Strongyloides stercoralis; Capillaria philippinensis; Angiostrongylus cantonensis; Hymenolepis nana; Diphyllobothrium latum; Echinococcus granulosus, E. multilocularis; Paragonimus westermani, P. caliensis; Chlonorchis sinensis; Opisthorchis felineas, G. Viverini, Fasciola hepatica Sarcoptes scabiei, Pediculus humanus; Phthirius pubis;* and *Dermatobia hominis*.

Fungi in general include but are not limited to: *Cryptococcus neoformans; Blastomyces dermatitidis; Aiellomyces dermatitidis; Histoplasfria capsulatum; Coccidioides immitis; Candids* species, including *C. albicans, C. tropicalis, C. parapsilosis, C. guilliermondii* and *C. krusei, Aspergillus* species, including *A. fumigatus, A. flavus* and *A. niger, Rhizopus* species; *Rhizomucor* species; *Cunninghammella* species; *Apophysomyces* species, including *A. saksenaea, A. mucor* and *A. absidia; Sporothrix schenckii, Paracoccidioides brasiliensis; Pseudallescheria boydii, Torulopsis glabrata;* and *Dermatophyres* species.

Inhibiting Passive ADCC

Also disclosed are methods, reagents, and pharmaceutical compositions for inhibiting or reducing passive ADCC. These methods reduce the cytotoxicity of immune effector cells in the subject by inhibiting passive ADCC.

In some embodiments, the immunological polypeptide is a fragment of an IgG immunoglobulin modified to not bind an Fc gamma receptor (FcγR). For example, the immunological polypeptide does not comprise amino acids 235-262 of SEQ ID No. 10, or functional equivalent thereof. For example, the polypeptide can be an IgG fragment that lacks a CD16a, CD32, or CD64 binding site. For example, this can be is a fragment of an IgG1, IgG2, IgG3 or IgG4 immunoglobulin. In some embodiments, the immunological polypeptide is a fragment from more than one subclass of antibody.

In some embodiments provided herein, are reagents, methods, and pharmaceutical compositions for reducing inflammation in a subject receiving anti-cancer therapy. The methods disclosed herein comprise administering a therapeutically effective amount of an immunological polypeptide comprising a region that binds to an Fc binding protein but does not comprise a region that binds to an Fc gamma receptor (FcγR); and administering an anti-cancer therapy comprising a monoclonal antibody drug, wherein the immunological polypeptide does not comprise amino acids 235-262 of SEQ ID No. 10, or functional equivalent thereof.

In some embodiments, the subject is being treated with a therapeutic antibody such as rituximab, tocilizumab, tositumomab, trastuzumab bevacizumab, brentuximab vedotin, cetuximab, daratumumab, ipilimumab, ofatumumab, panitumumab, alemtuzumab or pembrolizumab. Most therapeutic monoclonal antibody drugs are produced from mammalian host cell lines to target specific antigens. Side effects and reduced therapeutic efficacy can result from sequestration of the antibody by various native Fc binding proteins. The disclosed methods can decrease side effects of antibody mediated infusion toxicity (the so-called "first dose effect"), yet enhance antibody-based immunotherapy.

In some embodiments, provided herein are reagents, methods, and pharmaceutical compositions for treating a subject undergoing oncolytic HSV1 viral therapy. In other embodiments, provided herein are methods, reagents, and pharmaceutical compositions for enhancing oncolytic viral therapy in a subject, comprising administering a pharmaceutical composition to a subject comprising an polypeptide comprising a region that binds to a binds a Fc binding protein on a target cell but does not comprise a region that binds to a FcγR. For example, wherein the immunological polypeptide does not comprise amino acids 235-262 of SEQ ID No. 10, or functional equivalent thereof.

The methods can be used to inhibit passive ADCC early after oncolytic viral infection of a tumor so the virus can spread to other tumor cells. While it may be advantageous to inhibit passive ADCC early after oncolytic viral infection of a tumor so the virus can spread to other tumor cells, the disclosed methods can also be used to enhance passive ADCC after the tumor cells are infected to enhance killing of tumor cells.

Thus, in some embodiments, the methods disclosed herein provide a pharmaceutical composition comprising an immunological polypeptide comprising a domain that binds an FcγR on an immune effector cell and a non-overlapping domain that binds n Fc binding protein on a target cell. In certain embodiments the immunological polypeptide is an antibody, more specifically an IgG antibody and in particular an Fc fragment of an IgG antibody. Also within the scope of such immunological polypeptides is IgG containing antisera. A feature of the immunological polypeptides useful in the methods and comprising the pharmaceutical compositions disclosed herein is that the efficacy and utility of said IgG antibodies is independent of their antigenic specificity.

As above, the immune effector cell can be any immune cell that expresses an Fc gamma receptor. Fc gamma receptors include CD16a, CD16b, CD32, and CD64. Therefore in some embodiments, the immune effector cell is a T-cell, a B cell, a natural killer (NK) cell, a monocyte, a macrophage, a neutrophil or granulocyte, or a dendritic cell.

Differential Cytolysis Mediated by Ectopic Gene Expression (DC-MEGE)

Also disclosed herein are methods for identifying genes that modulate interaction of a virally infected cell and an immune effector cell. The method is referred to herein as differential cytolysis mediated by ectopic gene expression (DC-MEGE). This method provides for a comprehensive understanding of the interaction between human lymphocytes and each gene expressed by target cells infected with a virus.

The disclosed methods can comprise transfecting a host cell with an expression vector comprising a candidate viral gene and a reporter gene operably linked to an expression control sequence, exposing the transfected host cells and non-transfected host cells to a cytotoxic immune effector cell, and assaying the exposed transfected host cells and non-transfected host cells to measure cell death as a function of reporter gene expression or activity. In these methods, a decrease in cell death by the transfected host cells compared to non-transfected host cells is an indication that the viral gene suppressed the immune effector cell or in other words, protected the transfected host cell from the immune effector cell; and an increase in cell death by the transfected host cells compared to non-transfected host cells is an indication that the viral gene activated the immune effector cell or in other words, made the transfected host cell susceptible to the immune effector cell.

In particular embodiments, the reporter gene is a fluorescence gene, wherein the exposed transfected host cells and non-transfected host cells are assayed by flow cytometry to measure cell death as a function of fluorescence, wherein an increase in the percentage of fluorescent transfected host cells compared to non-transfected host cells is an indication that the viral gene protected the transfected host cell from the immune effector cell, and wherein a decrease in mean fluorescence by the transfected host cells compared to non-transfected host cells is an indication that the viral gene made the transfected host cell susceptible to the immune effector cell.

For example, a fluorescence reading where only non-infected, non-fluorescent cells are killed, and fluorescence increases, is an indication that the transfected target cell was protected from killing. A fluorescence reading where only infected, fluorescent cells are killed, and fluorescence decreases, is an indication that the transfected target cell was susceptible to killing. A fluorescence reading where there is no change in fluorescence is an indication that the target cell remained unchanged to the cytotoxic lymphocyte killing.

Examples of fluorescent protein genes includes: AcGFP1, Azami-Green, Azurite BFP, BFP, CFP, Citrine, Clover, CopGFP, Cycle 3 GFP, CyOFP1, CyPet, d1EGFP, d2ECFP, d2EGFP, d2EYFP, d4EGFP, daGFP, Dendra2, dKeima-Red, dKeima570, Dronpa-Green1, Dronpa-Green3, DsRed-Express, DsRed-Express2, DsRed-Max, DsRed-Monomer, DsRed.T3, DsRed1, DsRed2, dTomato, E2-Crimson, E2-Orange, E2-Red/Green, EBFP, EBFP2, ECFP, ecliptic pHluorin, EGFP, Emerald GFP, EosFP, EYFP, Fast-FT, Fluorescent Timer, FusionRed, GFP, GFPuv, HcRed1, hdKeima-Red, hdKeima570, hKikGR1, hKO, hmAzami-Green, hMGFP, hmKeima-Red, hmKeima8.5, hmKikGR1, hmKO, hmKO2, hmMiCy1, hmUkG1, hrGFP, IFP1.1, IFP1.4, IFP2.0, iRFP670, iRFP682, iRFP702, iRFP713, iRFP720, Kaede, KikGR1, KillerRed, Kohinoor, Kusabira-Orange, LanYFP, LSSmKate1, LSSmKate2, LSSmOrange, mAmetrine, mAmetrine1.1, mApple, mAzami-Green, mCardinal, mCerulean, mCherry, mCherry2, mClavGR2, mClover2, mClover3, mECFP, Medium-FT, mEGFP, mEmerald, mEos2, mEos3.2, mEos4a, mEos4b, mEYFP, mgfp5, mHoneydew, MiCy, mIFP, miniSOG, mKalama1, mKate2, mKeima-Red, mKikGR1, mKO, mKO2, mMaple, mMiCy1, mNectarine, mNeonGreen, mNeptune, mNeptune2, mNeptune2.5, mOrange, mOrange2, mPapayal, mPlum, mRaspberry, mRFP1, mRuby, mRuby2, mRuby3, mseCFP, mTagBFP2, mTangerine, mTFP1, mTurquoise, mTurquoise2, mUkG1, mVenus, mWasabi, PA-GFP, PA-TagRFP, pAcGFP1, pAcGFP1-1, pAcGFP1-C1, pAcGFP1-C2, pAcGFP1-C3, pAcGFP1-C In-Fusion Ready, pAcGFP1-N1, pAcGFP1-N2, pAcGFP1-N3, pAcGFP1-N In-Fusion Ready, pAG-S1, PAmCherry, PAmCherry1, pAmCyan, pAmCyan1-C1, pAmCyan1-N1, PAmKate, pAsRed2, pAsRed2-C1, pAsRed2-N1, pd1EGFP-N1, pd2ECFP-N1, pd2EGFP-N1, pd2EYFP-N1, pd4EGFP-N1, pDendra2, pDendra2-C, pDendra2-N, pDG1-S1, pDG3-S1, pdKeima-Red-S1, pdKeima570-S1, pDsRed-Express, pDsRed-Express-1, pDsRed-Express-C1, pDsRed-Express-N1, pDsRed-Express2, pDsRed-Express2-1, pDsRed-Express2-C1, pDsRed-Express2-N1, pDsRed-Monomer-C1, pDsRed-Monomer-C In-Fusion Ready, pDsRed-Monomer-N1, pDsRed-Monomer-N In-Fusion Ready, pDsRed2, pDsRed2-1, pDsRed2-C1, pDsRed2-N1, pE2-Crimson, pE2-Crimson-C1, pE2-Crimson-N1, pECFP, pECFP-1, pECFP-C1, pECFP-N1, pEGFP, pEGFP-1, pEGFP-C1, pEGFP-C2, pEGFP-C3, pEGFP-N1, pEGFP-N2, pEGFP-N3, pEYFP, pEYFP-1, pEYFP-C1, pEYFP-N1, pFusionRed-B, pFusionRed-C, pFusionRed-N, pGFP, pGFPuv, pGLO, pHcRed1, pHcRed1-1, pHcRed1-C1, pHcRed1-N1_1, phdKeima-Red-S1, phdKeima570-S1, phKikGR1-S1, phKO1-S1, phmAG1-S1, phMGFP, phmKeima-Red-S1, phmKO1-S1, phmUkG1-S1, pHTomato, pHuji, pKaede-S1, pKikGR1-S1, pKillerRed-B, pKillerRed-C, pKillerRed-N, pKindling-Red-B, pKindling-Red-N, pKO1-S1, pLSSmOrange-C1, pLSSmOrange-N1, pmAG1-S1, pmBanana, pmCherry, pmCherry-1, pmCherry-C1, pmCherry-N1, pMiCy1-S1, pmKate2-C, pmKate2-N, pmKeima-Red-S1, pmKikGR1-S1, pmKO1-S1, pmKO2-S1, pmMiCy1-S1, pmOrange, pmOrange2, pmOrange2-C1, pmOrange2-N1, pmPlum, pmRaspberry, pmStrawberry, pmUkG1-S1, pNirFP-C, pNirFP-N, pPA-TagRFP-C, pPA-TagRFP-N, pPAmCherry-C1, pPAmCherry-N1, pPAmCherry1-C1, pPAmCherry1-N1, pPhi-Yellow-B, pPhi-Yellow-C, pPhi-Yellow-N, pPhi-Yellow-PRL, pPS-CFP2-C, pPS-CFP2-N, pPSmOrange-C1, pPSmOrange-N1, pRSET-BFP, pRSET-CFP, pRSET-EmGFP, PS-CFP2, PSmOrange, PSmOrange2, pTagBFP-C, pTagBFP-N, pTagCFP-C, pTagCFP-N, pTagGFP2-C, pTagGFP2-N, pTagRFP-C, pTagRFP-N, pTagYFP-C, pTagYFP-N, ptd-Tomato-N1, ptdTomato, ptd-Tomato-C1, pTimer, pTimer-1, pTurboFP602-B, pTurboFP602-C, pTurboFP602-N, pTurboFP602-PRL, pTurboGFP-B, pTurboGFP-C, pTurboGFP-N, pTurboGFP-PRL, pTurboRFP-B, pTurboRFP-C, pTurboRFP-N, pTurboRFP-PRL, pTurboYFP-B, pTurboYFP-C, pTurboYFP-N, pTurboYFP-PRL, pZsGreen, pZsGreen1-1, pZsGreen1-C1, pZsGreen1-N1, pZsYellow, pZsYellow1-C1, pZsYellow1-N1, ratiometric pHluorin, Rhacostoma GFP, rsEGFP, rsEGFP2, rsTagRFP, Slow-FT, super-ecliptic pHluorin, superfolder GFP, TagBFP, TagCFP, TagGFP2, TagRFP, TagRFP-T, TagRFP657, TagYFP, tdTomato, TurboFP602, TurboFP635, TurboGFP, TurboRFP, TurboYFP, yeGFP, YFP, YPet, ZsGreen, ZsGreen1, and ZsYellow1. In particular embodiments, the gene encodes Green Fluorescent Protein (see, Chalfie et al., 1994, *Science* 263, 802-805).

The process can be repeated for each gene in a viral genome. For example, the method can further comprise of repeating the process for each gene individually, or for combinations of 2, 3, 4, 5, 6, 7, 8, 9, 10, 20, 30, 40, 50, or more genes in a viral genome.

These methods can be used with any immune effector cell(s) that is/are cytotoxic or secrete some biomarker (e.g., a cytokine) indicative of activation or suppression. For example, the cytotoxic immune effector cell can be a CD4+ T-cell, a CD8+ T-cell, a natural killer (NK) cell, a macrophage, a granulocyte, or a dendritic cell. The method described above can be repeated for each candidate immune effector cell alone, or in combination with other immune cells or bioactive agents.

The disclosed methods can also be used to assay the effects of candidate drugs on a gene's ability to affect cytolysis. For example, if a gene is found to protect a cell from killing by immune effector cells, a series of candidate drugs can be added in future assays to find a drug that inhibits the gene's protection.

A host cell is preferably selected based on its known susceptibility or resistance to killing by an immune effector cell when virally infected, expressing exogenous proteins, or in native status. Host cells can be primary cells isolated from an animal or a human subject. The host cells can be a cell line, such as an immortalized cell line. Host cells can include a single cell type, or a mixture of cells. Host cells can be cultured in suspension, on a surface (two-dimensional), or in a three-dimensional matrix.

The methods disclosed herein comprise exposing transfected host cells and non-transfected host cells to a cytotoxic immune effector cell. This step can involve co-culturing the host cells and cytotoxic immune effector cells under standard culture condition (37° C. with 5% $CO_2$) or relevant experimental settings that enhance or inhibit the function of immune cells and host cells.

Recombinant Oncolytic HSV

Glioblastoma multiforme (GBM) is a uniformly fatal disease despite the application of available combination therapies. Replication-competent viruses including oncolytic HSV ("oHSV") vectors, represent a promising therapeutic alternative.

As disclosed herein, the HSV Us8, UL12, UL30, US3, and Us12 genes make glioma cells more susceptible to killing by NK cells. Therefore, also disclosed herein is a recombinant oncolytic Herpes Simplex Virus (oHSV), comprising one or more activating mutations in an Us8 gene, one or more activating mutations in an UL12 gene, one or more activating mutations in an UL30 gene, one or more activating mutations in an Us3 gene, one or more activating mutations in an Us12 gene, or any combination thereof. Activating mutations of HSV genes are known in the art. See, for example, U.S. Pat. Nos. 8,092,791; 9,623,059; WO 2007052029; WO 2009052426; WO 2017013419; WO 2017132552; Varghese & Rabkin, 2002, *Cancer Gene Ther.* 9, 967-978; Grandi et al., 2009, *Expert Rev Neurother.* 9, 505-517; and Sokolowski et al., 2015, *Oncolytic Virother.* 4, 207-219. These modifications to HSV oncolytic viruses can enhance tumor killing of the oncolytic viruses.

The disclosed oHSV may be derived from several different types of herpes viruses. The Herpesviridae are a large family of DNA viruses that cause diseases in humans and animals. Herpes virus is divided into three subfamilies, alpha, beta, and gamma. Herpes viruses all share a common structure and are composed of relatively large double-stranded, linear DNA genomes encoding 100-200 genes encased within an icosahedral protein cage called the capsid which is itself wrapped in a lipid bilayer membrane called the envelope. The large genome provides many non-essential sites for introducing one or more transgenes without inactivating the virus (e.g., without completely inhibiting infection or replication). However, it should be appreciated that viral vectors are preferably modified (e.g., replication conditional, attenuated) so that they do not have undesirable effects (e.g., killing normal cells, causing disease).

As used herein, oncolytic Herpes virus refers to any one of a number of therapeutic viruses having a Herpes virus origin that are useful for killing cancer cells, particularly cancer stem cells, and/or inhibiting growth of a tumor, for example by killing cancer stem cells in the tumor. Typically, an oncolytic Herpes virus is a mutant version of a wild-type Herpes virus. In some cases, when the wild-type Herpes virus is of the subfamily alpha (i.e., is a Herpes simplex virus) the oncolytic Herpes viruses may be referred to as an oncolytic Herpes Simplex virus (oHSV). In some cases, the oHSV is a replication-conditional Herpes virus. Replication-conditional Herpes viruses are designed to preferentially replicate in actively dividing cells, such as cancer cells, in particular cancer stem cells. Thus, these replication-conditional viruses target cancer cells for oncolysis, and replicate in these cells so that the virus can spread to other cancer cells. In preferred embodiments, replication conditional Herpes viruses target cancer stem cells for oncolysis, and replicate in these cells so that the virus can spread to other cancer stem cells.

The disclosed oHSV may comprise any one of a number of mutations that affect expression of a viral gene. In most cases, a mutation is in virulence gene that contributes to the pathogenicity of the virus to a host organism. The mutation may be a point mutation, a deletion, an inversion, or an insertion. Typically the mutation is an inactivating mutation. As used herein, the term "inactivating mutation" is intended to broadly indicate a mutation or alteration to a gene wherein the expression of that gene is significantly decreased, or wherein the gene product is rendered nonfunctional, or its ability to function is significantly decreased.

Several types of replication-conditional herpes virus mutants have been developed and are useful in aspects of the methods disclosed herein. For example, one aspect involves viral mutants with defects in the function of a viral gene needed for nucleic acid metabolism, such as thymidine kinase (Martuza et al., 1991, *Science* 252:854-856), ribonucleotide reductase (RR) (Goldstein & Weller, 1988, *J. Virol.* 62:196-205; Boviatsis et al., 1994, *Gene Ther.* 0.1: 323-331; Boviatsis et al., 1994, *Cancer Res.* 54:5745-5751; Mineta et al., 1994, *Cancer Res.* 54:3363-3366), or uracil-N-glycosylase (Pyles and Thompson, 1994, *J Virol.* 68:4963-4972). Another aspect involves viral mutants with defects in the function of the γ-34.5 gene (Chambers et al., 1995, *Proc. Natl. Acad. Sci. USA* 92:1411-1415), which functions as a virulence factor by markedly enhancing the viral burst size of infected cells through suppression of the shutoff of host protein synthesis (Chou et al., 1990, *Science* 250:1262-1266; Chou and Roizman, 1992, *Proc. Natl. Acad. Sci. USA* 89:3266-3270). Other examples include G207 (Mineta et al., 1995, *Nat. Med* 1:938-943; U.S. Pat. No. 5,585,096, issued Dec. 17, 1996 to Martuza et al.), and MGH1 (Kramm et al., 1997, *Hum. Gene Ther.* 8:2057-2068), which possess deletions of both copies of γ-34.5 and an insertional mutation of RR.

The disclosed oHSV can comprise viruses that are based on herpes viruses, such as herpes simplex viruses (HSV), for example, HSV-1 (e. g., HSV-1 strain F or strain Patton) or HSV-2, that include an inactivating mutation in a virulence gene. In the case of herpes simplex viruses, this mutation can be an inactivating mutation in the γ-34.5 gene, which is the major HSV neurovirulence determinant.

Any of the viruses described above and herein and elsewhere can include an additional mutation or modification that is made to prevent reversion of the virus to wild type. For example, the virus can include a mutation in the ICP6 gene (SEQ ID NO: 26), which encodes the large subunit of ribonucleotide reductase.

The disclosed oHSV can also include sequences encoding a heterologous gene product, such as a vaccine antigen or an immunomodulatory protein. Virus carrying heterologous gene products may also be referred to as augmented viruses The effects of the disclosed oHSV can be augmented if the viruses also contain a heterologous nucleic acid sequence encoding one or more therapeutic agents, for example, a cytotoxin, an immunomodulatory protein (i.e., a protein that either enhances or suppresses a host immune response to an antigen), a tumor antigen, small interfering nucleic acid, an antisense RNA molecule, or a ribozyme.

Examples of immunomodulatory proteins include, e. g., cytokines (e. g., interleukins, alpha-interferon, beta-interferon, gamma-interferon, tumor necrosis factor, granulocyte macrophage colony stimulating factor (GM-CSF), macrophage colony stimulating factor (M-CSF), and granulocyte colony stimulating factor (G-CSF)), chemokines (e.g., neutrophil activating protein (NAP), macrophage chemoattractant and activating factor (MCAF), RANTES, and macrophage inflammatory peptides MIP-1a and MIP-1b), complement components and their receptors, immune system accessory molecules (e.g., B7.1 and B7.2), adhesion molecules (e.g., ICAM-1, 2, and 3), and adhesion receptor molecules.

Examples of tumor antigens that can be produced using the present methods include, in non-limiting examples, the E6 and E7 antigens of human papillomavirus, EBV-derived proteins (Van der Bruggen et al., 1991, *Science* 254: 1643-1647), mucins (Livingston et al., 1992, *Curr. Opin. Immun.* 4 (5): 624-629), such as MIJC1 (Burchell et al., 1989, *Int. J. Cancer* 44: 691-696), melanoma tyrosinase, and MZ2-E (Van der Bruggen et al., supra).

Therapeutic agents can also be an RNA molecule, such as an antisense RNA molecule that, by hybridization interactions, can be used to block expression of a cellular or pathogen mRNA. Alternatively, the RNA molecule can be a ribozyme (e.g., a hammerhead or a hairpin-based ribozyme) designed either to repair a defective cellular RNA, or to destroy an undesired cellular or pathogen-encoded RNA (see, e.g., Sullenger, 1995, *Chem. Biol.* 2 (5): 249-253; Czubayko et al., 1997, *Gene Ther.* 4 (9): 943-949; Rossi, 1997, *Ciba Found. Symp.* 209: 195-204; James et al., 1998, *Blood* 91 (2): 371-382; Sullenger, 1996, *Cytokines Mol. Ther.* 2 (3): 201-205; Hampel, 1998, *Prog. Nucleic Acid Res. Mol. Bio.* 58: 1-39; and Curcio et al., 1997, *Pharmacol. Ther.* 74 (3): 317-332).

In some embodiments, the therapeutic agent can be a small interfering nucleic acid molecule capable of inhibiting expression of a gene associated with the cancer, such as an oncogene. Small interfering nucleic acids (e.g., shRNAs, miRNAs) that inhibit the expression of these genes and their homologues are useful as therapeutic agents in certain embodiments of the methods. Oncogenes associated with various cancers are well known in the art and disclosed, in non-limiting examples, in Cooper, 1995, Oncogenes. Jones and Bartlett Publishers. and Vogelstein and Kinzler, 1998, The Genetic Basis of Human Cancer. McGraw-Hill the contents are incorporated herein by reference in their entirety.

A heterologous nucleic acid sequence can be inserted into the disclosed oHSV in a location that renders it under the control of a regulatory sequence of the virus. Alternatively, the heterologous nucleic acid sequence can be inserted as part of an expression cassette that includes regulatory elements, such as promoters or enhancers. Appropriate regulatory elements can be selected by those of ordinary skill in the art based on, for example, the desired tissue-specificity and level of expression. For example, a cell-type specific or tumor-specific promoter can be used to limit expression of a gene product to a specific cell type. This is particularly useful, for example, when a cytotoxic, immunomodulatory, or tumor antigenic gene product is being produced in a tumor cell in order to facilitate its destruction. In addition to using tissue-specific promoters, local administration of the viruses of the invention can result in localized expression and effect.

Examples of non-tissue specific promoters that can be used in the disclosed oHSV include the early Cytomegalovirus (CMV) promoter (U.S. Pat. No. 4,168,062) and the Rous Sarcoma Virus promoter (Norton et al., 1985, *Molec. Cell. Biol.* 5: 281). Also, HSV promoters, such as HSV-1 IE and IE 4/5 promoters, can be used.

Examples of tissue-specific promoters that can be used in the disclosed oHSV include, for example, prostate-specific antigen (PSA) promoter, which is specific for cells of the prostate; desmin promoter, which is specific for muscle cells (Li et al., 1989, *Gene* 78: 243; Li et al., 1991, *J. Biol. Chem.* 266: 6562; Li et al., 1993, *J Biol. Chem.* 268: 10403); enolase promoter, which is specific for neurons (Forss-Petter et al., 1986, *J. Neuroscience Res.* 16 (1): 141-156); beta-globin promoter, which is specific for erythroid cells (Townes et al., 1985, *EMBO J.* 4: 1715); tau-globin promoter, which is also specific for erythroid cells (Brinster et al., 1980, *Nature* 283: 499); growth hormone promoter, which is specific for pituitary cells (Behringer et al., 1988, *Genes Dev.* 2: 453); insulin promoter, which is specific for pancreatic beta cells (Selden et al., 1986, *Nature* 321: 545); glial fibrillary acidic protein promoter, which is specific for astrocytes (Brenner et al., 1994, *J. Neurosci.* 14: 1030); tyrosine hydroxylase promoter, which is specific for catecholaminergic neurons (Kim et al., 1993, *J. Biol. Chem.* 268: 15689); amyloid precursor protein promoter, which is specific for neurons (Salbaum et al., 1988, *EMBO J.* 7: 2807); dopamine beta-hydroxylase promoter, which is specific for noradrenergic and adrenergic neurons (Hoyle et al., 1994, *J Neurosci.* 14: 2455); tryptophan hydroxylase promoter, which is specific for serotonin/pineal gland cells (Boularand et al., 1995, *J. Biol. Chem.* 270: 3757); choline acetyltransferase promoter, which is specific for cholinergic neurons (Hersh et al., 1993, *J. Neurochem.* 61: 306); aromatic L-amino acid decarboxylase (AADC) promoter, which is specific for catecholaminergic/5-HT/D-type cells (Thai et al., 1993, *Mol. Brain Res.* 17: 227); proenkephalin promoter, which is specific for neuronal/spermatogenic epididymal cells (Borsook et al., 1992, *Mol. Endocrinol.* 6: 1502); reg (pancreatic stone protein) promoter, which is specific for colon and rectal tumors, and pancreas and kidney cells (Watanabe et al., 1990, *J. Biol. Chem.* 265: 7432); and parathyroid hormone-related peptide (PTHrP) promoter, which is specific for liver and cecum tumors, and neurilemoma, kidney, pancreas, and adrenal cells (Campos et al., 1992, *Mol. Endocrinol.* 6: 1642).

Examples of promoters that function specifically in tumor cells include the stromelysin 3 promoter, which is specific for breast cancer cells (Basset et al., 1990, *Nature* 348: 699); the surfactant protein A promoter, which is specific for non-small cell lung cancer cells (Smith et al., 1994, *Hum. Gene Ther.* 5: 29-35); the secretory leukoprotease inhibitor (SLPI) promoter, which is specific for SLPI-expressing carcinomas (Garver et al., 1994, *Gene Ther.* 1: 46-50); the tyrosinase promoter, which is specific for melanoma cells (Vile et al., 1994, *Gene Therapy* 1: 307; WO 94/16557); the stress inducible grp78/BiP promoter, which is specific for fibrosarcoma/tumorigenic cells (Gazit et al., 1995, *Cancer Res.* 55 (8): 1660); the AP2 adipose enhancer, which is specific for adipocytes (Graves, 1992, 1 Cell. *Biochem.* 49: 219); the a-1 antitrypsin transthyretin promoter, which is specific for hepatocytes (Grayson et al., 1988, *Science* 239: 786); the interleukin-10 promoter, which is specific for glioblastoma multiform cells (Nitta et al., 1994, *Brain Res.* 649: 122); the c-erbB-2 promoter, which is specific for pancreatic, breast, gastric, ovarian, and non-small cell lung cells (Harris et al., 1994, *Gene Ther.* 1: 170); the a-B-crystallin/heat shock protein 27 promoter, which is specific for brain tumor cells (Aoyama et al., 1993, *Int. J. Cancer* 55: 760); the basic fibroblast growth factor promoter, which is specific for glioma and meningioma cells (Shibata et al., 1991, *Growth Fact.* 4: 277); the epidermal growth factor receptor promoter, which is specific for squamous cell carcinoma, glioma, and breast tumor cells (Ishii et al., 1993, *Proc. Natl. Acad. Sci. U.S.A.* 90: 282); the mucin-like glycoprotein (DF3, MUC1) promoter, which is specific for breast carcinoma cells (Abe et al., 1993, *Proc. Natl. Acad. Sci. U.S.A.* 90: 282); the mts1 promoter, which is specific for metastatic tumors (Tulchinsky et al., 1992, *Proc. Natl. Acad. Sci. U.S.A.* 89: 9146); the NSE promoter, which is specific for small-cell lung cancer cells (Forss-Petter et al., 1990, *Neuron* 5: 187); the somatostatin receptor promoter, which is specific for small cell lung cancer cells (Bombardieri et al., 1995, *Eur. J. Cancer* 31A: 184; Koh et al., 1995, *Int.* 1 *Cancer* 60: 843); the c-erbB-3 and c-erbB-2 promoters, which are specific for breast cancer cells (Quin et al., 1994, *Histopathology* 25: 247); the c-erbB4 promoter, which is specific for breast and gastric cancer cells (Rajkumar et al., 1994, *Breast Cancer Res. Trends* 29: 3); the thyroglobulin promoter, which is specific for thyroid carcinoma cells (Mariotti et al., 1995, *J. Clin. Endocrinol. Meth.* 80: 468); the a-fetoprotein promoter, which is specific for hepatoma cells (Zuibel et al., 1995, *J. Cell. Phys.* 162: 36); the villin promoter, which is specific for gastric cancer cells (Osborn et al., 1988, *Virchows Arch. A. Pathol. Anat. Histopathol.* 413: 303); and the albumin promoter, which is specific for hepatoma cells (Huber, 1991, *Proc. Natl. Acad. Sci. U.S.A.* 88: 8099).

The disclosed oHSV can be used to treat a subject having (e.g., harboring) or at risk of having a cancer stem cell (CSC) and/or a tumor having CSCs (e.g., a tumor for which sustained growth is dependent on CSCs; such tumors may also be referred to as a CSC-dependent tumor). Whether a subject is deemed "at risk" of having a CSC or a tumor having CSCs is a determination that may be within the discretion of the skilled practitioner caring for the subject. Any suitable diagnostic test and/or criteria can be used. For example, a subject may be considered "at risk" of having a CSC or a tumor having CSCs if (i) the subject has a mutation, genetic polymorphism, gene or protein expression profile, and/or presence of particular substances in the blood, associated with increased risk of developing or having cancer relative to other members of the general population not having mutation or genetic polymorphism; (ii) the subject has one or more risk factors such as having a family history of cancer, having been exposed to a carcinogen or tumor-promoting agent or condition, e.g., asbestos, tobacco smoke, aflatoxin, radiation, chronic infection/inflammation, etc., advanced age; (iii) the subject has one or more symptoms of cancer, etc.

In some embodiments, the cancer is a colon carcinoma, a pancreatic cancer, a breast cancer, an ovarian cancer, a prostate cancer, a squamous cell carcinoma, a cervical cancer, a lung carcinoma, a small cell lung carcinoma, a bladder carcinoma, a squamous cell carcinoma, a basal cell carcinoma, an adenocarcinoma, a sweat gland carcinoma, a sebaceous gland carcinoma, a papillary carcinoma, a papillary adenocarcinoma, a cystadenocarcinoma, a medullary carcinoma, a bronchogenic carcinoma, a renal cell carcinoma, a hepatocellular carcinoma, a bile duct carcinoma, a choriocarcinoma, a seminoma, an embryonal carcinoma, a Wilms' tumor, melanoma, or a testicular tumor. In one embodiment, the cancer is a glioma. In one embodiment, the cancer is a breast or prostate carcinoma. Other cancers will be known to one of ordinary skill in the art.

In particular embodiments, the cancer is a brain cancer. In some embodiments, the cancer is a glioma. A glioma is a type of primary central nervous system (CNS) tumor that arises from glial cells. In addition to the brain, gliomas can also affect the spinal cord or any other part of the CNS, such as the optic nerves. The gliomas for which the methods of the invention are useful to treat include ependymomas, astrocytomas, oligodendrogliomas, and mixed gliomas, such as oligoastrocytomas. In some embodiments, the gliomas contain cancer stem cells that are CD133+. In some embodiments, the glioma is a glioblastoma.

Gliomas are further categorized according to their grade, which is determined by pathologic evaluation of the tumor. Low-grade gliomas are well-differentiated (not anaplastic); these are benign and portend a better prognosis for the patient. High-grade gliomas are undifferentiated or anaplastic; these are malignant and carry a worse prognosis. Of numerous grading systems in use, the most common is the World Health Organization (WHO) grading system for astrocytoma. The WHO system assigns a grade from 1 to 4, with 1 being the least aggressive and 4 being the most aggressive. Various types of astrocytomas are given corresponding WHO grades. WHO Grade 1 includes, for example, pilocytic astrocytoma; WHO Grade 2 includes, for example, diffuse or low-grade astrocytoma; WHO Grade 3 includes, for example, anaplastic (malignant) astrocytoma; and WHO Grade 4 includes, for example, glioblastoma multiforme (most common glioma in adults). Accordingly, in some embodiments the methods of the invention are useful for treating patients (subjects) with WHO Grade 1, Grade 2, Grade 3, or Grade 4 gliomas.

Also disclosed are methods of inducing a systemic immune response to cancer in a subject, which involve administering to the subject an oHSV disclosed herein. The herpes virus can be administered, for example, to a tumor of the subject. In addition, the patient can have or be at risk of developing metastatic cancer, and the treatment can be carried out to treat or prevent such cancer.

Recombinant HSV Vaccine

Also as disclosed herein, HSV gE and gI enhance passive ADCC and promote clearance of HSV1 infection by FcγR-bearing immune cells. Therefore, disclosed is an HSV vaccine that comprises a viral vector comprising the HSV Us7 and Us8 genes that encode gE and gI. These genes can be operably connected, collectively or independently, to an expression control sequence that promotes earlier and/or higher expression of gE and gI in infected cells to promote passive ADCC.

In some embodiments, the vector is an attenuated HSV vector. Methods to construct expression vectors containing genetic sequences and appropriate transcriptional and translational control elements are well established and described previously (Kambara, et al., 2005, *Cancer Res.* 65, 2832-9). These methods include in vitro recombinant DNA techniques, synthetic techniques, and in vivo genetic recombination. Such techniques are described in Sambrook et al., Molecular Cloning, A Laboratory Manual (Cold Spring Harbor Press, Plainview, N.Y., 1989), and Ausubel et al., Current Protocols in Molecular Biology (John Wiley & Sons, New York, N.Y., 1989).

Expression vectors generally contain regulatory sequences necessary elements for the translation and/or transcription of the inserted coding sequence. For example, the coding sequence is preferably operably linked to a promoter and/or enhancer to help control the expression of the desired gene product.

Promoters used in biotechnology are of different types according to the intended type of control of gene expression. They can be generally divided into constitutive promoters, tissue-specific or development-stage-specific promoters, inducible promoters, and synthetic promoters. An enhancer is a sequence of DNA that functions at no fixed distance from the transcription start site and can be either 5' or 3' to the transcription unit. Furthermore, enhancers can be within an as well as within the coding sequence itself. They are usually between 10 and 300 bp in length, and they function in cis. Enhancers function to increase transcription from nearby promoters. Enhancers also often contain response elements that mediate the regulation of transcription. Promoters can also contain response elements that mediate the regulation of transcription. Enhancers often determine the regulation of expression of a gene. While many enhancer sequences are now known from mammalian genes (globin, elastase, albumin, α-fetoprotein and insulin), typically one will use an enhancer from a eukaryotic cell virus for general expression. Preferred examples are the SV40 enhancer on the late side of the replication origin (bp 100-270), the cytomegalovirus early promoter enhancer, the polyoma enhancer on the late side of the replication origin, and adenovirus enhancers.

In preferred embodiments, the promoter is an immediate-early (IE) promoter, such as the cytomegalovirus (CMV) promoter/enhancer, or EF1a, CAG, SV40, PGK1, Ubc, human beta actin promoter, etc.

Treatment

The compositions disclosed can be used therapeutically in combination with a pharmaceutically acceptable carrier. By "pharmaceutically acceptable" is meant a material that is not biologically or otherwise undesirable, i.e., the material may be administered to a subject without causing any undesirable biological effects or interacting in a deleterious manner with any of the other components of the pharmaceutical composition in which it is contained. The carrier is selected to minimize any degradation of the active ingredient and to minimize any adverse side effects in the subject, as would be well known to one of skill in the art.

When the polypeptide or viral vector disclosed herein is prepared for administration, it can be combined with a pharmaceutically acceptable carrier, diluent or excipient to form a pharmaceutical formulation, or unit dosage form. The total active ingredients in such formulations include from 0.1 to 99.9% by weight of the formulation. A "pharmaceutically acceptable" substance is a carrier, diluent, excipient, and/or salt that is compatible with the other ingredients of the formulation, and not deleterious to the recipient thereof. The active ingredient for administration may be present as a powder or as granules; as a solution, a suspension or an emulsion.

The vectors or polypeptides (active ingredients) can be formulated and administered to treat a variety of disease states by any means that produces contact of the active ingredient with the agent's site of action in the body of the organism. They can be administered by any conventional means available for use in conjunction with pharmaceuticals, either as individual therapeutic active ingredients or in a combination of therapeutic active ingredients. They can be administered alone, but are generally administered with a pharmaceutical carrier selected on the basis of the chosen route of administration and standard pharmaceutical practice.

In general, water, suitable oil, saline, aqueous dextrose (glucose), and related sugar solutions and glycols such as propylene glycol or polyethylene glycols are suitable carriers for parenteral solutions. Solutions for parenteral administration contain the active ingredient, suitable stabilizing agents and, if necessary, buffer substances. Antioxidizing agents such as sodium bisulfate, sodium sulfite or ascorbic acid, either alone or combined, are suitable stabilizing agents. Also used are citric acid and its salts and sodium ethylenediaminetetraacetic acid (EDTA). In addition, parenteral solutions can contain preservatives such as benzalkonium chloride, methyl- or propyl-paraben and chlorobutanol. Suitable pharmaceutical carriers are described in Remington's Pharmaceutical Sciences, a standard reference text in this field.

Additionally, standard pharmaceutical methods can be employed to control the duration of action. These are well known in the art and include control release preparations and can include appropriate macromolecules, for example polymers, polyesters, polyamino acids, polyvinyl, pyrolidone, ethylenevinylacetate, methyl cellulose, carboxymethyl cellulose or protamine sulfate. The concentration of macromolecules as well as the methods of incorporation can be adjusted in order to control release. Additionally, the agent can be incorporated into particles of polymeric materials such as polyesters, polyamino acids, hydrogels, poly (lactic acid) or ethylenevinylacetate copolymers. In addition to being incorporated, these agents can also be used to trap the compound in microcapsules.

Pharmaceutical formulations containing the therapeutic agents disclosed herein can be prepared by procedures known in the art using well known and readily available ingredients. The therapeutic agents can also be formulated as solutions appropriate for parenteral administration, for instance by intramuscular, subcutaneous or intravenous routes. The pharmaceutical formulations of the therapeutic agents can also take the form of an aqueous or anhydrous solution or dispersion, or alternatively the form of an emulsion or suspension.

The herein disclosed compositions, including pharmaceutical composition, may be administered in a number of ways depending on whether local or systemic treatment is desired, and on the area to be treated. These parenteral (including subcutaneous, intravenous, intramedullary, intraarticular, intramuscular, or intraperitoneal injection), topical, transdermal, and oral. Administration may occur in a single dose or in repeat administrations. The vectors or polypeptides disclosed herein may be administered in combination with other therapeutic agents such as monoclonal antibodies and intravenous IgG.

As used herein the terms treatment, treat, or treating refers to a method of reducing the effects of a disease or condition or symptom of the disease or condition. Thus in the disclosed method, treatment can refer to a 10%, 20%, 30%, 40%, 50%, 60%, 70%, 80%, 90%, or 100% reduction in the severity of an established disease or condition or symptom of the disease or condition. For example, a method for treating a disease is considered to be a treatment if there is a 10% reduction in one or more symptoms of the disease in a subject as compared to a control. Thus the reduction can be a 10%, 20%, 30%, 40%, 50%, 60%, 70%, 80%, 90%, 100%, or any percent reduction in between 10% and 100% as compared to native or control levels. It is understood that treatment does not necessarily refer to a cure or complete ablation of the disease, condition, or symptoms of the disease or condition.

As used herein, the terms prevent, preventing, and prevention of a disease or disorder refers to an action, for example, administration of a therapeutic agent, that occurs before or at about the same time a subject begins to show one or more symptoms of the disease or disorder, which inhibits or delays onset or exacerbation of one or more symptoms of the disease or disorder. As used herein, references to decreasing, reducing, or inhibiting include a change of 10%, 20%, 30%, 40%, 50%, 60%, 70%, 80%, 90% or greater as compared to a control level. Such terms can include but do not necessarily include complete elimination.

The pharmaceutical compositions may be given following, preceding, in lieu of, or in combination with, other therapies in the subject. The subject may have been administered a vaccine or other composition in order to stimulate an immune response.

Methods of Making Polypeptides

A cell engineered to express the polypeptides disclosed herein is provided. The engineered cell can be propagated in cell culture (e.g., as opposed to being a part of a living animal ("in vivo")). For example, the cell may be a mammalian cell, e.g., a CHO cell or a human cell or a mouse hybridoma cell. Examples of other types of cells that may be used for expression the polypeptides disclosed herein include mouse myeloma cells (e.g., NSO), human embryonic kidney cells (e.g., HEK293), monkey kidney cells (e.g., COS), human epithelial carcinoma cells (e.g., HeLa), human fibrosarcoma cells (e.g., HT-1080), baby hamster kidney cells, yeast cells, insect cells, and others (see, e.g., Fernandez et al. (eds.) *Gene Expression Systems*, Academic Press, 1999). Any cell compatible with the disclosed polypeptides and appropriate culture conditions may be used.

Methods of making polypeptides, such as those that simultaneously bind an FcγR and an Fc binding domain protein, are known in the art. One method which may be employed is the method of Kohler, G. et al. (1975) *Continuous Cultures Of Fused Cells Secreting Antibody Of Predefined Specificity" Nature* 256:495-497 or a modification thereof. In one embodiment, the desired polypeptide which interacts with the immune effector cell or a protein present on the surface of an immune effector cell that expresses such an activating receptor are obtained using host cells that over-express such molecules.

Also disclosed are modifications to disclosed polypeptides that do not significantly affect their properties and variants that have enhanced or decreased activity. Modification of polypeptides is routine practice in the art and need not be described in detail herein. Examples of modified polypeptides include polypeptides with conservative substitutions of amino acid residues, one or more deletions or additions of amino acids which do not significantly deleteriously change the functional activity, or use of chemical analogs. Amino acid residues which can be conservatively substituted for one another include but are not limited to: glycine/alanine; valine/isoleucine/leucine; asparagine/glutamine; aspartic acid/glutamic acid; serine/threonine; lysine/arginine; and phenylalanine/tryosine. These polypeptides also include glycosylated and nonglycosylated polypeptides, as well as polypeptides with other post-translational modifications, such as, for example, glycosylation with different sugars, acetylation, and phosphorylation. Preferably, the amino acid substitutions would be conservative, i.e., the substituted amino acid would possess similar chemical properties as that of the original amino acid. Such conservative substitutions are known in the art, and examples have been provided above. Other methods of modification include using coupling techniques known in the art, including, but not limited to, enzymatic means, oxidative substitution and chelation. Modifications can be used, for example, for attachment of labels for immunoassay, such as the attachment of radioactive moieties for radioimmunoassay. Modified polypeptides are made using established procedures in the art and can be screened using standard assays known in the art.

The invention also encompasses fusion proteins comprising one or more fragments or regions from the disclosed polypeptides. In one embodiment, a fusion polypeptide is provided that comprises at least 10 contiguous amino acids of an IgG Fc region.

Polypeptides of the invention may be conveniently prepared using solid phase peptide synthesis (Merrifield, B. (1986) "Solid Phase Synthesis," *Science* 232(4748):341-347; Houghten, R. A. (1985) General Method For The Rapid Solid-Phase Synthesis Of Large Numbers Of Peptides: Specificity Of Antigen-Antibody Interaction At The Level Of Individual Amino Acids" *Proc. Natl. Acad. Sci.* (USA.) 82(15):5131-135; Ganesan, A. (2006) "Solid-Phase Synthesis In The Twenty-First Century" *Mini Rev. Med. Chem.* 6(1):3-10).

Vectors containing polynucleotides that encode the disclosed polypeptides can be introduced into a host cell by any of a number of appropriate means, including electroporation, transfection employing calcium chloride, rubidium chloride, calcium phosphate, DEAE-dextran, or other substances; microprojectile bombardment; lipofection; and infection (e.g., where the vector is an infectious agent such as vaccinia virus). The choice of introducing vectors or polynucleotides will often depend on features of the host cell.

Any host cells capable of over-expressing heterologous DNAs can be used for the purpose of isolating the genes encoding the disclosed polypeptides. Non-limiting examples of suitable mammalian host cells include but are not limited to COS, HeLa, and CHO cells.

A number of embodiments of the invention have been described. Nevertheless, it will be understood that various modifications may be made without departing from the spirit and scope of the invention. Accordingly, other embodiments are within the scope of the following claims.

EXAMPLES

Example 1: A Novel Function of Immunoglobulin G in Immune Recognition

Materials and Methods

Viruses, Bacteria, Antibody and Proteins.

HSV1 F strain was purchased from ATCC, Manassas, Va. Generating Us8 deficient HSV1 F was described previously (Suenaga et al., 2014, *Microbiology and Immunology* 58, 513-522). R8411, a HSV1 F strain which expresses luciferase was provided by Bernard Roizman (Zerboni et al., 2013, *J Virol* 87, 2791-2802). Wild type (WT) newman strain (ATCC, 25904) and protein A deficient (Spa-) newman were a gift from Dr Timothy Frost (Dublin, Ireland), and grew in tryptic soy broth (Patel et al., 1987, *Infect Immun* 55, 3103-3110). Antibody specific for CD3(HIT3a), CD14 (M5E2), CD19(HIB19), CD56 (N901), CD16a (3G8), CD253 (RIK2), CD69 (FN50), CD62L (DREG56), CD107a (H4a3), CD3ζ (pY142) (K25-407.69), CD3ζ (6B10.2), CD3 (17A2), CD62L (MEL-14), CD27 (LG.3A10) CD69 (H1.2F3), NKp46 (29A1.4), Anti-HSV1 gE (9H3), Anti-HSV1 gC (1C8), and Anti-HSV1 gB (T111) were purchased from BD Biosciences, Franklin Lakes, N.J.; Biolegend, San Diego, Calif.; Beckman Coulter, Brea, Calif.; Abcam, Cambridge, Mass.; R&D Systems, Minneapolis, Minn.; Sigma-Aldrich, St. Louis, Mo.; and Millipore, Burlington, Va. Anti-HSV1 gD (ID3) was provided by Roselyn J. Eisenberg and Gary Cohen. Anti-HSV1 gE (9H3) was purchased from Abcam. Biotinylated CD16a and HuIgG1 Fc was purchased from Sino Biological, Beijing, China, IgG1Fc(ΔCD16) was made by cloning human IgG1 Fc aa262-466 (SEQ ID NO: 2) into a pFuse vector (InvivoGen, San Diego, Calif.) after IL2 signal peptide, expressed in BHK cells and purified using protein A agarose beads (Thermofisher). Pooled human IgG (GamaStan, Grifols USA, Los Angeles, Calif.), which contains HSV1 specific antibody, was purchased from Ohio State University pharmacy, Columbus, Ohio.

Human IgG Fc (12724, Scripps Laboratories, San Diego, Calif.) was validated as containing no Fab, and did not bind cells infected with Us8-HSV1 viruses. Rituximab (Genentech, South San Francisco, Calif.) and Darzalex (Janssen Pharmaceuticals, Fremont, Calif.) were purchased from Ohio State University pharmacy.

Cloning of HSV1 Genes.

Individual HSV1 genes were amplified from HSV1 F strain DNA (sequence accession number: GU734771) with gene specific primers, which are flanked with SpeI site at the 5' and PacI site at the 3' end, respectively (e.g., SEQ ID NOs: 25, 27-170), and cloned into a pCDH vector (System Bioscience, Palo Alto, Calif., CD510B) using conventional methods.

Culture and Transfection of Human Glioma Spheres.

Glioma cells were derived from primary human brain tumors and grown in DMEM/F12 (Life Technology, Carlsbad, Calif.) supplemented with B27 (1:50), heparin (5 ug/mL), basic FGF (bFGF) (20 ng/mL), and EGF (20 ng/mL) as described previously (Mao et al., 2013, *Proc Natl Acad Sci USA* 110, 8644-8649). Except as noted otherwise, #83 glioma cells were used throughout this study (Mao et al., 2013, *Proc Natl Acad Sci USA* 110, 8644-8649). For one single transfection, ten million glioma cells were washed once with DMEM/F12 media, and resuspended in 100 μl of basic nucleofector solution (Lonza Inc., Allendale, N.J.). Subsequently, the cell suspension was mixed with 6 μg of plasmid expressing HSV1 genes and nucleofected using program A33 (Amaxa GmBH, Koeln, Germany). Following nucleofection, cells were immediately mixed with 1 ml media and transferred into one well of 6-well plates containing 4 ml DMEM/F12 with all supplements.

Differential Cytolysis Mediated by Ectopic Gene Expression.

24 h after transfection, glioma cells were resuspended and centrifuged down at 50 g for 5 min to remove cell debris and dead cells. Subsequently, $1 \times 10^4$ glioma cells were resuspended with 100 μl DMEM/F12 media and seeded into each well of a U bottom 96-well plate. Purified human NK cells were resuspended in RPMI media (Life Technology, Carlsbad, Calif.) supplemented with 10% heat inactivated FBS (Sigma-Aldrich, St. Louis, Mo.) to a final concentration of $5 \times 10^6$/ml of media, and 100 μl of NK cells were added to culture with transfected glioma cells. In a parallel control experiment, 100 μl RPMI 1640 media supplemented with 10% FBS, instead of human NK cells, was added to the seeded glioma cells. Culture samples were collected using LSRII (BD Biosciences, Franklin Lakes, N.J.) at 5 h of culture. Living glioma cells were gated in based on their forward scatter (FSC) and side scatter (SSC) and measured for the percentage of GFP+ cells.

Differential cytotoxicity contributed by the expression of individual viral gene was calculated with the formula:

$$\Delta GFP = \frac{GFP\ \%(+nk) - GFP\ \%(-nk)}{GFP\ \%(-nk)} * 100\%,$$

wherein
ΔGFP=change in GFP;
GFP %(+nk)=percentage of GFP in presence of NK cells;
GFP %(−nk)=percentage of GFP in absence of NK cells Virus Production, Purification and Inactivation.

Vero cells were seeded at a density of $7 \times 10^6$ cells per 100 mm dish and inoculated with 2.5 pfu per cell of HSV-1 F strain or #30 mutants (Suenaga et al. 2014, *Microbiology and Immunology* 58, 513-522). At 24 hours post-inoculation, culture media and cell debris were collected. After three freeze-thaw cycles to release virus, cell debris was removed by low speed centrifugation (2,000×g for 5 minutes), samples were loaded on a 5 ml 35% sucrose gradient and centrifuged in a Beckman SW27 rotor at 25,000 rpm for 1 hour. Virus pellet was collected, washed and concentrated in PBS. To inactivate viruses, purified HSV1 viruses were treated with 0.2% Trition-100 for 30 min. Inactivated viruses were diluted to 0.1 ug/ml for coating plates.

Plaque Assay.

Briefly, sequentially diluted viruses were loaded on single layer of Vero cells and incubated at 37° C.; pooled human IgG (final concentration 0.1%) was added 1 h later to restrain viral spread. Plaques were counted after 48 h culture. To determine the effect of human IgG3, human IgG Fc, Rituximab, daratumumab, and human IgG on the infectivity of HSV1, 1 ug/ml of these reagents were added into sequentially diluted viruses and incubated at room temperature for 30 min prior to a plaque assay. Treated viruses were tittered with standard plaque assay and all results were normalized to PBS control.

Human NK Cell Isolation and Stimulation Condition.

All NK cells used herein were freshly enriched from peripheral blood leukopacks of healthy donors (American Red Cross, Columbus, Ohio) using RosetteSep cocktail (StemCell Technologies, Cambridge, Mass.) as previously described (Yu et al. 2010, *Blood* 115, 274-281). A half million isolated human NK cells were incubated with media, or media supplement with 5 ug/ml protein A or protein G for 30 min prior to stimulation. $1 \times 10^5$ infected or transfected glioma cells, or K562 cells were used in the culture with $5 \times 10^5$ NK cells. For all CD107a staining, CD107a antibody was added at the beginning of the cell culture. Flat 96 well plates (MaxiSorp, Thermo Fisher Scientific, Waltham, Mass.) were coated with 50 ul protein A (0.1 ug/ul), protein G (0.1 ug/ul), or wt or Us8-HSV1 F (0.1 ug/ul) overnight at 4 C°.

Chromium Release Cytotoxicity Assay.

Glioma cells were labeled by incubating $5 \times 10^5$ cells in 50 µCi $^{51}$Cr for 90 min at 37° C. Radiolabeled cells were washed 3 times and resuspended in complete RPMI 1640 media, and seeded in U bottom 96-well plates in triplicates at a concentration of $5 \times 10^4$ cells/ml. In some cases, antibodies or IgG products (5 ug/ml) were added into radiolabeled target cells and incubated on ice for 30 minutes for binding or blocking certain interactions. Effector cells were added in specified effector-to-target ratios (E:T, x-axis on FIG. 1D) and incubated at 37° C. for 4-6 hours. Cytolysis was then measured and calculated as previously described (Dai et al., 2017, *Immunity*, 47, 159-170)).

CD3ζ Phosphorylation Staining.

One-half million NK cells were rested at 37° C. for 1 h and then stimulated with $H_2O_2$ (11 mM), IL12(10 ng/ml)+IL18(10 ng/ml), $2 \times 10^5$ transfected glioma cells, or $1 \times 10^8$ cfu of bacteria for 1 h. NK cells were fixed using Phosflow Fix Buffer I (BD), permeabilized with Phosflow™ Perm Buffer III (BD Biosciences, Franklin Lakes, N.J.), blocked with normal mouse immunoglobulin, and then stained with anti-CD3ζ (pY142) and anti CD3ζ antibodies. Phosphatase inhibitor (Roche, South San Francisco, Calif.) was supplemented in all the staining steps.

Modeling Structure of gE-Fc-CD16a Complex and Protein A-Fc-CD16a Complex.

Docking predictions for gE-Fc (RCSB Protein Data Bank ID: PDB ID: 2GJ7) and CD16a-Fc (RCSB Protein Data Bank ID: PDB ID: IE4K) were conducted on the ZDOCK online server. For gE-Fc, only the gE subunits were uploaded to the server, and residues 225, 245-247, 249-250, 256, 258, 311, 316, 318-322, 324, and 338-342 were specified as contact residues (Patel et al., 1987, *Infect Immun* 55, 3103-3110). In the case of CD16a-Fc, residues 252-258, 307, 309-311, 314-315, 382, 428, and 433-436 on Fc (SEQ ID NO: 11) were specified as contact residues (Patel et al., 1987, *Infect Immun* 55, 3103-3110).

CD16a Binding.

Transfected glioma cells or bacteria were first incubated for 30 min on ice with PBS with or without IgG1Fc (ΔCD16), IgG1Fc (Scripps Laboratories, San Diego, Calif.), rituximab, or hu IgG (GamaStan, Grifols), respectively. After one wash with FACS buffer, samples were incubated on ice with biotinylated CD16a, and 20 minutes later apc-streptavidin (BD Biosciences, Franklin Lakes, N.J.) was added and samples were kept on ice for another 20 min. After two washes with FACS buffer, cells or bacteria were immediately checked on LSRII flow cytometer (BD Biosciences, Franklin Lakes, N.J.).

Mouse Experiments.

8-to-12 weeks old female C57BL/6 and BALB/c mice (Jackson Laboratory, CITY) were used for all the studies. For survival studies, BALB/c mice were injected intraperitoneally (i.p.) with $3 \times 10^6$ pfu HSV1 F strain virus. PBS, 200 µg human IgG3 (Sigma-Aldrich, St. Louis, Mo.), 200 ug human IgG Fc (Scripps Laboratories, San Diego, Calif.), 200 µg Rituximab or 200 µg Darzalex were given via i.p. injection at 4 hours prior to virus challenge, and at 24 hours and 72 hours after virus challenge. For bioluminescence imaging to track virus load, BALB/c mice were injected i.p with $1.2 \times 10^5$ pfu of R8411 virus (Zerboni, L. et al. *J Virol* 87, 2791-2802 (2013)). To study the clearance of HSV1 by human IgG1, BALB/c mice were injected i.p with 200 µg rituximab at 4 hours prior to virus challenge, and at 24 hours after virus challenge. Each mouse was given 3 mg luciferin potassium 10 minutes prior to isoflurane anesthesia to ensure consistent photon flux. Images were taken using an IVIS Spectrum (Perkin Elmer, Waltham, Mass.) at 18 h and 84 h post infection. Each group was recorded for 4 sections of 2 minute exposure. Bioluminescence values were measured from the whole mouse and calculated as photon flux (photons/s) using Living Image 4.0 (Perkin Elmer, Waltham, Mass.). To study the effect of protein A on NK cells in vivo, mice were injected intravenously (i.v.) with 40 µg silicone beads and protein A conjugated beads (AlphaBio, Racho Santa Margarita, Calif.). 24-48 h after beads completed this inoculation, blood, spleen and lung were collected and mononuclear cells were isolated from these tissues and stained using antibodies against mouse antigens. For in vitro mouse NK cell stimulation and cytotoxicity, NK cells were enriched from spleens of 8 to 12 weeks old C57BL/6 and BALB/c mice using an NK cell isolation kit (Miltenyi Biotec, Cambridge, Mass.) following manufacturer's instruction.

Statistics.

Two-sample t test was used to compare two independent groups and paired t test was used to compare two paired groups. Data transformation was performed if the original distribution was non-normal. Linear mixed models were used to account for the covariance structure due to repeated measures from the same donor when three or more groups were compared. P values were adjusted for multiple comparisons by Holm's procedure. A p value of <0.05 was considered significant. Experiments were repeated at least three or more times. Data are displayed as mean±SEM.

Results

Differential Cytolysis Mediated by Ectopic Gene Expression (DC-MEGE) Identified HSV1 gE as a Human NK Cell Activator.

Figure 1B:
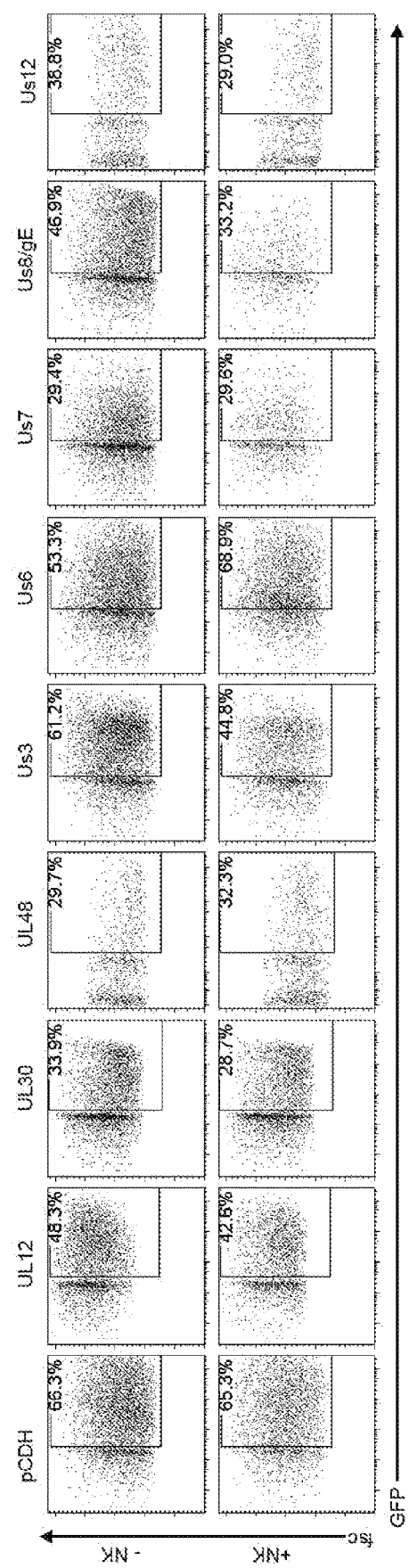
Figure 1C:
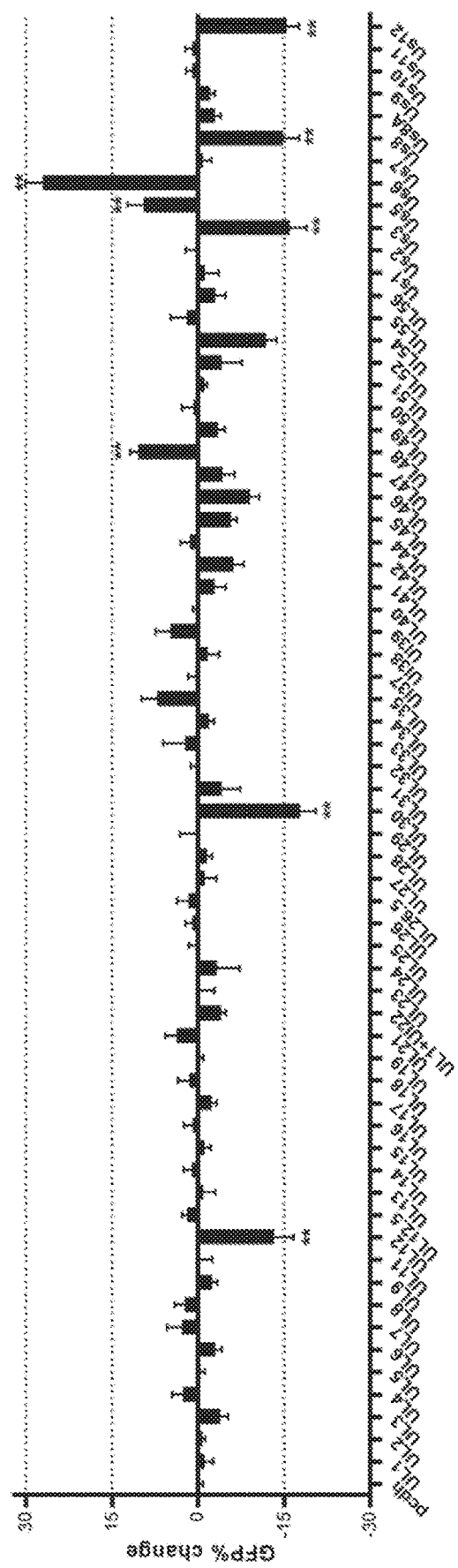
Figure 1D:
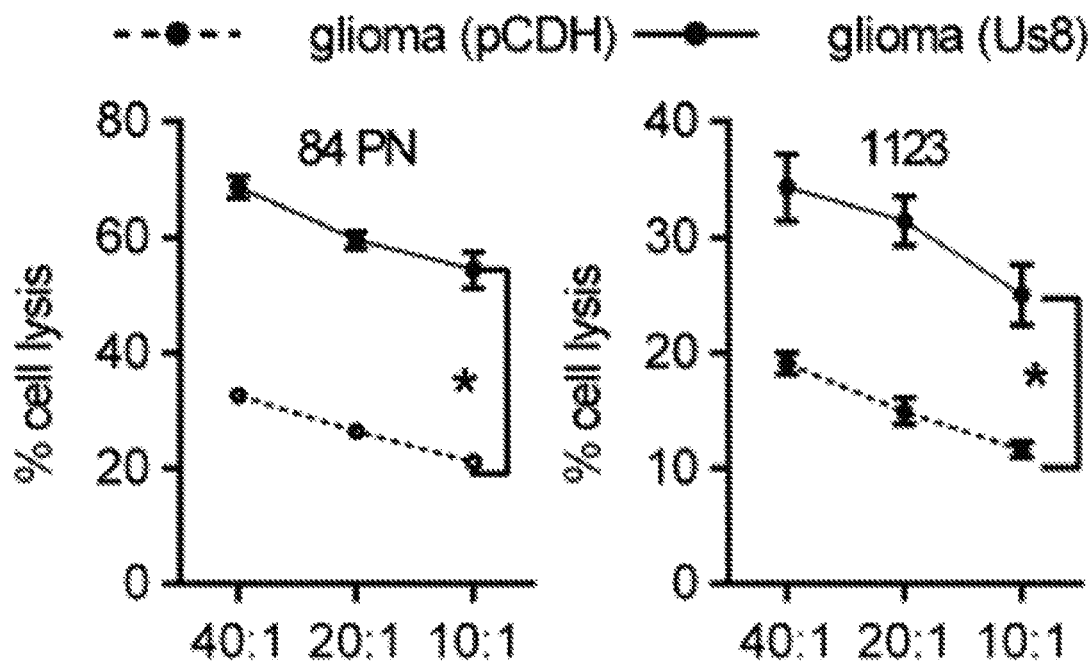

The HSV1 genome contains 84 open reading frames, encoding 74 unique viral proteins (Szpara et al., 2010, *J Virol* 84, 5303-5313), however very few of them have been studied for their roles in immune recognition or evasion (Imai et al., 2013, *PLoS One* 8, e72050; Chisholm et al., 2007, *The Journal of Infectious Diseases* 195, 1160-1168; Huard & Fruh, 2000, *Eur J Immunol* 30, 509-515). To gain a comprehensive understanding of the interaction between human NK cells and HSV1, DC-MEGE were developed to measure how NK cells respond to glioma cells expressing a single HSV1 gene (FIG. 1A). Each HSV1 gene was cloned upstream of the "self-cleaving" T2a sequence and green fluorescence protein (GFP); as a consequence, fluorescence reveals expression of viral proteins (Szymczak et al., 2004, *Nat Biotechnol* 22, 589-594). Glioma cells were transfected with an individual HSV1 gene, and subsequently cultured with or without fresh human NK cells. The percentage of GFP+ living glioma cells were recorded in parallel as GFP(+NK) % when NK cells are present, or GFP(−NK) % when glioma cells are cultured alone. When expression of a HSV1 viral protein made glioma cells susceptible to NK cell cytolysis, GFP+ glioma cells were preferably killed by NK cells, therefore, GFP(+NK) % would be less than GFP(−NK) %, or vice versa when HSV1 viral protein made glioma cells resistant to NK cell cytolysis (FIG. 1A). Applying the DC-MEGE assay, 65 HSV1 genes were screened, demonstrating that glioma cells expressing UL12, UL30, Us3, Us8 and Us12 were more susceptible to NK cell cytolysis, while expression of UL48, Us5, or Us6 made glioma cells resistant to NK cell cytolysis (FIGS. 1B and 1C).

Figure 1E:
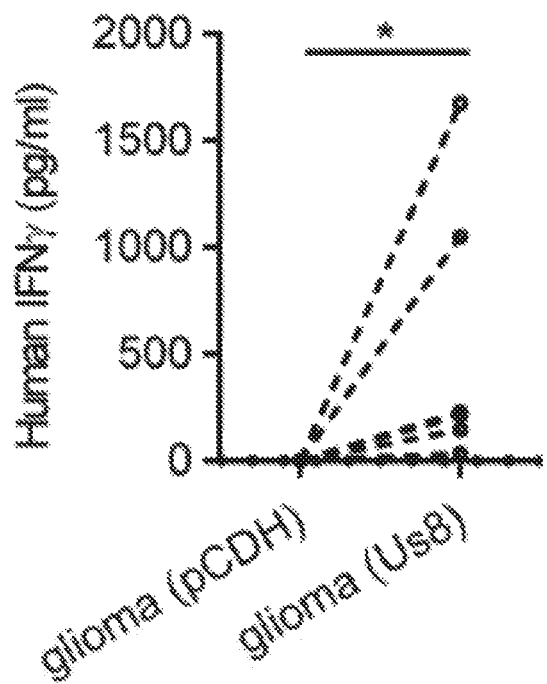
Figure 1F:
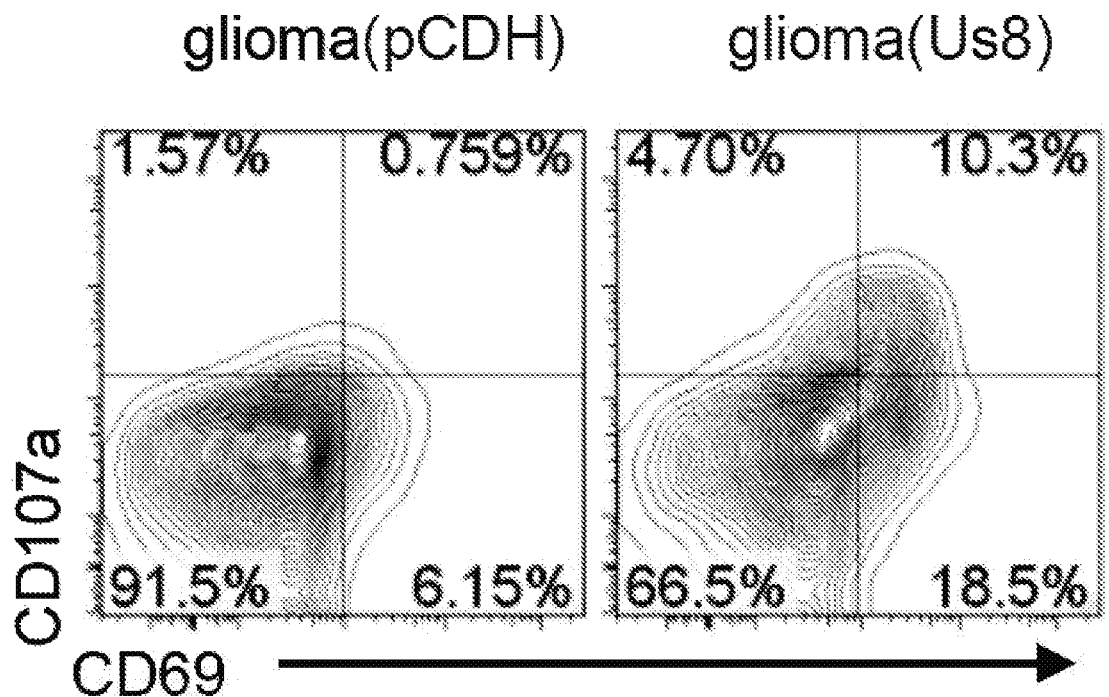
Figure 1G:
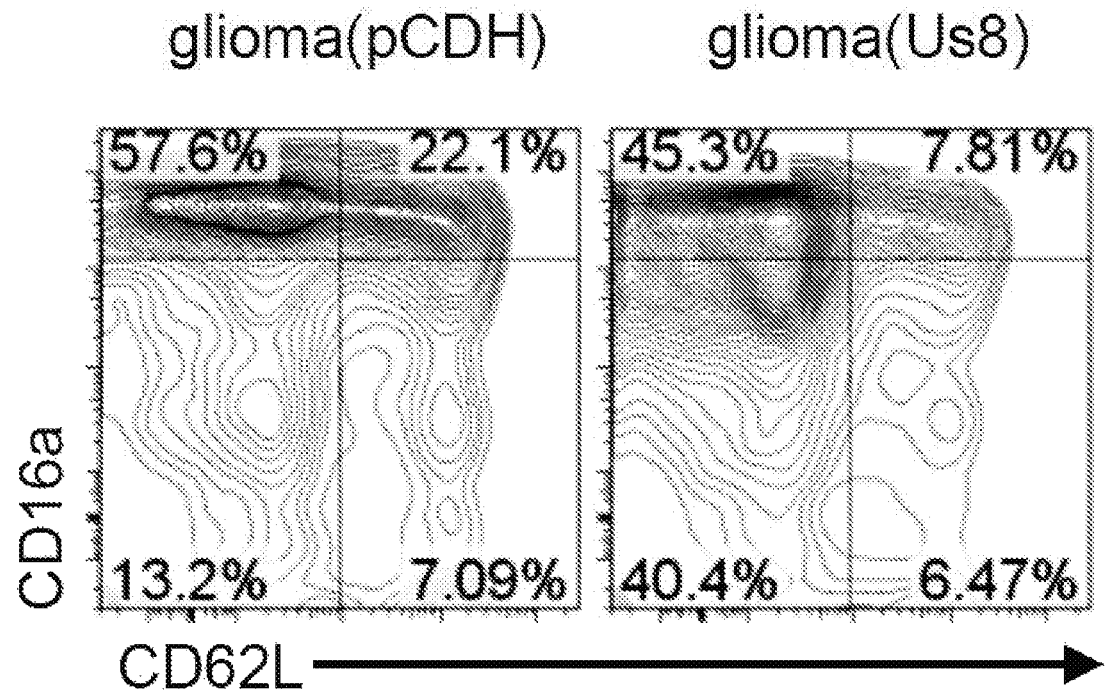
Figure 1H:
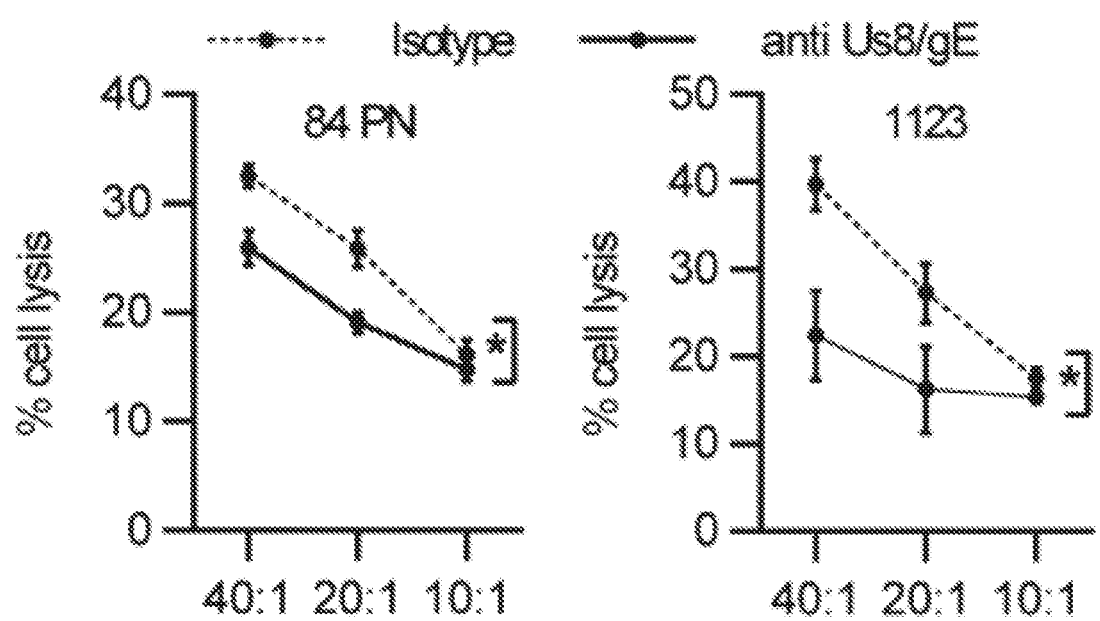
Figure 6:
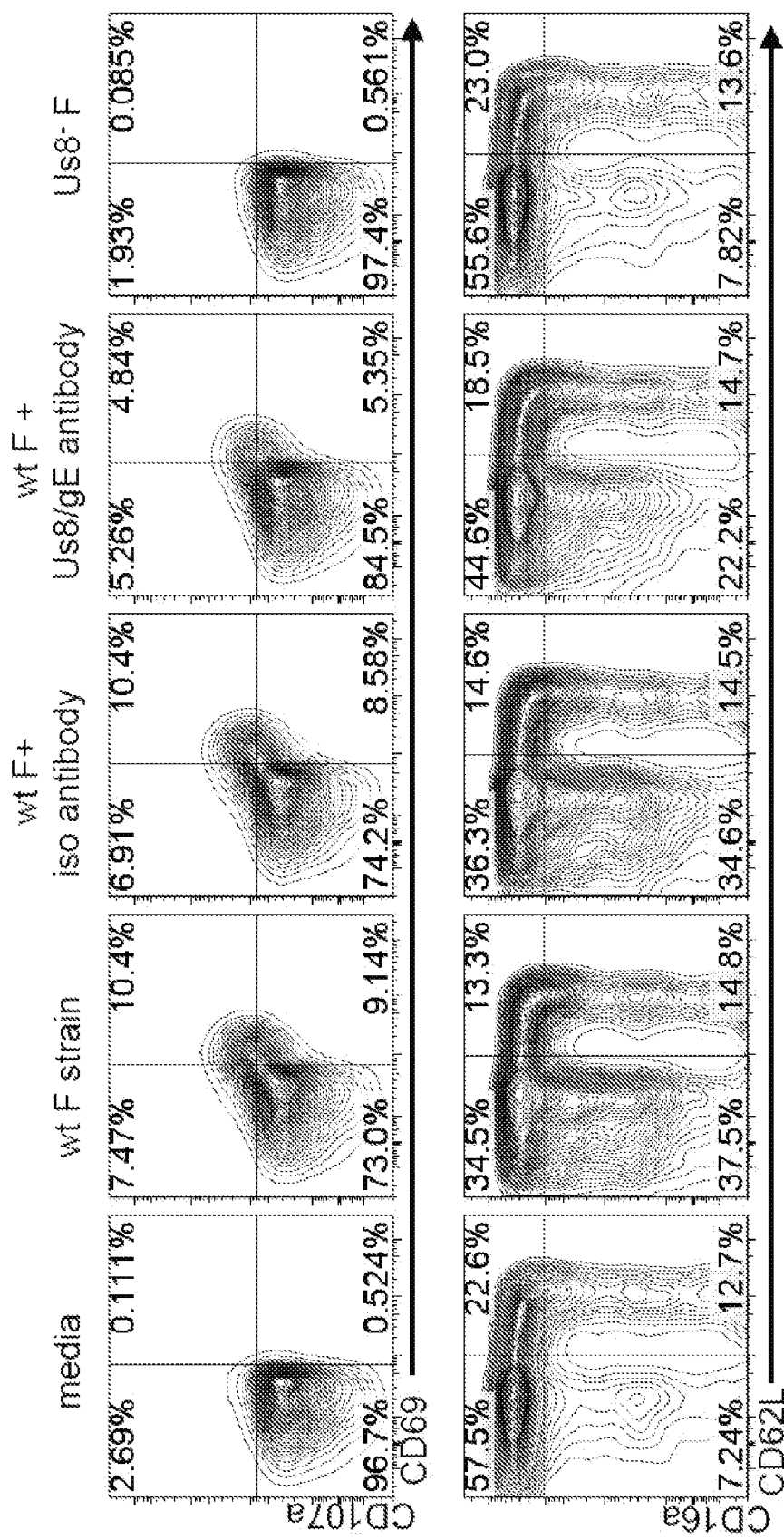
FIG. 6 shows the phenotype of primary human NK cells after culture for 7 hours in plates coated with inactivated pure wild type or Us8-deficient HSV1 F strain viruses. Isotype or Us8/gE-specific antibody was added to interfere with the interaction between NK cells and coated F strain viruses. Representative contour staining of 7 donors is shown.

HSV1 Us8 encodes gE, which alone is a low affinity human IgG Fc receptor, binding human IgG1, IgG2 and IgG4 at the CH2-CH3 interface (Sprague et al., 2006, *PLoS Biol* 4, e148). DC-MEGE results were validated using a $^{51}$Cr release assay against a human mesenchymal glioma cell line #1123 and a human proneural glioma cell line #84 (Mao et al., 2013, *Proc Natl Acad Sci USA* 110, 8644-8649), shown in FIG. 1D. Glioma cells expressing Us8 (referred as glioma Us8 hereafter) also induced human primary NK cells to secret IFN-γ (FIG. 1E), express CD69 and CD107a (FIG. 1F), and cleave CD62L and CD16a (FIG. 1G), which are characteristic phenotypes of activated human NK cells. NK cytotoxicity towards glioma Us8 was attenuated by a gE specific mouse monoclonal antibody (Abcam) (FIG. 1h). Wild type (wt) HSV1 F strain viruses (of which gE is a major protein component) and a mutant HSV1 F strain with targeted-deletion of Us8 (Us8$^-$) (Suenaga et al., 2014, *Microbiology and Immunology* 58, 513-522) were purified. NK cells were cultured in plates coated with inactivated pure viruses. NK cells were only activated by wild-type (wt) but not Us8$^-$ F strain viruses (FIGS. 1I, 6), and activation of NK cells by wt HSV1 was also inhibited by the anti-Us8 antibody (FIGS. 1I, 6). Taken together, these results demonstrated that direct interaction between gE and human NK cells contributed to the functional enhancement of NK cells.

Human IgG Links gE and NK Cell Activation.

Figure 7:
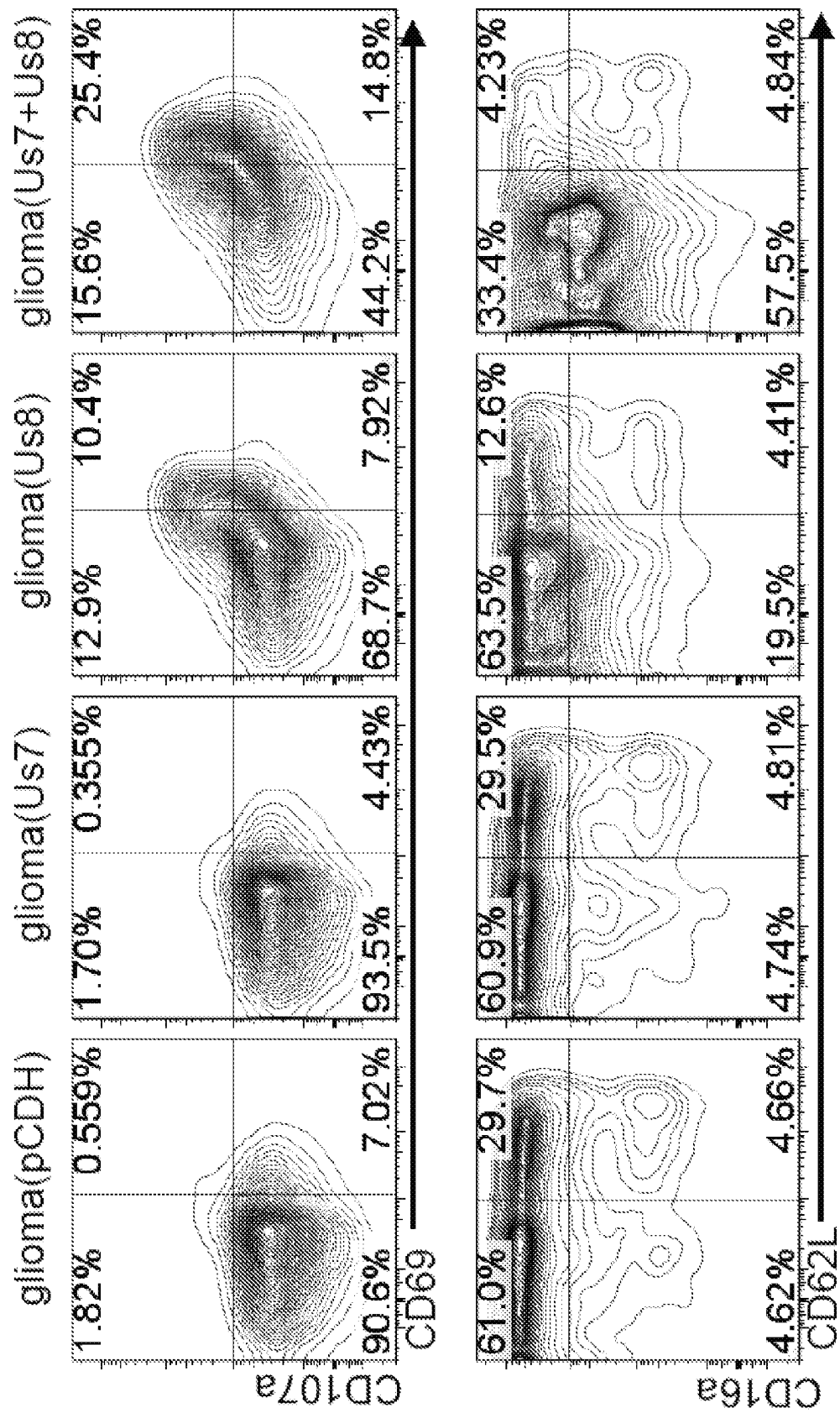
FIG. 7 shows the phenotype of primary human NK cells after being cultured for 7 hours with glioma cells expressing different HSV1 genes. A representative contour plot from one of 8 donors is shown.

HSV1 gE can form heterodimers with glycoprotein I (gI), encoded by HSV1 Us7, and the resultant gE/gI complex is the high affinity viral Fc receptor for human IgG (Sprague et al., 2006, *PLoS Biol* 4, e148; Johnson et al., 1988, *J Virol* 62, 1347-1354). Glioma cells expressing Us7 (glioma Us7, hereafter) did not activate NK cells (FIGS. 1B, 1C, 2A, 2B); however, glioma cells expressing both Us7 and Us8 (glioma Us7+Us8) activated NK cells much more potently than glioma Us8 (FIGS. 2A 2B, 7), suggesting IgG-binding function of gE may be involved in NK cell activation.

Figure 2A:
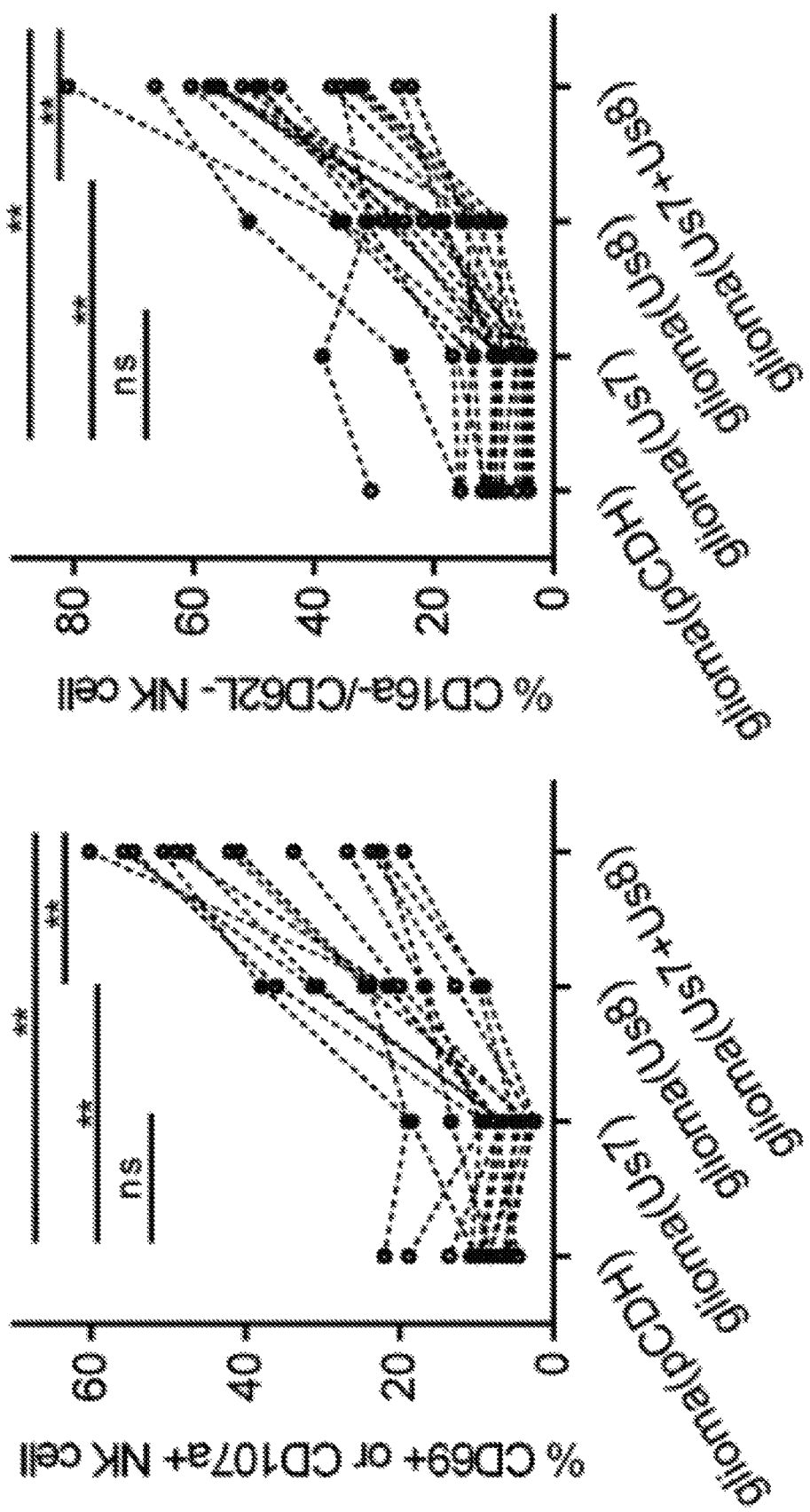
FIGS. 2A to 2G show IgG-linked gE and NK cell activation.
Figure 2B:
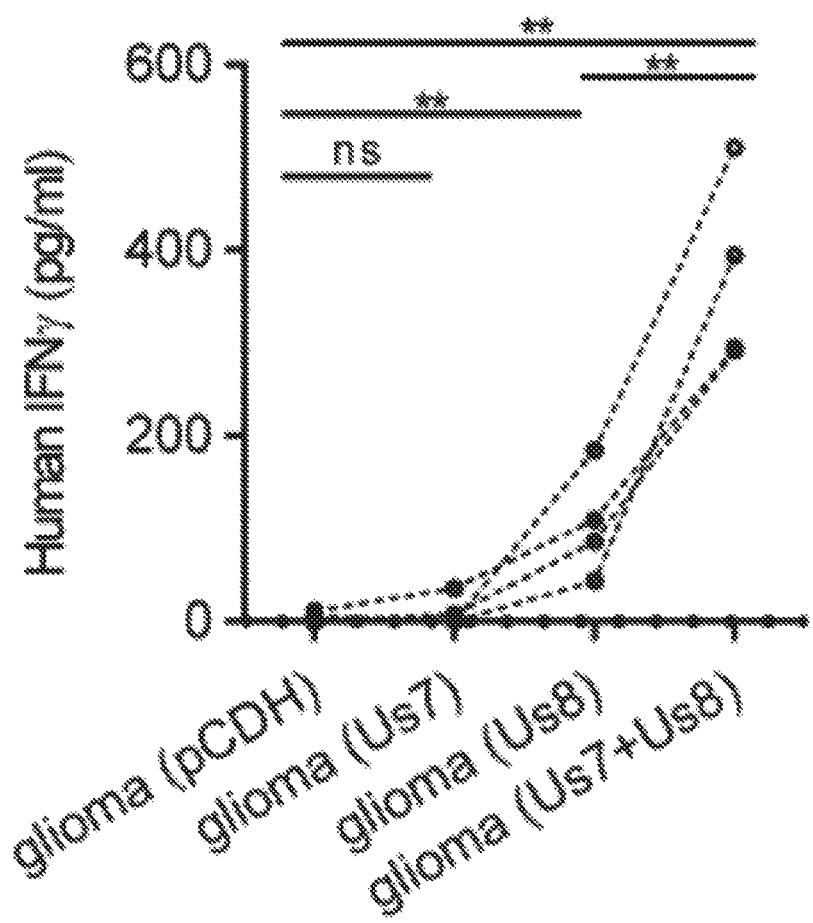
Figure 2C:
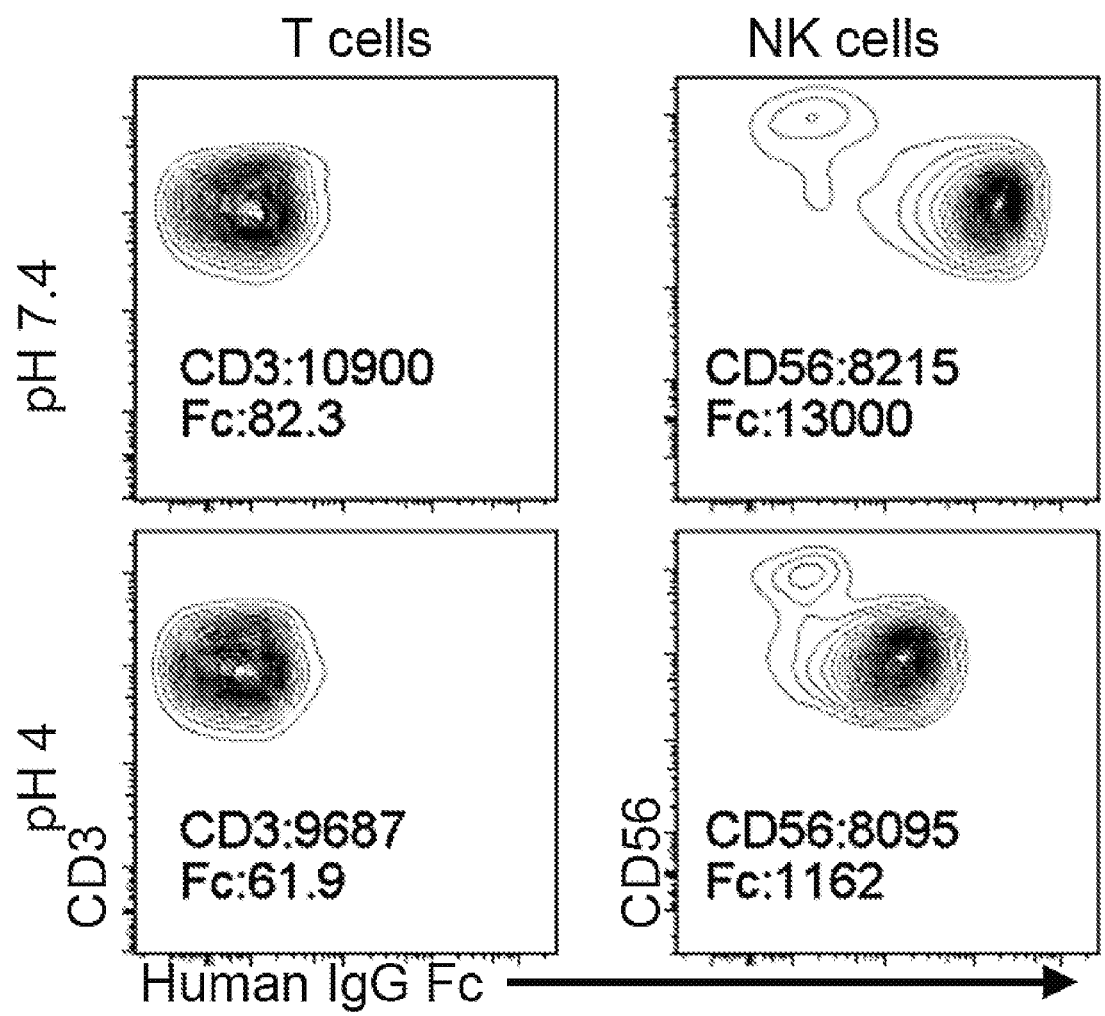
Figure 2D:
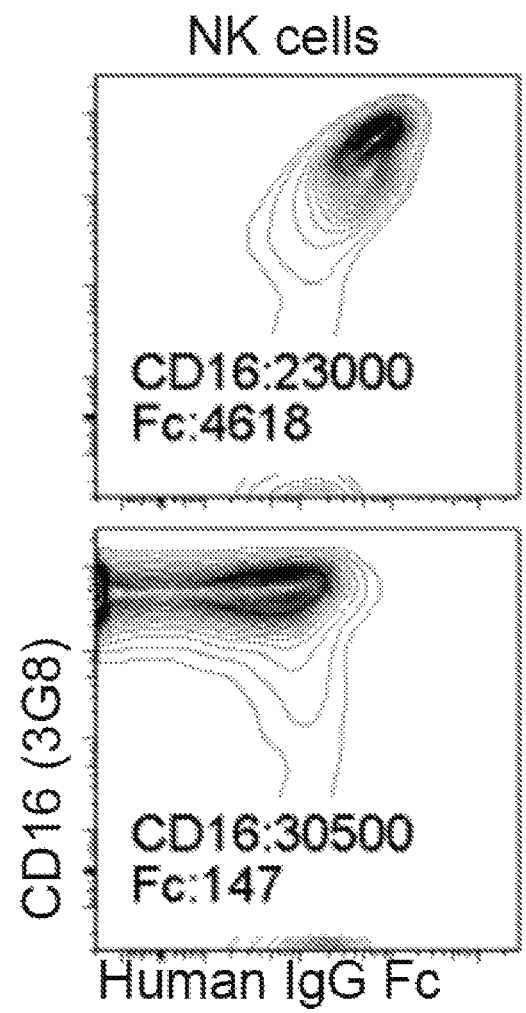
Figure 2E:
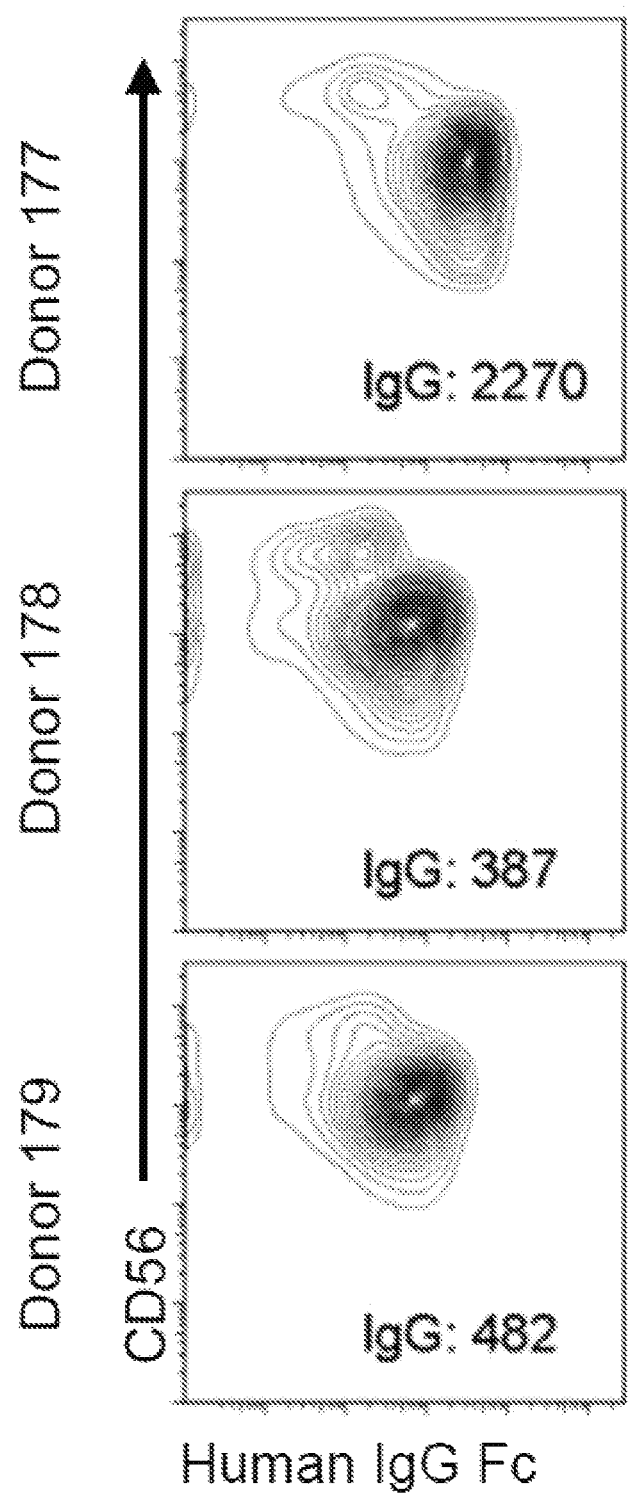
Figure 2F:
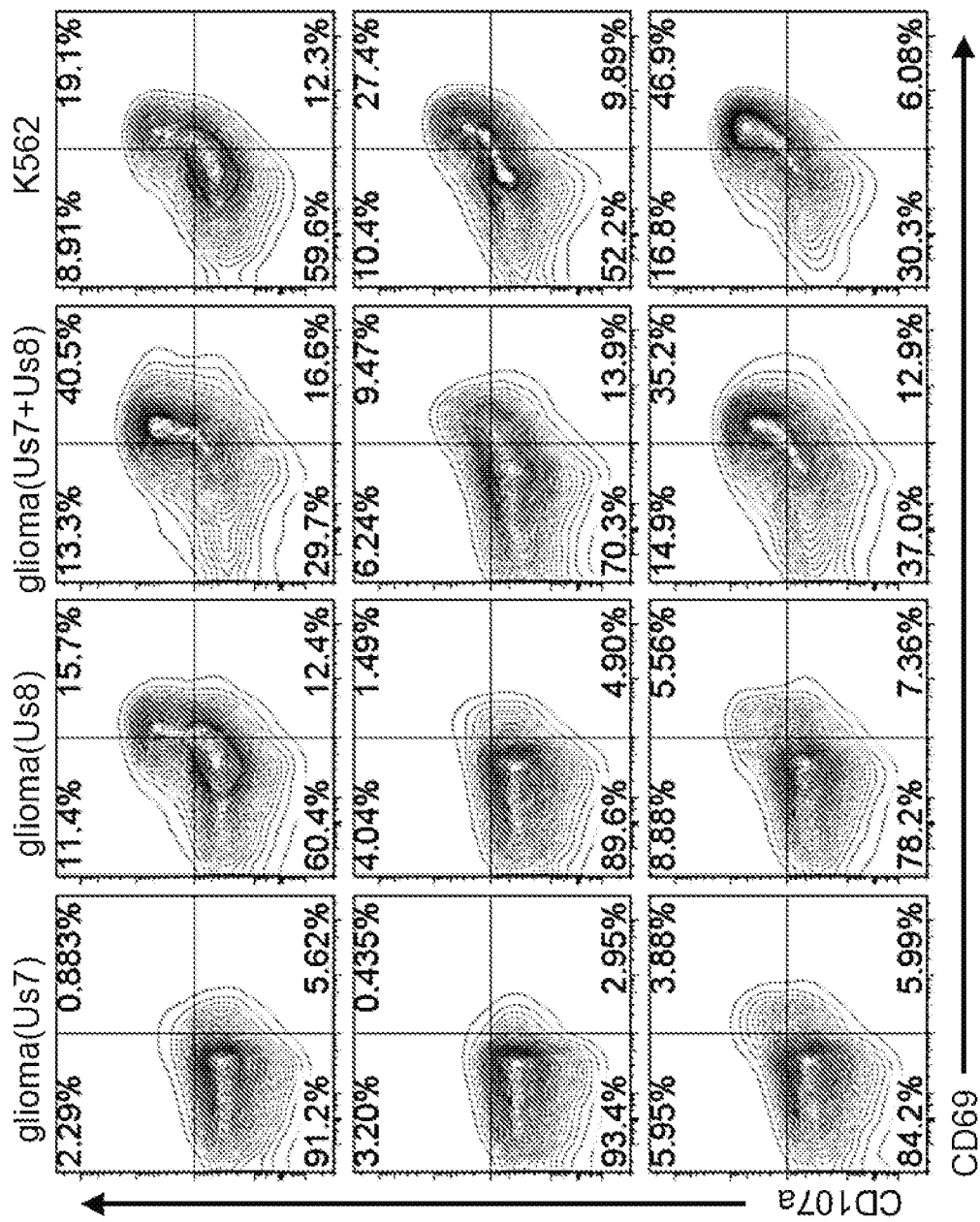
Figure 2G:
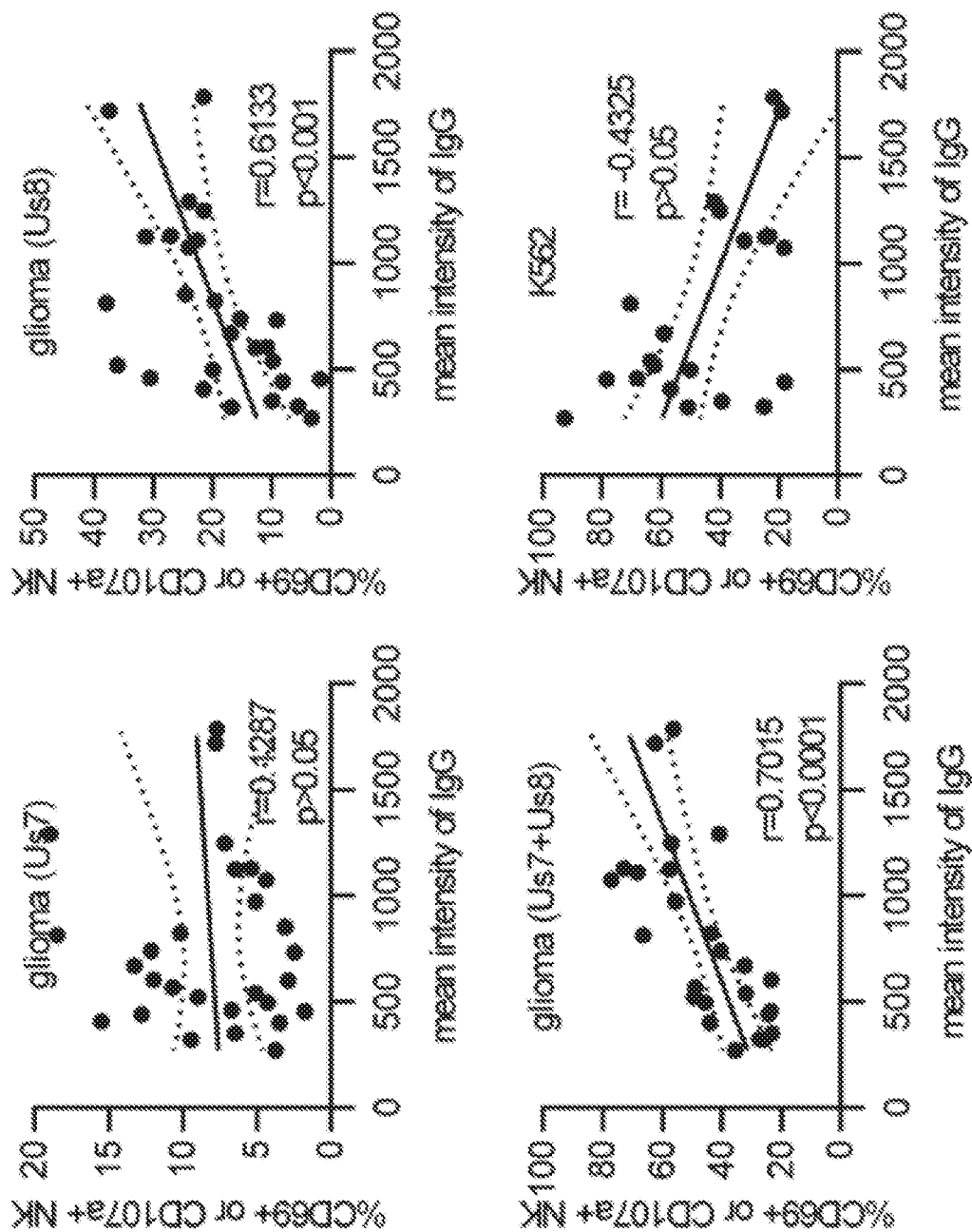
Figure 8:
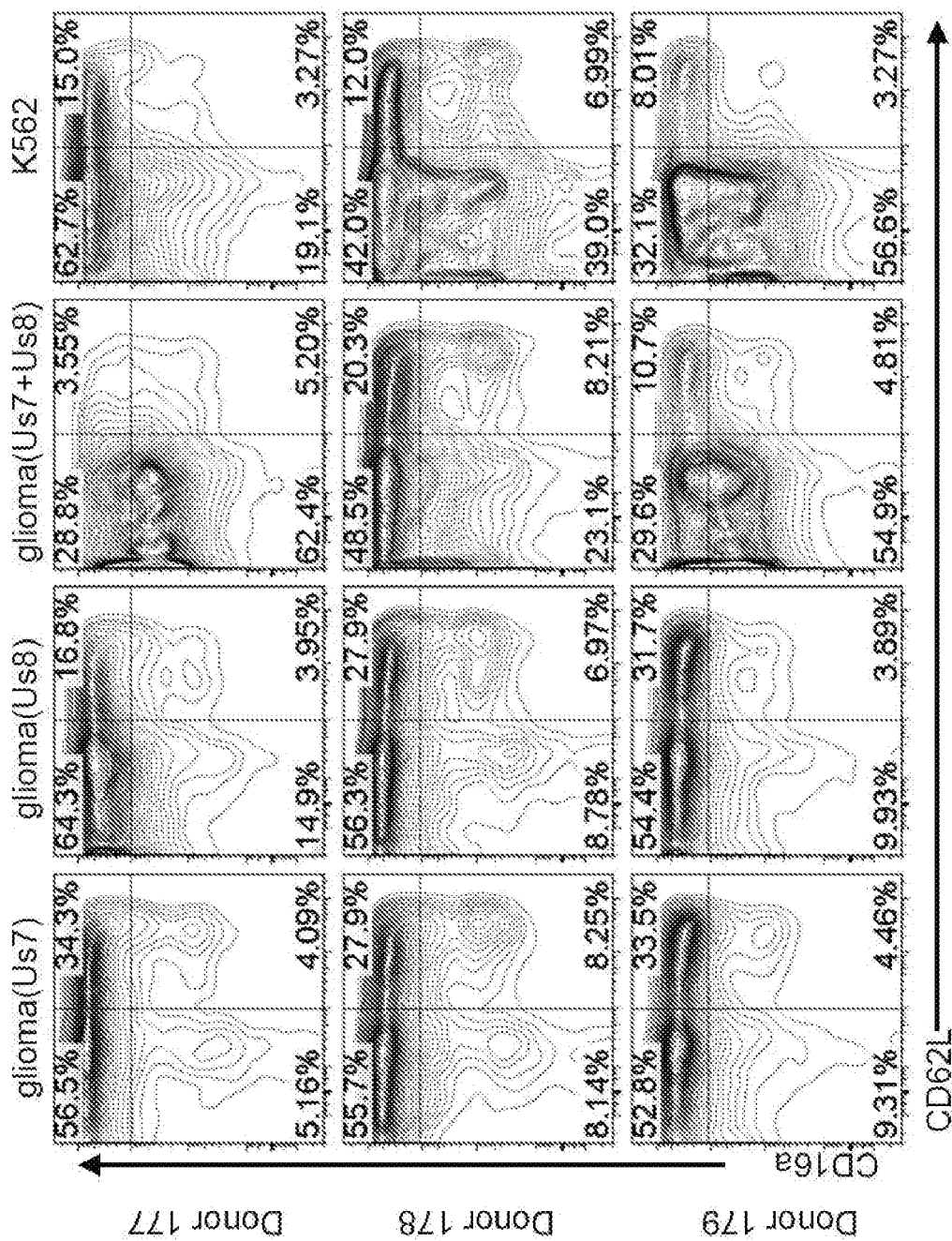
FIG. 8 shows the phenotype of NK cells from different donors after being cultured for 7 hours with transfected glioma cells or K562 cells.
Figure 27A:
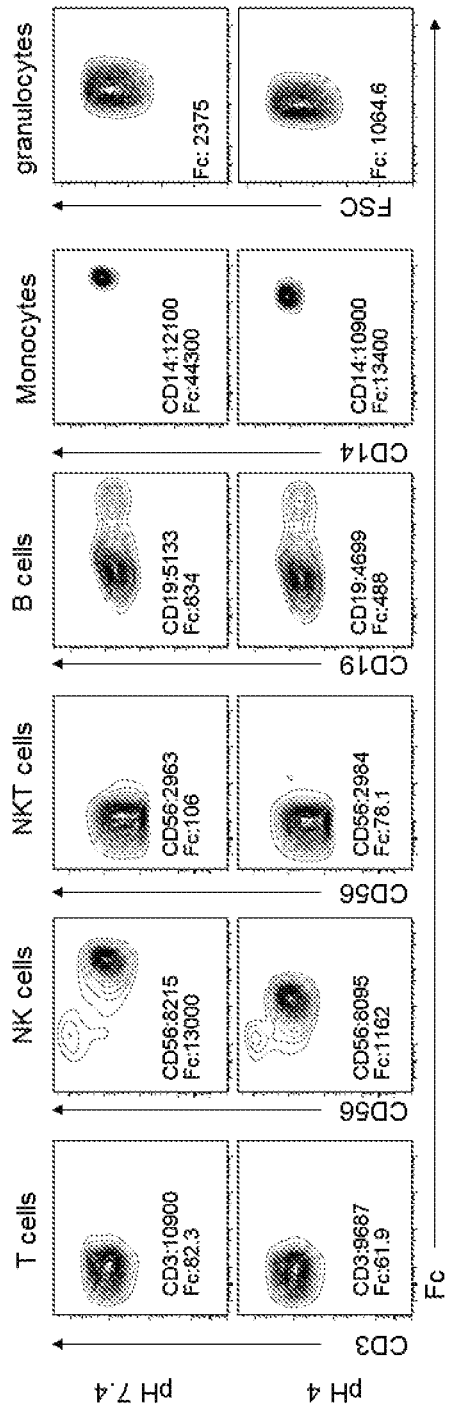
FIGS. 27A and 27B show that human primary NK cells, B cells, monocytes and granulocytes are naturally coated with human IgG molecules, which is accessible for protein A binding. Human PBMC were washed with pH7.4 or pH4 media, and subsequently stained with fluorescently labeled lineage markers and mouse anti-human IgG Fc antibody as shown in FIG. 27A, or fluorescently labeled lineage markers and protein A as shown in FIG. 27B. Mean intensity of cell markers, human Fc and protein A are shown.
Figure 27B:
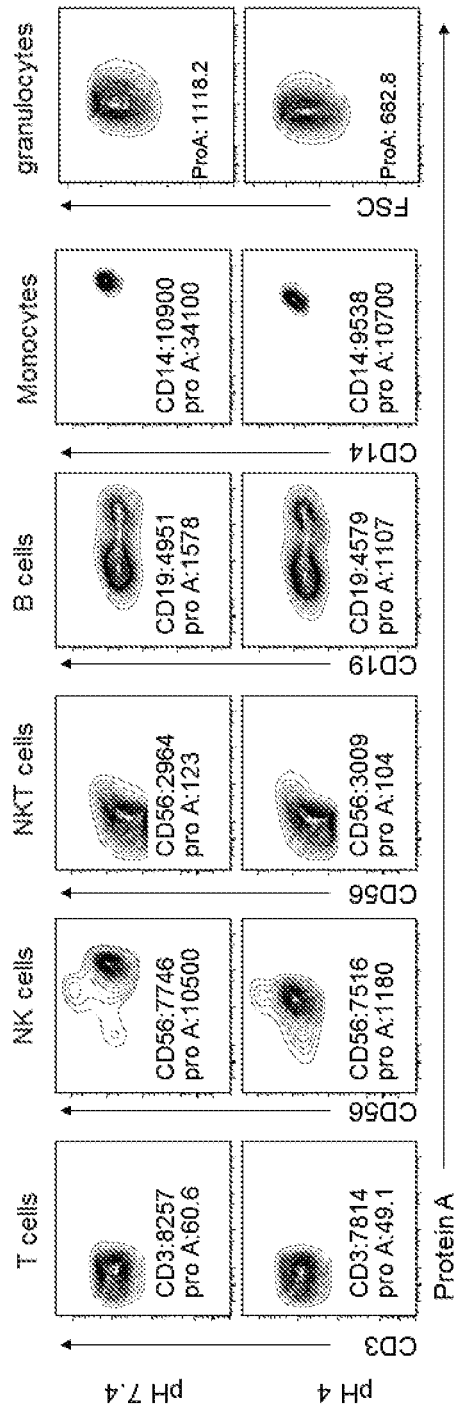

Although human IgG was not supplemented in the glioma-NK cell co-culture, IgG molecules were shown to be naturally present on the surface of primary human NK cells (FIG. 2C). Washing NK cells briefly with acidic media (RPMI1640 plus 10% FBS) adjusted to pH4.0 with acetic acid) decreased surface IgG (FIG. 2C) and increased binding of an anti-human CD16 antibody (3G8) (Perussia et al., 1984, *J Immunol* 133, 180-189) that competes with human IgG for the same binding site on CD16a (FIG. 2D), demonstrating IgG molecules are anchored on human NK cells via CD16a. In addition to NK cells, B cells, monocytes and granulocytes were shown to be naturally coated with human IgG molecules, via non-covalent binding, revealed by acidic media treatment which removed most of the IgG from the cell surface (FIG. 27A). These surface IgG molecules provide interaction sites for protein A binding (FIG. 27B). Primary NK cells from a variety of healthy human donors had very different levels of surface IgG (FIG. 2E) and their response to stimulus varied (FIGS. 2F and 8). The response (measured by the percentage of CD69+ or CD107a+ NK cells) of human NK cells towards glioma Us8 correlated with the level of surface IgG; and the correlation became even stronger when NK cells were cultured with glioma Us7+Us8 (FIG. 2G). In contrast, the response of NK cells to K562 cells, which are leukemia cells negative for MHC I molecule and widely used as an activating control for NK cells, showed no correlation with surface IgG (FIG. 2G). Taken together, human IgG was shown to link gE and NK cell activation.

CD16a, IgG Fc and HSV1 gE Form a Ternary Complex Essential for NK Cell Activation.

Figure 3A:
FIGS. 3A to 3K show that IgG bridging was essential for NK cell activation by HSV gE.
Figure 3B:
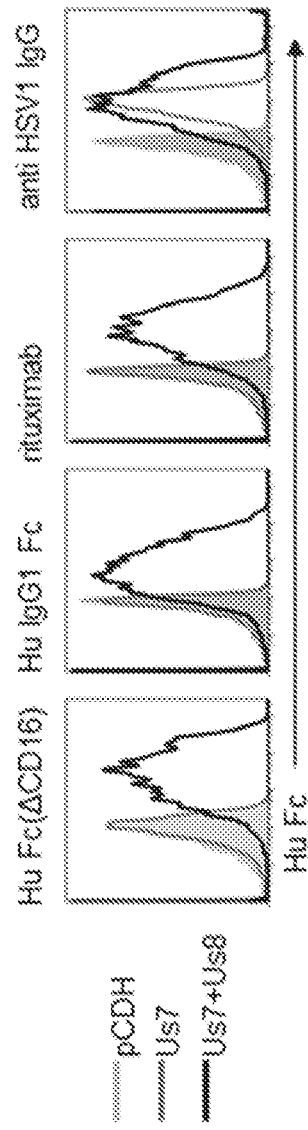

Human CD16a binding sites on IgG Fc are located far apart from the CH2-CH3 interface where gE binds IgG (Sondermann et al., 2000, *Nature* 406, 267-273; Sprague et al. 2006, *PLoS Biol* 4, e148), leading to the hypothesis that IgG, gE and CD16a could form a ternary complex. Structure modeling using the known gE-IgG Fc and CD16a-IgG Fc crystal structure supported the conclusion that gE and CD16a could bind the same IgG Fc molecule without interfering with each other (FIG. 3A). To validate the existence of such a CD16a-IgGFc-gE complex, experiments were conducted to determine whether the extracellular domain of CD16a could bind glioma Us7+Us8 in the presence of different human IgG products. IgG1 Fc(ΔCD16) is a recombinant human IgG1 Fc fragment without the CD16a binding sites; while IgG1 Fc has intact CD16a binding sites. Consistent with the crystal structure (FIG. 3A), CD16a binding sites played no role in the binding between Fc and HSV1 gE as both IgG1 Fc(ΔCD16) and IgG1 Fc bound to glioma Us7+Us8 efficiently (FIG. 3B, left and middle left). Although no direct interaction existed between CD16a and glioma Us7+Us8 (FIG. 3C left), CD16a was found to bound glioma Us7+Us8 when IgG1Fc was present and this interaction was dependent on the CD16a binding sites on IgG1Fc (FIG. 3C middle left and middle), thus proving the formation of CD16a-IgGFc-gE complex.

Figure 3C:
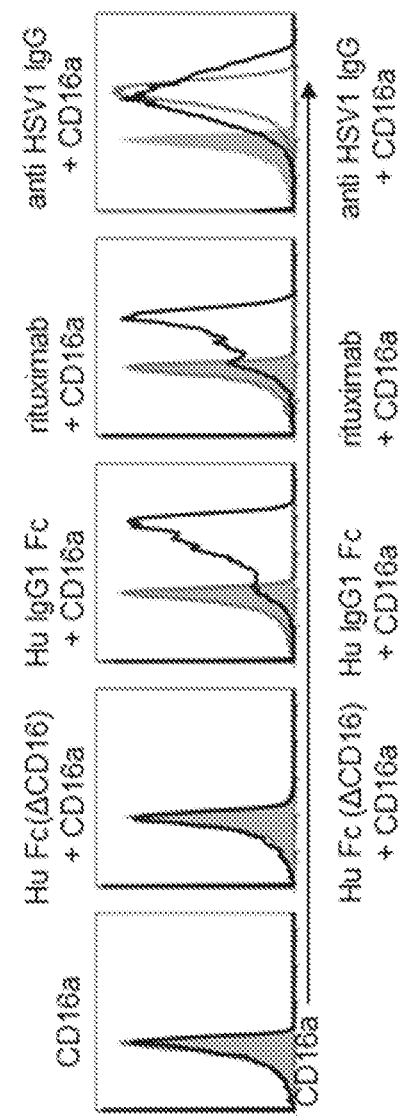
Figure 3D:
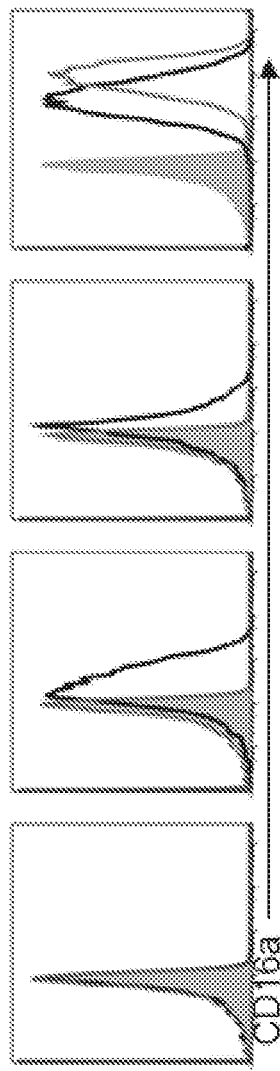
Figure 3E:
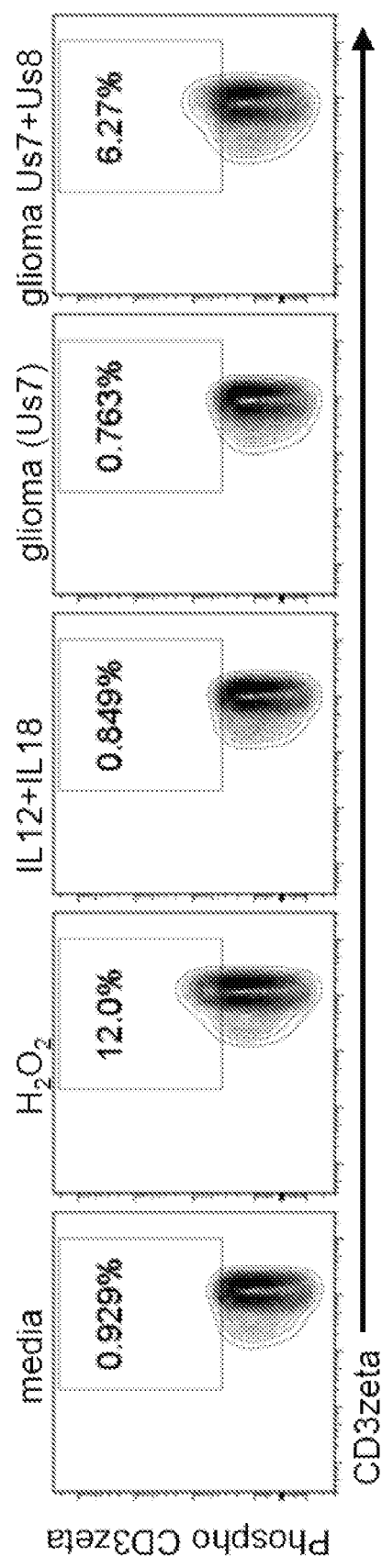

Human HSV1 specific IgG contains antibodies that specifically recognize gE or gI (FIG. 3B, middle right), and its presence allowed CD16a to bind glioma cells expressing an HSV1 gene via the classical interaction between CD16a and antigen-antibody complex (FIG. 3C, middle right). Similar CD16a binding tests were also performed using Rituximab (a humanized IgG1 monoclonal antibody against human CD20) (Edwards et al., 2004, *N Engl J Med* 350, 2572-2581) (FIGS. 3B and 3C, right), or glioma cells infected with Us8-HSV1 or wild type HSV1 (FIG. 3D), which again confirmed CD16a, IgG Fc and HSV1 gE formed a ternary complex. Furthermore, phosphorylation of CD3ζ specifically occurred when NK cells were stimulated with $H_2O_2$ (positive control) or in culture with glioma Us7+Us8, but not with IL12+IL18 (FIG. 3E), demonstrating gE activated NK cells through CD16a-CD3ζ axis.

Figure 3F:
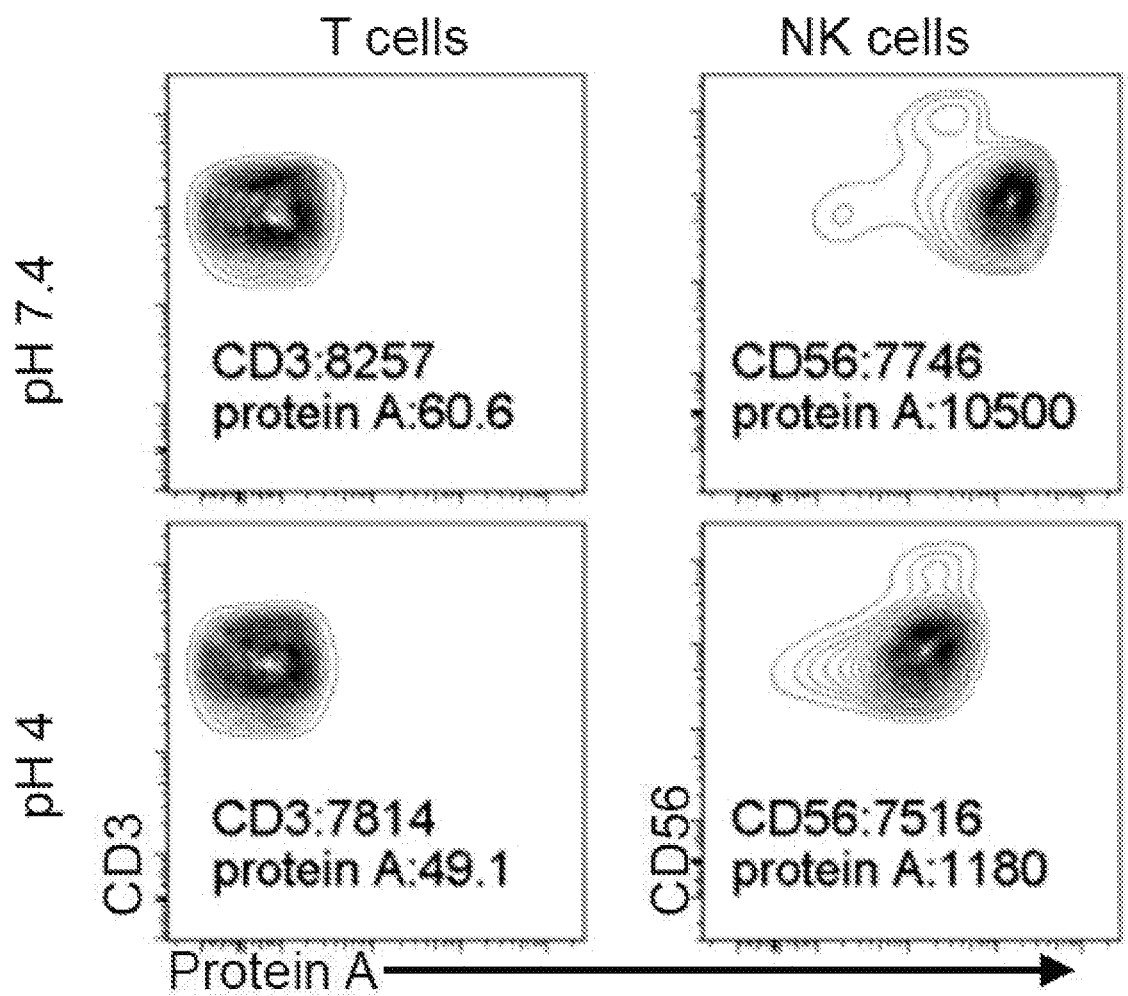
Figure 3G:
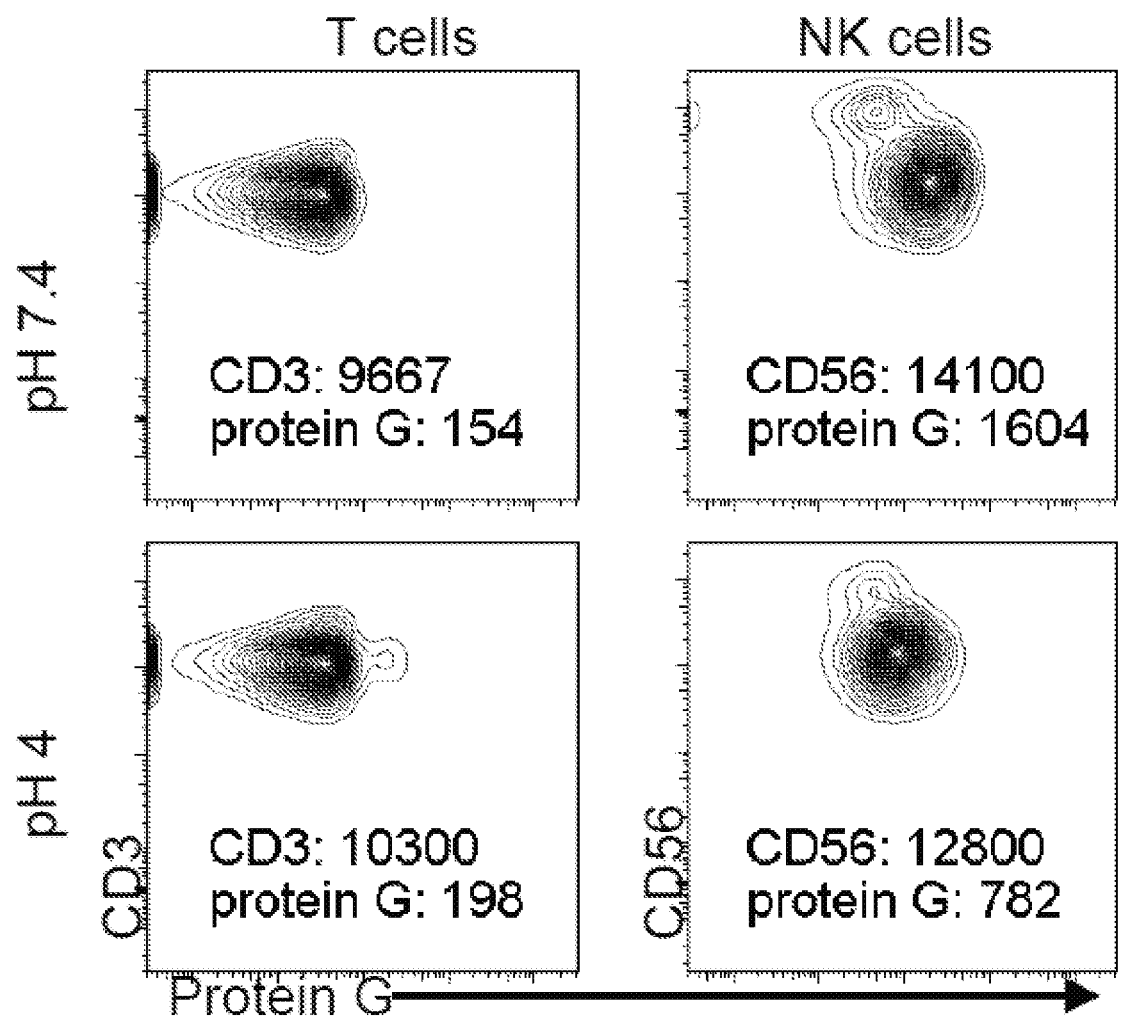
Figure 9A:
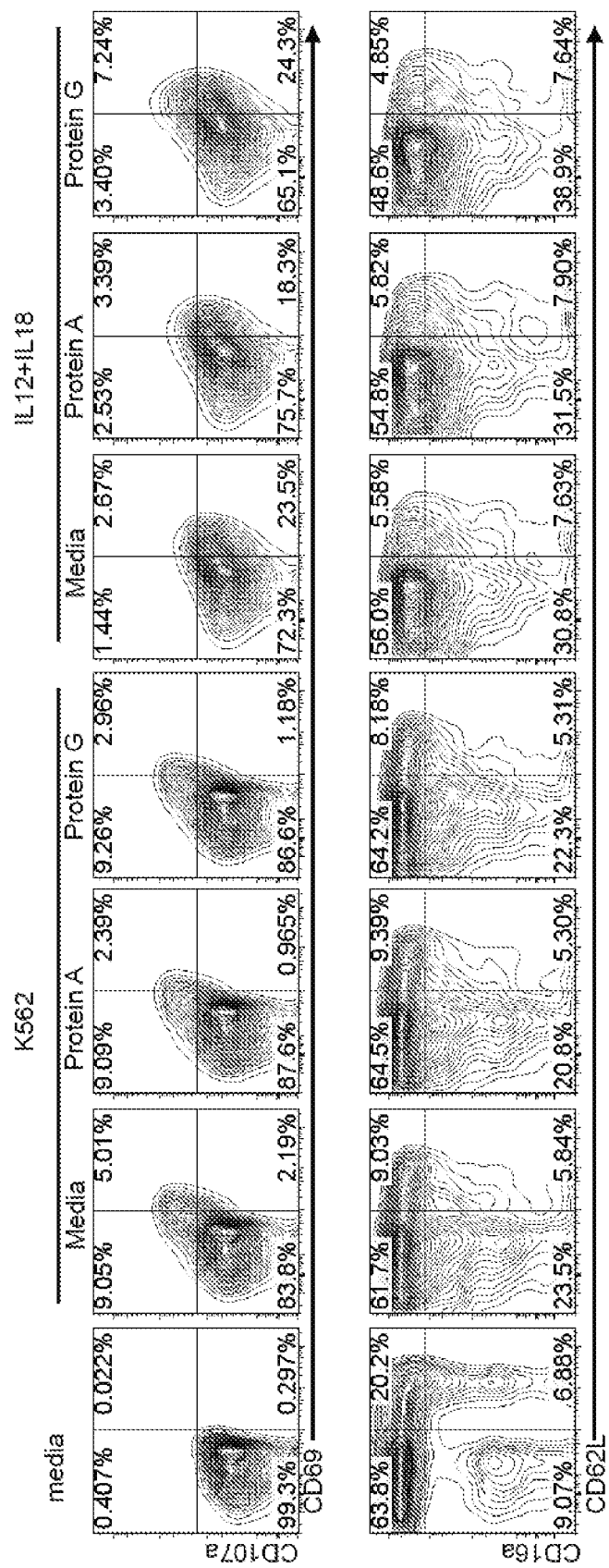
FIGS. 9A and 9B show primary human NK cells treated with protein A or protein G, and subsequently cultured with K562 cells, IL12+IL18 or transfected glioma cells. Phenotyping was performed at 7 hours of culture. A representative contour plot from one of 8 donors is shown.
Figure 9B:
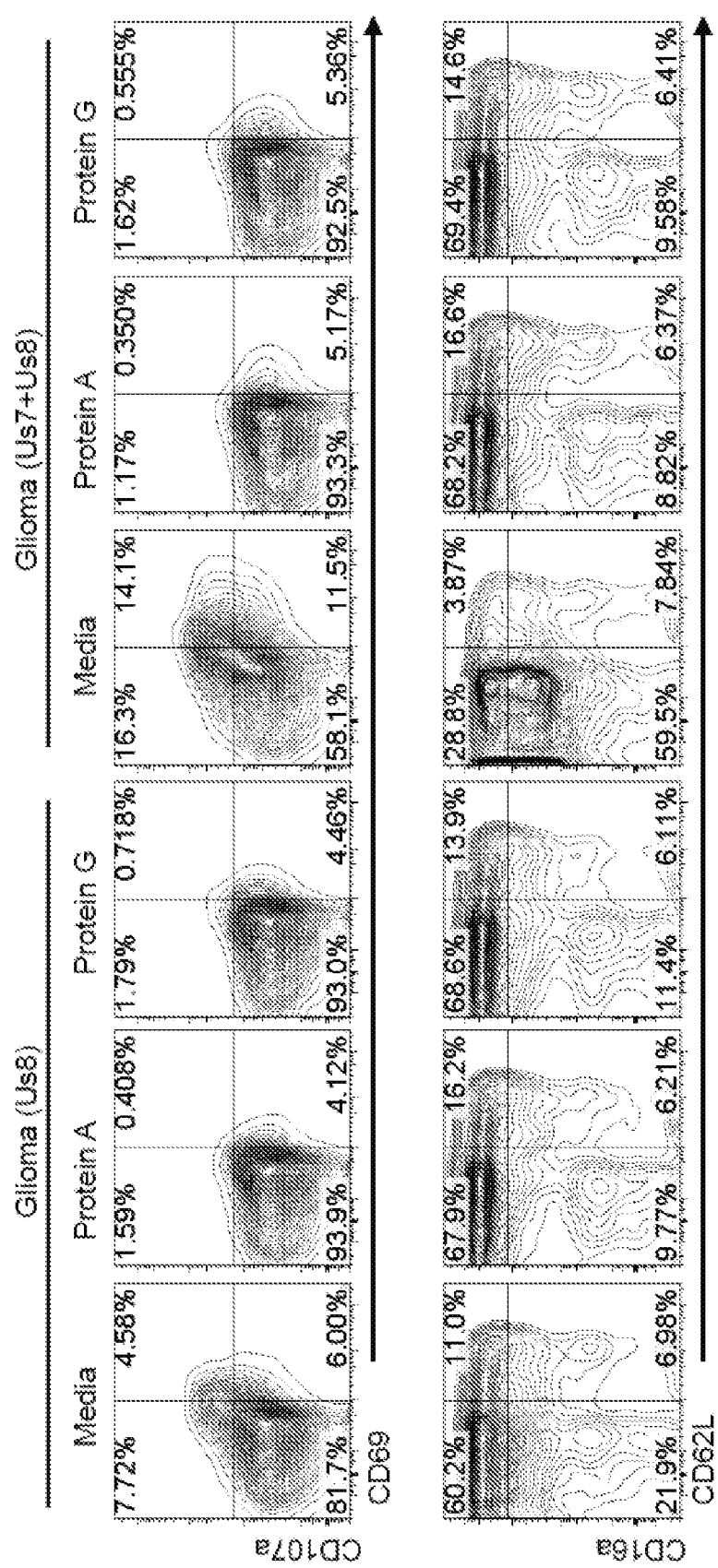
Figure 10A:
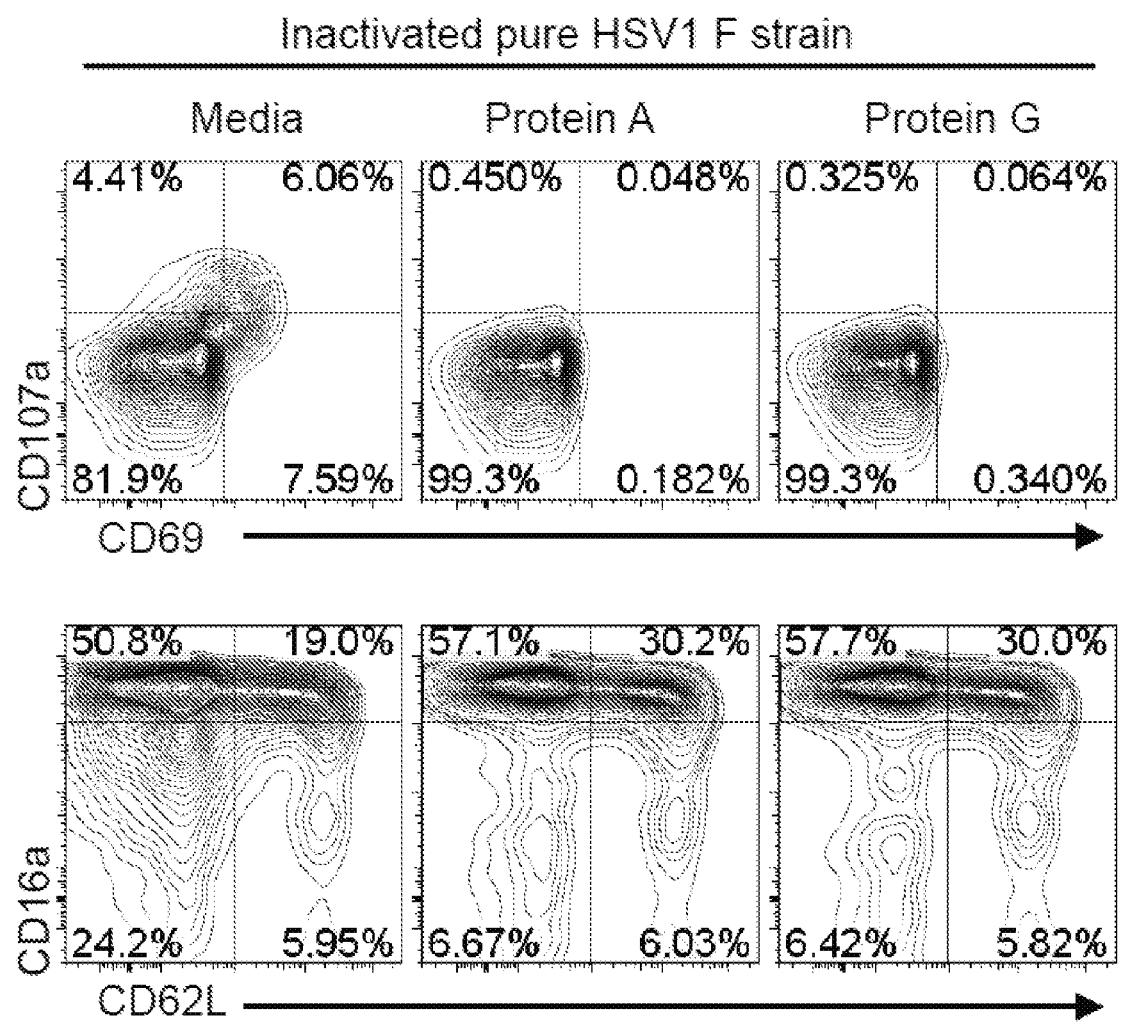
FIGS. 10A and 10B show human NK cells treated with medium alone, protein A or protein G, and subsequently cultured in plates coated with inactivated wildtype HSV1 F strain. Phenotyping was performed after 7 hours of culture. A representative contour plot from one donor (FIG. 10A) and statistical summary for 5 donors (FIG. 10B) are shown.
Figure 10B:
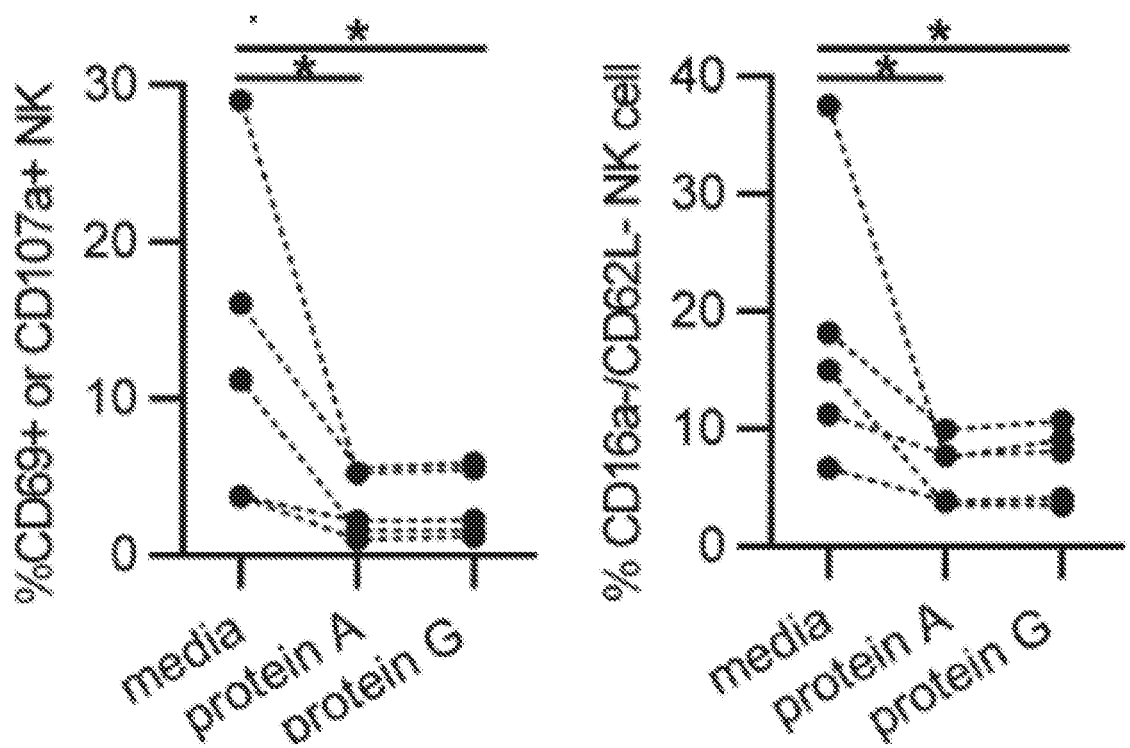
Figure 11A:
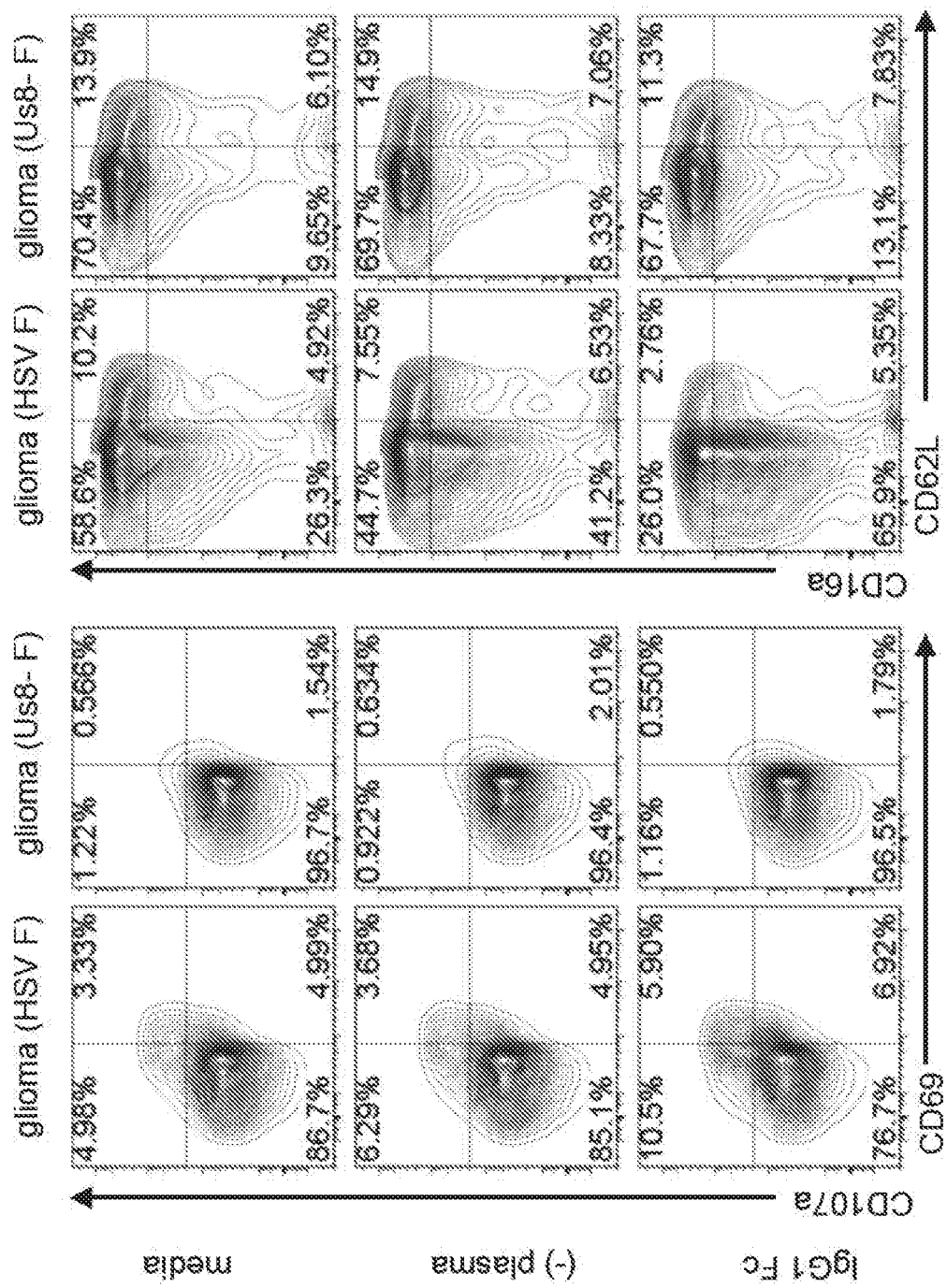
FIGS. 11A to 11D show NK cells cultured with infected glioma cells (FIG. 11A, 11B), or transfected glioma cells (FIG. 11C, 11D), in the presence of medium alone, HSV1 non-immune plasma ((−) plasma) or human IgG1 Fc, and stained after 7 h of culture. A representative contour plot from one donor (FIGS. 11A and 11C) and statistical summary of 7-9 donors (FIGS. 11B and 11D) are shown.
Figure 11B:
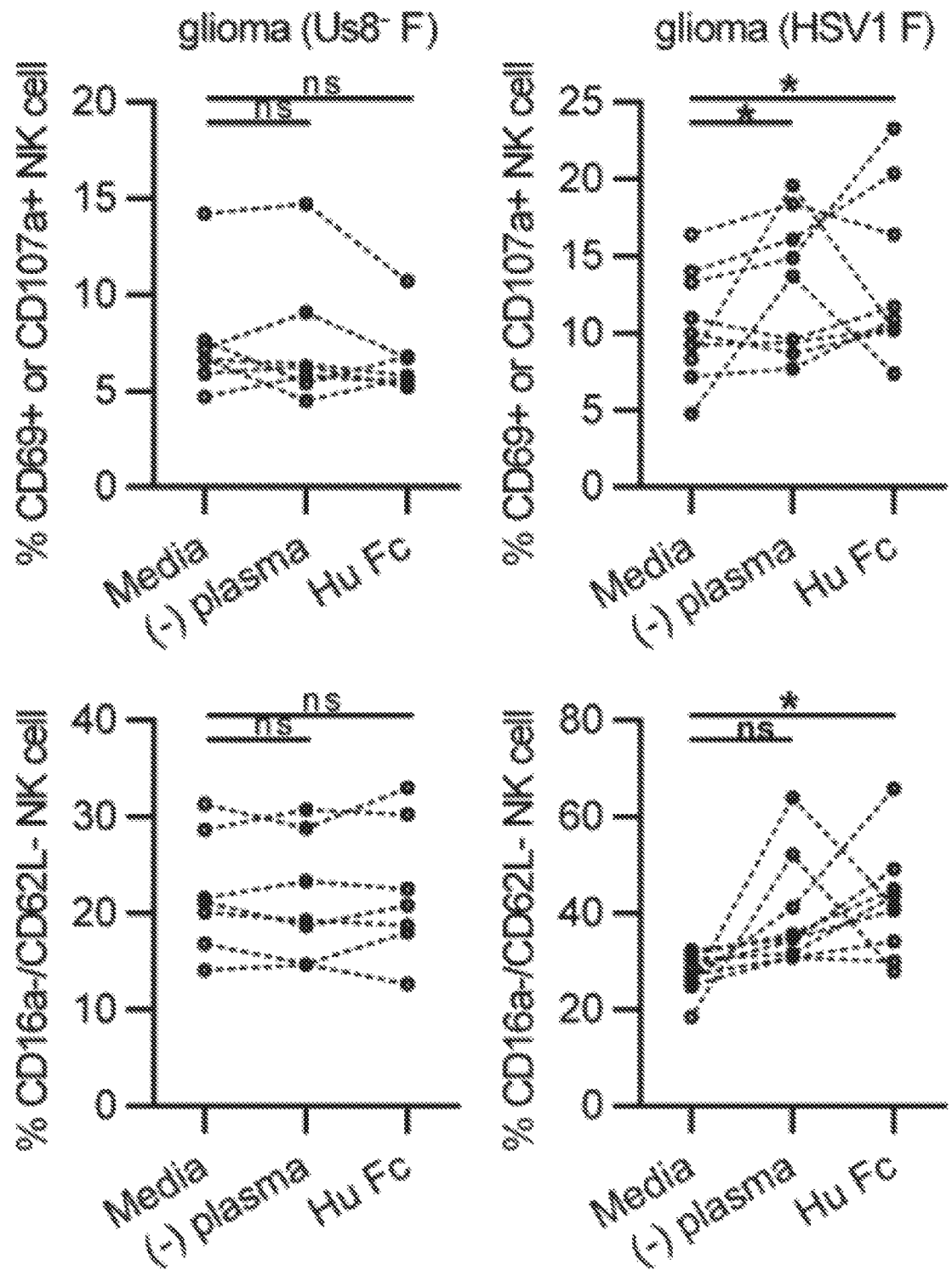
Figure 11C:
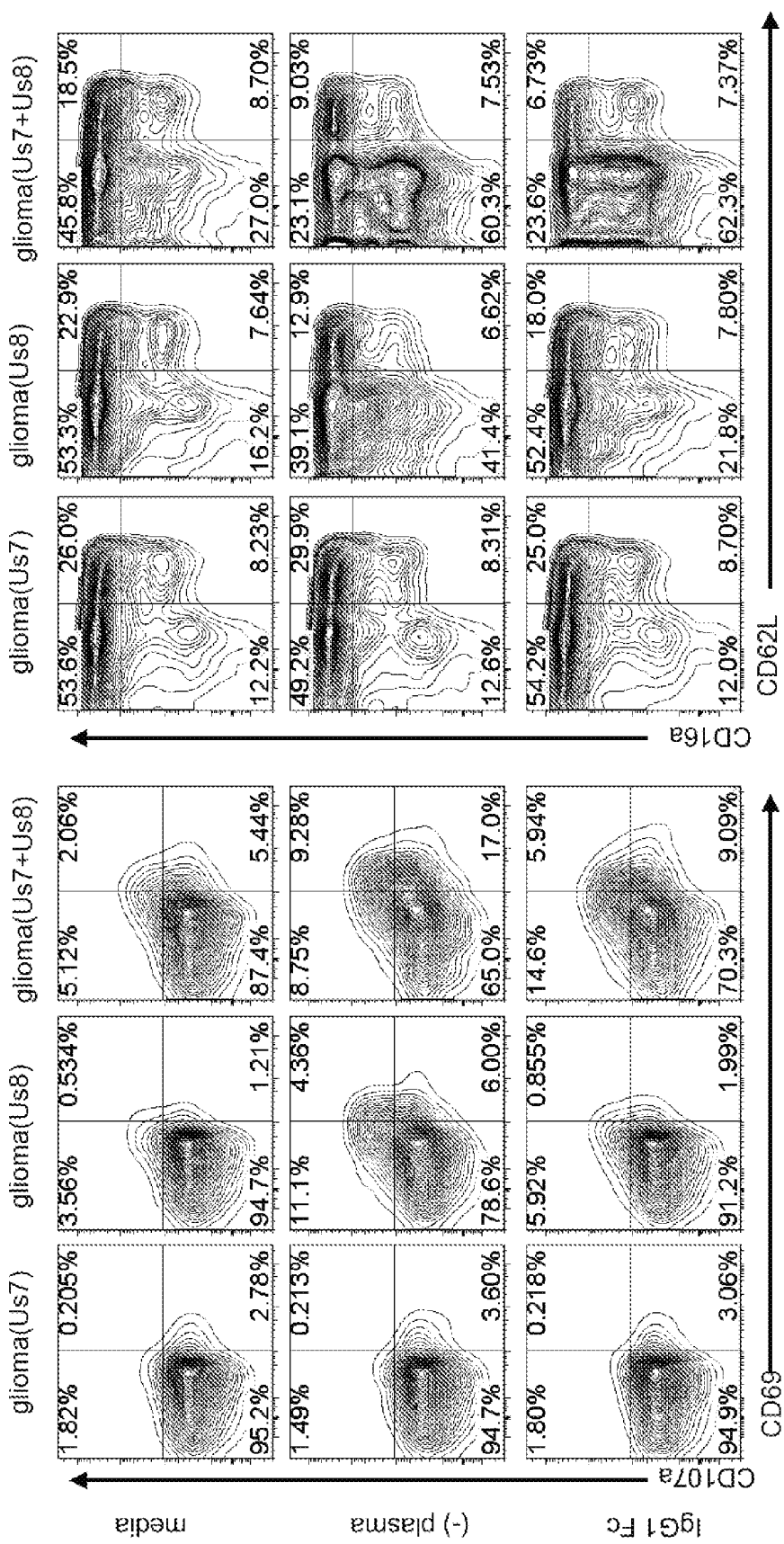
Figure 11D:
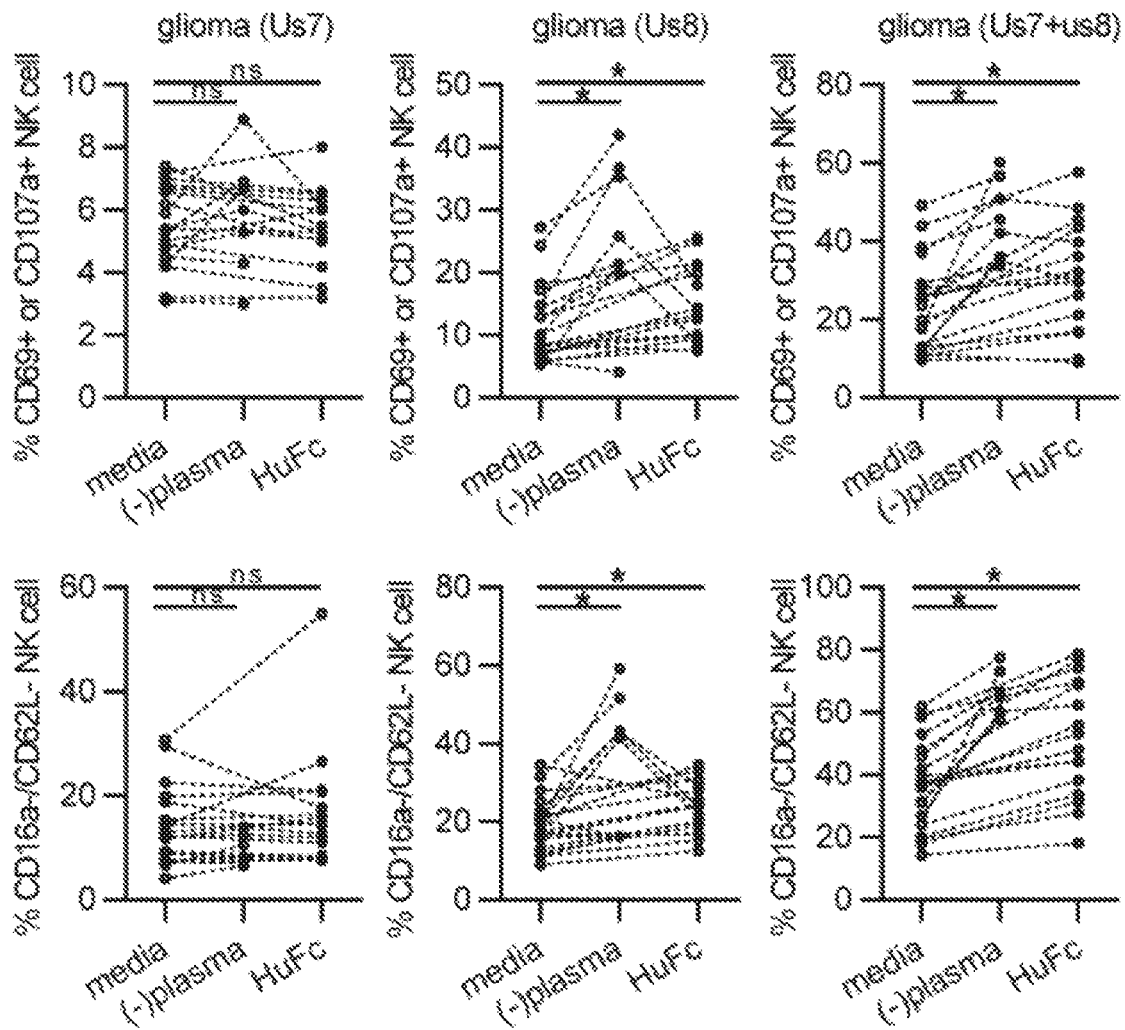

IgG-binding proteins, protein A from *Staphylococcus aureus* and protein G from group G *Streptococcus*, bind IgG mainly at the CH2-CH3 interface (Sauer-Eriksson et al., 1995, *Structure* 3, 265-278; Deis et al., 2015, *Proc Natl Acad Sci US A* 112, 9028-9033). Protein A and protein G were shown to also bind primary human NK cells via IgG present on the membrane of NK cells (FIGS. 3F and 3G), which also suggested that surface IgG coated on primary NK cells were fully accessible for gE to bind. To test the essentiality of IgG to NK cell activation by HSV1 gE, primary human NK cells were incubated with an excess of protein A or protein G to occupy all CH2-CH3 interface prior to culturing the NK cells with different stimuli. Pre-incubation with protein A or protein G completely inhibited all functional enhancements of NK cell by gE (FIGS. 3H-3J and 9). This treatment did not change human NK cells' responses to K562 cells or IL12+IL18 (FIG. 9). Additionally, plates coated with pure and inactivated wt HSV1 virus could no longer activate NK cells that were pre-incubated with protein A or protein G (FIGS. 10A and 10B). Taken together, these results supported the conclusion that IgG Fc bridged the interaction between NK cells and target cells expressing HSV1 gE, and resulted in NK cell activation.

Passive ADCC Promotes the Clearance of HSV1 Infection In Vivo.

Figure 3H:
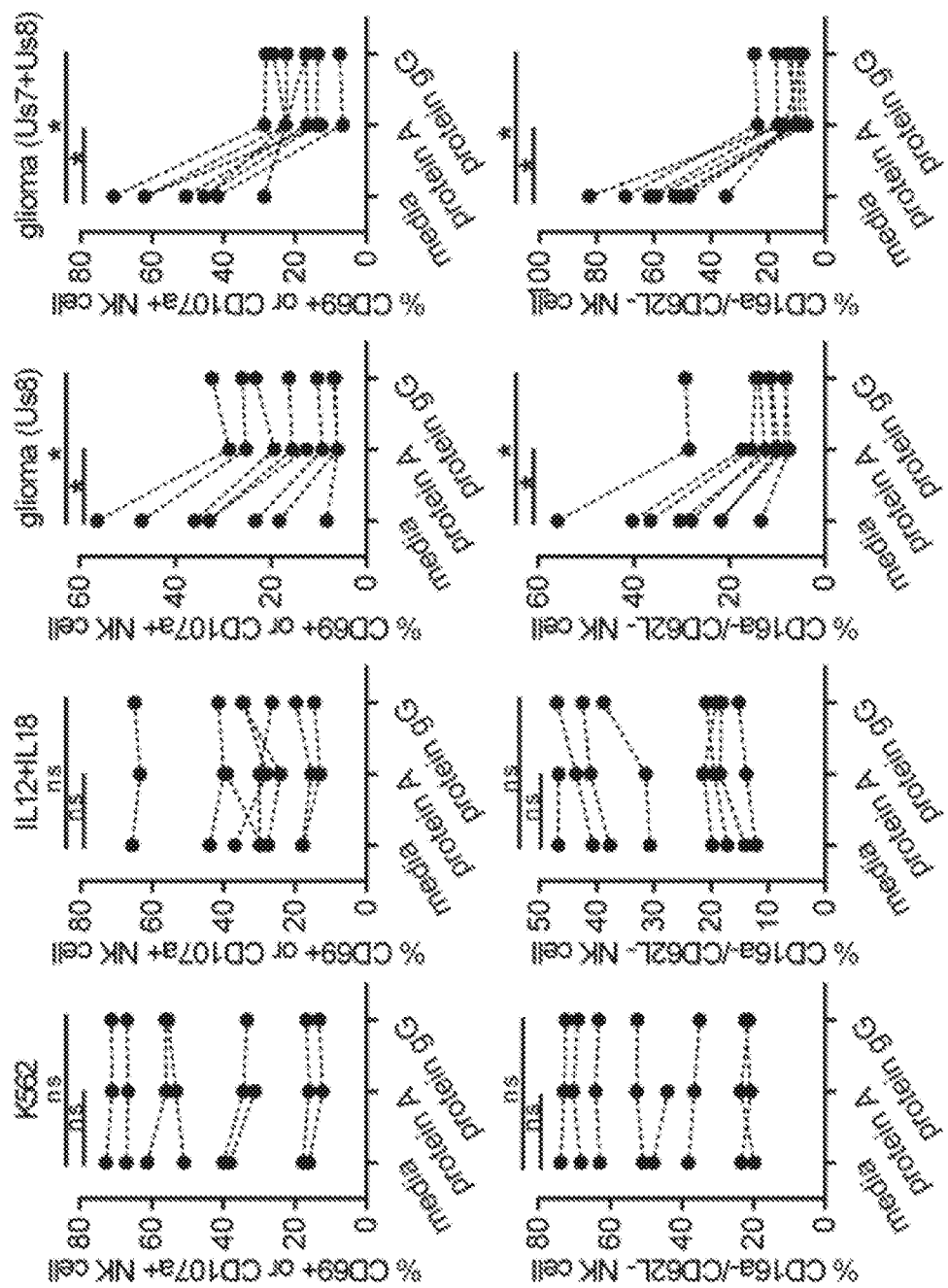
Figure 3I:
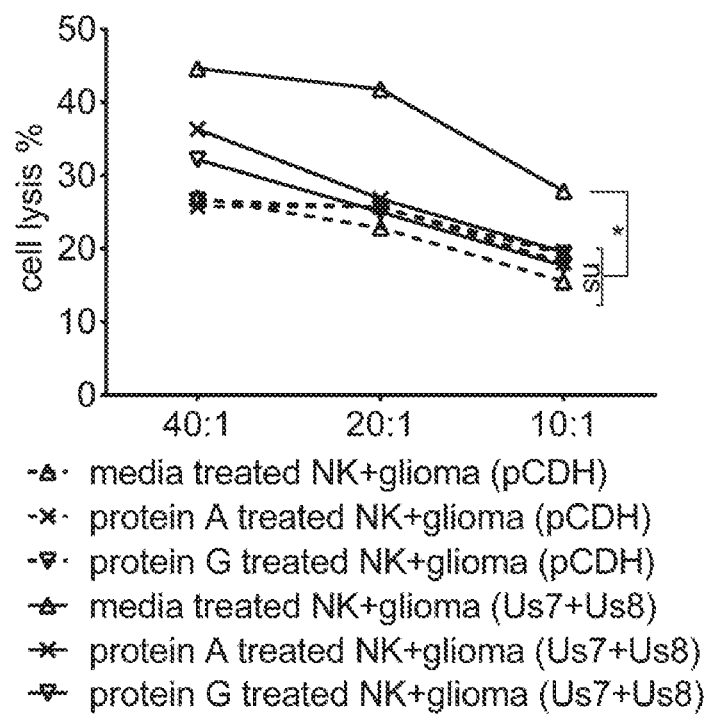
Figure 3J:
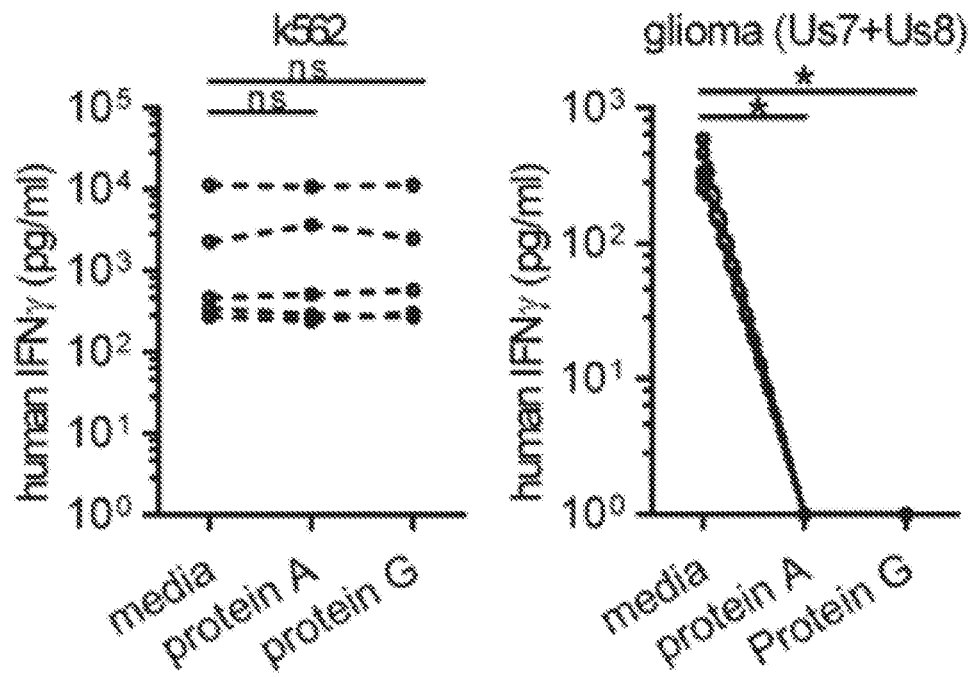
Figure 3K:
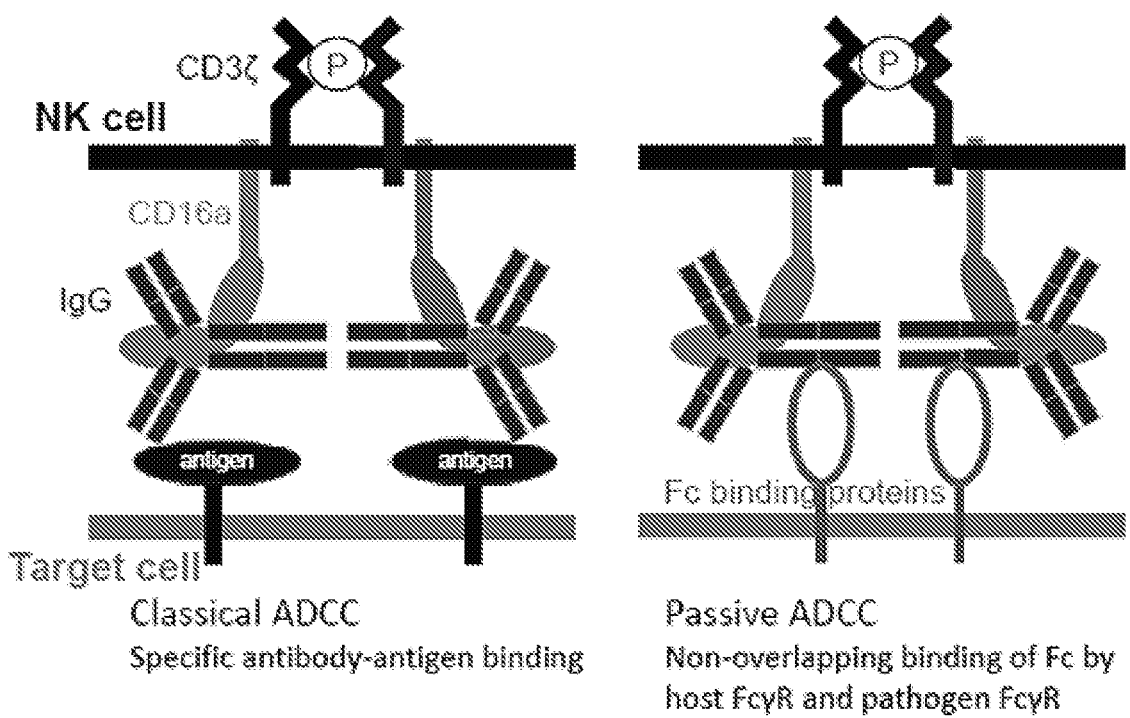
Figure 4A:
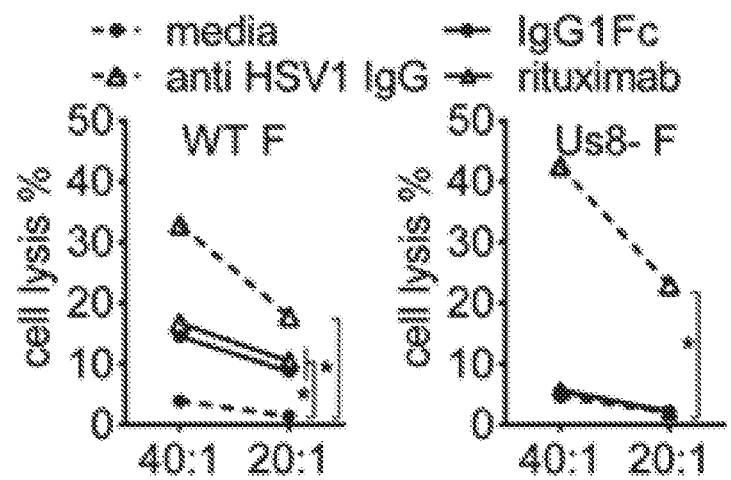
FIGS. 4A to 4F show that passive ADCC promotes viral clearance in vivo.
Figure 4B:
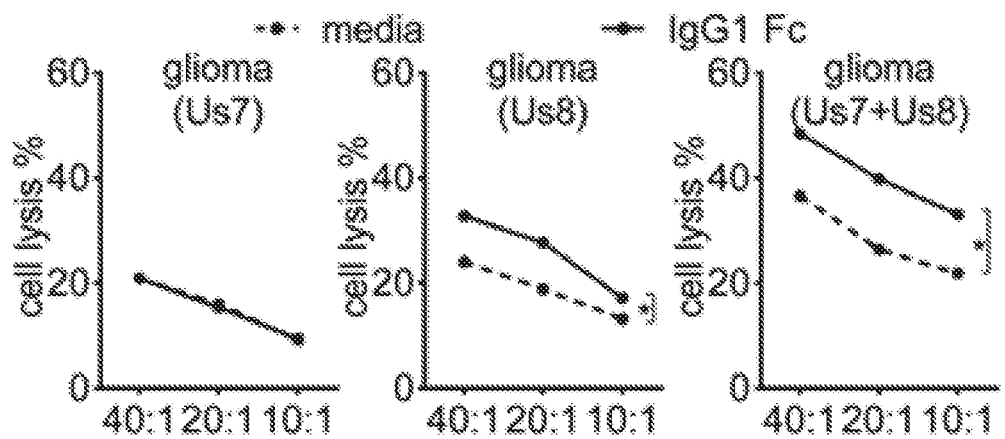

Human NK cell activation by gE represents a previously unappreciated immunostimulation mechanism which is solely bridged by IgG Fc, and differs from classical IgG functions by requiring no antigen-specific antibody (FIG. 3K). This type of NK cell activation was named passive ADCC (FIG. 3K). The above experiments were all conducted without adding human IgG to the interaction, and NK cell activation by gE was mediated by IgG already present on primary NK cells (FIGS. 3H-3J). During primary HSV1 infection in vivo, infected cells are likely to be coated with human IgG due to the expression of gE and the abundance of IgG in human serum. To test whether the non-immune IgG coating on infected cells could provide additional anchoring/activating sites for CD16a(+) NK cells, non-HSV1 non-immune plasma [(−) plasma] or IgG1 Fc fragments were added in culture. Both (−) plasma and IgG1 Fc further enhanced activation of NK cells by infected or transfected glioma cells in a gE dependent manner (FIGS. 11A-11D). NK cytotoxicity toward glioma cells infected with wt or us8⁻ F was enhanced by HSV1-specific IgG (classical ADCC, FIG. 3K), however human IgG1 Fc and an antibody targeting an irrelevant antigen (i.e rituximab) also enhanced NK cell cytotoxicity to glioma cells infected with wt F but not Us8⁻ F strain (FIG. 4A), or glioma cells expressing gE (FIG. 4B).

Figure 4C:
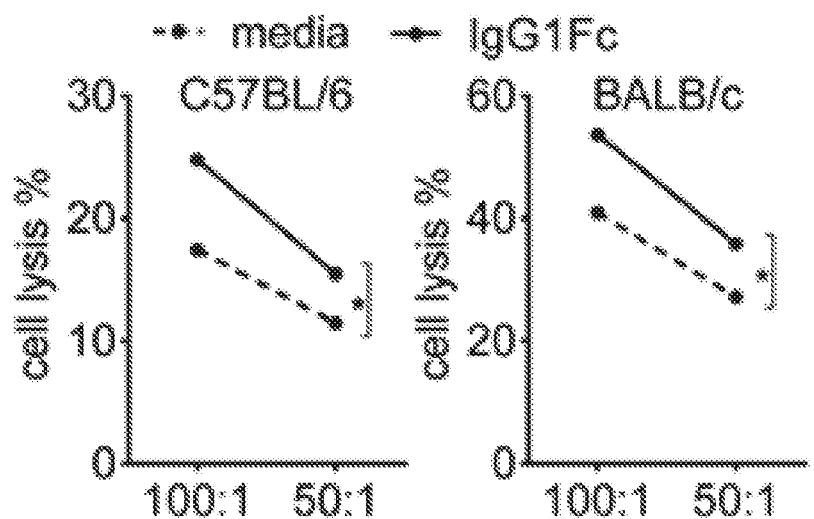
Figure 4D:
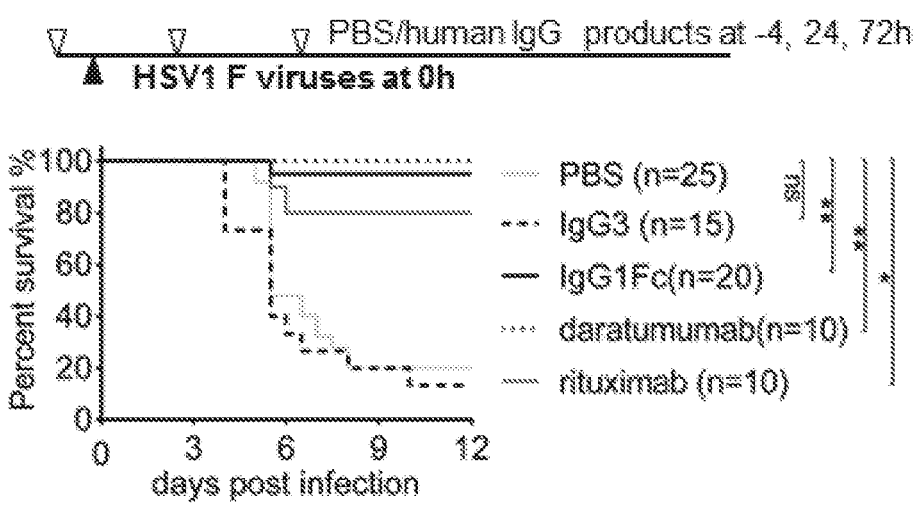
Figure 4E:
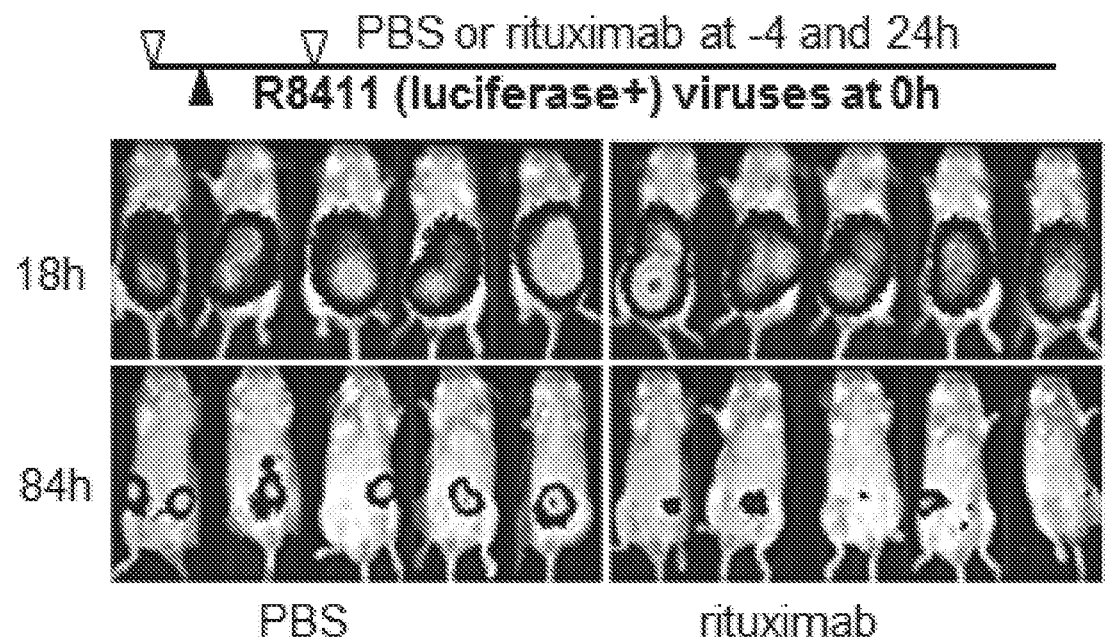
Figure 4F:
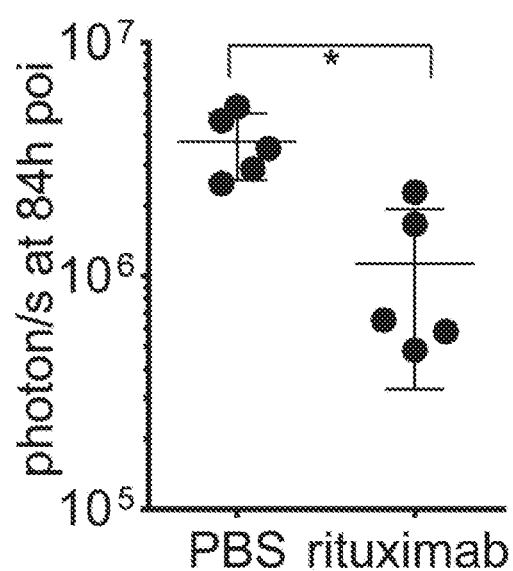
Figure 12A:
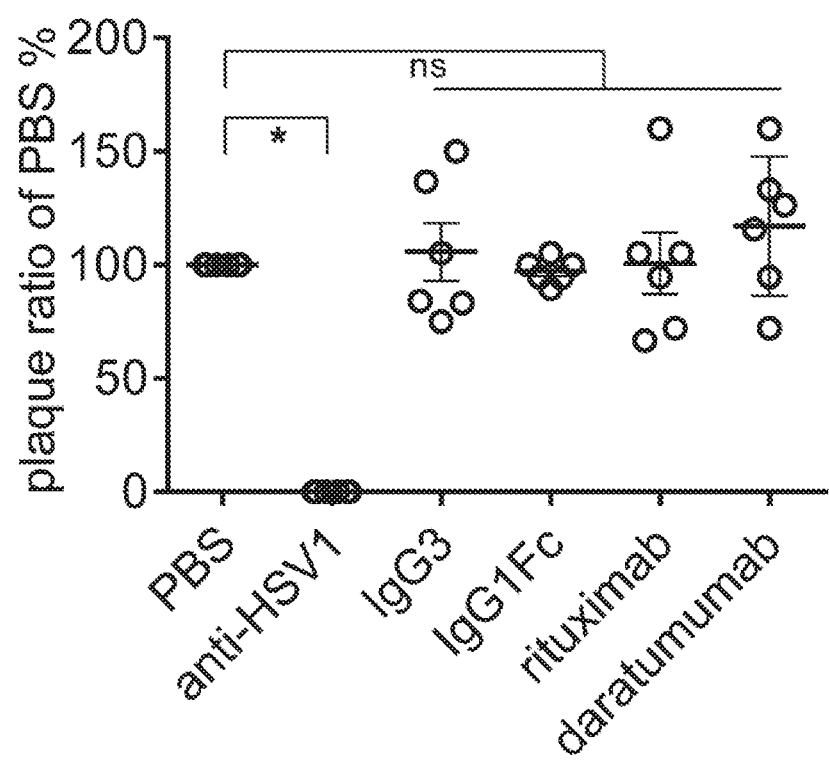
FIG. 12A shows serial diluted HSV1 F strain mixed with PBS or IgG products, incubated for 30 min at room temperature, and titred on Vero cells for infectivity. All numbers are normalized to PBS treatment (negative control). Human IgG contained anti-HSV1 IgG (positive control).
Figure 12B:
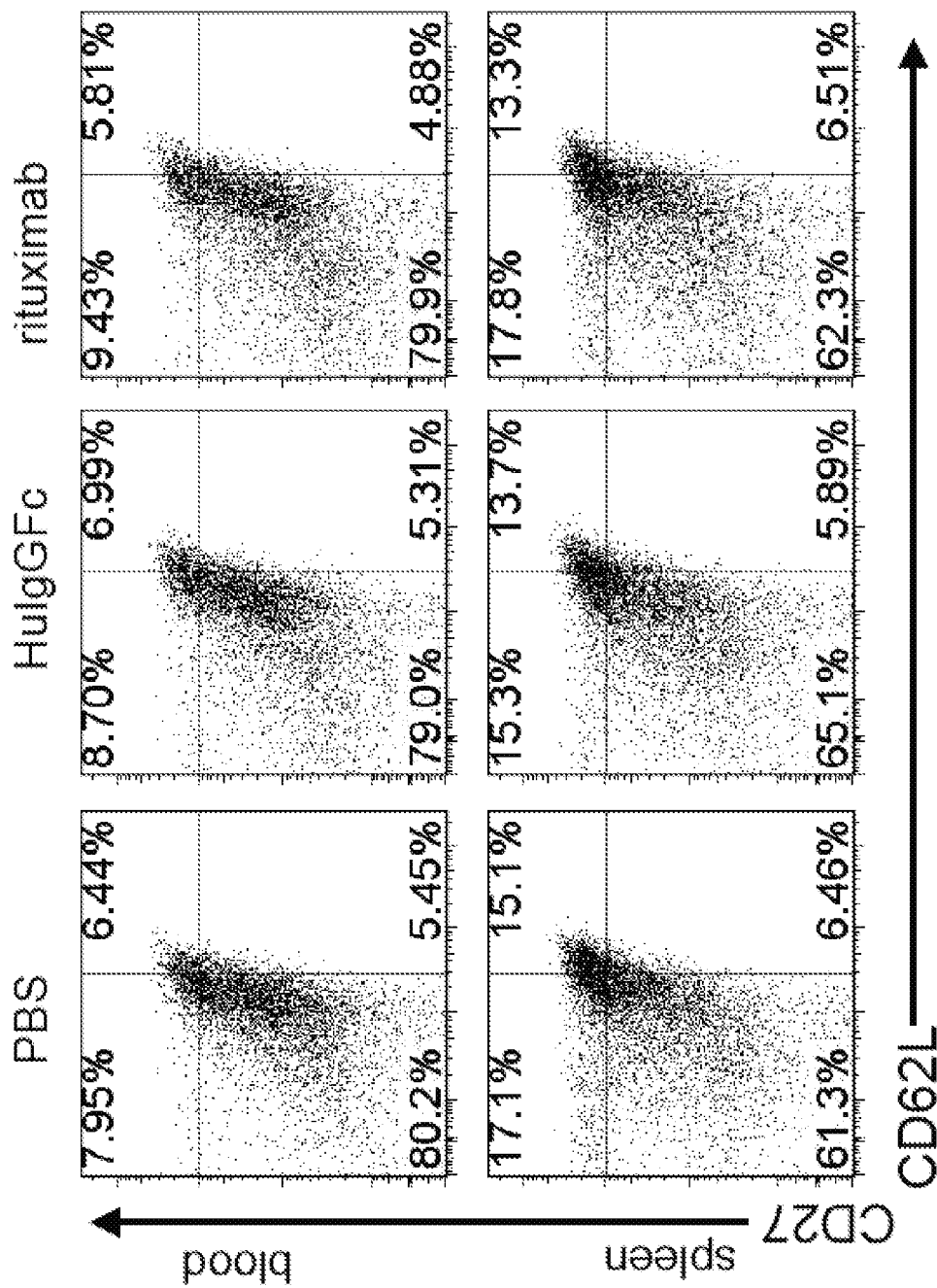
FIG. 12B shows the phenotype of NK cells from BALB/c mice that were injected with human IgG Fc or rituximab for 24 hours.

HSV1 gE does not bind mouse IgG (Chapman et al., 1999, *J Biol Chem* 274, 6911-6919), however mouse FcγR binds human IgG with high affinity (Ober et al., 2001, *Int Immunol* 13, 1551-1559), and thus supplementing human IgG should be able to bridge mouse NK cells and HSV1 infected cells, promote immune activation and clearance of HSV1 infection. Consistent with this hypothesis, NK cells isolated from C57BL/6 and BALB/c mice displayed enhanced cytotoxicity towards glioma Us7+Us8 in the presences of human IgG Fc fragments (FIG. 4C). To demonstrate that passive ADCC could be an important mechanism for clearing HSV1 infection in vivo, BALB/c mice were injected with PBS, human IgG3, human IgG Fc fragments, daratumumab (a human IgG1 antibody directed against human CD38) or rituximab, four hours before and at 24 h and 72 h after virus challenge (FIG. 4D). Each of these reagents did not affect the infectivity of HSV1 viruses when NK cells were absent (FIG. 12A), nor their in vivo administration alone changed phenotypes of NK cells in vivo (FIG. 12B), human IgGFc fragments, daratumumab and rituximab alleviated HSV1 infection symptoms and provided mice complete protection from lethal HSV1 infection (FIG. 4D). HSV1 gE is required for the cell-to-cell spread of HSV1 in vivo (Polcicova et al., 2005, *J Virol* 79, 11990-12001), therefore the Us8⁻ F strain was not used in vivo to confirm dependence on gE for this kind of protection. However, human IgG3, which does not bind HSV1 gE (Sprague et al., 2006, *PLoS Biol* 4, e148), failed to provide any protection against HSV1 infection (FIG. 4F), suggesting an gE-IgG interaction is critical for protection against lethal HSV1 infection by human IgG products. Furthermore, tracking virus infection in vivo using a HSV1 F strain expressing luciferase (Zerboni et al., 2013, *J Virol* 87, 2791-2802) revealed that rituximab increased clearance of HSV1 infection (FIG. 4E, 4F). Taken together, IgG Fc bridging viral Fc receptor and immune Fc receptor provides robust protection against HSV1 infection when pathogen-specific antibody is not available.

Bacterial IgG Binding Proteins Activate NK Cells Through the IgG Fc-Mediated Bridging.

Figure 5A:
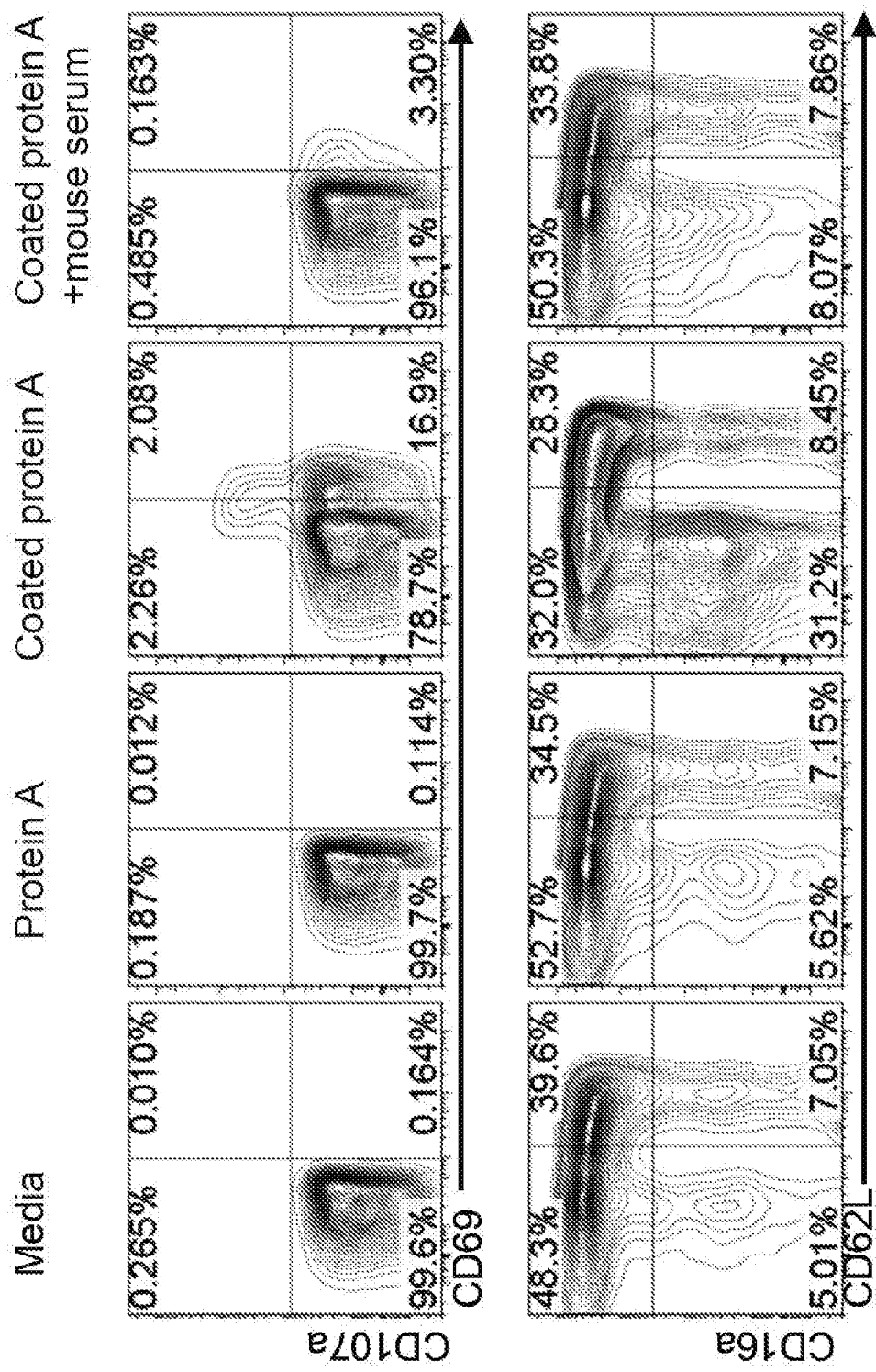
FIGS. 5A to 5H show bacterial IgG-binding proteins activate NK cells through IgG bridging.
Figure 5B:
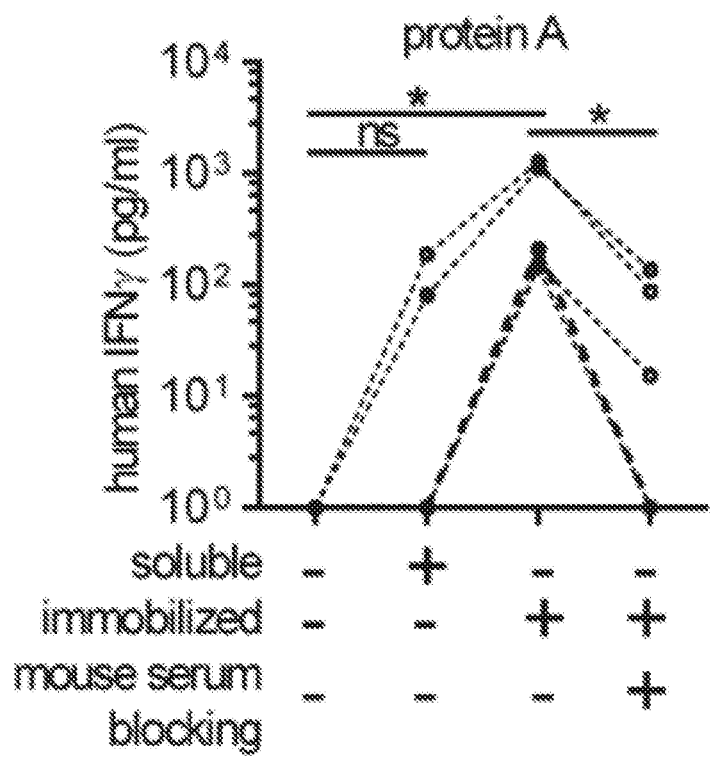
Figure 5C:
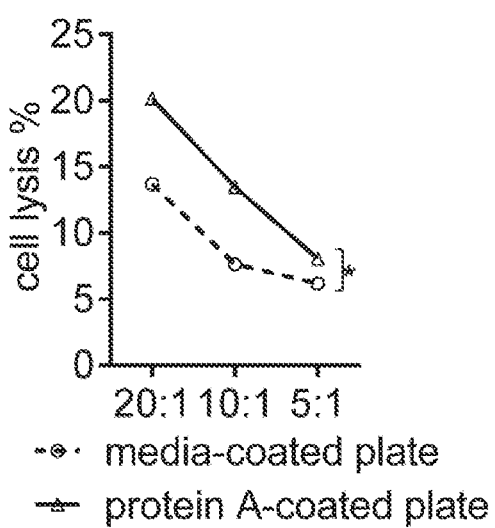

Experiments were conducted to test whether IgG binding proteins from other pathogens can activate NK cell through the same mechanism. Although protein A bound IgG Fc presented on the surface of human NK cells (FIGS. 3F and 3G), adding pure protein A directly in culture failed to activate human NK cells (FIG. 5A), because monomeric forms of protein A did not cause accumulation of CD16a prerequisite for CD3ζ auto phosphorylation. However, primary human NK cells were activated after culturing in protein A-coated plates (FIG. 5A), produced IFN-γ (FIG. 5B) and showed enhanced NK cytotoxicity (FIG. 5C). These NK cell functional enhancements were abrogated when protein A coated plates were blocked with mouse serum (FIG. 5A), because mouse IgG blocked all potential interactions between human IgG and protein A/G.

Figure 5D:
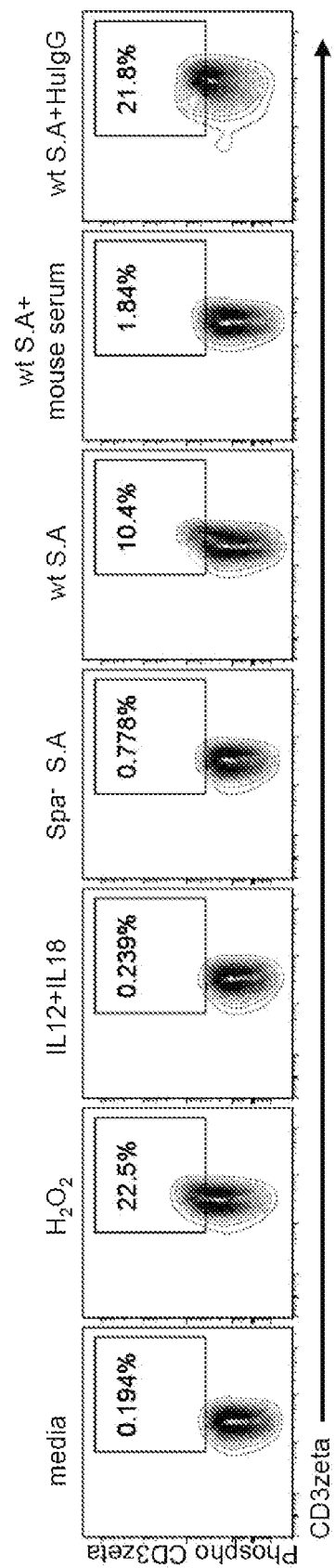
Figure 5E:
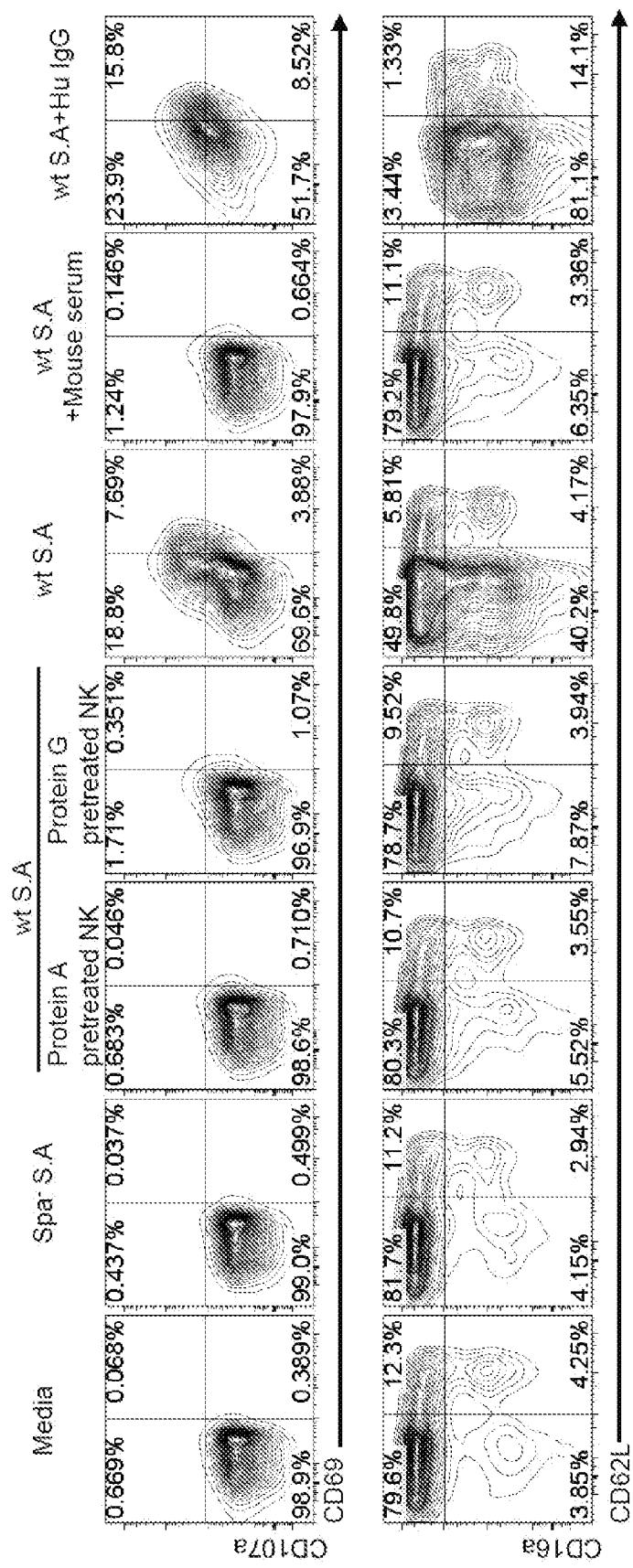
Figure 13A:
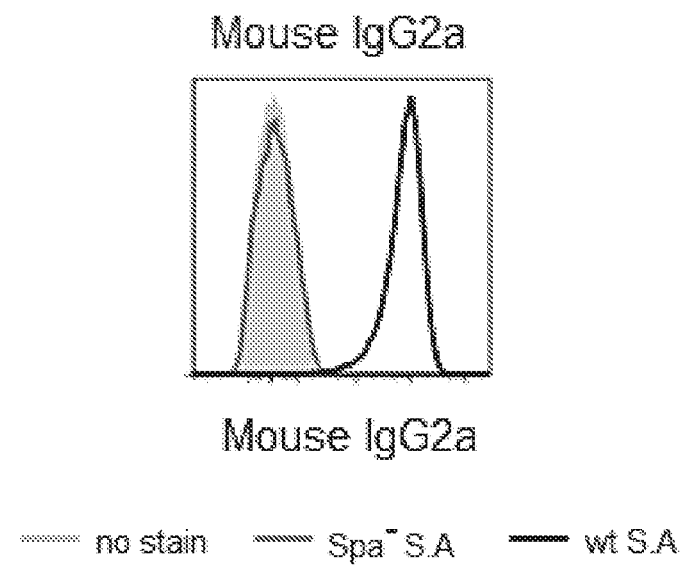
FIG. 13A shows binding of mouse IgG2a to bacteria.
Figure 13B:
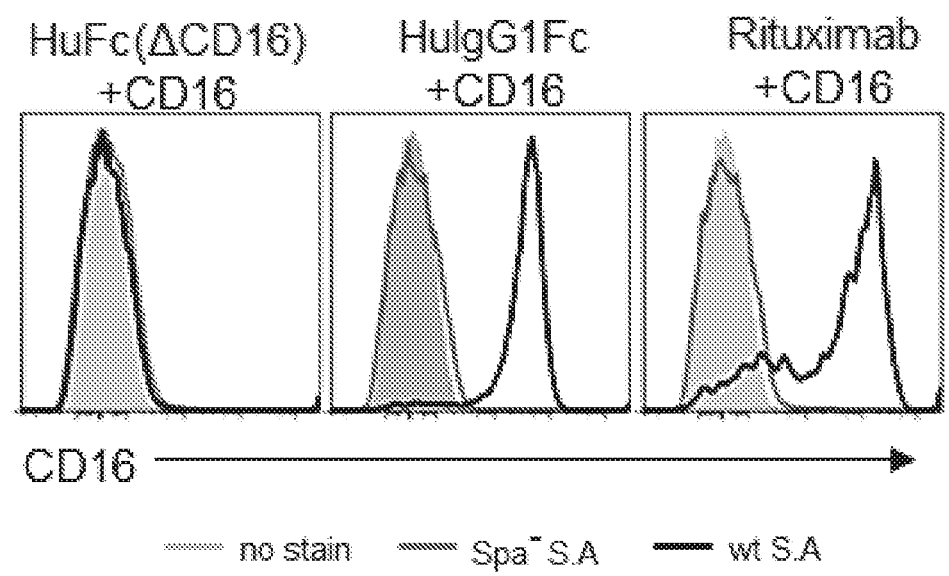
FIG. 13B shows binding of CD16a to bacteria in the presence of human IgG products.
Figure 14A:
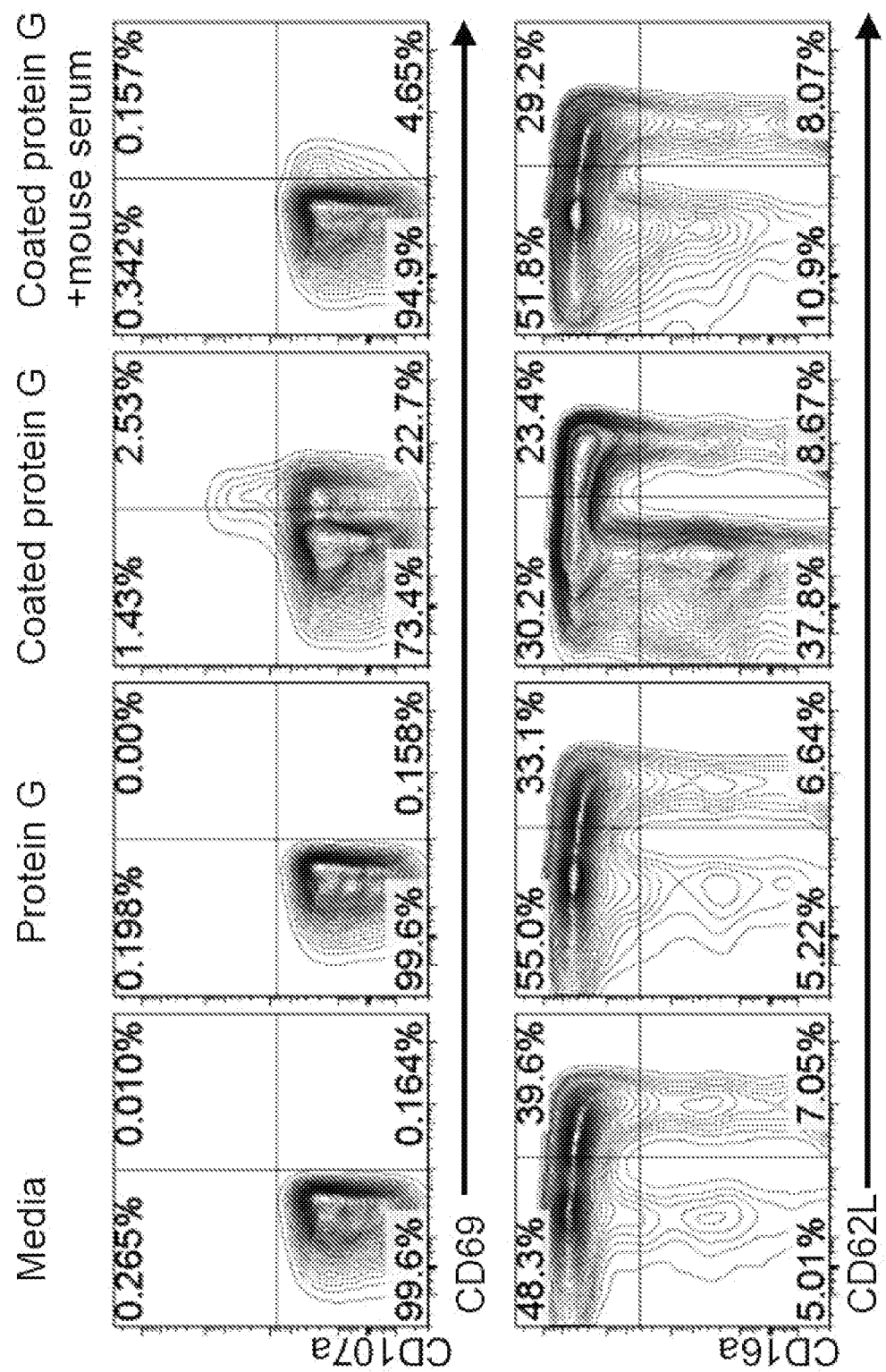
FIGS. 14A and 14B show the phenotype (FIG. 14A) and IFN γ production (FIG. 14B) of primary human NK cells after culture with soluble Streptococcus protein G, or in plates coated with protein G, or in protein G coated plates which were blocked with mouse serum before NK cell culture. Each dotted line in FIG. 14B represents one donor (mean of triplicates, n=6).
Figure 14B:
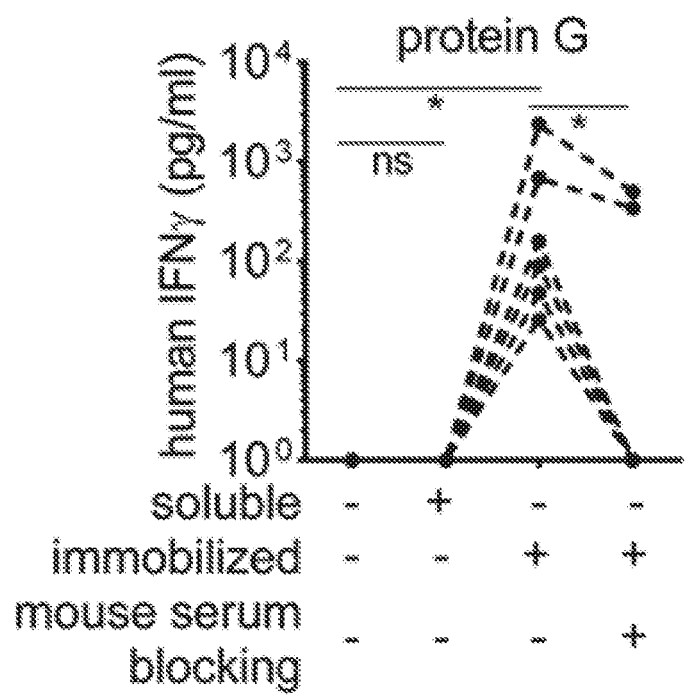
Figure 14C:
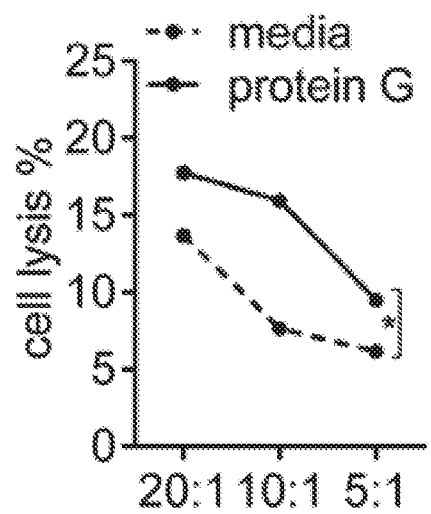
FIG. 14C shows human NK cells cultured in plates coated with media or protein A for 30 min, wherein cytotoxicity was assessed against glioma cells. These results are shown as mean±sem.

The formation of a CD16a-Fc-protein A complex was tested using wild type *Staphylococcus aureus* (S.A.) newman strain (wt) and a protein A deficient newman strain (Spa) (Patel et al., 1987, *Infect Immun* 55, 3103-3110) (FIG. 13A). CD16a bound S.A when either full human IgG (rituximab) or IgG1 Fc fragments were present and protein A was indispensable for this interaction (FIG. 13B). Phosphorylation of CD3ζ by S.A depended on protein A as protein A deficiency or blocking of protein A with mouse serum canceled CD3ζ phosphorylation. Furthermore, pre-incubating S.A with human IgG slightly enhanced CD3ζ phosphorylation (FIG. 5D). Phenotypes of NK cells cultured with S.A mirrored the result of CD3ζ phosphorylation. Activation of NK cells by wt S.A was inhibited by pre-incubating wt S.A with mouse serum, and enhanced by human IgG (FIG. 5E). NK cell activation by wt S.A was also abolished if primary human NK cells were pretreated with either soluble monomeric protein A or protein G (FIG. 5E). Furthermore, human NK cells were activated by *Streptococcus* protein G in a similar fashion (FIGS. 14A-14C). Taken together, these results demonstrate that bacterial IgG binding proteins activated human NK cells through Fc bridge and CD16a.

Figure 5F:
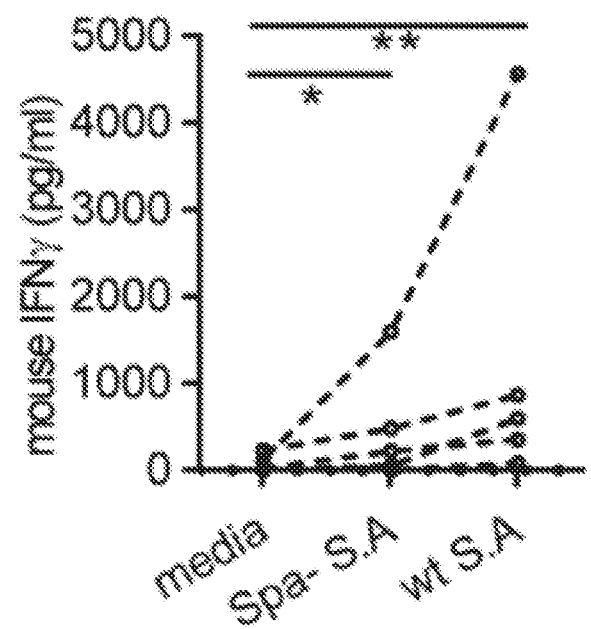
Figure 5G:
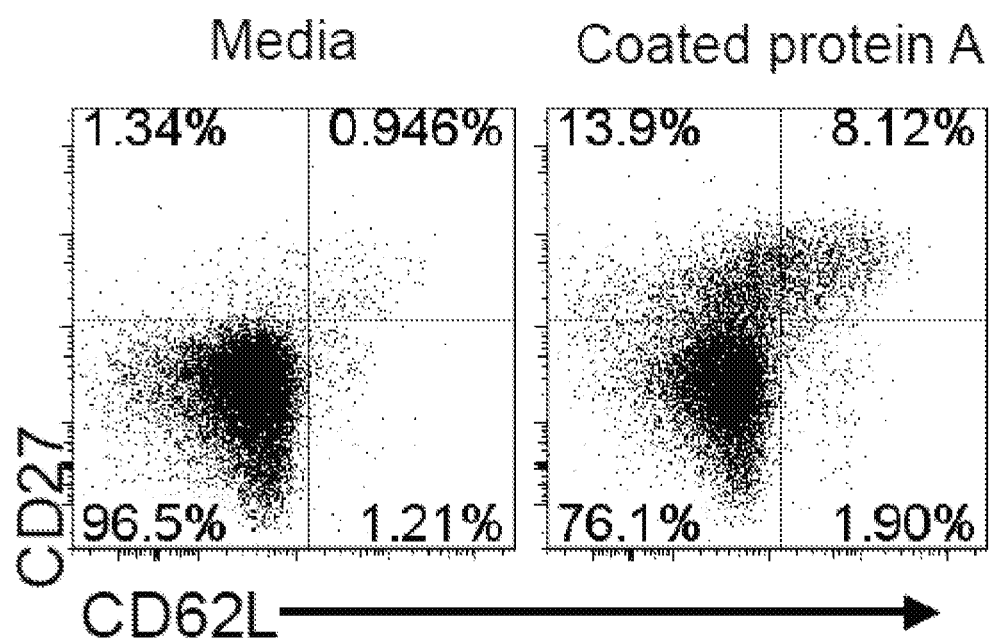
Figure 5H:
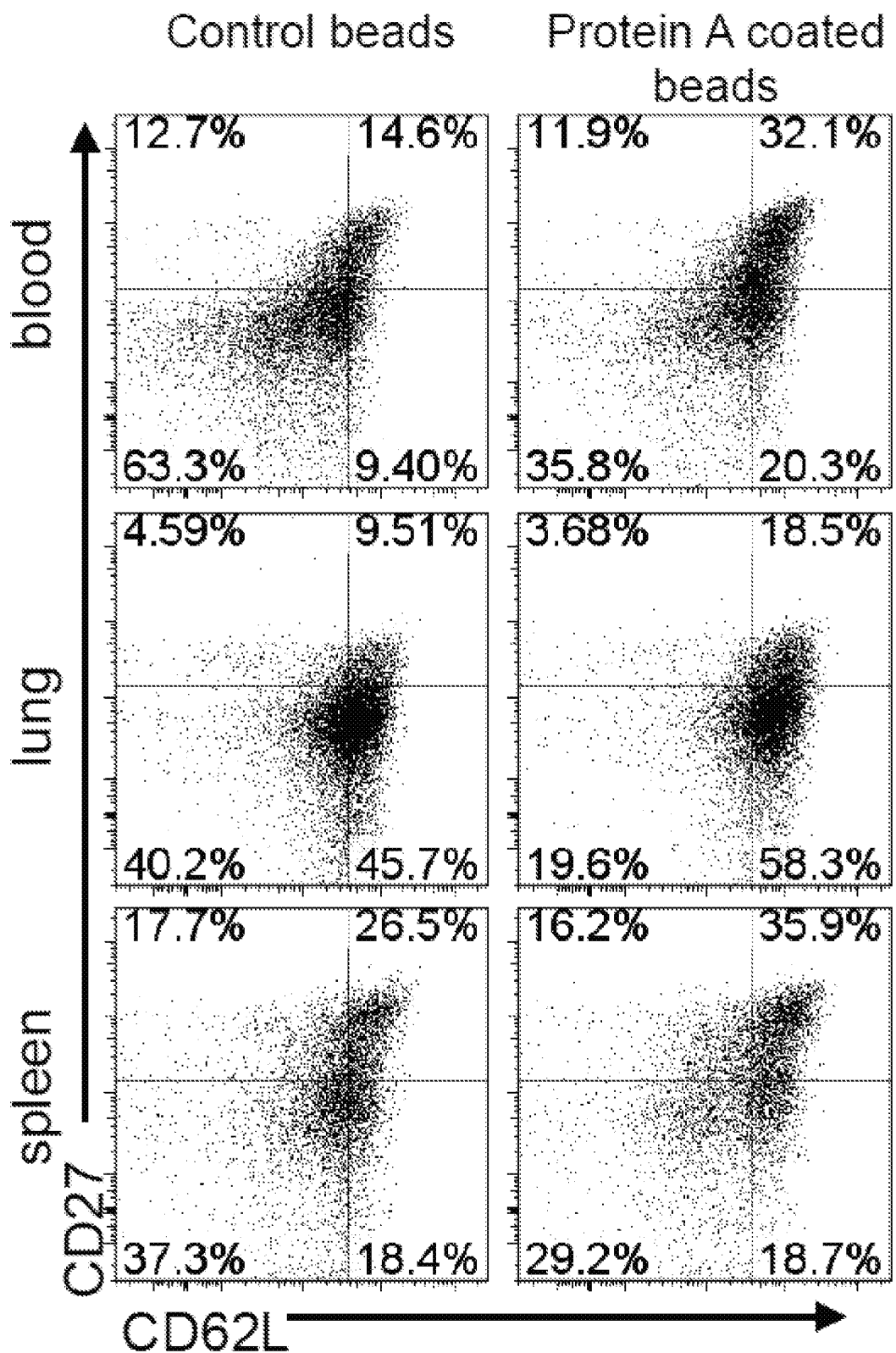
Figure 15A:
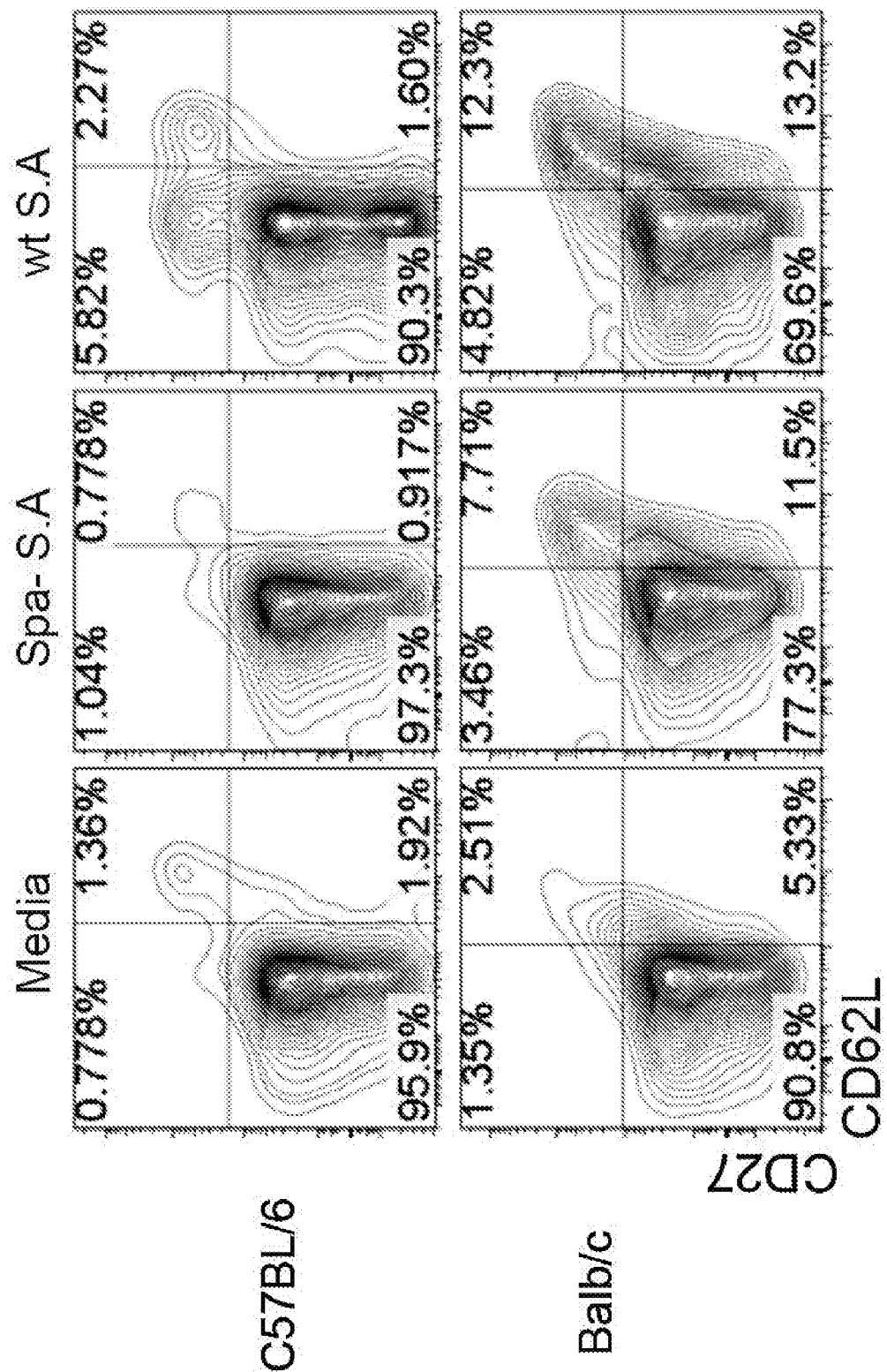
FIG. 15A shows the phenotype of mouse spleen NK cells from C57BL/6 and BALB/c after 24 hours culture with bacteria. This represents one of three experiments.
Figure 15B:
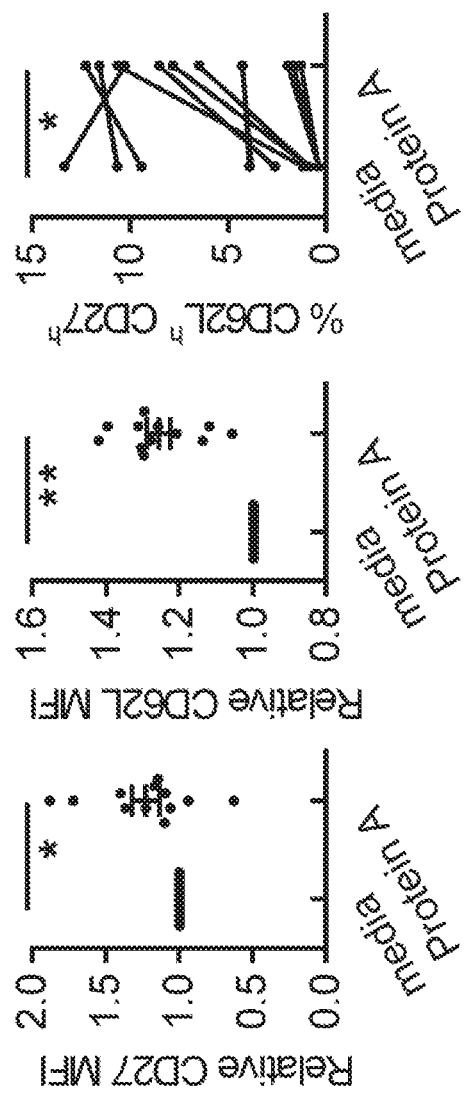
FIG. 15B shows NK cells isolated from mouse spleen cultured in plates pre-coated with media or protein A and stained at 24 h of culture. CD62L and CD27 intensity are relative to media coated plates (n=12).
Figure 15C:
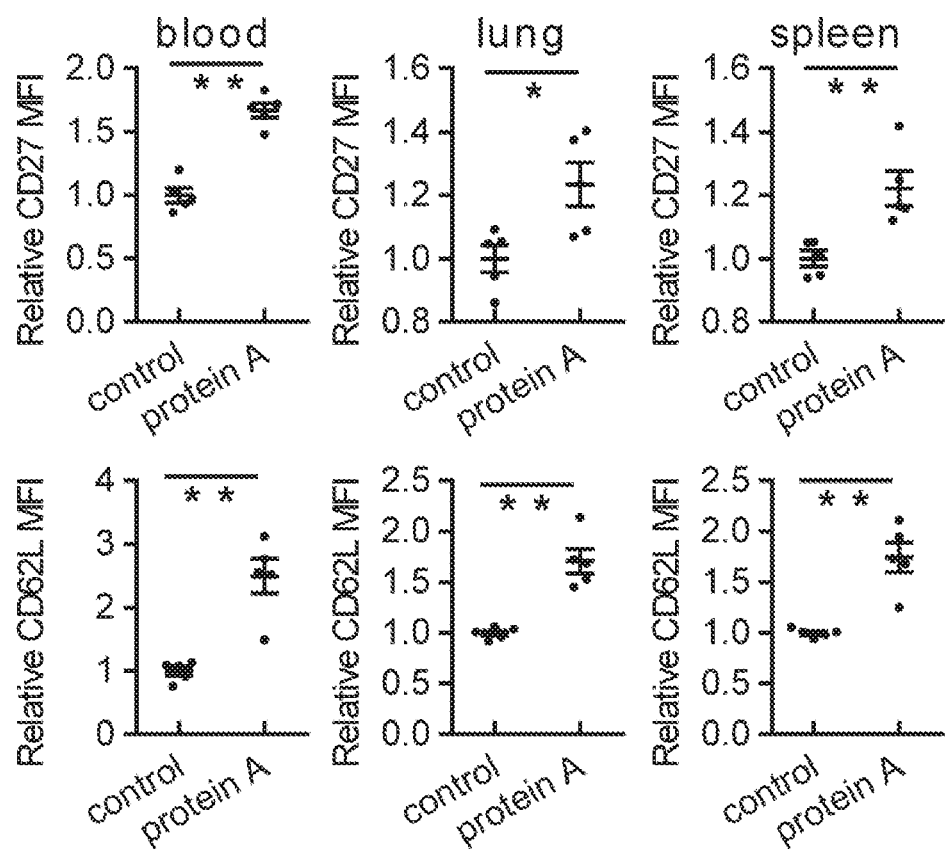
FIG. 15C shows the phenotypes of NK cells from BALB/c mice that were injected with control silicone beads or protein A-conjugated silicone beads. A statistical summary (n=5) is shown.
Figure 15D:
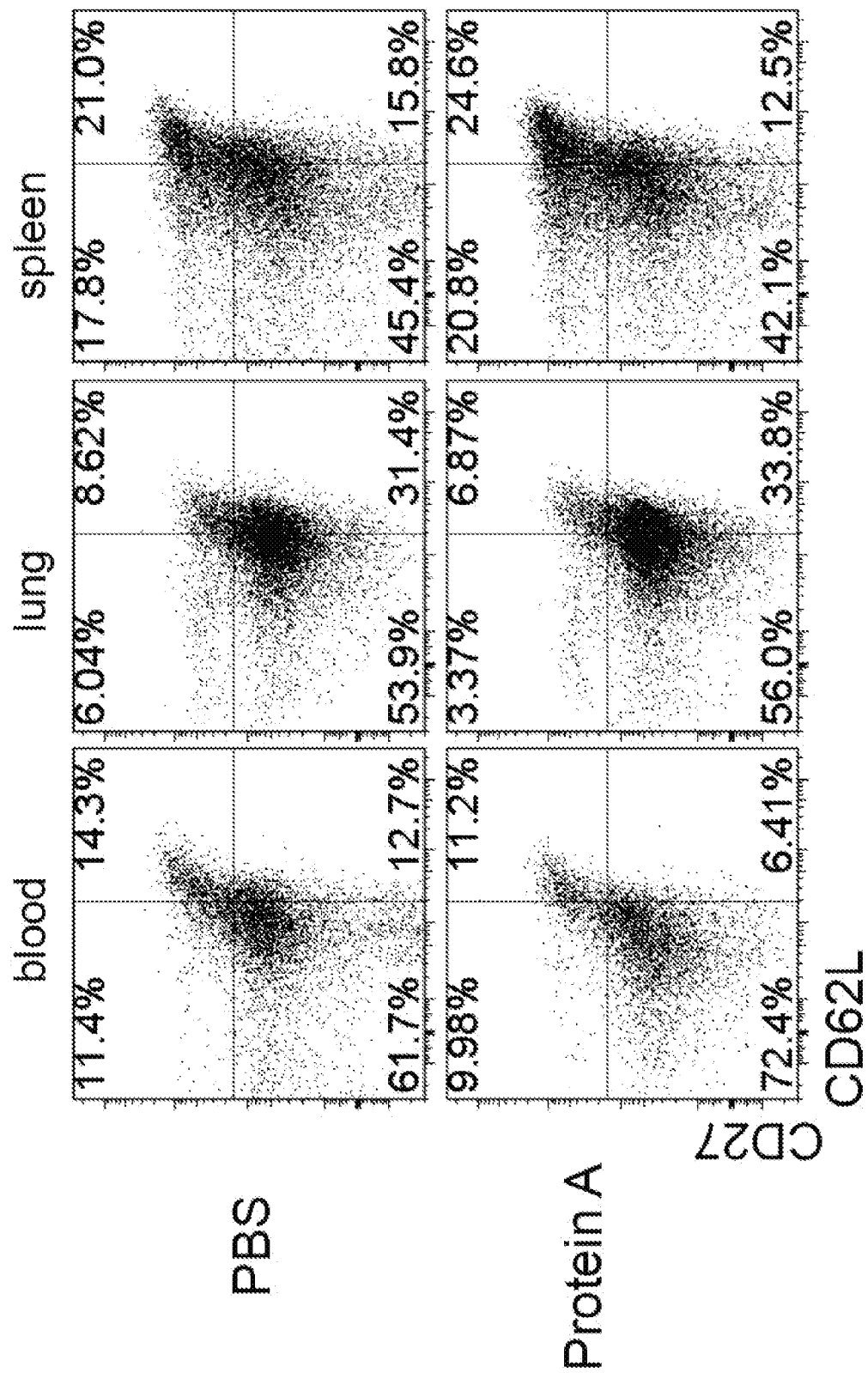
FIG. 15D shows the phenotype of NK cells from BALB/c mice injected with soluble protein A for 24 hours. The Figures represent one of 3 experiments.

Additionally, mouse NK cells cultured with wildtype S.A produced more IFNγ than spa-S.A (FIG. 5F), and expressed more early activation marker CD27 and CD62L (in contrast to a loss of CD62L in activated human NK cells) (Peng, H. et al. *J Immunol* 190, 4255-4262 (2013); Hayakawa & Smyth, 2006, *J Immunol* 176, 1517-1524) (FIG. 15A). A similar phenotype was observed when mouse NK cells were cultured in protein A-coated plates (FIGS. 5G and 15B). S.A produces many inflammatory factors (Fournier & Philpott, 2005, *Clin Microbiol Rev* 18, 521-540 (2005)). To avoid confounding of results by bystander activation, mice were injected with protein A-coated silicone beads to study if oligomeric protein A could activate NK cell in vivo. NK cells from mice injected with protein A conjugated silicone beads adopted a more activating phenotype compared with NK cells from mice injected with control silicon beads (FIGS. 5H and 15C). However, injection of soluble protein A did not cause any phenotypic changes on mouse NK cells compared to PBS control (FIG. 15D). Taken together these results demonstrate that protein A activated mouse NK cells in vitro and in vivo.

Discussion

As demonstrated by the results set forth above, an unbiased cytotoxicity assay, DC-MEGE, illustrated interactions of human NK cells and host tumor cells following HSV1 infection (FIG. 1A). With the exception of Us12 (Huard & Fruh, 2000, *Eur Immunol* 30, 509-515) and Us3 (Imai et al., 2013, *PLoS One* 8, e72050), this is the first time the remaining viral genes have been reported as significant for their regulation of NK cell cytotoxicity. DC-MEGE is therefore useful to study how NK cells interact with other pathogens.

HSV1 gE/gI complexes have been shown to participate in "antibody bipolar bridging", whereby a single HSV1-specific IgG antibody simultaneously binds to a HSV1-antigen using its Fab region and to gE/gI via its Fc region (Frank & Friedman, 1989, *Journal of virology* 63, 4479-4488). It has been proposed that such antibody bipolar bridging could block access of the Fc portion of an antibody to FcγR expressed on innate immune effector cells, and thereby reduce classical ADCC and presumably provide a mechanism for immune evasion following HSV1 infection (Dubin et al., 1991, *Journal of virology* 65, 7046-7050; Corrales-Aguilar et al., 2014, *PLoS Pathog* 10, e1004131). This seems to contradict the disclosed finding that gE or the gE/gI complex promotes activation and cytotoxicity of human NK cells (FIGS. 2A, 2B). However previous studies suggesting an NK-inhibition of HSV1 gE/gI were all conducted in the presence of HSV1-specific antibody (Frank & Friedman, 1989, *Journal of virology* 63, 4479-4488; Dubin et al., 1991, *Journal of virology* 65, 7046-7050; Corrales-Aguilar et al., 2014, *PLoS Pathog* 10, e1004131); thus these results were all relative to classical ADCC, whereas the actual function of HSV1 gE binding non-immune IgG under the condition of primary viral infection was not assessed.

Disclosed herein is an unappreciated immunostimulatory role of HSV1 gE/gI. Crystal structure, in vitro and in vivo functional validation demonstrated that IgG Fc bridged gE and CD16a (FIG. 3C), and the resultant ternary complex transduced an intracellular signal that activated NK cells (FIG. 3E), and promoted clearance of HSV1 infection. The disclosed work suggests that during primary HSV1 infection when anti-HSV1 antibody is not yet available, NK cells can utilize "passive ADCC" to clear HSV1-infected cells (FIG. 4D-4F). This result is consistent with the observation that most primary HSV1 infections in man are clinically asymptomatic. It is also highly likely that passive ADCC is at least in part responsible for the rapid NK cell clearance of oncolytic HSV1 in the setting of malignant glioma (Alvarez-Breckenridge et al., 2012, *Nat Med* 18, 1827-1834 (2012)).

This disclosure has also established a functional role for surface IgG, anchored by its Fc domain to CD16a expressed on the NK cell surface, and a new mechanism by which NK cells are able to recognize pathogens in the absence of specific antigen recognition. As demonstrated herein, HSV1 infected host cells, as well as protein A and protein G, are capable of activating human NK cells by binding NK cell surface IgG. Protein A has long been proposed as a virulent factor for *Staphylococcus aureus* newman strain, and Spa⁻ *Staphylococcus aureus* newman strain. causes milder symptoms in mice than wt S.A (Palmqvist et al., 2002, *Microb Pathog* 33, 239-249). The disclosed findings that coated protein A and wt S.A. activated NK cells, and Spa⁻ S.A. did not activate NK cells, provide a mechanistic explanation for this phenotype. This new mechanism of innate immune cell activation has broad implications for clinical toxicity observed during infection, given that many viruses and bacteria encode proteins capable of binding the Fc domain of human IgG (Litwin et al., 1992, *J Virol* 66, 3643-3651; Sprague et al., 2008, *Journal of Virology* 82, 3490-3499; Loukas et al., 2001, *Infect Immun* 69, 3646-3651; De Miranda-Santos & Campos-Neto, 1981, *J Exp Med* 154, 1732-1742).

Example 2: Use of IgG-Binding Proteins Protein A and Protein G to Capture Monocytes and Increase the Efficacy of Generating Dendritic Cells and Macrophages In Vitro Dendritic cells and macrophages are highly specialized antigen-presenting cells (APC), which account for a very small percentage (~0.2%) of human blood mononuclear cells. Accordingly, dendritic cells and macrophages are generated from in vitro culture of monocytes for numerous therapeutic purposes.

Conventional procedures for generating dendritic cells and macrophages involve: (1) plating PBMC or monocytes on culture dishes, (2) incubating cells at 37° C. for few hours to allow monocytes to attached to the plate, (3) removing non-adherent cells by vigorously washing the plates with media, and (4) treating adherent cells with GM-CSF (for macrophage) or GMCSF and IL4 (for dendritic cells) for one week. While this protocol yields consistent results, cells were lost during step 2 and 3, and a relative large amount of monocytes or PBMC were required for generating enough dendritic cells and macrophages for downstream uses.

Figure 23A:
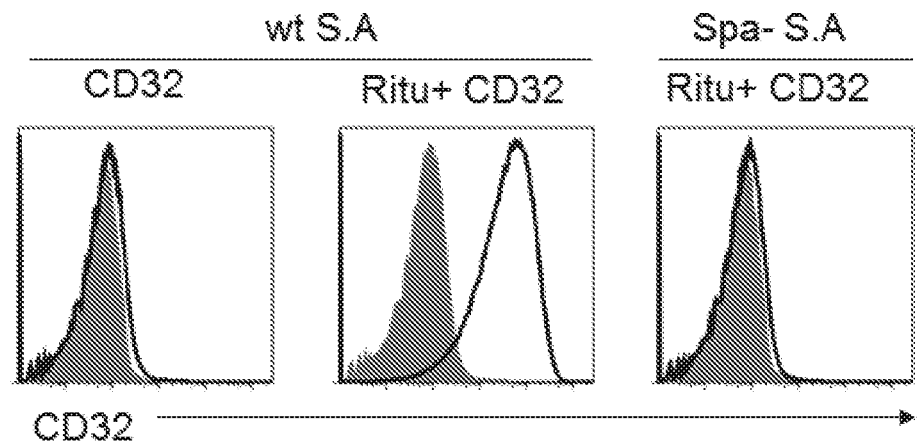
FIGS. 23A and 23B show that the binding of human Fcγ receptor CD32 and CD64 to Staphylococcus aureus required the presence of human IgG and protein A. Wild type (wt) or protein A deficient (Spa-) Staphylococcus aureus bacteria were incubated with fluorescently labeled human Fcγ receptor CD32 as show in in FIG. 23A and CD64 as shown in FIG. 23B in the absence or presence of humanized antibody rituximab (Ritu). Filled grey histograms represent unstained bacteria.
Figure 23B:
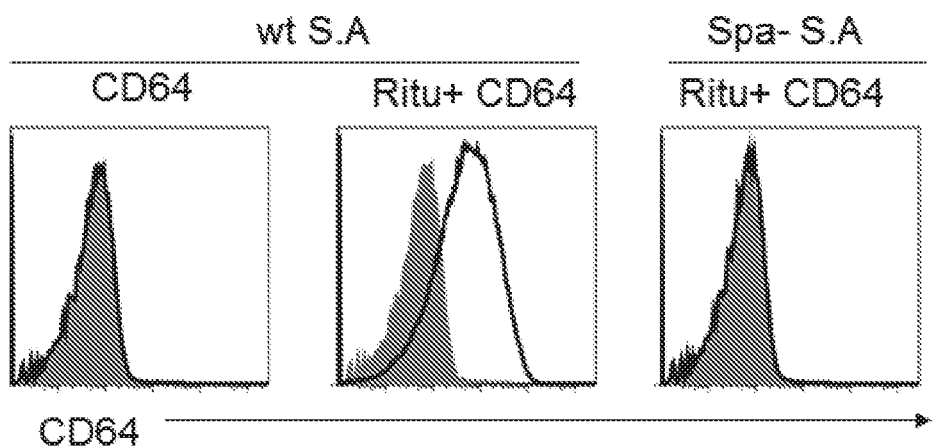

Like natural killer cells, primary monocytes are also coated on the surface with IgG molecules, which are anchored on monocytes by Fcγ receptors, including CD64, CD32 and CD16a and provide interaction sites for protein A to bind. Binding of human Fcγ receptor CD32 and CD64 to *Staphylococcus aureus* (S.A) required the presence of human IgG and protein A. Wild type (wt) or protein A deficient (Spa-) S.A bacteria were incubated with fluorescent labeled human Fcγ receptor CD32 and CD64 in the absence or presence of humanized antibody rituximab (Ritu) (FIGS. 23A and 23B). These results confirmed that protein A, IgG and CD32/CD64 formed ternary complexes in a way similar to protein A/IgG/CD16 complex. CD64, the high affinity FcγR, is majorly expressed by monocytes, macrophages and dendritic cells.

Figure 17A:
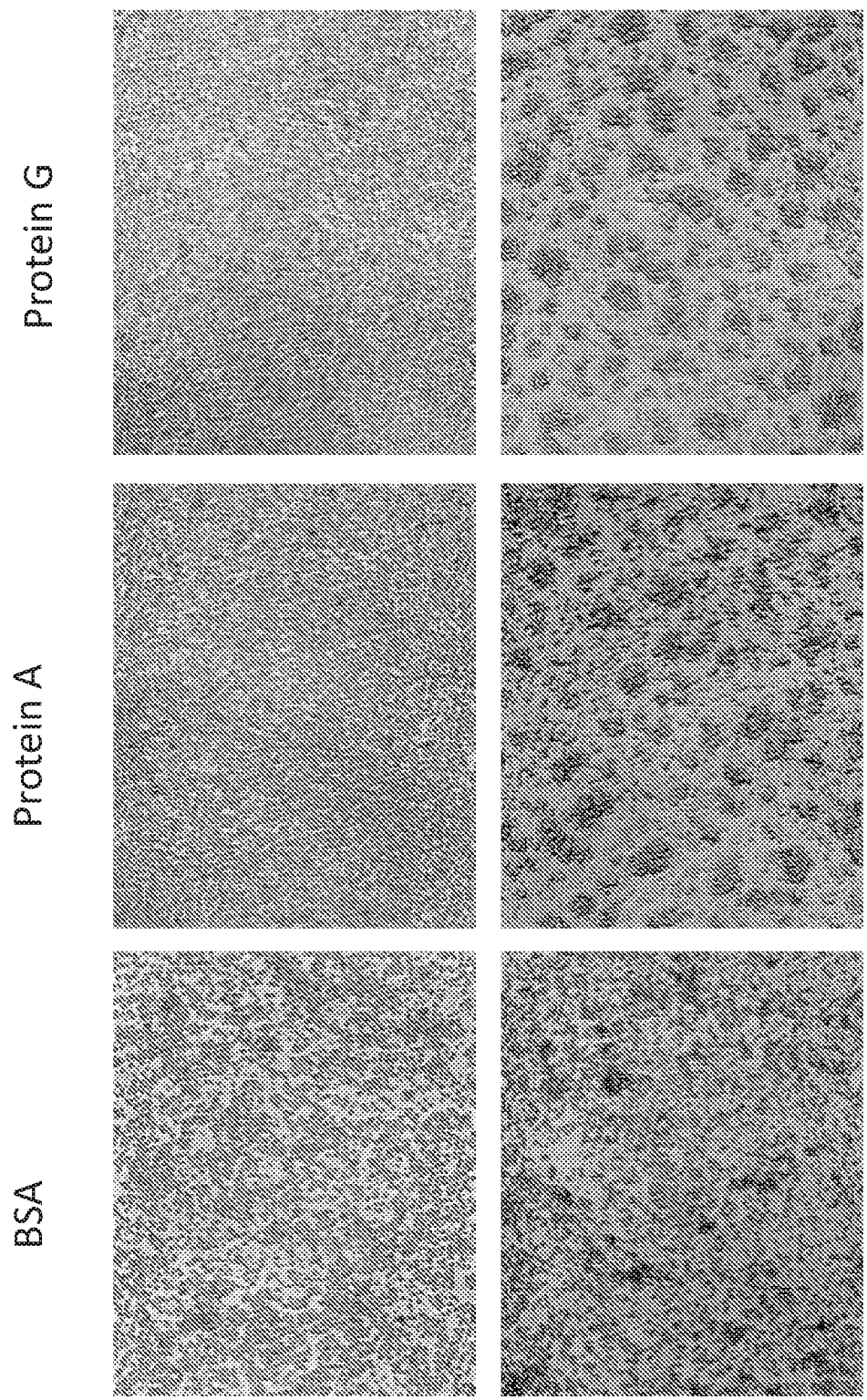
FIGS. 17A-17C show morphological and functional changes of human monocytes treated with bacterial IgG-binding proteins.
Figure 17B:
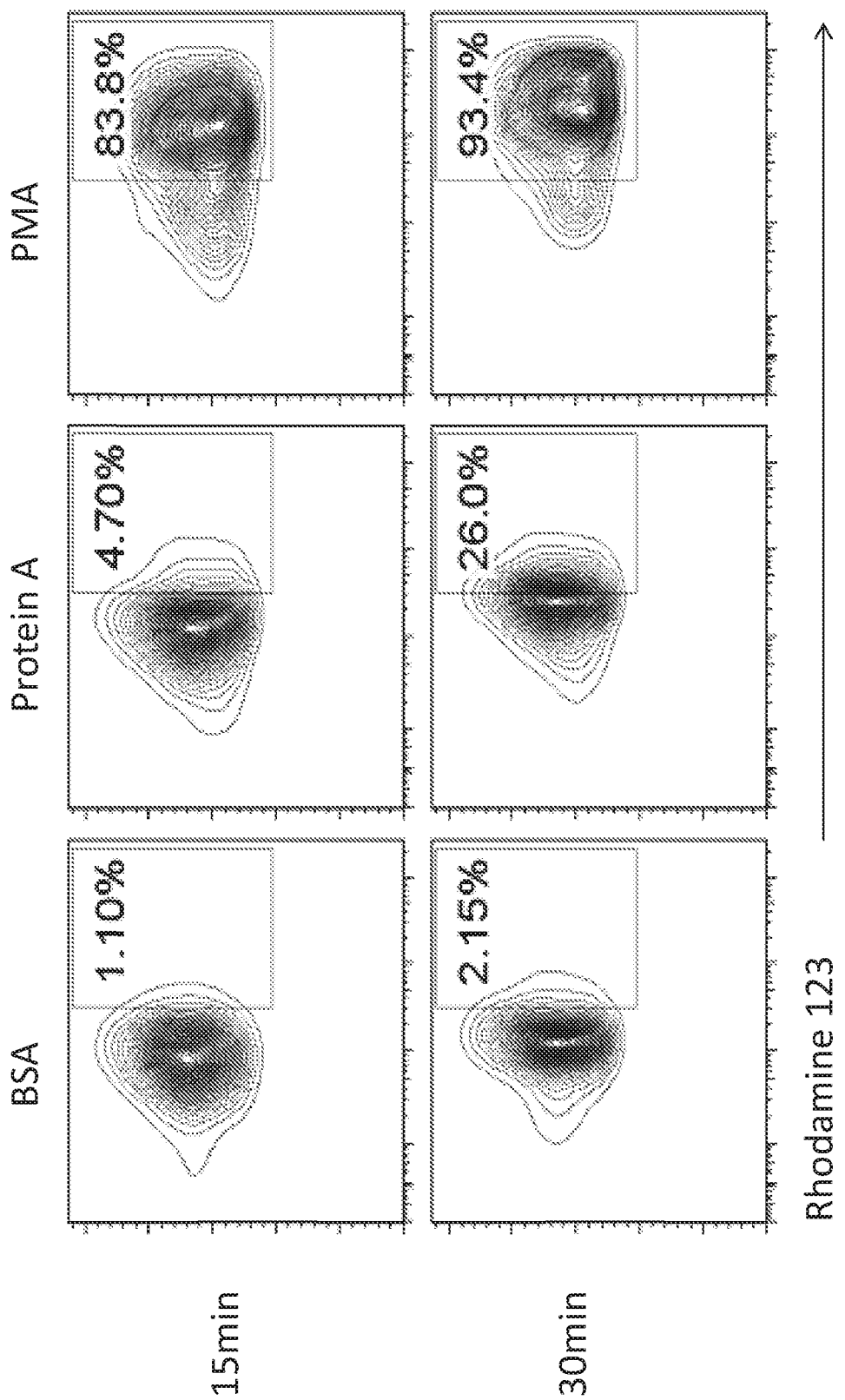
Figure 17C:
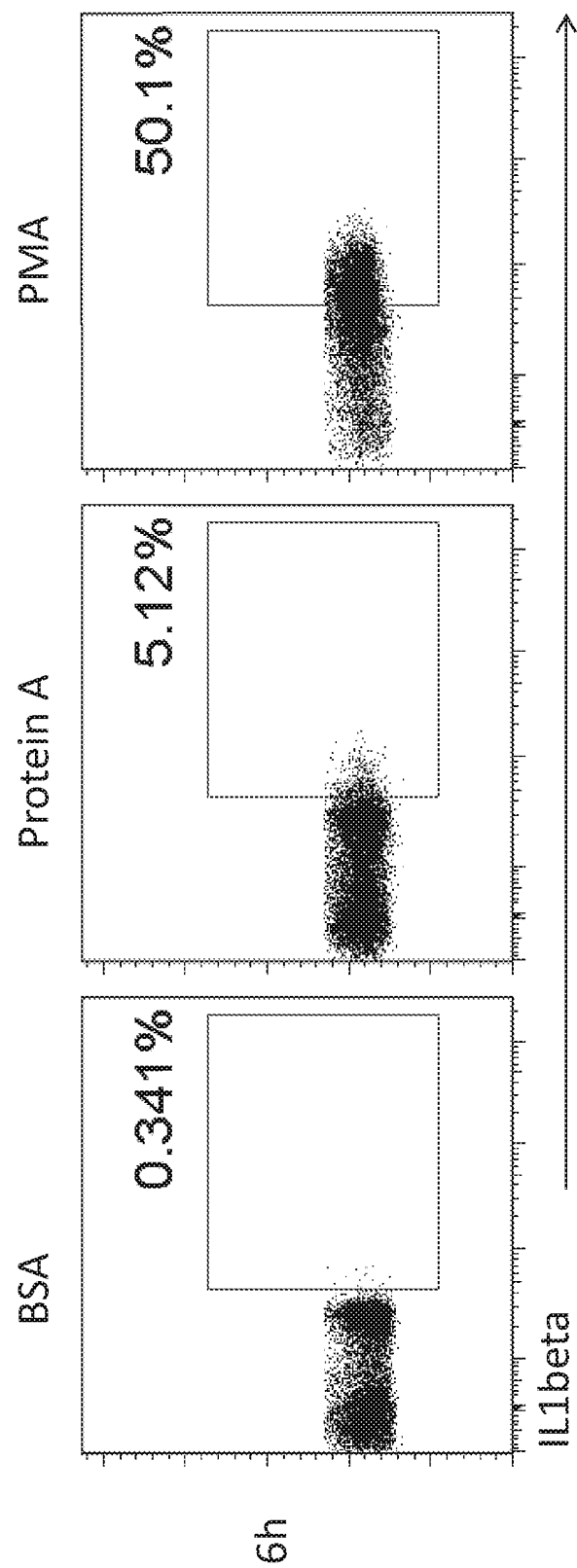
Figure 18:
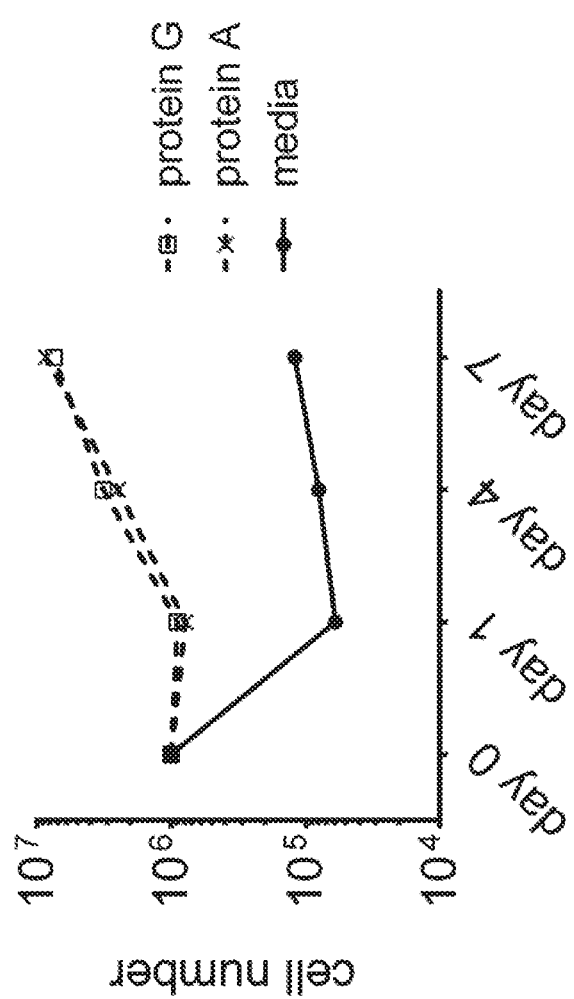
FIG. 18 shows that culture plates pre-coated with protein A and protein G increased efficacy of generating dendritic cells from human monocytes. One million purified human monocytes were seeded in plates on day 0 and cultured with media supplemented with 20 ng/ml GM-CSF and IL4 (long/ml) to generate dendritic cells. Cells unattached to the plate were removed on day 1. Cells attached to plates were counted on day 1, day 4 and day 7.
Figure 19:
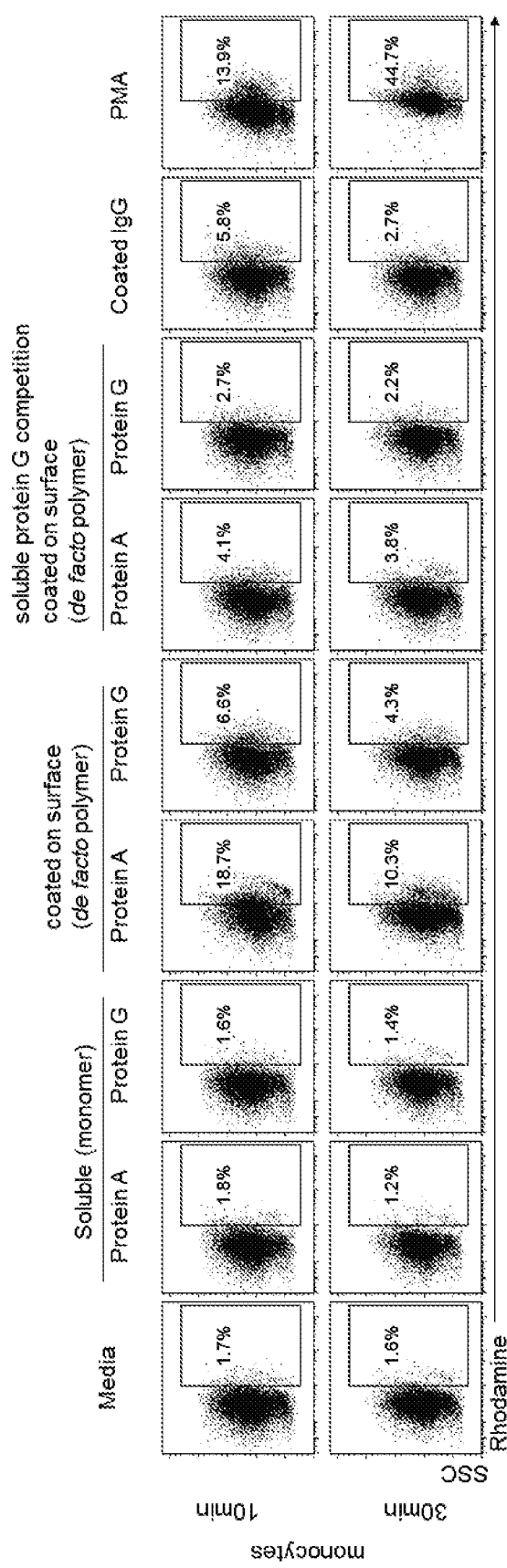
FIG. 19 shows that immobilized protein A and protein G induced respiration burst in primary human monocytes. Freshly isolated human monocytes were cultured under the indicated conditions in the presence of dihydrorhodamine123 (DHR123) for 10 min or 30 min. Cells were analyzed using flow cytometry.
Figure 20:
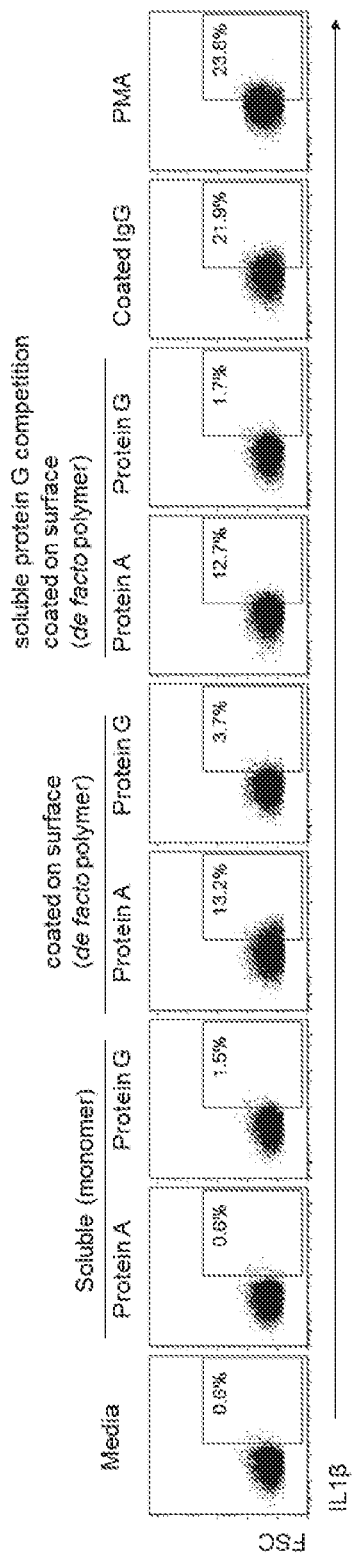
FIG. 20 shows that immobilized protein A and protein G induced the production of IL1β in primary human monocytes. Freshly isolated human monocytes were cultured under the indicated conditions for 6 hours and stained for IL1β.
Figure 21:
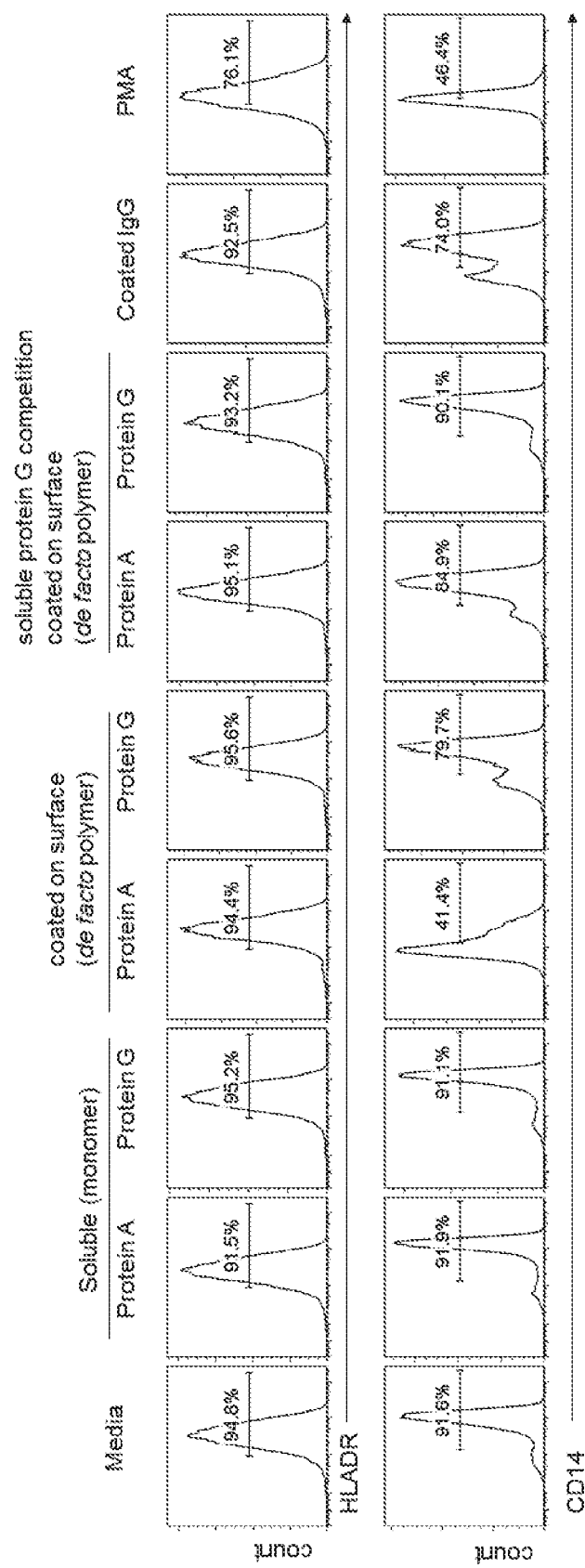
FIG. 21 shows that immobilized protein A and protein G changed the phenotype of primary human monocytes. Freshly isolated human monocytes were cultured under the indicated conditions for 6 hours and stained for HLA-DR and CD14.
Figure 22:
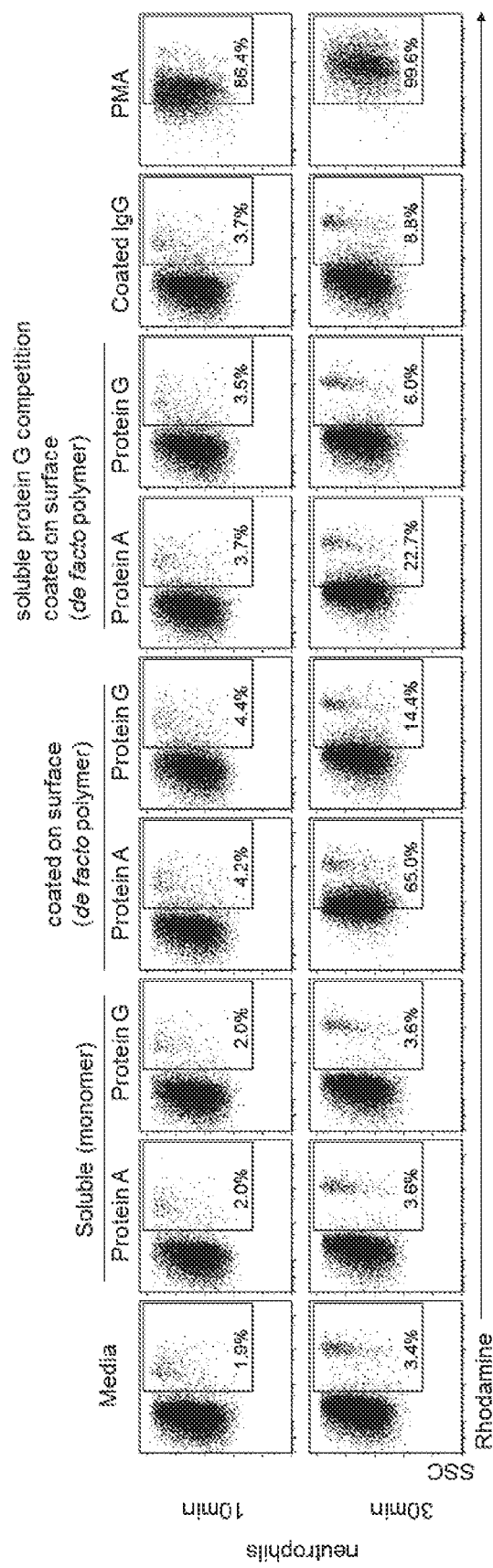
FIG. 22 shows that immobilized protein A and protein G induced respiration burst in primary human neutrophils. Freshly isolated human neutrophils were cultured under the indicated conditions in the presence of DHR 123 for 10 min or 30 min. Cells were analyzed using flow cytometry.

Protein A and protein G can bind IgG coated on NK cells and monocytes. Therefore, protein A or protein G molecule coated on a plate should be able to bind surface IgG of monocytes and thus increase adhesion of monocytes. By plating the same amount of monocytes in different plates, monocytes were found to attach more firmly to protein A or protein G treated plates than to bovine serum treated plates during the first few hours, and monocytes culture in plate A or protein G coated plates started to form colonies, an indication of activation (FIG. 17A). Further experiments using protein A coated plate showed that other than increasing adhesion of monocytes, protein A coated plates also increased metabolic activity of monocytes, induced monocytes to produce IL1β and changed the phenotype of primary human monocytes after 6 hours (FIG. 17B, 17C, FIG. 19, FIG. 20, and FIG. 21). Similarly, immobilized protein A and protein G induced respiration burst in primary human neutrophils (FIG. 22). Therefore, instead of culturing monocytes in regular plates, monocytes or PBMC were cultured in plates coated with protein A or protein G for generating dendritic cells or macrophages. This reduced loss of cells at steps 2 and 3 and required much less starting monocytes and PBMC for generating equal amount of dendritic cells and macrophage (FIG. 18).

Figure 24:
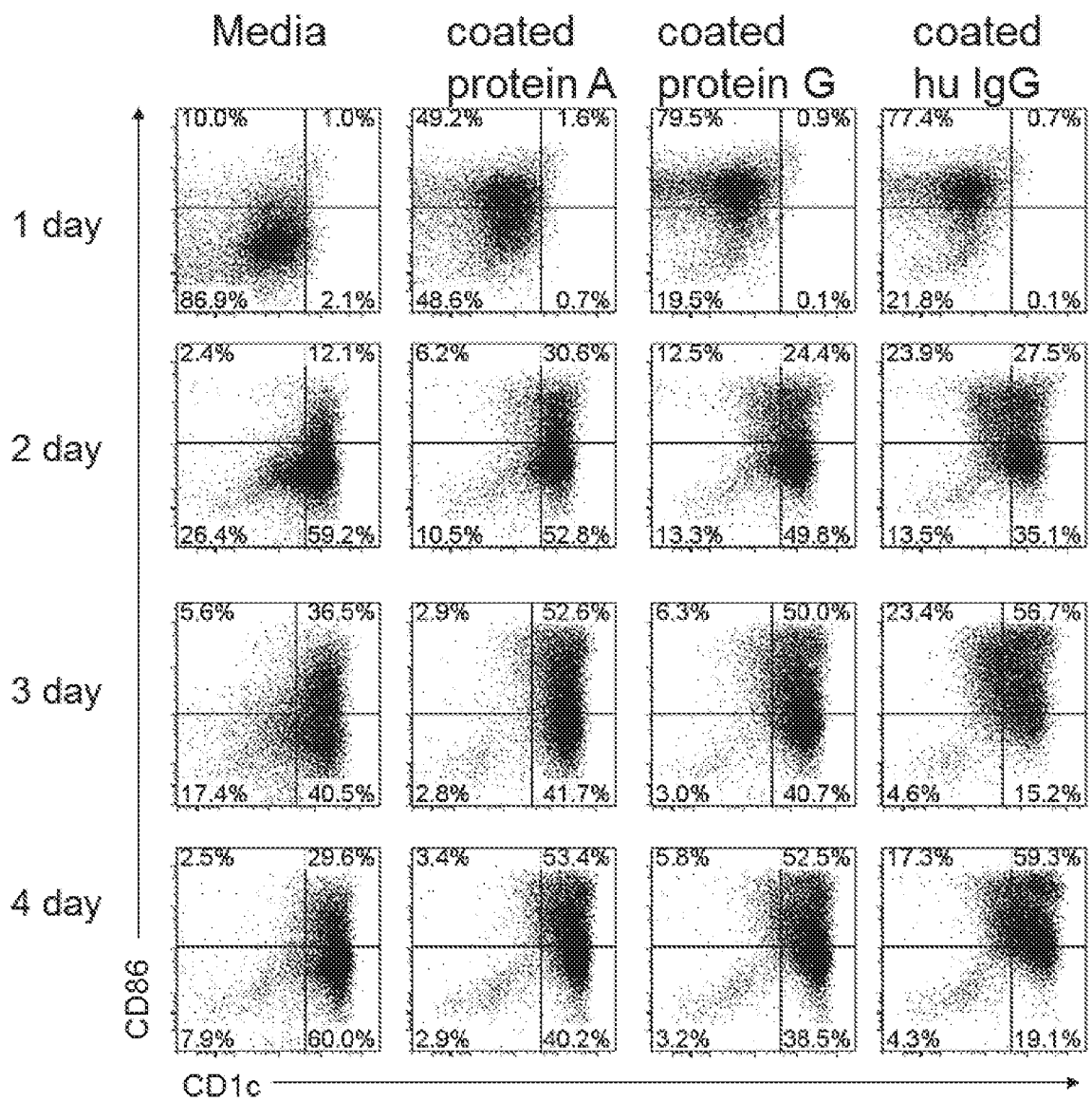
FIG. 24 shows that immobilized protein A, protein G and human IgG changed the phenotype of monocyte-derived dendritic cells. Freshly isolated human monocytes were cultured in the presence of IL4 and GM-CSF in treated plates for specified times and stained for CD86 and CD1c.
Figure 25:
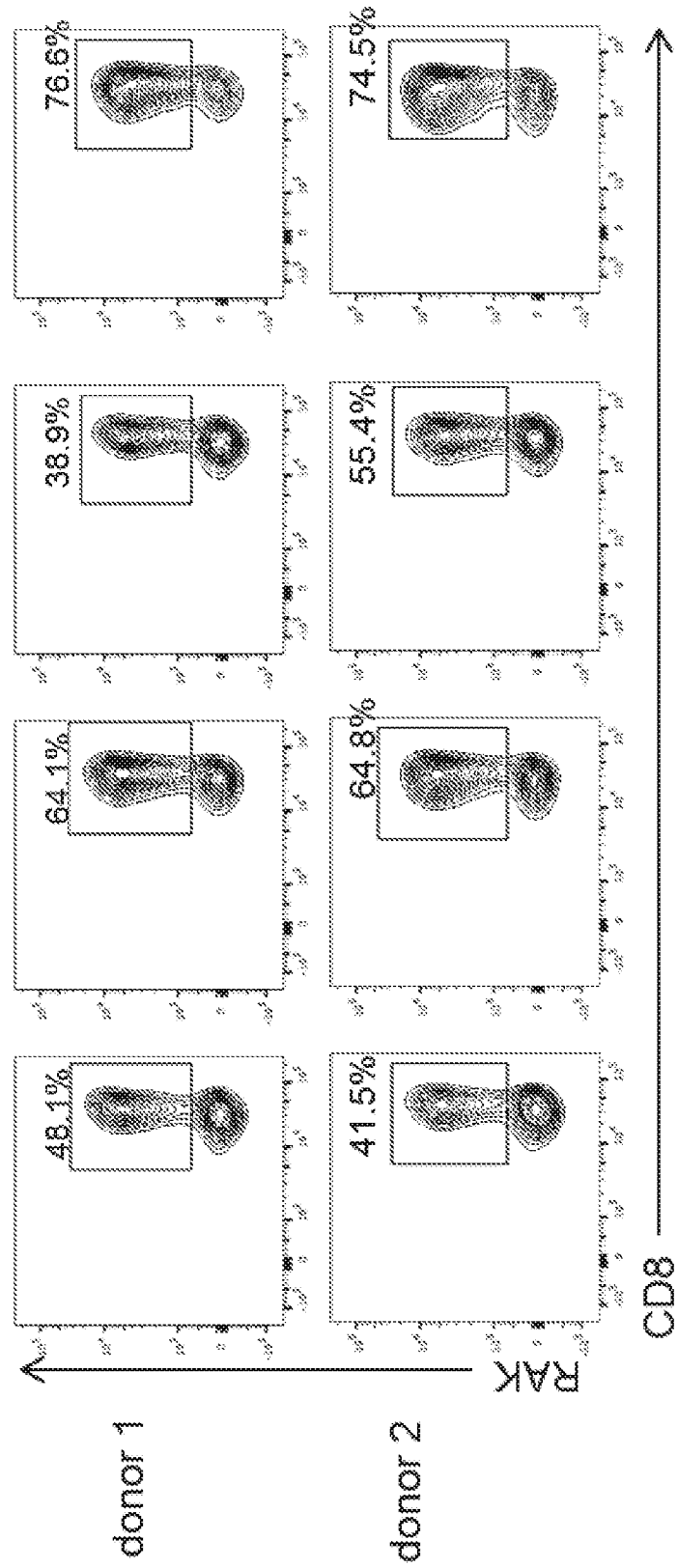
FIG. 25 shows that immobilized protein A, protein G and human IgG changed the function of monocyte-derived dendritic cells. Dendritic cells were generated from monocytes cultured in plates for 5 days, activated and loaded with Epstein-Barr virus (EBV) replication activator BamHI Z leftward reading frame 1 (BZLF1) peptide for 24 hours, and cultured with autologous T cells for 10 days. EBV-specific cytotoxic T cells were determined by tetramer staining.
Figure 26:
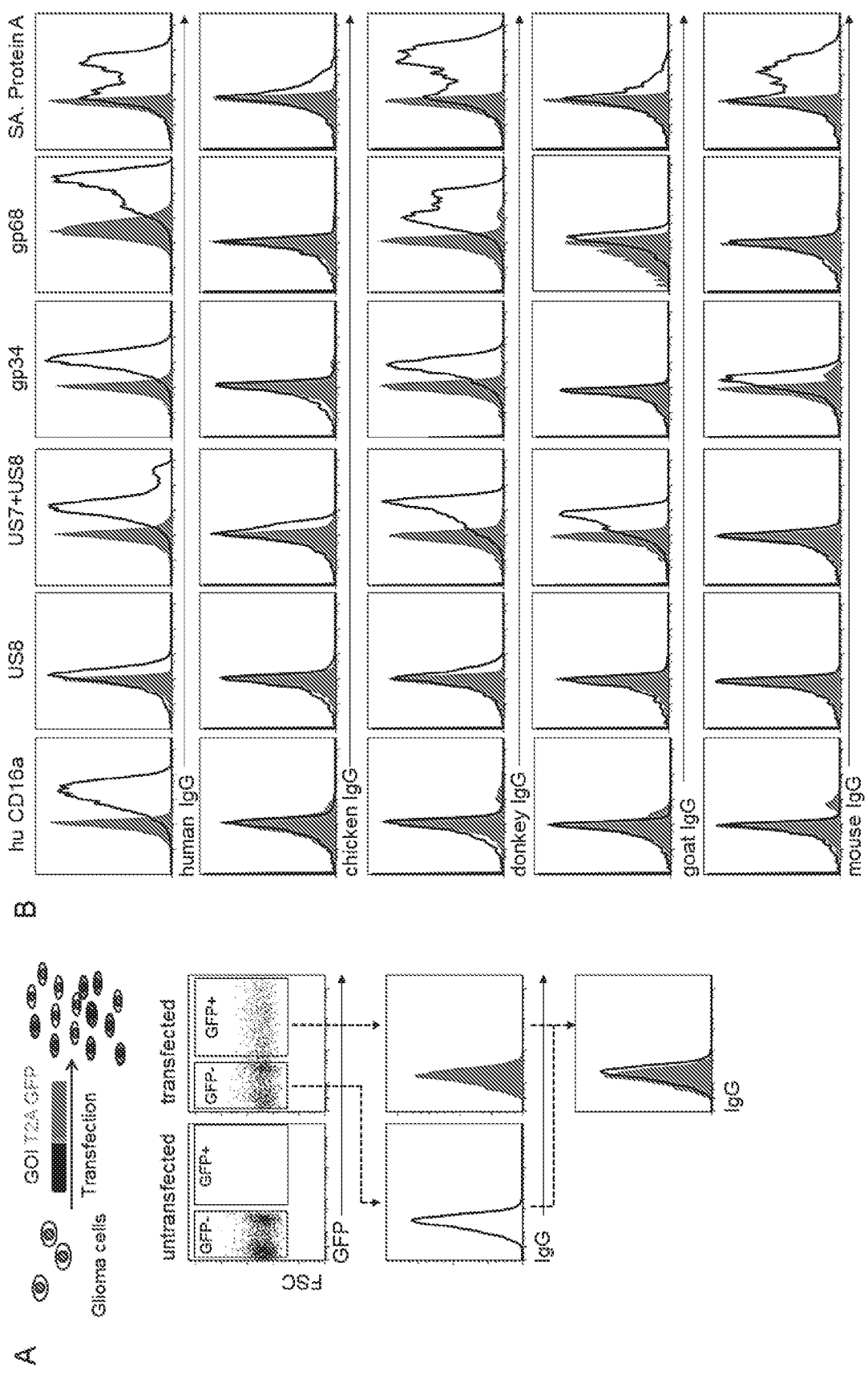
FIGS. 26A and 26B show binding of human and pathogen IgG-binding proteins to IgG molecules from different species. The experimental procedures used are shown in FIG. 26A and representative results are shown in FIG. 26B for determining interactions between different IgG and IgG-binding proteins using flow cytometry. IgG-binding proteins were cloned individually to fuse with 2A protein from the Thosea asigna virus and green fluorescent protein (GFP), wherein GFP reports expression of IgG-binding protein. To determine interactions between IgG and IgG-binding proteins, glioma cells were transfected with IgG binding protein and incubated with fluorescently labeled IgG from different species. Samples were read by flow cytometry, and GFP+ (heavy black line) and GFP− cells (filled gray histogram) were analyzed for fluorescent signal intensity and overlaid with each other.

Dendritic cells generated from plates pre-coated with protein A, protein G or human IgG expressed a higher amount of costimulator molecule CD86 (FIG. 24). Upon loading with Epstein Barr Virus (EBV) antigenic peptide and coculturing with autologous T cells, these dendritic cells also tended to induce more EBV specific cytotoxic T cells (FIG. 25).

Previous studies reported that protein A binds TNFR1 and activates epithelial cells, and protein G does not bind TNFR1 and not activate epithelial cells (reference PMID: 15247912). While it is possible that monocyte attachment and activation by protein A may partially contribute to binding TNFR1 which is expressed on monocytes, protein G increased monocyte attachment can be explained by binding surface IgG on monocytes because the existence of the ternary complex of protein G-IgG-CD16 and the present data showing protein G activates NK cells through binding surface IgG.

Example 3: Activation of NK Cells Using CMV

Figure 29A:
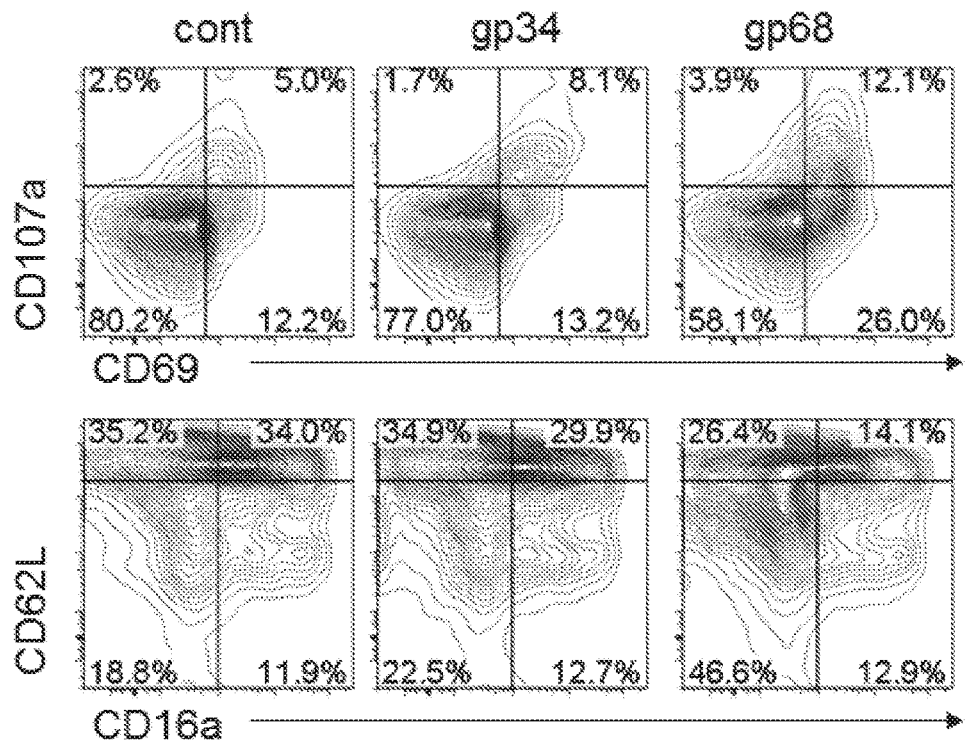
FIGS. 29A and 29B show the phenotypes of primary human NK cells after being cultured for 7 hours with transfected glioma cells.
Figure 29B:
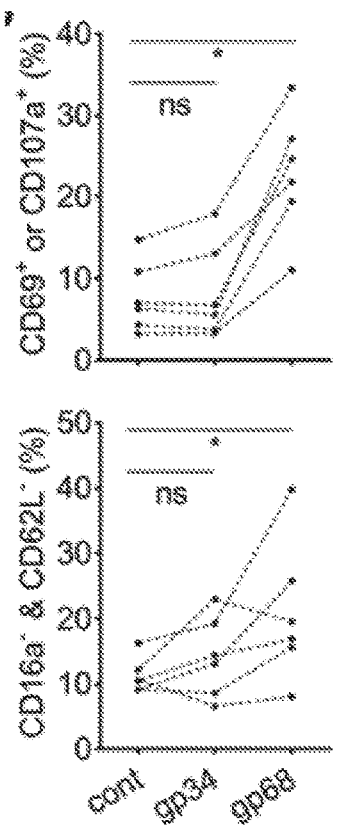

Both CMV gp34 and gp68 are IgG-binding proteins capable of binding both humanized antibody rituximab and human IgG through portions of their Fc (FIGS. 28A and 28B). CD16a does not directly interact with glioma cells expressing either gp34 or gp68 (FIG. 28C), however it can bind glioma cells expressing gp68 in the presence of rituximab or human IgG1 Fc fragment, but does not bind to the glioma cells expressing gp34 even when human IgG Fc is present (FIGS. 28D and 28E). Therefore, gp68 is capable of forming a ternary complex with human IgG1 Fc and CD16a. Additionally, primary human NK cells cultured with glioma cells expressing gp68 showed activated phenotypes, which was represented by the increase of CD69 and CD107a, and the decrease of CD62L and CD16a (FIGS. 29A and 29B).

Figure 30:
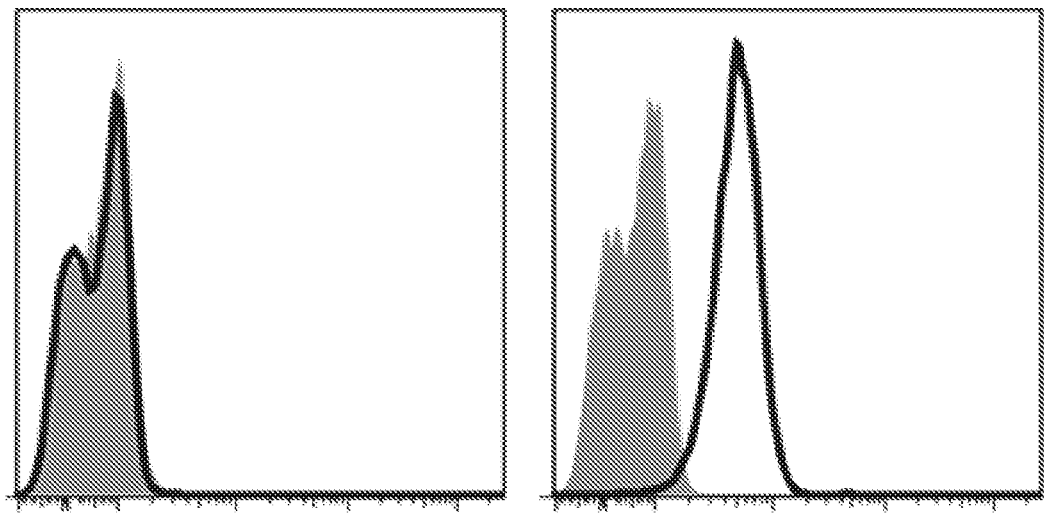
FIG. 30 demonstrates that mouse cytomegalovirus infection allows 3T3 cells to bind non-immune mouse IgG. 3T3 cells were not infected (filled grey) or infected with murine cytomegalovirus (MCMV; heavy black) for 24 h, and incubated with fluorescent labeled IgG. Cells were collected using flow cytometry.

MCMV infection also allowed 3T3 to bind non immune mouse IgG (FIG. 30), indicating that MCMV produce IgG-binding protein(s).

Unless defined otherwise, all technical and scientific terms used herein have the same meanings as commonly understood by one of skill in the art to which the disclosed invention belongs. Publications cited herein and the materials for which they are cited are specifically incorporated by reference.

Those skilled in the art will recognize, or be able to ascertain using no more than routine experimentation, many equivalents to the specific embodiments of the invention described herein. Such equivalents are intended to be encompassed by the following claims.

| | |
|---|---|
| SEQ ID NO: 1:<br>IgG1 Fc (binds both human FcγR and pathogen IgG binding protein) | EPKSCDKTHTCPPCPAPELLGGPSVFLFPPKPKDTLMISRTPE<br>VTCVVVDVSHEDPEVKFNWYVDGVEVHNAKTKPREEQYN<br>STYRVVSVLTVLHQDWLNGKEYKCKVSNKALPAPIEKTISK<br>AKGQPREPQVYTLPPSRDELTKNQVSLTCLVKGFYPSDIAVE<br>WESNGQPENNYKTTPPVLDSDGSFFLYSKLTVDKSRWQQG<br>NVFSCSVMHEALHNHYTQKSLSLSPGK |
| SEQ ID NO: 2:<br>IgG1 Fc (binds only pathogen IgG binding protein) | FPPKPKDTLMISRTPEVTCVVVDVSHEDPEVKFNWYVDGVE<br>VHNAKTKPREEQYNSTYRVVSVLTVLHQDWLNGKEYKCK<br>VSNKALPAPIEKTISKAKGQPREPQVYTLPPSRDELTKNQVS<br>LTCLVKGFYPSDIAVEWESNGQPENNYKTTPPVLDSDGSFFL<br>YSKLTVDKSRWQQGNVFSCSVMHEALHNHYTQKSLSLSPG<br>K |
| SEQ ID NO: 3:<br>IgG binding protein A | MKKKNIYSIR KLGVGIASVT LGTLLISGGV TPAANAAQHD<br>EAQQNAFYQV LNMPNLNADQ RNGFIQSLKD<br>DPSQSANVLG EAQKLNDSQA PKADAQQNNF<br>NKDQQSAFYE ILNMPNLNEA QRNGFIQSLK<br>DDPSQSTNVL GEAKKLNESQ APKADNNFNK EQQNAFYEIL<br>NMPNLNEEQR NGFIQSLKDD PSQSANLLSE<br>AKKLNESQAP KADNKFNKEQ QNAFYEILHL<br>PNLNEEQRNG FIQSLKDDPS VSKEILAEAK<br>KLNDAQAPKE EDNKKPGKED GNKPGKEDGN<br>KPGKEDNKKP GKEDGNKPGK EDNNKPGKED<br>GNKPGKEDNN KPGKEDGNKP GKEDGNKPGK<br>EDGNGVHVVK PGDTVNDIAK ANGTTADKIA<br>ADNKLADKNM IKPGQELVVD KKQPANHADA<br>NKAQALPETG EENPFIGTTV FGGLSLALGA<br>ALLAGRRREL |
| SEQ ID NO: 4:<br>IgG binding protein G | MEKEKKVKYF LRKSAFGLAS VSAAFLVGST VFAVDSPIED<br>TPIIRNGGEL TNLLGNSETT LALRNEESAT<br>ADLTAAAVAD TVAAAAAENA GAAAWEAAAA<br>ADALAKAKAD ALKEFNKYGV SDYYKNLINN<br>AKTVEGIKDL QAQVVESAKK ARISEATDGL SDFLKSQTPA<br>EDTVKSIELA EAKVLANREL DKYGVSDYHK<br>NLINNAKTVE GVKELIDEIL AALPKTDTYK LILNGKTLKG<br>ETTTEAVDAA TAEKVFKQYA NDNGVDGEWT |

-continued

|                                                      |                                                                                                                                                                                                                                                                                                                                                                                                                                                                                                                          |
|------------------------------------------------------|--------------------------------------------------------------------------------------------------------------------------------------------------------------------------------------------------------------------------------------------------------------------------------------------------------------------------------------------------------------------------------------------------------------------------------------------------------------------------------------------------------------------------|
|                                                      | YDDATKTFTV TEKPEVIDAS ELTPAVTTYK<br>LVINGKTLKG ETTTKAVDAE TAEKAFKQYA<br>NDNGVDGVWT YDDATKTFTV TEMVTEVPGD<br>APTEPEKPEA SIPLVPLTPA TPIAKDDAKK DDTKKEDAKK<br>PEAKKDDAKK AETLPTTGEG SNPFFTAAAL<br>AVMAGAGALA VASKRKED                                                                                                                                                                                                                                                                                                          |
| SEQ ID NO: 5:<br>Glycoprotein E                      | MARGAGLVFF VGVWVVSCLA AAPRTSWKRV TSGEDVVLL<br>PAPAGPEERT RAHKLLWAAE PLDACGPLRP SWVALWPPRR<br>VLETVVDAAC MRAPEPLAIA YSPPFPAGDE GLYSELAWRDR<br>VAVVNESLVI YGALETDSGL YTLSVVGLSD EARQVASVVLV<br>VEPAPVPTPT PDDYDEEDDA GVSERTPVSV PPPTPPRRPP VA<br>PPTHPRVI PEVSHVRGVT VHMETPEAIL FAPGETFGTN VSIHA<br>IAHDDGPYAM DVVWMRFDVP SSCAEMRIYE ACLYHPQLPE<br>CLSPADAPC AVSSWAYRLA VRSYAGCSRT TPPPRCFAEARM<br>EPVPGLAWL ASTVNLEFQH ASPQHAGLYL CVVYVDDHIHA<br>WGHMTISTAA QYRNAVVEQH LPQRQPEPVE PTRPHVRAPPP<br>APSARGPLRL GAVLGAALLL AALGLSAWAC MTCWRRRSW |
|                                                      | RAVKSRASAT GPTYIRVADS ELYADWSSDS EGERDGSLWQ<br>DPPERPDSPS TNGSGFEILS PTAPSVYPHS EGRKSRRPLT TFGS<br>GSPGRRHSQA SYSSVLW                                                                                                                                                                                                                                                                                                                                                                                                      |
| SEQ ID NO: 6:<br>IgG1<br>(GenBank<br>Accession No:<br>AAC82527.1) | ASTKGPSVFP LAPSSKSTSG GTAALGCLVK DYFPEPVTVS<br>WNSGALTSGV HTFPAVLQSS<br>GLYSLSSVVT VPSSSLGTQT YICNVNHKPS NTKVDKKVEP<br>KSCDKTHTCP PCPAPELLGG<br>PSVFLFPPKP KDTLMISRTP EVTCVVVDVS HEDPEVKFNW<br>YVDGVEVHNA KTKPREEQYN<br>STYRVVSVLT VLHQDWLNGK EYKCKVSNKA LPAPIEKTIS<br>KAKGQPREPQ VYTLPPSRDE<br>LTKNQVSLTC LVKGFYPSDI AVEWESNGQP ENNYKTTPPV<br>LDSDGSFFLY SKLTVDKSRW<br>QQGNVFSCSV MHEALHNHYT QKSLSLSPGK                                                                                                                           |
| SEQ ID NO: 7:<br>IgG2<br>(GenBank<br>Accession No:<br>AAB59393.1) | ASTKGPSVFP LAPCSRSTSE STAALGCLVK DYFPEPVTVS<br>WNSGALTSGV HTFPAVLQSS<br>GLYSLSSVVT VPSSNFGTQT YTCNVDHKPS NTKVDKTVER<br>KCCVECPPCP APPVAGPSVF<br>LFPPKPKDTL MISRTPEVTC VVVDVSHEDP EVQFNWYVDG<br>VEVHNAKTKP REEQFNSTFR<br>VVSVLTVVHQ DWLNGKEYKC KVSNKGLPAP IEKTISKTKG<br>QPREPQVYTL PPSREEMTKN<br>QVSLTCLVKG FYPSDISVEW ESNGQPENNY KTTPPMLDSD<br>GSFFLYSKLT VDKSRWQQGN<br>VFSCSVMHEA LHNHYTQKSL SLSPGK                                                                                                                              |
| SEQ ID NO: 8:<br>IgG3<br>(GenBank<br>Accession No:<br>AA52805.1) | ASTKGPSVFP LAPCSRSTSG GTAALGCLVK DYFPEPVTVS<br>WNSGALTSGV HTFPAVLQSS<br>GLYSLSSVVT VPSSSLGTQT YTCNVNHKPS NTKVDKRVEL<br>KTPLGDTTHT CPRCPEPKSC<br>DTPPPCPRCP EPKSCDTPPP CPRCPEPKSC DTPPPCPRCP<br>APELLGGPSV FLFPPKPKDT<br>LMISRTPEVT CVVVDVSHED PEVQFKWYVD<br>GVEVHNAKTK PREEQYNSTF RVVSVLTVLH<br>QDWLNGKEYK CKVSNKALPA PIEKTISKTK GQPREPQVYT<br>LPPSREEMTK NQVSLTCLVK<br>GFYPSDIAVE WESSGQPENN YNTTPPMLDS DGSFFLYSKL<br>TVDKSRWQQG NIFSCSVMHE<br>ALHNRFTQKS LSLSPGK                                                                 |
| SEQ ID NO: 9:<br>IgG4<br>(GenBank<br>Accession No:<br>AAB5934.1) | ASTKGPSVFP LAPCSRSTSE STAALGCLVK DYFPEPVTVS<br>WNSGALTSGV HTFPAVLQSS GLYSLSSVVT<br>VPSSSLGTKT YTCNVDHKPS NTKVDKRVES KYGPPCPSCP<br>APEFLGGPSV<br>FLFPPKPKDT LMISRTPEVT CVVVDVSQED PEVQFNWYVD<br>GVEVHNAKTK PREEQFNSTY<br>RVVSVLTVLH QDWLNGKEYK CKVSNKGLPS SIEKTISKAK<br>GQPREPQVYT LPPSQEEMTK<br>NQVSLTCLVK GFYPSDIAVE WESNGQPENN YKTTPPVLDS<br>DGSFFLYSRL TVDKSRWQEG<br>NVFSCSVMHE ALHNHYTQKS LSLSLGK                                                                                                                             |
| SEQ ID NO: 10:<br>IgG1<br>(S6B291) | MEFGLSWLFLVAILKGVQCEVQLLESGGDLVQPGGSLRLSC<br>AASGFTFSTYAMSWVRQAP<br>GKGLEWVSGIGDSGHSIYYADSVKGRFTISRDNSKNTLYLQ<br>MNSLRAEDTAVYYCATGSQ<br>WPGDYWGQGTLVTVSSASTKGPSVFPLAPSSKSTSGGTAAL<br>GCLVKDYFPEPVTVSWNSG<br>ALTSGVHTFPAVLQSSGLYSLSSVVTVPSSSLGTQTYICNVN |

-continued

| | |
|---|---|
| | HKPSNTKVDKRVEPKSCD<br>KTHTCPPCPAPELLGGPSVFLFPPKPKDTLMISRTPEVTCVVV<br>DVSHEDPEVKFNWYVDG<br>VEVHNAKTKPREEQYNSTYRVVSVLTVLHQDWLNGKEYK<br>CKVSNKALPAPIEKTISKAKG<br>QPREPQVYTLPPSRDELTKNQVSLTCLVKGFYPSDIAVEWES<br>NGQPENNYKTTPPVLDSD<br>GSFFLYSKLTVDKSRWQQGNVFSCSVMHEALHNHYTQKSL<br>SLSPGK |
| SEQ ID NO: 11: FcγRI FG-loop | MGKHRY |
| SEQ ID NO: 12: UL12 | MESTVGPACP PGRTVTKRPW ALAEDTPRGP DSPPKRPRPN<br>SLPLTTTFRP LPPPPQTTSA VDPSSHSPVN<br>PPRDQHATDT ADEKPRAASP ALSDASGPPT PDIPLSPGGT<br>HARDPDADPD SPDLDSMWSA SVIPNALPSH<br>ILAETFERHL RGLLRGVRAP LAIGPLWARL DYLCSLAVVL<br>EEAGMVDRGL GRHLWRLTRR GPPAAADAVA<br>PRPLMGFYEA ATQNQADCQL WALLRRGLTT<br>ASTLRWGPQG PCFSPQWLKH NASLRPDVQS<br>SAVMFGRVNE PTARSLLFRY CVGRADDGGE<br>AGADTRRFIF HEPSDLAEEN VHTCGVLMDG<br>HTGMVGASLD ILVCPRDIHG YLAPVPKTPL<br>AFYEVKCRAK YAFDPMDPSD PTASAYEDLM<br>AHRSPEAFRA FIRSIPKPSV RYFAPGRVPG<br>PEEALVTQDQ AWSEAHASGE KRRCSAADRA<br>LVELNSGVVS EVLLFGAPDL GRHTISPVSW<br>SSGDLVRREP VFANPRHPNF KQILVQGYVL DSHFPDCPPH<br>PHLVTFIGRH RTSAEEGVTF RLEDGAGALG<br>AAGPSKASIL PNQAVPIALI ITPVRIDPEI YKAIQRSSRL<br>AFDDTLAELW ASRSPGPGPA AAETTSSSPT TGRSSR |
| SEQ ID NO: 13: UL30 | MFSGGGGPLS PGGKSAARAA SGFFAPAGPR GASRGPPPCL<br>RQNFYNPYLA PVGTQQKPTG PTQRHTYYSE<br>CDEFRFIAPR VLDEDAPPEK RAGVHDGHLK<br>RAPKVYCGGD ERDVLRVSG GFWPRRSRLW<br>GGVDHAPAGF NPTVTVFHVY DILENVEHAY<br>GMRAAQFHAR FMDAITPTGT VITLLGLTPE<br>GHRVAVHVYG TRQYFYMNKE EVDRHLQCRA<br>PRDLCERMAA ALRESPGASF RGISADHFEA<br>EVVERTDVYY YETRPALFYR VYVRSGRVLS YLCDNFCPAI<br>KKYEGGVDAT TRFILDNPGF VTFGWYRLKP<br>GRNNTLAQPA APMAFGTSSD VEFNCTADNL AIEGGMSDLP<br>AYKLMCFDIE CKAGGEDELA FPVAGHPEDL VIQISCLLYD<br>LSTTALEHVL LFSLGSCDLP ESHLNELAAR<br>GLPTPVVLEF DSEFEMLLAF MTLVKQYGPE FVTGYNIINF<br>DWPFLLAKLT DIYKVPLDGY GRMNGRGVFR<br>VWDIGQSHFQ KRSKIKVNGM VNIDMYGIIT DKIKLSSYKL<br>NAVAEAVLKD KKKDLSYRDI PAYYAAGPAQ<br>RGVIGEYCIQ DSLLVGQLFF KFLPHLELSA VARLAGINIT<br>RTIYDGQQIR VFTCLLRLAD QKGFILPDTQ GRFRGAGGEA<br>PKRPAAARED EERPEEEGED EDEREEGGGE<br>REPEGARETA GRHVGYQGAR VLDPTSGFHV<br>NPVVVFDFAS LYPSIIQAHN LCFSTLSLRA<br>DAVAHLEAGK DYLEIEVGGR RLFFVKAHVR ESLLSILLRD<br>WLAMRKQIRS RIPQSSPEEA VLLDKQQAAI KVVCNSVYGF<br>TGVQHGLLPC LHVAATVTTI GREMLLATRE<br>YVHARWAAFE QLLADFPEAA DMRAPGPYSM RIIYGDTDSI<br>FVLCRGLTAA GLTAVGDKMA SHISRALFLP<br>PIKLECEKTF TKLLLIAKKK YIGVIYGGKM LIKGVDLVRK<br>NNCAFINRTS RALVDLLFYD DTVSGAAAAL AERPAEEWLA<br>RPLPEGLQAF GAVLVDAHRR ITDPERDIQD<br>FVLTAELSRH PRAYTNKRLA HLTVYYKLMA RRAQVPSIKD<br>RIPYVIVAQT REVEETVARL AALRELDAAA<br>PGDEPAPPAA LPSPAKRPRE TPSPADPPGG ASKPRKLLVS<br>ELAEDPAYAI AHGVALNTDY YFSHLLGAAC<br>VTFKALFGNN AKITESLLKR FIPEVWHPPD<br>DVAARLRTAG FGAVGAGATA EETRRMLHRA FDTLA |
| SEQ ID NO: 14: Us5 | MSLRAVWHLG LLGSLVGAVL AATHRGPAAN<br>TTDPLTHAPV SPHPSPLGGF AVPLVVGGLC<br>AVVLGAACLL ELLRRTCRGW GRYHPYMDPV VV |
| SEQ ID NO: 15: Us3 | MKPVLVLAIL AVLFLRLADS VPRPLDVVVS EIRSAHFRVE<br>ENQCWFHMGM LYFKGRMSGN FTEKHFVNVG<br>IVSQSYMDRL QVSGEQYHHD ERGAYFEWNI<br>GGHPVTHTVD MVDITLSTRW GDPKKYAACV |

|  |  |
|---|---|
| | PQVRMDYSSQ TINWYLQRSM RDDNWGLLFR<br>TLLVYLFSLV VLVLLTVGVS ARLRFI |
| SEQ ID NO:<br>16: Us12 | MVQIQFHQGE PLGHKKEKPP PVSPPSPPPI RRVTVITKDE<br>DTLRSVQHFL WMVRLYGTVV FQTSATIATT<br>ILFMLIPWRV TTPYLRDTLP FWSTLLPCAL RCHAYWLERQ<br>RRPGTLMLVM VYTTLTTISV STIGLCFDRT<br>VVIQAYVLSS MLCVWCTGLA WLMAWNMQRR<br>LAILCLLSFM LPILWLFIAV QSWEPYQRII LALTVSFIYG<br>LKIVLIRDTL TVLYRSPSNC YTDGDLLRTA<br>MLLYMDQ VIM FLLVVVPLTA PIWYPNYAGA<br>LGRTAHWLFH K |
| SEQ ID NO:<br>17: Us7 | MRIQLLLVST LVASIVATRV EDMATFRTEK<br>QWQQDLQYRR EFVKRQLAPK PKSNIVVSHT<br>VSCVIDGGNM TSVWRFEGQF NPHIASEVIL HDTSGLYNVP<br>HEVQNDGQVL TVTVKRSAPA DIAKVLISLK<br>PVQLSSGQYE CRPQLQLPWV PRPSSFMYDS<br>YRLWYEKRWL TIILYVFMWT<br>YLVTLLQYCI VRFIGTRLFY FLQRNITIRF TGKPTYNLLT<br>YPVKG |
| SEQ ID NO:<br>18: Us8 | MRRWLRLLVG LGCCWVTLAH AGNPYEDDDY<br>YYYREDEPRQ HGEPNYVAPP ARQFRFPPLN<br>NVSSYQASCV VKDGVLDAVW RVQGTFYPEK<br>GIVARVGWSG RRGRKWGRLH APECLVETTE<br>AVFRLRQWVP TDLDHLTLHL VPCTKCKPMW<br>CQPRYHIRYF SYGNSVDNLR RLHYEYRHLE<br>LGVVIAIQMA MVLLLGYVLA RTVYRVSSAY<br>YLRWHACVPQ KCEKSLC |
| SEQ ID NO:<br>19: Us6 | MDLLIRLGFL LMCALPTGEE RSSRDPKTLL SLSPRQQACV<br>PRTKSHRPVC YNDTGDCTDA DDSWKQLGED<br>FAHQCLQAAK KRPKTHKSRP NDRNLEGRLT<br>CQRVRRLLPC DLDIHPSHRL LTLMNNCVCD<br>GAVWNAFRLI ERHGFFAVTL YLCCGITLLV VILALLCSIT<br>YESTGRGIRR CGS |
| SEQ ID NO:<br>20: UL48 | MDLLVDELFA DMNADGASPP PPRPAGGPKN TPAAPPLYAT<br>GRLSQAQLMP SPPMPVPPAA LFNRLLDDLG<br>FSAGPALCTM LDTWNEDLFS ALPTNADLYR ECKFLSTLPS<br>DVVEWGDAYV PERTQIDIRA HGDVAFPTLP<br>ATRDGLGLYY EALSRFFHAE LRAREESYRT VLANFCSALY<br>RYLRASVRQL HRQAHMRGRD RDLGEMLRAT<br>IADRYYRETA RLARVLFLHL YLFLTREILW<br>AAYAEQMMRP DLFDCLCCDL ESWRQLAGLF<br>QPFMFVNGAL TVRGVPIEAR RLRELNHIRE<br>HLNLPLVRSA ATEEPGAPLT TPPTLHGNQA RASGYFMVLI<br>RAKLDSYSSF TTSPSEAVMR EHAYSRARTK<br>NNYGSTIEGL LDLPDDDAPE EAGLAAPRLS FLPAGHTRRL<br>STAPPTDVSL GDELHLDGED VAMAHADALD<br>DFDLDMLGDG DSPGPGFTPH DSAPYGALDM<br>ADFEFEQMFT DALGIDEYGG |
| SEQ ID NO:<br>21: FcγRIIA | MTMETQMSQN VCPRNLWLLQ PLTVLLLLAS<br>ADSQAAAPPK AVLKLEPPWI NVLQEDSVTL<br>TCQGARSPES DSIQWFHNGN LIPTHTQPSY RFKANNNDSG<br>EYTCQTGQTS LSDPVHLTVL SEWLVLQTPH<br>LEFQEGETIM LRCHSWKDKP LVKVTFFQNG KSQKFSHLDP<br>TFSIPANHS HSGDYHCTGN IGYTLFSSKP<br>VTITVQVPSM GSSSPMGIIV AVVIATAVAA IVAAVVALIY<br>CRKKRISANS TDPVKAAQFE PPGRQMIAIR KRQLEETNND<br>YETADGGYMT LNPRAPTDDD KNIYLTLPPN DHVNSNN |
| SEQ ID NO:<br>22: FcγRIIB | MGILSFLPVL ATESDWADCK SPQPWGHMLL<br>WTAVLFLAPV AGTPAAPPKA VLKLEPQWIN<br>VLQEDSVTLT CRGTHSPESD SIQWFHNGNL IPTHTQPSYR<br>FKANNNDSGE YTCQTGQTSL SDPVHLTVLS<br>EWLVLQTPHL EFQEGETIVL RCHSWKDKPL VKVTFFQNGK<br>SKKFSRSDPN FSIPANHSH SGDYHCTGNI<br>GYTLYSSKPV TITVQAPSSS PMGIIVAVVT GIAVAAIVAA<br>VVALIYCRKK RISALPGYPE CREMGETLPE KPANPTNPDE<br>ADKVGAENTI TYSLLMHPDA LEEPDDQNRI |
| SEQ ID NO:<br>23: gI | MPCRPLQGLV LVGLWVCATS LVVRGPTVSL<br>VSNSFVDAGA LGPDVVEED LLILGELRFV<br>GDQVPHTTYY DGGVELWHYP MGHKCPRVVH<br>VVTVTACPRR PAVAFALCRA TDSTHSPAYP<br>TLELNLAQQP LLRVQRATRD YAGVYVLRVW |

| | -continued |
|---|---|
| | VGDAPNASLF VLGMAIAAEG TLAYNGSAYG<br>SCDPKLLPSS APRLAPASVY QPAPNQASTP STTTSTPSTT<br>IPAPSTTIPA PQASTTPFPT GDPKPQPPGV NHEPPSNATR<br>ATRDSRYALT VTQIIQIAIP ASIIALVFLG SCICFIHRCQ<br>RRYRRSRRPI YSPQMPTGIS CAVNEAAMAR LGAELKSHPS<br>TPPKSRRRSS RTPMPSLTAI AEESEPAGAA GLPTPPVDPT<br>TPTPTPPLLV |
| SEQ ID NO:<br>24: FcγRIIIa | MWQLLLPTAL LLLVSAGMRT EDLPKAVVFL<br>EPQWYRVLEK DSVTLKCQGA YSPEDNSTQW<br>FHNESLISSQ ASSYFIDAAT VDDSGEYRCQ TNLSTLSDPV<br>QLEVHIGWLL LQAPRWVFKE EDPIHLRCHS<br>WKNTALHKVT YLQNGKGRKY FHHNSDFYIP<br>KATLKDSGSY FCRGLVGSKN VSSETVNITI TQGLAVSTIS<br>SFFPPGYQVS FCLVMVLLFA VDTGLYFSVK TNIRSSTRDW<br>KDHKFKWRKD PQDK |
| SEQ ID NO:<br>25; UL1<br>forward | gtctacacta gtatggggat tttgggttgg gtcggg |
| SEQ ID NO:<br>26; ICP6 | MASRPAASSP VEARAPVGGQ EAGGPSAATQ<br>GEAAGAPLAH GHHVYCQRVN GVMVLSDKTP<br>GSASYRISDS NFVQCGSNCT MIIDGDVVRG RPQDPGAAAS<br>PAPFVAVTNI GAGSDGGTAV<br>VAFGGTPRRS AGTSTGTQTA DVPAEALGGP PPPPRFTLGG<br>GCCSCRDTRR RSAVFGGEGD<br>PVGPAEFVSD DRSSDSDSDD SEDTDSETLS HASSDVSGGA<br>TYDDALDSDS SSDDSLQIDG<br>PVCRPWSNDT APLDVCPGTP GPGADAGGPS AVDPHAPTTG<br>AGAGLAADPA VARDDAEGLS<br>DPRPRLGTGT AYPVPLELTP ENAEAVARFL GDAVNREPAL<br>MLEYFCRCAR EETKRVPPRT<br>FCSPPRLTED DFGLLNYALV EMQRLCLDVP PVPPNAYMPY<br>YLREYVTRLV NGFKPLVSRS<br>VRLYRILGVL VHLRIRTREA SFEEWLRSKE VALDFGLTER<br>LREHEAQLVI LAQALDHYDC<br>LIHSTPHTLV ERGLQSALKY EEFYLKRFGG HYMESVFQMY<br>TRIAGFLACR ATRGMRHIAL<br>GREGSWWEMF KFFFHRLYDH QIVPSTPAML<br>NLGTRNYYTS SCYLVNPQAT TNKATLRAIT<br>SNVSAILARN GGIGLCVQAF NDSGPGTASV MPALKVLDSL<br>VAAHNKESAR PTGACVYLEP<br>WHTDVRAVLR MKGVLAGEEA QRCDNIFSAL<br>WMPDLFFKRL IRHLDGEKNV TWTLFDRDTS<br>MSLADFHGEE FEKLYQHLEV MGFGEQIPIQ ELAYGIVRSA<br>ATTGSPFVMF KDAVNRHYIY<br>DTQGAAIAGS NLCTEIVHPA SKRSSGVCNL GSVNLARCVS<br>RQTFDFGRLR DAVQACVLMV<br>NIMIDSTLQP TPQCTRGNDN LRSMGIGMQG LHTACLKLGL<br>DLESAEFQDL NKHIAEVMLL<br>SAMKTSNALC VRGARPFNHF KRSMYRAGRF<br>HWERFPDARP RYEGEWEMLR QSMMKHGLRN<br>SQFVALMPTA ASAQISDVSE GFAPLFTNLF SKVTRDGETL<br>RPNTLLLKEL ERTFSGKRLL<br>EVMDSLDAKQ WSVAQALPCL EPTHPLRRFK<br>TAFDYDQKLL IDLCADRAPY VDHSQSMTLY<br>VTEKADGTLP ASTLVRLLVH AYKRGLKTGM<br>YYCKVRKATN SGVFGGDDNI VCTSCAL |
| SEQ ID NO:<br>27 UL1<br>forward | gtctacacta gtatggggat tttgggttgg gtcggg |
| SEQ ID NO:<br>28: UL1<br>reverse | gtctacttaa ttaagatgcg ccgggagtgg ggtcgtc |
| SEQ ID NO:<br>29: UL2<br>forward | gtctacacta gtatgaagcg ggcctgcagc cgaag |
| SEQ ID NO:<br>30: UL2<br>reverse | gtctacttaa ttaaaaccga ccagtcgatg ggtg |
| SEQ ID NO:<br>31: UL3<br>forward | gtctacacta gtatggttaa acctctggtc tcatac |

| | |
|---|---|
| SEQ ID NO: 32: UL3 reverse | gtctacttaa ttaactcggc ccccgaggcc agcatg |
| SEQ ID NO: 33: UL4 forward | gtctacacta gtatgtccaa tccacagacg accatc |
| SEQ ID NO: 34: UL4 reverse | gtctacttaa ttaaggaccc caaaagtttg tctgcg |
| SEQ ID NO: 35: UL5 forward | gtctacacta gtatggcggc ggccggcggg gag |
| SEQ ID NO: 36: UL5 reverse | gtctacttaa ttaaatatac aatgaccacg ttcggatcg |
| SEQ ID NO: 37: UL6 forward | gtctacacta gtatgaccgc accacgctcg cgg |
| SEQ ID NO: 38: UL6 reverse | gtctacttaa ttaatcgtcg gccgtcgcgg cggccatcc |
| SEQ ID NO: 39: UL7 forward | gtctacacta gtatggccgc cgcgacggcc gac |
| SEQ ID NO: 40: UL7 reverse | gtctacttaa ttaaacaaaa ctgataaaac agcgacg |
| SEQ ID NO: 41: UL8 forward | gtctacacta gtatggacac cgcagatatc gtgtgg |
| SEQ ID NO: 42: UL8 reverse | gtctacttaa ttaaggcaaa cagaaacgac atcttg |
| SEQ ID NO: 43: UL9 forward | gtctacacta gtatgccttt cgtgggggc gcggag |
| SEQ ID NO: 44: UL9 reverse | gtctacttaa ttaatagggt gctaaagttc accg |
| SEQ ID NO: 45: UL10 forward | gtctacacta gtatgggacg cccggccccc ag |
| SEQ ID NO: 46: UL10 reverse | gtctacttaa ttaaccaacg gcggacggtg ctgtac |
| SEQ ID NO: 47: UL11 forward | gtctacacta gtatgggcct ctcgttctcc ggggc |
| SEQ ID NO: 48: UL11 reverse | gtctacttaa ttaattcgct atcggacatg ggggtg |
| SEQ ID NO: 49: UL12 forward | gtctacacta gtatggagtc cacggtaggc cc |
| SEQ ID NO: 50: UL12 reverse | gtctacttaa ttaagcgaga cgacctcccc gtcg |

-continued

| | |
|---|---|
| SEQ ID NO: 51: UL13 forward | gtctacacta gtatggatga gtcccgcaga cagcg |
| SEQ ID NO: 52: UL13 reverse | gtctacttaa ttaacgacag cgcgtgccgc gcgcac |
| SEQ ID NO: 53: UL14 forward | gtctacacta gtatggaccg agatgccgcc cacg |
| SEQ ID NO: 54: UL14 reverse | gtctacttaa ttaattcgcc atcgggatag tcccg |
| SEQ ID NO: 55: UL15 forward | gtctacacta gtatgtttgg tcagcagctg gcgtc |
| SEQ ID NO: 56: UL15 reverse | gtctacttaa ttaacgaaac gcgtgtgatg ggagcg |
| SEQ ID NO: 57: UL16 forward | gtctacacta gtatggcgca gctgggaccc cggcg |
| SEQ ID NO: 58: UL16 reverse | gtctacttaa ttaattcggg atcgcttgag gaggcccg |
| SEQ ID NO: 59: UL17 forward | gtctacacta gtatgaacgc gcacttggcc aacgaggtc |
| SEQ ID NO: 60: UL17 reverse | gtctacttaa ttaagcgaga acggccgttc ccgga |
| SEQ ID NO: 61: UL18 forward | gtctacacta gtatgctggc ggacggcttt gaaac |
| SEQ ID NO: 62: UL18 reverse | gtctacttaa ttaagggata gcgtataacg gg |
| SEQ ID NO: 63: UL19 forward | gtctacacta gtatggccgc tcccaaccgc gaccc |
| SEQ ID NO: 64: UL19 reverse | gtctacttaa ttaacagagc cagtcccttg agcggggatg |
| SEQ ID NO: 65: UL20 forward | gtctacacta gtatgaccat gcgggatgac cttcctc |
| SEQ ID NO: 66: UL20 reverse | gtctacttaa ttaagaacgc gacgggtgca ttcaag |
| SEQ ID NO: 67: UL21forward | gtctacacta gtatggagct tagctacgcc acc |
| SEQ ID NO: 68: UL21 reverse | gtctacttaa ttaacacaga ctgtccgtgt ttgg |
| SEQ ID NO: 69: UL22 forward | gtctacacta gtatggggaa tggtttatgg ttcg |

-continued

| | |
|---|---|
| SEQ ID NO: 70: UL22 reverse | gtctacttaa ttaattcgcg tctccaaaaa aacgggacac |
| SEQ ID NO: 71: UL23 forward | gtctacacta gtatggcttc gtacccctgc catc |
| SEQ ID NO: 72: UL23 reverse | gtctacttaa ttaagttagc ctcccccatc tcccgggcaa acg |
| SEQ ID NO: 73: UL24forward | gtctacacta gtatggccgc gagaacgcgc agc |
| SEQ ID NO: 74: UL24 reverse | gtctacttaa ttaattcgga ggcggctcgg ggtttg |
| SEQ ID NO: 75: UL25 forward | gtctacacta gtatggaccc gtactgccca tug |
| SEQ ID NO: 76: UL25 reverse | gtctacttaa ttaaaaccgc cgacaggtac tgtgg |
| SEQ ID NO: 77: UL26 forward | gtctacacta gtatggcagc cgatgccccg ggag |
| SEQ ID NO: 78: UL26 reverse | gtctacttaa ttaagcgggc ccccatcatc tgagag |
| SEQ ID NO: 79: UL26.5 forward | gtctacacta gtatgaaccc cgttccggca tcgggc |
| SEQ ID NO: 80: UL26.5 reverse | gtctacttaa ttaagcgggc ccccatcatc tgagag |
| SEQ ID NO: 81: UL27 forward | gtctacacta gtatgcgcca gggcgccccc gc |
| SEQ ID NO: 82: UL27 reverse | gtctacttaa ttaacaggtc gtcctcgtcg gcgtc |
| SEQ ID NO: 83: UL28 forward | gtctacacta gtatggccgc cccggtgtcc gagccc |
| SEQ ID NO: 84: UL28 reverse | gtctacttaa ttaacggggg cccgtcgtgc cccc |
| SEQ ID NO: 85: UL29 forward | gtctacacta gtatggagac aaagcccaag acggc |
| SEQ ID NO: 86: UL29 reverse | gtctacttaa ttaacagcat atccaacgtc aggtctc |
| SEQ ID NO: 87: UL30 forward | gtctacacta gtatgttttc cggtggcggc gg |
| SEQ ID NO: 88: UL30 reverse | gtctacttaa ttaatgctag agtatcaaag gctc |
| SEQ ID NO: 89: UL31forward | gtctacacta gtatgtatga caccgacccc catc |

| | |
|---|---|
| SEQ ID NO: 90: UL31 reverse | gtctacttaa ttaacggcgg aggaaactcg tcgaatg |
| SEQ ID NO: 91: UL32forward | gtctacacta gtgcccagcc atggcaactt cg |
| SEQ ID NO: 92: UL32 reverse | gtctacttaa ttaatacata ggtacacagg gtgtgc |
| SEQ ID NO: 93: UL33 forward | gtctacacta gtgaagttgc catggctggg c |
| SEQ ID NO: 94: UL33 reverse | gtctacttaa ttaagccccg cagaatctgg tgcaggtc |
| SEQ ID NO: 95: UL34 forward | gtctacacta gtatggcggg actgggcaag ccc |
| SEQ ID NO: 96: UL34 reverse | gtctacttaa ttaataggcg cgcgccagca ccaac |
| SEQ ID NO: 97: UL35 forward | gtctacacta gtatggccgt cccgcaattt cac |
| SEQ ID NO: 98: UL35 reverse | gtctacttaa ttaacggggt cccgggcgtc gaagg |
| SEQ ID NO: 99: UL36 forward | gtctacacta gtatgatcgc gggcacccca ccgcac |
| SEQ ID NO: 100: UL36 reverse | gtctacttaa ttaagcccag taacatgcgc acgtgatg |
| SEQ ID NO: 101: UL37 forward | gtctacacta gtatggcaga ccgcggtctc ccgtccg |
| SEQ ID NO: 102: UL37 reverse | gtctacttaa ttaattggta actcgttaac ggcaagtc |
| SEQ ID NO: 103: UL38 forward | gtctacacta gtatgaagac caatccgcta cccg |
| SEQ ID NO: 104: UL38reverse | gtctacttaa ttaacgcgca tgcccgccac tcgcc |
| SEQ ID NO: 105: UL39 forward | gtctacacta gtatggccag ccgcccagcc gc |
| SEQ ID NO: 106: UL39 reverse | gtctacttaa ttaacagcgc gcagctcgtg cagac |
| SEQ ID NO: 107: UL40 forward | gtctacacta gtatggattc cgcggcccca g |
| SEQ ID NO: 108: UL40 reverse | gtctacttaa ttaacagatc gttgacgacc gc |

-continued

| | |
|---|---|
| SEQ ID NO: 109: UL41 forward | gtctacacta gtatgggttt gttcgggatg atgaag |
| SEQ ID NO: 110: UL41 reverse | gtctacttaa ttaactcgtc ccagaatttg gccag |
| SEQ ID NO: 111: UL42 forward | gtctacacta gtatgacgga ttcccctggc ggtg |
| SEQ ID NO: 112: UL42 reverse | gtctacttaa ttaaggggaa tccaaaacca gac |
| SEQ ID NO: 113: UL43 forward | gtctacacta gtatgctccg caacgacagc cacc |
| SEQ ID NO: 114: UL43 reverse | gtctacttaa ttaaatcgcc cgaccgcccg cccgttg |
| SEQ ID NO: 115: UL44 forward | gtctacacta gtgctttgcc gggaacgcta gc |
| SEQ ID NO: 116: UL44 reverse | gtctacttaa ttaaccgccg atgacgctgc cgcgac |
| SEQ ID NO: 117: UL45 forward | gtctacacta gtatgcctct gcgggcatcg gaac |
| SEQ ID NO: 118: UL45 reverse | gtctacttaa ttaacggcag ccccagcgcg ttgc |
| SEQ ID NO: 119: UL46 forward | gtctacacta gtctggacgc ggcataactc cgac |
| SEQ ID NO: 120: UL46 reverse | gtctacttaa ttaaccggct ccggcgtcct tcgcgtttaa g |
| SEQ ID NO: 121: UL47 forward | gtctacacta gtatgtcggc tcgcgaaccc gc |
| SEQ ID NO: 122: UL47 reverse | gtctacttaa ttaatgggcg tggcgggcct cccag |
| SEQ ID NO: 123: UL48 forward | gtctacacta gtatggacct cttggtcgac gagctg |
| SEQ ID NO: 124: UL48 reverse | gtctacttaa ttaacccacc gtactcgtca attccaag |
| SEQ ID NO: 125: UL49 forward | gtctacacta gtatgacctc tcgccgctcc gtgaag |
| SEQ ID NO: 126: UL49 reverse | gtctacttaa ttaactcgac gggccgtctg g |
| SEQ ID NO: 127: UL49A forward | gtctacacta gtctcatctt cctgttaggg acgatg |
| SEQ ID NO: 128: UL49A reverse | gtctacttaa ttaaggcgtg cccggcagcc agtag |

| | |
|---|---|
| SEQ ID NO: 129: UL50 forward: | gtctacacta gtgtccctaa caggaagatg agtcag |
| SEQ ID NO: 130: UL50 reverse | gtctacttaa ttaaaatacc ggtagagcca aaacc |
| SEQ ID NO: 131: UL51 forward | gtctacacta gtatggcttc tcttctcggg gc |
| SEQ ID NO: 132: UL51 reverse | gtctacttaa ttaattgacc caaaacacac ggagctgc |
| SEQ ID NO: 133: UL52 forward | gtctacacta gtatggggca ggaagacggg aac |
| SEQ ID NO: 134: UL52 reverse | gtctacttaa ttaaagacga cggttgagag gtgctgc |
| SEQ ID NO: 135: UL53 forward | gtctacacta gtatgctcgc cgtccgttcc ctgcag |
| SEQ ID NO: 136: UL53 reverse | gtctacttaa ttaatacatc aaacaggcgc ctctggatc |
| SEQ ID NO: 137: UL54 forward | gtctacacta gtatggcgac tgacattgat atgctaattg |
| SEQ ID NO: 138: UL54 reverse | gtctacttaa ttaaaaacag ggagttgcaa taaaatatt tgc |
| SEQ ID NO: 139: UL55 forward | gtctacacta gtcttttgca ctatgacagc gacc |
| SEQ ID NO: 140: UL55 reverse | gtctacttaa ttaacgcctt aattttaatc ttgac |
| SEQ ID NO: 141: UL56 forward | gtctacacta gtcatccatg gcttcggagg cggcgc |
| SEQ ID NO: 142: UL56 reverse | gtctacttaa ttaaccgcca caggaatacc agaataatg |
| SEQ ID NO: 143: RS1 forward | gtctacacta gtatggcgtc ggagaacaag cagcg |
| SEQ ID NO: 144: RS1 reverse | gtctacttaa ttaacagcac cccgtccccc tcgaacgcg |
| SEQ ID NO: 145: US1 forward | gtctacacta gtatggccga catttcccca gg |
| SEQ ID NO: 146 US1 reverse: | gtctacttaa ttaacggccg gagaaacgtg tcgctg |
| SEQ ID NO: 147: US2 forward | gtctacacta gtatgggcgt tgttgtcgtc aacg |

-continued

| | | |
|---|---|---|
| SEQ ID NO: 148: US2 reverse | gtctacttaa ttaacagggt ggtaaccgga tagcagatg | |
| SEQ ID NO: 149: US3 forward | gtctacacta gtatggcctg tcgtaagttt tgtcg | |
| SEQ ID NO: 150: US3 reverse | gtctacttaa ttaatttctg ttgaaacagc ggcaaac | |
| SEQ ID NO: 151: US4 forward | gtctacacta gtcatcatgt cgccgggcgc catg | |
| SEQ ID NO: 152: US4 reverse | gtctacttaa ttaacccgcg ttcggacggc aggcac | |
| SEQ ID NO: 153: US5 forward | gtctacacta gtatgtctct gcgcgcagtc tg | |
| SEQ ID NO: 154: US5 reverse | gtctacttaa ttaatacgac aactgggtcc atgtagg | |
| SEQ ID NO: 155: US6 forward | gtctacacta gtgtgtggtg cgttccggta tg | |
| SEQ ID NO: 156: US6 reverse | gtctacttaa ttaagtaaaa caagggctgg tgcgag | |
| SEQ ID NO: 157: US7 forward | gtctacacta gtgtcccgtt ccgggatgcc gtg | |
| SEQ ID NO: 158: US7 reverse | gtctacttaa ttaataccaa caggggaggc gttg | |
| SEQ ID NO: 159: US8 forward | gtctacacta gtgacatgga tcgcggggcg gtg | |
| SEQ ID NO: 160: US8 reverse | gtctacttaa ttaaccagaa gacggacgaa tcgg | |
| SEQ ID NO: 161: US8A forward | gtctacacta gtatggatcc ggctttgaga tc | |
| SEQ ID NO: 162: US8A reverse | gtctacttaa ttaatgcgcc tcgggcaatt gacgtc | |
| SEQ ID NO: 163: US9 forward | gtctacacta gtatgacgtc ccggctctcc g | |
| SEQ ID NO: 164: US9 reverse | gtctacttaa ttaagcggag cagccacatc aggag | |
| SEQ ID NO: 165: US10 forward | gtctacacta gtgtgataat gatcaagcgg cgg | |
| SEQ ID NO: 166: US10 reverse | gtctacttaa ttaagcacag gggtggggtt agg | |
| SEQ ID NO: 167: US11 forward | gtctacacta gtgtggctct cgagatgagc cag | |

| SEQ ID NO: 168: US11 reverse | gtctacttaa ttaatacaga cccgcgagcc gtacgtg |
| --- | --- |
| SEQ ID NO: 169: US12 forward | gtctacacta gtatgtcgtg ggccctggaa atggc |
| SEQ ID NO: 170: US12 reverse | gtctacttaa ttaaacgggt taccggatta cggggac |

What is claimed is:

1. A method of treating a subject infected with a pathogen expressing an Fc-binding protein comprising administering to the subject a therapeutically effective amount of a pharmaceutical composition consisting of an Fc fragment of a human immunoglobulin G 1 (IgG1) antibody that binds to an FcγR on an immune effector cell at a first region and the pathogen-encoded Fc binding protein at a second region, wherein the first region is different than the second region, and wherein the pathogen-encoded Fc binding protein is glycoprotein E (gE) or 68 kDa-glycoprotein (gp68).

2. A method for treating a cancer in a subject undergoing oncolytic viral therapy comprising administering to the subject a therapeutically effective amount of a pharmaceutical composition consisting of an Fc fragment of a human immunoglobulin G 1 (IgG1) antibody that binds to the pathogen-encoded Fc binding protein but does not bind to an FcγR on an immune effector cell, and wherein the pathogen-encoded Fc binding protein is glycoprotein E (gE) or 68 kDa-glycoprotein (gp68).

3. The method of claim 1, wherein the Fc fragment of the IgG1 antibody comprises SEQ ID NO: 1.

4. The method of claim 1, wherein the FcγR is CD16a.

5. The method of claim 1, wherein the pathogen is herpes simplex virus 1 (HSV-1).

6. The method of claim 1, wherein the pathogen is a cytomegalovirus.

7. The method of claim 2, wherein the Fc fragment of the IgG1 antibody comprises SEQ ID NO: 2.

8. The method of claim 2, wherein the oncolytic viral therapy comprises administering to the subject a recombinant oncolytic herpes simplex virus (oHSV).

9. A method of activating natural killer (NK) cells in a subject infected with a pathogen, comprising administering to the subject a pharmaceutical composition consisting of an Fc fragment of a human immunoglobulin G 1 (IgG1) antibody that binds to an FcγR on an immune effector cell at a first region and the pathogen-encoded Fc binding protein at a second region, wherein the first region is different than the second region, and wherein the pathogen-encoded Fc binding protein is glycoprotein E (gE) or 68 kDa-glycoprotein (gp68).

10. The method of claim 7, wherein the pathogen is herpes simplex virus 1 (HSV-1).

11. The method of claim 7, wherein the pathogen is a cytomegalovirus.

12. The method of claim 7, wherein the FcγR is CD16a.

13. The method of claim 7, wherein the Fc fragment of the IgG1 antibody comprises SEQ ID NO: 1.

* * * * *